(12) United States Patent
Yen et al.

(10) Patent No.: US 8,193,206 B2
(45) Date of Patent: Jun. 5, 2012

(54) PYRIMIDINE COMPOUNDS

(75) Inventors: Chi-Feng Yen, Taipei County (TW);
Cheng-Kung Hu, Hsinchu (TW);
Ming-Chen Chou, Taipei (TW);
Chen-Tso Tseng, Taipei (TW);
Chien-Huang Wu, Taipei County (TW);
Ying-Huey Huang, Changhua (TW);
Shu-Jen Chen, Taipei (TW); Chi-Hsin Richard King, Holladay, UT (US)

(73) Assignee: TaiGen Biotechnology Co., Ltd., Taipei (TW)

( * ) Notice: Subject to any disclaimer, the term of this patent is extended or adjusted under 35 U.S.C. 154(b) by 701 days.

(21) Appl. No.: 12/330,132

(22) Filed: Dec. 8, 2008

(65) Prior Publication Data

US 2009/0143302 A1 Jun. 4, 2009

Related U.S. Application Data

(63) Continuation-in-part of application No. 11/451,897, filed on Jun. 13, 2006, now abandoned.

(60) Provisional application No. 60/690,267, filed on Jun. 14, 2005, provisional application No. 60/798,596, filed on May 8, 2006.

(51) Int. Cl.
*A61K 31/505* (2006.01)
*A61K 31/506* (2006.01)

(52) U.S. Cl. ........................................................ 514/275

(58) Field of Classification Search .................... 514/275
See application file for complete search history.

(56) References Cited

U.S. PATENT DOCUMENTS

| | | | |
|---|---|---|---|
| 3,759,921 A | 9/1973 | Paget | |
| 4,285,946 A | 8/1981 | Kampe et al. | |
| 5,034,560 A | 7/1991 | Cesa et al. | |
| 6,420,354 B1 | 7/2002 | Marquess et al. | |
| 7,501,412 B2 | 3/2009 | Fujio et al. | |
| 2005/0124640 A1 | 6/2005 | Cardozo et al. | |
| 2005/0197350 A1 | 9/2005 | Sekiguchi et al. | |
| 2006/0281712 A1 | 12/2006 | Yen et al. | |
| 2006/0293324 A1 | 12/2006 | Yen et al. | |
| 2007/0167459 A1 | 7/2007 | Habashita et al. | |
| 2008/0070894 A1 | 3/2008 | Kawamura et al. | |

FOREIGN PATENT DOCUMENTS

| | | |
|---|---|---|
| AU | 2005247943 | 12/2005 |
| AU | 2006295260 | 4/2007 |
| AU | 2006297089 | 4/2007 |
| AU | 2006318383 | 5/2007 |
| AU | 2007227602 | 9/2007 |
| EP | 0443862 | 8/1991 |
| EP | 834507 | 8/1998 |
| EP | 1571146 | 9/2005 |
| EP | 1595869 | 11/2005 |
| EP | 1852432 | 11/2007 |
| JP | 1992-211040 | 3/1994 |
| JP | 2001-518094 | 10/2001 |
| JP | 2003-519139 | 6/2003 |
| JP | 2003-527303 | 9/2003 |
| JP | 2004-300156 | 10/2004 |
| RU | 2189976 | 10/2000 |
| WO | WO 93/01498 | 1/1993 |
| WO | WO93/03018 | 2/1993 |
| WO | WO 95/13312 | 5/1995 |
| WO | WO 95/23609 | 9/1995 |
| WO | WO 97/20823 | 6/1997 |
| WO | WO 97/46250 | 12/1997 |
| WO | WO 98/24782 | 6/1998 |
| WO | WO 98/43969 | 10/1998 |
| WO | WO 99/50249 | 10/1999 |
| WO | WO 99/65897 | 12/1999 |
| WO | WO 00/20358 | 4/2000 |
| WO | WO00/27826 | 5/2000 |
| WO | WO00/53595 | 9/2000 |
| WO | WO 01/47897 | 7/2001 |
| WO | WO 01/47915 | 7/2001 |
| WO | WO 02/50065 | 6/2002 |
| WO | WO 02/057259 | 7/2002 |
| WO | WO 03/024448 | 3/2003 |
| WO | WO03/026666 | 4/2003 |
| WO | WO 03/028641 | 4/2003 |
| WO | WO03/082855 | 10/2003 |
| WO | WO2004/002964 | 1/2004 |
| WO | WO2004/005281 | 1/2004 |

(Continued)

OTHER PUBLICATIONS

Database WPI Week 200376; Thomson Scientific, London, GB, An 2003-812528; XP002598940. Purandare et al. "Identification of Chemokine Receptor CCR4 Antagonist"; Bioorganic & Medicinal Chemistry Letters, Pergamon, Elsevier Science; 15(10):2671, (2005).

Database WPI Week 200634, Thomson Scientific, London, GB; An 2006-331425; XP002598941.

Database WPI Week 200652; Thomson Scientific, London, GB; An 2006-506849; XP002598942.

Larsen et al., "Hylan and Hylan Derivatives in Drug Deliver," Cosmetic and Pharmaceutical Applications of Polymers, 147-157, 1991.

(Continued)

*Primary Examiner* — James D Anderson
*Assistant Examiner* — Gregg Polansky
(74) *Attorney, Agent, or Firm* — Occhiuti Rohlicek & Tsao LLP

(57) ABSTRACT

This invention relates to a method for treating inflammatory diseases or immune diseases, developmental or degenerative diseases, or tissue injuries. The method includes administering to a subject in need thereof an effective amount of one or more compounds of formula (I). Each variable in this formula is defined in the specification.

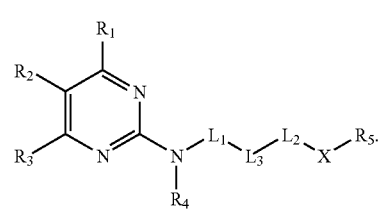

15 Claims, No Drawings

FOREIGN PATENT DOCUMENTS

| WO | WO 2004/052862 | 6/2004 |
| --- | --- | --- |
| WO | WO 2004/067516 | 8/2004 |
| WO | WO 2004/069823 | 8/2004 |
| WO | WO2004/074260 | 9/2004 |
| WO | WO 2005/028427 | 3/2005 |
| WO | WO2005/085212 | 9/2005 |
| WO | WO2006/025567 | 3/2006 |
| WO | WO2006/090853 | 8/2006 |
| WO | WO2007/129195 | 11/2007 |

OTHER PUBLICATIONS

Lofas, "Dextarn modified self-assembled monolayer surfaces for use in biointeraction analysis with surface Plasmon resonance," Pure & Appl. Chem. 67:829-834, 1995.

Goendoes et al., "An Efficient Synthesis of cis- and trns-2-Aminocyclohexanecarboxamides and Their N-Substituted Derivates," Liebigs Ann. Chem. 591-593, 1991.

Roberts et al., Synthesis of Some 4-Substituted Biocyclo[2.2.2]octane-1-carboxylic Acids, JACS, 75:637-640; 1953.

Kanuma et al., "Discovery of 4-(dimethylamino)quinazolines as potent and selective antagonists for the melanin-concentrating hormone receptor 1", Bioorganic & Medicinal Chemistry Letters 15:2565-2569, 2005.

Campagna et al., "A Convenient Synthesis of Nitriles from Primary Amides Under Mild Conditions," Tetrahedron Letters; the International Organ for the Rapid Publication of Preliminary Communications in Organic Chemistry, 1913-1816, 1977.

Klenke et al., "Nitrile Reduction in the Presence of Boc-Protected Amino Groups by Catalytic Hydrogeneration over Palladium-Activated Raney-Nickel" J. Org. Chem. 66:2480-2483, 2001.

Kuo et al. "A convenient new procedure for converting primary amides into nitriles" Chem. Commun. 2007, 301-303.

Li et al. "Preparation of Fluorescent Nonpetidic Neuropeptide Y Receptor Ligands: Analogues of the Quinazoline-type Antiobesity Y Antagonist CGP 71683A" Arch. Pharm, Pharm. Med. Chem. 2003, 336, 585-590.

MedicineNet.com, "Definition of Retinopathy", 2003, downloaded from http://www.medterms.com/script/main/art.asp?articlekey=22185 on Aug. 14, 2009, p. 1 of 1.

MedicineNet.com, "Definition of Ischemia", 1998, downloaded from http://www.medterms.com/script/main/art.asp?articlekey=4052 on Aug. 14, 2009, p. 1 of 1.

Suggitt et al.,; "50 Years of Preclinical Anticancer Drug Screening: Empirical to Target-Driven Approaches"; Clinical Cancer Research, 2005, vol. 11, pp. 971-981.

Gura, "Systems for Identifying New Drugs are Often Faulty"; Science, 1997, vol. 278, 1041-1042.

CAS RN 355420-13-2, STN Entry Date Sep. 10, 2001 Benzaldehyde, 3-bromo-4-(2,4-dinitrophenoxy)-5-methoxy:,2-[5-fl uoro-4-(4-morpholinyl)-2-pyrimidinyl] hy dr azone.

CAS RN 401590-15-6, STN Entry Date Mar. 18 2}A2 Benzaldehy de, 4-[(2-chloro-5-fl uoro-4-pyrimidinyl)oxy] -3-ethoxy-, 2-[5-fl uoro-4-(4-morpholinyl)-2-pyrimidinyl]hydrazone.

CAS RN 831774-92-6, STN Entry Date Feb. 15, 2005 Benzaldehyde, 4-IU -1(2.4-dichlorophenyl)methylf-2,3,6,7 -tetrahydro-1,3-dimethyl-2,6-dioxo-1H-purin-8-ylloxy1-3-methoxy-, 1-12-[5-fluoro-4-(4-morpholinyl)-2-pyrimidinyllhydrazonel.

CAS RN 353509 -l!-Z,STN Entry DateZgAug. 2001 Benzaldehy de, 4-[(2-chloro-5-fl uoro-4-pyrimidinyl)oxy] -, 2-[5-fl uoro-4-(4-morpholinyl)-2-pyri midinyl]hy dr azone.

CAS RN 872521-21-6, STN Entry Date Jan. 24, 2006 Benzaldehyde, 3-[(2-chloro-S-fluoro-4-pyrimidinyl)oxy]-4-methoxy-, 2-[5-fl uoro-4-(4-morpholinyl)-2-pyrimidinyl] hy dr azone.

CAS RN 353509-72-3, STN Entry Date Aug. 29, 2001 Benzaldehyde, 4-[(2-chloro-5-fl uoro-4-pyrimidinyl)oxy]-3-methoxy-, 2-[5-fl uoro-4-(4-morpholinyl)-2-pyrimidinyl] hyd r azone.

CAS RN 444801-00-7, STN Entry Date Aug. 24 }OD2 Benzaldehy de, 4-(2,4-dinitrophenoxy)-3-iodo-5-methoxy-, 2-[5-fl uoro-4-(4-morpholinyl)-2-pyrimidinyl] hy dr azone.

CAS RN 790195-80-1, STN Entry Date Nov. 29, 2004, 4-[2-1[(cyclohexylamino)carbonyl]aminol-6-methyl-4-pyrimidinyl-laminol]- benzenecarboximidamide.

CAS RN 401579-82-6, STN Entry Date Mar. 18, 2002 N-cyclohexyl-N'-(4,6-dichloro-2-pyrimidinyl) -urea.

CAS RN 400839-99-8, STN Entry Date Mar. 14, 2002 N-cyclohexyl-N'-(4,6-dimethoxy-2-pyrimidinyl)-urea.

CAS RN 400839-40-9, STN Entry Date Mar. 14, 2002 N-cyclohexyl-N'-(5 -methyl-2-pyrimidinyl) -urea.

CAS RN 378776-29-5, STN Entry Date Dec. 27, 2001 N-cyclohexyl-2-[(4,6 -diphenyl-2-pyrimidinyl)amino] -acetamide.

Database CAplus Accession No. 1996:101040 & CAS RN 17361r-24-0.

Database CAplus Accession No. 1991:449603 & CAS RN 134840-01-0.

Strekowski, L. et al, Anti-Cancer Drug Design, 1988, 3(2), 79-89.

PYRIMIDINE COMPOUNDS

CROSS REFERENCE TO RELATED APPLICATIONS

This application is a continuation-in-part application of U.S. Utility application Ser. No. 11/451,897, filed Jun. 13, 2006, which claims priority to U.S. Provisional Application Ser. No. 60/690,267, filed Jun. 14, 2005 and U.S. Provisional Application Ser. No. 60/798,596, filed May 8, 2006. The contents of all of the three prior applications are incorporated herein by their reference.

BACKGROUND

Chemokines are a family of cytokines that regulate the adhesion and transendothelial migration of leukocytes during an immune or inflammatory reaction (Mackay C. R., Nat. Immunol., (2001) 2:95; Olson et al., Am. J. Physiol. Regul. Integr. Comp. Physiol., (2002) 283:R7). Chemokines also regulate T cells and B cells trafficking and homing, and contribute to the development of lymphopoietic and hematopoietic systems (Ajuebor et al., Biochem. Pharmacol., (2002) 63:1191). Approximately 50 chemokines have been identified in humans. They can be classified into 4 subfamilies, i.e., CXC, CX3C, CC, and C chemokines, based on the positions of the conserved cysteine residues at the N-terminal (Onuffer et al., Trends Pharmacol Sci., (2002) 23:459). The biological functions of chemokines are mediated by their binding and activation of G protein-coupled receptors (GPCRs) on the cell surface. Take CXCR4 receptor for example, it can be activated by Stromal-derived factor-1 or SDF-1, a member of CXC chemokines.

SDF-1 was originally cloned from bone marrow stromal cell lines and found to act as a growth factor for progenitor B cells (Nishikawa et al., Eur. J. Immunol., (1988) 18:1767). SDF-1 also induces bone marrow colonization of hematopoietic precursor cells during embryogenesis (Bleul et al., J. Exp. Med., (1996) 184:1101). The physiological function of SDF-1 is mediated by CXCR4 receptor. Mice lacking SDF-1 or CXCR4 receptor show lethal abnormality in bone marrow myelopoiesis, B cell lymphopoiesis, and cerebellar development (Nagasawa et al., Nature, (1996) 382:635; Ma et al., Proc. Natl. Acad. Sci., (1998) 95:9448; Zou et al., Nature (1998) 393:595; Lu et al., Proc. Natl. Acad. Sci. (2002) 99:7090). CXCR4 receptor is expressed broadly in a variety of tissues, particularly in immune and central nervous systems, and has been described as the major co-receptor for HIV-1/2 on T lymphocytes. Although initial interest in CXCR4 antagonism focused on its potential application to AIDS treatment (Bleul et al., Nature (1996) 382:829), it is now becoming clear that CXCR4 receptor and SDF-1 are also involved in other pathological conditions such as rheumatoid arthritis, asthma, and tumor metastases (Buckley et al., J. Immunol., (2000) 165:3423). CXCR4 receptor and SDF-1 are also found widely expressed in many tissues during embryonic development. Further, the CXCR4/SDF-1 pathway has been shown to be critically involved in the regeneration of several tissue injury models. Specifically, it has been found that the SDF-1 level is elevated at an injured site and CXCR4-positive cells actively participate in the tissue regenerating process.

SUMMARY

This invention is based on the discovery that certain pyrimidine compounds are effective in treating inflammatory and immune diseases (e.g., retinopathy), developmental or degenerative diseases, or tissue injuries through their binding to chemokine receptors (e.g., CXCR3 or CXCR4 receptors). In addition, these compounds, when used in combination with G-CSF growth factor, exhibited synergistic effects in stem cells and endothelial progenitor cells mobilization.

In one aspect, this invention features pyrimidine compounds of formula (I) and their salts:

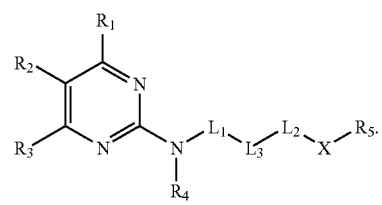

(I)

In this formula, X is —N($R_a$)— or —O—; or X, together with $R_5$, is $C_3$-$C_{20}$ heterocycloalkyl; or X, together with $L_2$ and $L_3$, is $C_3$-$C_{20}$ heterocycloalkyl; each of $L_1$ and $L_2$, independently, is $C_1$-$C_{10}$ alkylene, $C_1$-$C_{10}$ heteroalkylene, —C(O)—, or deleted; or $L_1$, together with $L_3$, $R_4$, and the nitrogen attached to $R_4$, is $C_3$-$C_{20}$ heterocycloalkyl, or $L_2$, together with $L_3$ and X, is $C_3$-$C_{20}$ heterocycloalkyl; $L_3$ is —N($R_b$)—, —O—, aryl, heteroaryl, or $C_3$-$C_{20}$ cycloalkyl; or $L_3$, together with $L_1$, $R_4$, and the nitrogen attached to $R_4$, is $C_3$-$C_{20}$ heterocycloalkyl; or $L_3$, together with $L_2$ and X, is $C_3$-$C_{20}$ heterocycloalkyl; each of $R_1$, $R_2$, and $R_3$, independently, is H, $C_1$-$C_{10}$ alkyl, $C_3$-$C_{20}$ cycloalkyl, $C_3$-$C_{20}$ heterocycloalkyl, aryl, heteroaryl, halo, CN, O$R_c$, COO$R_c$, OC(O)$R_c$, C(O)$R_c$, C(O)N$R_c R_d$, or N$R_c R_d$; $R_4$ is H, $C_1$-$C_{10}$ alkyl, $C_3$-$C_{20}$ cycloalkyl, $C_3$-$C_{20}$ heterocycloalkyl, aryl, or heteroaryl; and $R_5$ is $C_3$-$C_{20}$ cycloalkyl, $C_3$-$C_{20}$ heterocycloalkyl, aryl, heteroaryl, or $C_1$-$C_{10}$ alkyl substituted with $C_3$-$C_{20}$ cycloalkyl, $C_3$-$C_{20}$ heterocycloalkyl, or N($R_e R_f$); or $R_5$, together with X, is $C_3$-$C_{20}$ heterocycloalkyl; in which each of $R_a$, $R_b$, $R_c$, $R_d$, $R_e$, and $R_f$, independently, is H, $C_1$-$C_{10}$ alkyl, $C_3$-$C_{20}$ cycloalkyl, $C_3$-$C_{20}$ heterocycloalkyl, aryl, heteroaryl, or —C(O)R; R being H, $C_1$-$C_{10}$ alkyl, $C_3$-$C_{20}$ cycloalkyl, $C_3$-$C_{20}$ heterocycloalkyl, aryl, or heteroaryl.

Referring to formula (I), a subset of the pyrimidine compounds described above are those in which X can be —N($R_a$)—, each of $L_1$ and $L_2$, independently, can be $C_1$-$C_{10}$ alkylene, —C(O)—, or deleted; and $L_3$ can be —N($R_b$)—, —O—, aryl, or $C_3$-$C_{20}$ cycloalkyl. As one example, in certain pyrimidine compounds, $L_3$ is —N($R_b$)—. In these compounds, $R_5$ can be $C_3$-$C_{20}$ cycloalkyl (e.g., 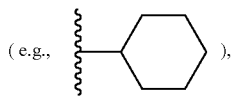 ), $C_1$-$C_{10}$ alkyl substituted with $C_3$-$C_{20}$ cycloalkyl (e.g., 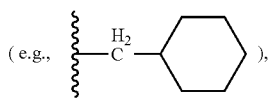 ), or $C_3$-$C_{20}$ heterocycloalkyl substituted with $C_1$-$C_{10}$ alkyl (e.g., 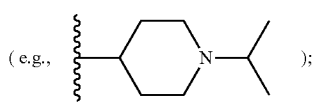);

$R_b$ can be $C_1$-$C_{10}$ alkyl substituted with N(R'R"), in which each of R' and R", independently, is H, $C_1$-$C_{10}$ alkyl, $C_3$-$C_{20}$ cycloalkyl, $C_3$-$C_{20}$ heterocycloalkyl, aryl, or heteroaryl; and $R_1$ can be $C_3$-$C_{20}$ heterocycloalkyl (e.g., 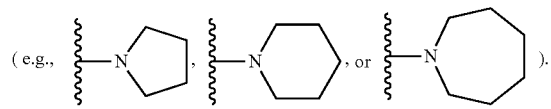).

As another example, in certain pyrimidine compounds, $L_3$ can be aryl (e.g., phenylene). In these compounds, $R_5$ can be $C_1$-$C_{10}$ alkyl substituted with $C_3$-$C_{20}$ heterocycloalkyl (e.g., 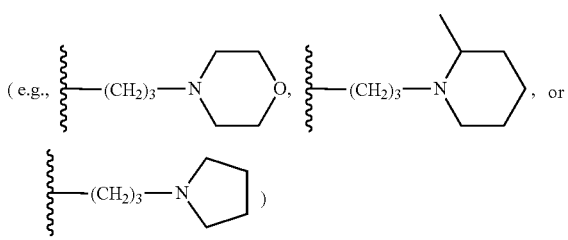)

or $C_1$-$C_{10}$ alkyl substituted with $N(R_eR_f)$

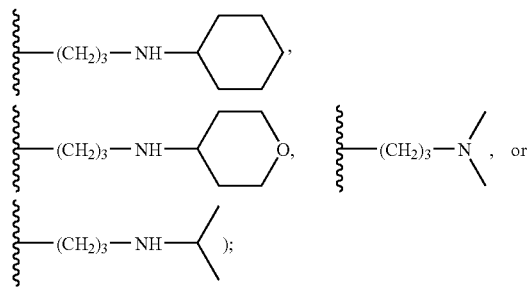

or $R_5$, together with X, is $C_3$-$C_{20}$ heterocycloalkyl

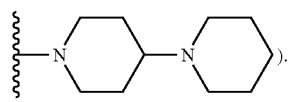).

$R_3$ can be H, halo $C_1$-$C_{10}$ alkyl, $OR_c$, $NR_cR_d$, or $C_3$-$C_{20}$ heterocycloalkyl optionally substituted with $C_1$-$C_{10}$ alkyl, $C_3$-$C_{20}$ cycloalkyl, $C_3$-$C_{20}$ heterocycloalkyl, aryl, OR', C(O)R', COOR', C(O)N(R'R"), $SO_2R'$, C(S)N(R'R"), $OSO_3R'$, or $PO(OR')_2$, in which each of R' and R", independently, is H, $C_1$-$C_{10}$ alkyl, $C_3$-$C_{20}$ cycloalkyl, $C_3$-$C_{20}$ heterocycloalkyl, aryl, or heteroaryl. In certain embodiments, $R_3$ can be H, Cl, $CH_3$, OPh,

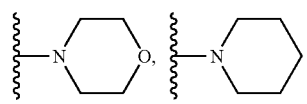

optionally substituted with OH,

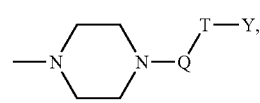

optionally substituted with $C_1$-$C_{10}$ alkyl, $C_3$-$C_{20}$ cycloalkyl, $C_3$-$C_{20}$ heterocycloalkyl, aryl, OH, C(O)R', COOR', C(O)N(R'R"), $SO_2R'$, C(S)N(R'R"), $OSO_3R'$, $PO(OR')_2$, or NH(R') substituted with OH or NHC(O)R". In one embodiment, $R_3$ is

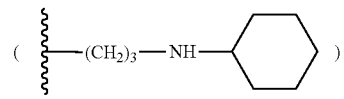

wherein Q is C(O) or a bond, T is alkylene, and Y is OH or COOH. As another example, in certain pyrimidine compounds, $L_3$ can be $C_3$-$C_{20}$ cycloalkyl (e.g., cyclohexylene). In these compounds, $R_5$ can be $C_1$-$C_{10}$ alkyl substituted with $N(R_eR_f)$ ( 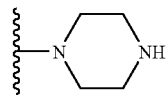 )

and $R_3$ can be $C_3$-$C_{20}$ heterocycloalkyl substituted with $C_1$-$C_{10}$ alkyl, $C_3$-$C_{20}$ cycloalkyl, $C_3$-$C_{20}$ heterocycloalkyl, aryl, OR', C(O)R', COOR', C(O)N(R'R"), $SO_2R'$, or C(S)N(R'R"), in which each of R' and R", independently, is H, $C_1$-$C_{10}$ alkyl, $C_3$-$C_{20}$ cycloalkyl, $C_3$-$C_{20}$ heterocycloalkyl, aryl, or heteroaryl.

The term "alkyl" refers to a saturated or unsaturated, linear or branched hydrocarbon moiety, such as —$CH_3$, —$CH_2$—$CH$=$CH_2$, or branched —$C_3H_7$. The term "alkylene" refers to a divalent, saturated or unsaturated, linear or branched hydrocarbon moiety, such as —$CH_2$— or —CH=CH—. The term "heteroalkylene" refers to an alkylene moiety having at least one heteroatom (e.g., N, O, or S). The term "cycloalkyl" refers to a saturated or unsaturated, non-aromatic, cyclic hydrocarbon moiety, such as cyclohexyl or cyclohexen-3-yl. The term "heterocycloalkyl" refers to a saturated or unsaturated, non-aromatic, cyclic moiety having at least one ring heteroatom (e.g., N, O, or S), such as 4-tetrahydropyranyl or 4-pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkylene, heteroalkylene, cycloalkyl, heterocycloalkyl, aryl, and heteroaryl mentioned herein include both substituted and unsubstituted moieties, unless specified otherwise. Possible substituents on cycloalkyl, heterocycloalkyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyl, halogen, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. On the other hand, possible substituents on alkyl, alkylene, or heteroalkylene include all of the above-recited substituents except $C_1$-$C_{10}$ alkyl, $C_2$-$C_{10}$ alkenyl, and $C_2$-$C_{10}$ alkynyl. Cycloalkyl, heterocycloalkyl, aryl, and heteroaryl can also be fused with each other.

In another aspect, this invention features pyrimidine compounds of formula (I) shown above in which X is —N($R_a$)— or —O—; each of $L_1$ and $L_2$, independently, is $C_1$-$C_{10}$ alkylene, $C_1$-$C_{10}$ heteroalkylene, —C(O)—, or deleted; $L_3$ is —N($R_b$)—, $C_3$-$C_{20}$ cycloalkyl, aryl, heteroaryl, or deleted; $R_1$ is H, $C_1$-$C_{10}$ alkyl, $C_3$-$C_{20}$ cycloalkyl, aryl, heteroaryl, halo, CN, $OR_c$, $COOR_c$, $OC(O)R_c$, $C(O)R_c$, $C(O)NR_cR_d$, or $NR_cR_d$; each of $R_2$ and $R_3$, independently, is H, $C_1$-$C_{10}$ alkyl, $C_3$-$C_{20}$ cycloalkyl, $C_3$-$C_{20}$ heterocycloalkyl, aryl, heteroaryl, halo, CN, $OR_e$, $COOR_e$, $OC(O)R_e$, $C(O)R_e$, $C(O)NR_eR_f$, or $NR_eR_f$; and each of $R_4$ and $R_5$, independently, is H, $C_1$-$C_{10}$ alkyl, $C_3$-$C_{20}$ cycloalkyl, $C_3$-$C_{20}$ heterocycloalkyl, aryl, or heteroaryl; or $R_4$ and $R_5$ together are $C_1$-$C_{10}$ alkylene or $C_1$-$C_{10}$ heteroalkylene; in which each of $R_a$, $R_b$, $R_c$, $R_d$, $R_e$, and $R_f$ independently, is H, $C_1$-$C_{10}$ alkyl, $C_3$-$C_{20}$ cycloalkyl, $C_3$-$C_{20}$ heterocycloalkyl, aryl, or heteroaryl; or a salt thereof.

Referring to formula (I), a subset of the just-described pyrimidine compounds are those in which X is —N($R_a$)—; each of $L_1$ and $L_2$, independently, is $C_1$-$C_{10}$ alkylene; $L_3$ is deleted; $R_1$ is $NR_cR_d$; each of $R_2$ and $R_3$, independently, is H, $C_1$-$C_{10}$ alkyl, halo, or $C_3$-$C_{20}$ cycloalkyl; and each of $R_4$ and $R_5$, independently, is H or $C_3$-$C_{20}$ cycloalkyl; or $R_4$ and $R_5$ together are $C_1$-$C_{10}$ alkylene or $C_1$-$C_{10}$ heteroalkylene. In these compounds, $R_5$ can be

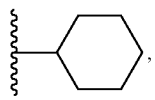

or $R_4$ and $R_5$ together can be —$CH_2CH_2$—; one of $R_c$ and $R_d$ can be $C_1$-$C_{10}$ alkyl substituted with N(RR') or aryl, in which each of R and R', independently, is H, $C_1$-$C_{10}$ alkyl, $C_3$-$C_{20}$ cycloalkyl, $C_3$-$C_{20}$ heterocycloalkyl, aryl, or heteroaryl

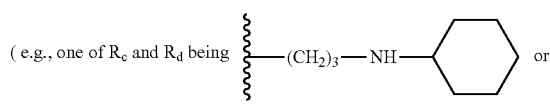

(e.g., one of $R_c$ and $R_d$ being

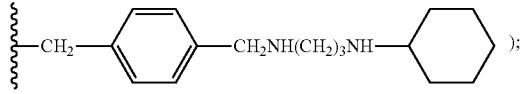

);

$R_3$ can be

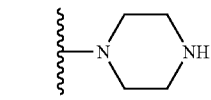

substituted with $C_1$-$C_{10}$ alkyl, which is in turn substituted with $C_3$-$C_{20}$ heterocycloalkyl or OR, R being H, $C_1$-$C_{10}$ alkyl, $C_3$-$C_{20}$ cycloalkyl, $C_3$-$C_{20}$ heterocycloalkyl, aryl, or heteroaryl. In one embodiment, $R_3$ is

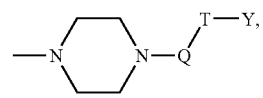

wherein Q is C(O) or a bond, T is alkylene, and Y is OH or COOH.

In still another aspect, this invention features a method for treating an inflammatory or immune disease, a developmental or degenerative disease, or a tissue injury. The method includes administering to a subject in need thereof an effective amount of one or more pyrimidine compounds of formula (I) shown above.

The term "treating" or "treatment" refers to administering one or more pyrimidine compounds to a subject, who has an above-described disease, a symptom of such a disease, or a predisposition toward such a disease, with the purpose to confer a therapeutic effect, e.g., to cure, relieve, alter, affect, ameliorate, or prevent the above-described disease, the symptom of it, or the predisposition toward it.

An inflammatory disease is characterized by a local or systemic, acute or chronic inflammation. Examples include retinopathy, inflammatory dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), inflammatory bowel diseases (e.g., Crohn's disease and ulcerative colitis), hypersensitivity lung diseases (e.g., hypersensitivity pneumonitis, eosinophilic pneumonia, delayed-type hypersensitivity, interstitial lung disease or ILD, idiopathic pulmonary fibrosis, and ILD associated with rheumatoid arthritis), asthma, and allergic rhinitis.

An immune disease is characterized by a hyper- or hypo-reaction of the immune system. Examples include autoimmune diseases (e.g., rheumatoid arthritis, psoriatic arthritis, systemic lupus erythematosus, myasthenia gravis, juvenile onset diabetes, glomerulonephritis, autoimmune throiditis, ankylosing spondylitis, systemic sclerosis, and multiple sclerosis), acute and chronic inflammatory diseases (e.g., systemic anaphylaxis or hypersensitivity responses, drug allergies, insect sting allergies, graft rejection, including allograft rejection, and graft-versus-host disease), Sjogren's syndrome, human immunodeficiency virus infection, cancer (e.g., brain, breast, prostate, colon, kidney, ovary, thyroid, lung, and haematopoietic cancer), and tumor metastasis.

Developmental diseases are growth or differentiation related disorders that lead to loss-of-function or gain-of-function. Degenerative diseases generally refer to change of a tissue to a lower or less functional form. Examples of a developmental or degenerative disease include spinal muscular atrophy, Duchenne muscular dystrophy, Parkinson's disease, and Alzheimer's disease. Tissue injuries can be caused by oxidative stress (e.g., ischemia-reperfusion in stroke or myocardial infarction), complement activation, graft rejection, chemicals (e.g., alcohol-induced liver damage or mucosal tissue injuries in cancer therapy), viral infection (e.g., glomerular injuries associated with hepatitis C infection), and mechanical forces (e.g., sports injury). Examples of tissue injuries include brain injury, heart injury, liver damage, skeletal muscle injury, kidney damage, pancreatic injury, lung injury, skin injury, and gastrointestinal tract injury.

A subject in need of treatment of an above-described disease can also be concurrently administered with a pyrimidine compound described above and one or more other therapeutic agents. Examples of such a therapeutic agent include a G-CSF growth factor, a steroidal or a non-steroidal anti-inflammatory drug, a COX2 inhibitor, a leukotriene receptor inhibitor, a prostaglandin modulator, a TNF modulator, and an immunosuppressive agent (e.g., cyclosporine A). The term "concurrently administered" refers to administering a pyrimidine compound and one or more other therapeutic agents at the same time or at different times during the period of treatment.

In still another aspect, this invention features a method for enhancing migration of bone marrow-derived cells to blood. The method includes administering to a subject in need thereof an effective amount of one or more pyrimidine compounds of formula (I) shown above. The term "bone marrow-derived cells" refers to cells originating from bone marrow. Examples of bone marrow-derived cells include, but are not limited to, CD34+ cells and CD133+ cells. Preferably, bone marrow-derived cells are stem cells or endothelial progenitor cells. An effective amount of a very late antigen-4 (VLA-4) inhibitor can be used together with the pyrimidine compounds in this method. Examples of a VLA-4 inhibitor can be found in, e.g., U.S. Pat. No. 6,495,525.

In still another aspect, this invention features a chemical synthetic method. The method includes reacting a compound of the formula

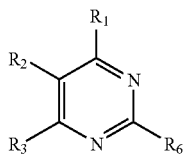

with a compound of the formula

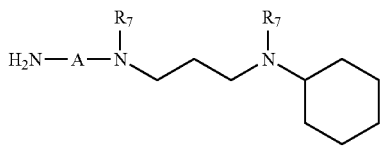

to give a compound of formula (II):

(II)

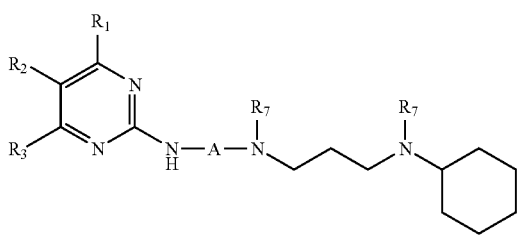

In this formula, A is phenylene, cyclohexylene,

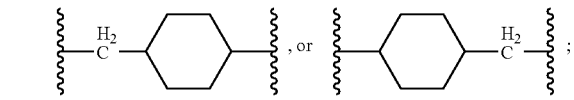

each of $R_1$, $R_2$, and $R_3$, independently, is H, $C_1$-$C_{10}$ alkyl, $C_3$-$C_{20}$ cycloalkyl, $C_3$-$C_{20}$ heterocycloalkyl, aryl, heteroaryl, halo, CN, $OR_a$, $COOR_a$, $OC(O)R_a$, $C(O)R_a$, $C(O)NR_aR_b$, or $NR_aR_b$; $R_6$ is halo; and $R_7$ is a amino-protecting group (e.g., t-butoxycarbonyl, benzyloxycarbonyl, acetyl, phenylcarbonyl, or trialkylsilyl); in which each of $R_a$ and $R_b$, independently, is H, $C_1$-$C_{10}$ alkyl, $C_3$-$C_{20}$ cycloalkyl, $C_3$-$C_{20}$ heterocycloalkyl, aryl, heteroaryl, or —C(O)R; R being H, $C_1$-$C_{10}$ alkyl, $C_3$-$C_{20}$ cycloalkyl, $C_3$-$C_{20}$ heterocycloalkyl, aryl, or heteroaryl.

The method can further include deprotecting the compound of formula (II) to give a compound of formula (III):

(III)

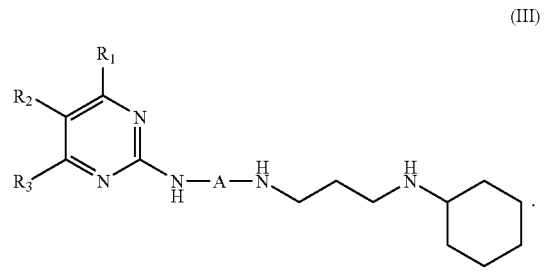

In a subset of compounds of formula (III), $R_1$ is $N(R_aR_b)$, in which $R_a$ and $R_b$, independently, is H, $C_1$-$C_{10}$ alkyl, $C_3$-$C_{20}$ cycloalkyl, $C_3$-$C_{20}$ heterocycloalkyl, aryl, or heteroaryl. In these compounds, one of $R_a$ and $R_b$ can be

In another subset of compounds of formula (III), $R_3$ is

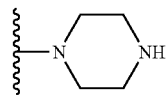

optionally substituted with $C_1$-$C_{10}$ alkyl, $C_3$-$C_{20}$ cycloalkyl, $C_3$-$C_{20}$ heterocycloalkyl, or aryl.

Referring to formula (II), when $R_3$ is halo, a compound of formula (II) can further react with a compound of the formula

to give a compound of formula (IV):

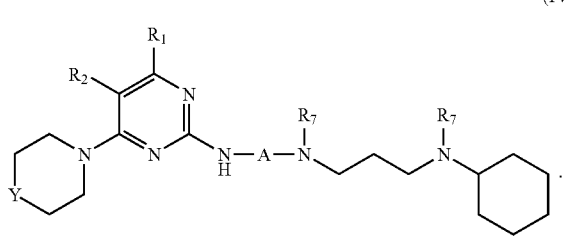

(IV)

In this formula, Y is —O—, —CH$_2$—, or —N(R$_c$)—, in which R$_c$ is H, C$_1$-C$_{10}$ alkyl, C$_3$-C$_{20}$ cycloalkyl, C$_3$-C$_{20}$ heterocycloalkyl, aryl, heteroaryl, or halo. The compound of formula (IV) can be deprotected to give a compound of formula (V):

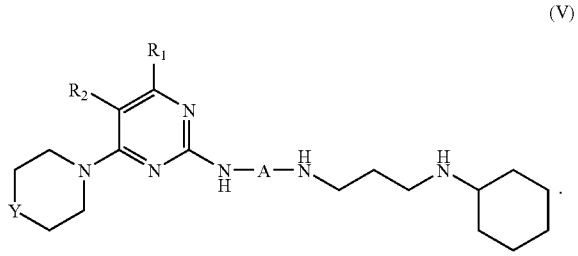

(V)

Referring to formula (IV), when Y is NH, a compound of formula (IV) can further react with a compound of the formula

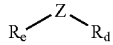

to give a compound of formula (VI):

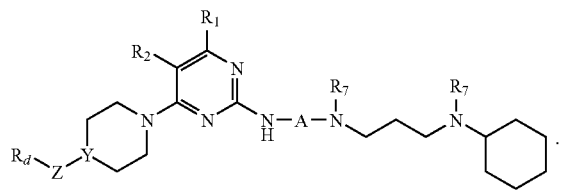

in which Z is —CH$_2$— or —C(O)—; R$_d$ is C$_1$-C$_{10}$ alkyl, C$_3$-C$_{20}$ cycloalkyl, C$_3$-C$_{20}$ heterocycloalkyl, aryl, or heteroaryl; and R$_e$ is halo. The compound of formula (VI) can be deprotected to give a compound of formula (VII):

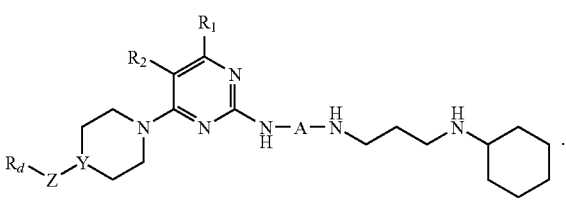

As another example, when Y is NH, a compound of formula (IV) can further react with a compound of the formula

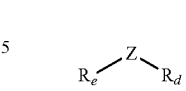

to give an imine compound, followed by reducing the imine compound to give a compound of formula (VI). In the formula

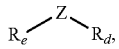

Z is —C(O)—; R$_d$ is C$_1$-C$_{10}$ alkyl, C$_3$-C$_{20}$ cycloalkyl, C$_3$-C$_{20}$ heterocycloalkyl, aryl, or heteroaryl; and R$_e$ is H. As another example, when Y is NH, a compound of formula (IV) can further react with a compound of the formula

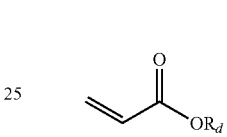

to give an ester compound, followed by hydrolyzing the ester compound to give a compound of formula (VIII):

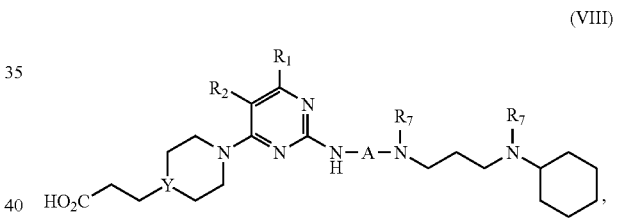

(VIII)

in which R$_d$ is C$_1$-C$_{10}$ alkyl, C$_3$-C$_{20}$ cycloalkyl, C$_3$-C$_{20}$ heterocycloalkyl, aryl, or heteroaryl. The compound of formula (VIII) can be deprotected to give a compound of formula (IX):

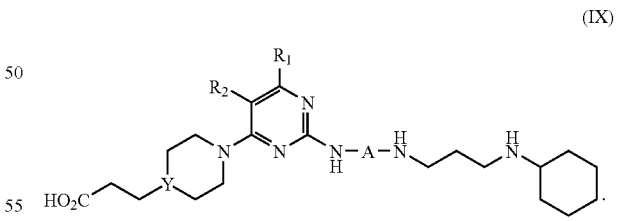

(IX)

As a further example, when Y is NH, a compound of formula (IV) can further react with a compound of the formula

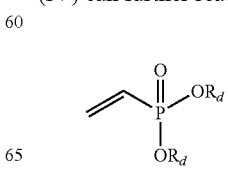

to give a compound of formula (X):

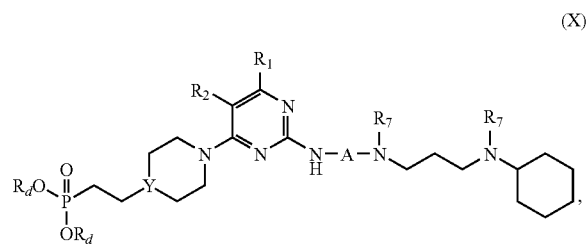
(X)

in which $R_d$ is $C_1$-$C_{10}$ alkyl, $C_3$-$C_{20}$ cycloalkyl, $C_3$-$C_{20}$ heterocycloalkyl, aryl, or heteroaryl. The compound of formula (X) can be deprotected to give a deprotected compound, followed by hydrolyzing the deprotected compound to give a compound of formula (XI):

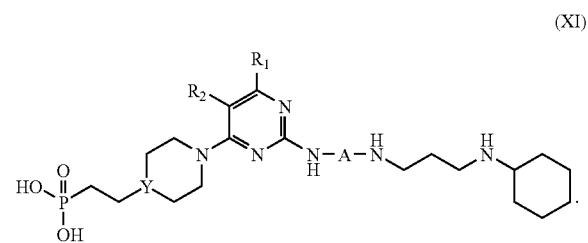
(XI)

Referring to formula (II), when $R_3$ is halo, a compound of formula (II) can further react with a compound of the formula $R_cOH$ to give a compound of formula (XII):

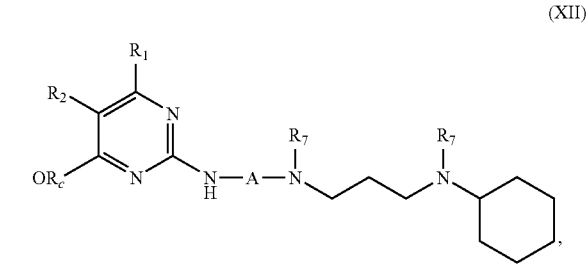
(XII)

in which $R_c$ is $C_1$-$C_{10}$ alkyl, $C_3$-$C_{20}$ cycloalkyl, $C_3$-$C_{20}$ heterocycloalkyl, aryl, or heteroaryl. The compound of formula (XII) can be deprotected to give a compound of formula (XIII):

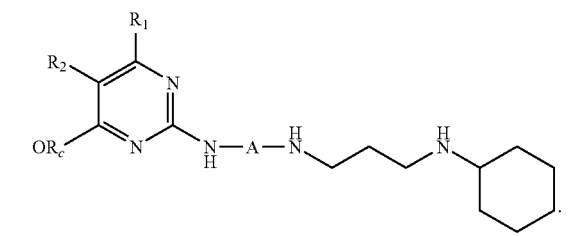
(XIII)

Referring to formula (II), when $R_2$ is CN, the compound of formula (II) can be reduced to give a compound of formula (XIV):

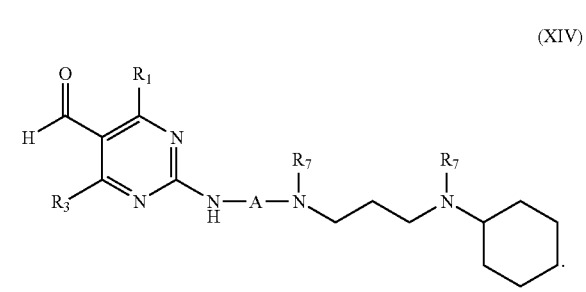
(XIV)

The compound of formula (XIV) can further react with a compound of the formula $R_cNH_2$ to give an imine compound, followed by reducing the imine compound to give a compound of formula (XV):

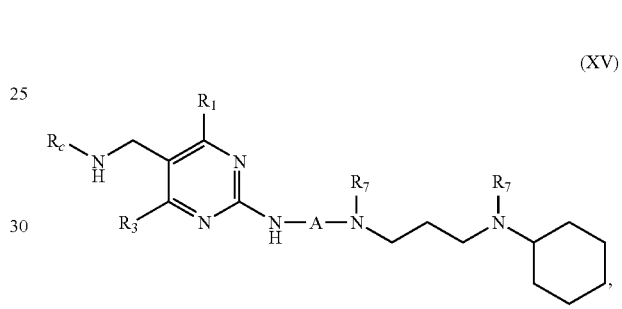
(XV)

in which $R_c$ is $C_1$-$C_{10}$ alkyl, $C_3$-$C_{20}$ cycloalkyl, $C_3$-$C_{20}$ heterocycloalkyl, aryl, or heteroaryl. The compound of formula (XV) can be deprotected to give a compound of formula (XVI):

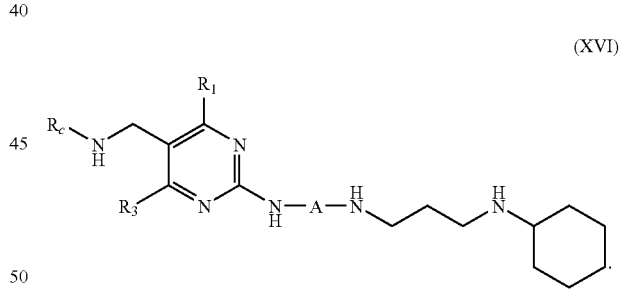
(XVI)

In a further aspect, the invention features a chemical synthetic method that includes reacting a compound of the formula with a compound of the formula

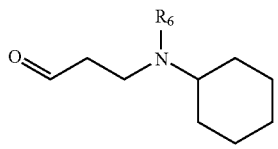

to give a compound of formula (XVII):

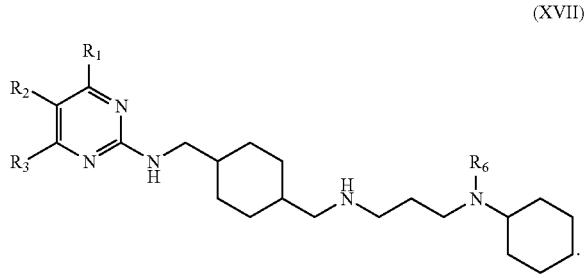

(XVII)

In formula (XVII), each of $R_1$ and $R_2$, independently, is H, $C_1$-$C_{10}$ alkyl, $C_3$-$C_{20}$ cycloalkyl, $C_3$-$C_{20}$ heterocycloalkyl, aryl, heteroaryl, halo, CN, $OR_a$, $COOR_a$, $OC(O)R_a$, $C(O)R_a$, $C(O)NR_aR_b$, or $NR_aR_b$; $R_3$ is halo; and $R_6$ is a amino-protecting group; in which each of $R_a$ and $R_b$, independently, is H, $C_1$-$C_{10}$ alkyl, $C_3$-$C_{20}$ cycloalkyl, $C_3$-$C_{20}$ heterocycloalkyl, aryl, heteroaryl, or —C(O)R; R being H, $C_1$-$C_{10}$ alkyl, $C_3$-$C_{20}$ cycloalkyl, $C_3$-$C_{20}$ heterocycloalkyl, aryl, or heteroaryl. The method can further include protecting the compound of formula (XX), followed by reacting the protected compound of formula (XVII) with a compound of the formula

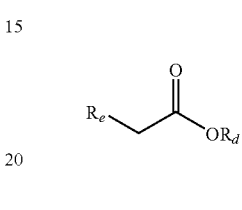

to give a compound of formula (XVIII):

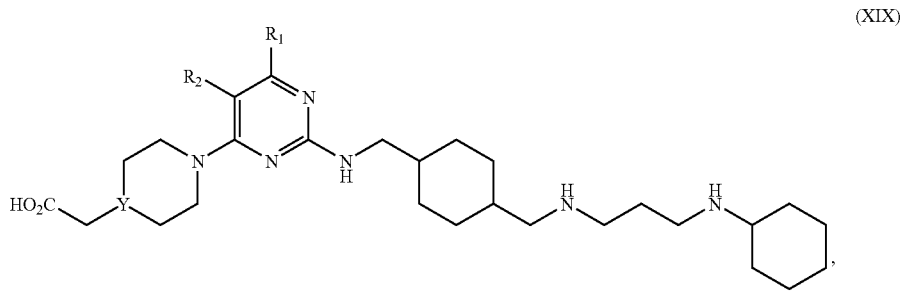

(XVIII)

In formula (XVIII), $R_7$ is a amino-protecting group; and Y is —O—, —CH$_2$—, or —N($R_c$)—, in which $R_c$ is H, $C_1$-$C_{10}$ alkyl, $C_3$-$C_{20}$ cycloalkyl, $C_3$-$C_{20}$ heterocycloalkyl, aryl, heteroaryl, or halo.

Referring to formula (XVIII), when Y is NH, the method can further include: (1) reacting the compound of formula (XVIII) with a compound of the formula

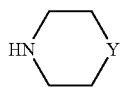

to give an ester compound; (2) hydrolyzing the ester compound to give an acid compound; and (3) deprotecting the acid compound to give a compound of formula (XIX):

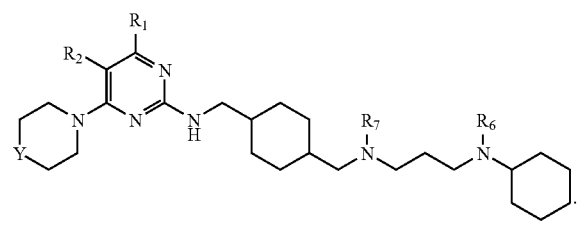

(XIX)

in which $R_d$ is $C_1$-$C_{10}$ alkyl, $C_3$-$C_{20}$ cycloalkyl, $C_3$-$C_{20}$ heterocycloalkyl, aryl, or heteroaryl; and $R_e$ is halo.

In addition, this invention encompasses a pharmaceutical composition that contains an effective amount of at least one of the above-mentioned pyrimidine compounds and a pharmaceutically acceptable carrier.

The pyrimidine compounds described above include the compounds themselves, as well as their salts, prodrugs, and solvates, if applicable. A salt, for example, can be formed between an anion and a positively charged group (e.g., amino) on a pyrimidine compound. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a pyrimidine compound. Suitable cations include sodium ion, potassium ion, magnesium ion, calcium ion, and an ammonium cation such as tetramethylammonium ion. The pyrimidine compounds also include those salts containing quaternary nitrogen atoms. Examples of prodrugs include esters and other pharmaceutically acceptable derivatives, which, upon administration to a subject, are capable of providing active pyrimidine compounds. A solvate refers to a complex formed between an active pyrimidine compound and a pharmaceutically acceptable solvent. Examples of pharmaceutically acceptable solvents include water, ethanol, isopropanol, ethyl acetate, acetic acid, and ethanolamine.

Also within the scope of this invention is a composition containing one or more of the pyrimidine compounds described above for use in treating an above-described disease, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

Shown below are exemplary compounds, compounds 1-268, of this invention:

Compound 1

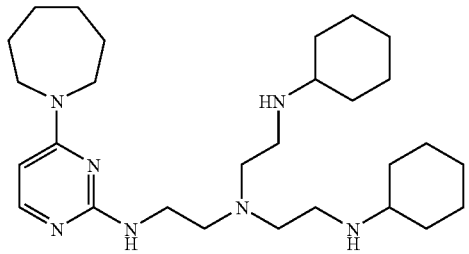

Compound 2

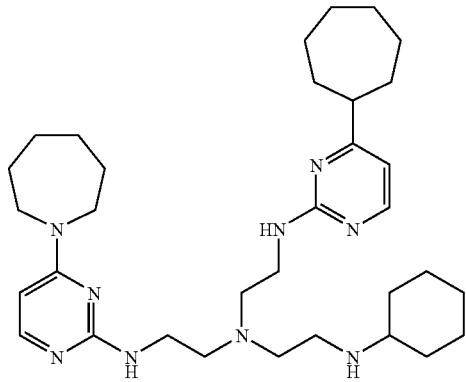

Compound 3

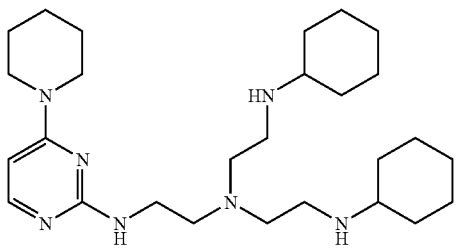

Compound 4

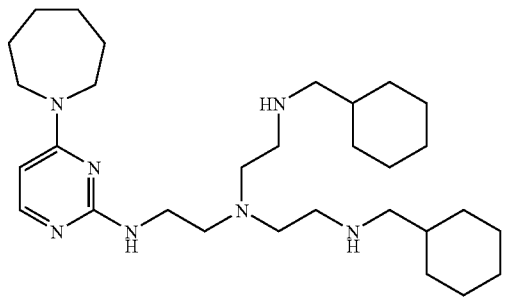

Compound 5

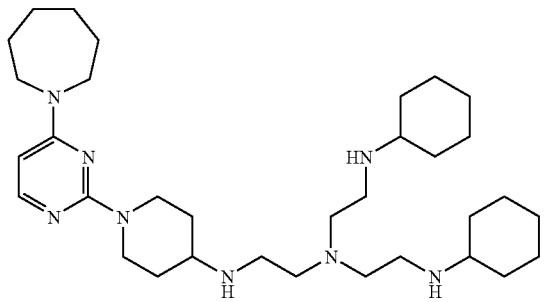

Compound 6

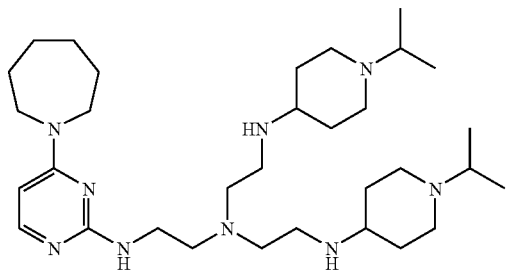

Compound 7

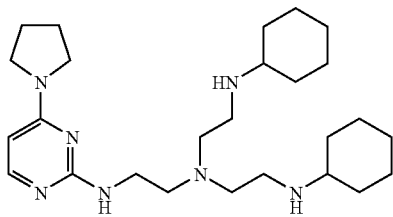

Compound 8

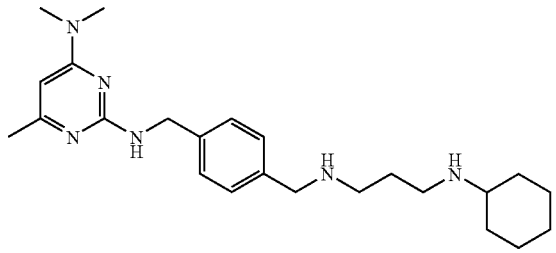

-continued
Compound 9
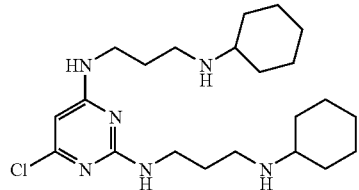
Compound 10
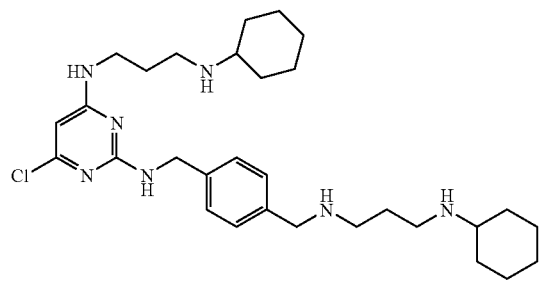
Compound 11
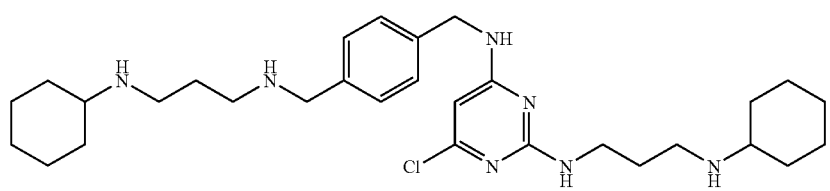
Compound 12
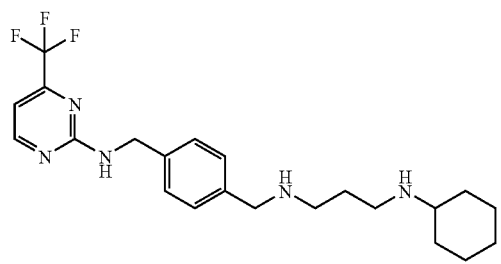
Compound 13
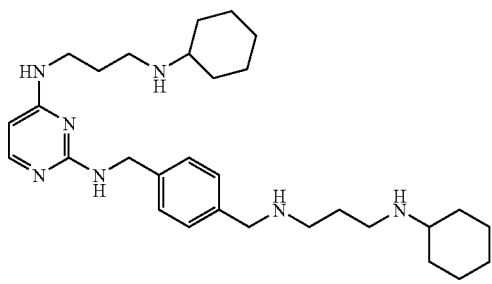
Compound 14
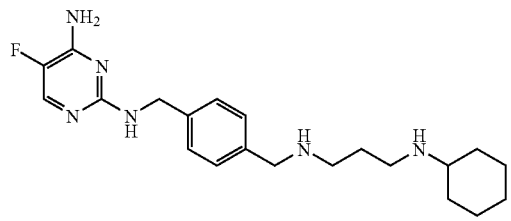
Compound 15
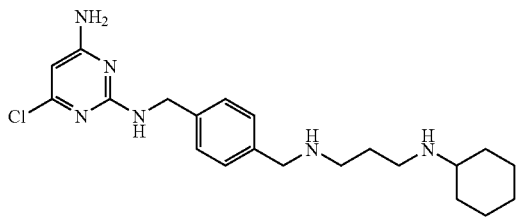
Compound 16
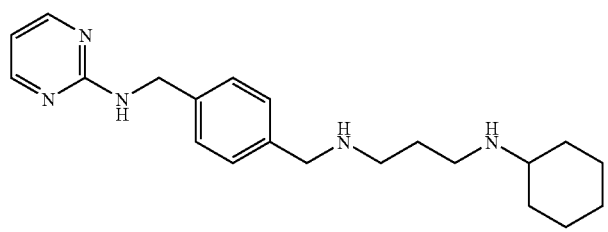
Compound 17
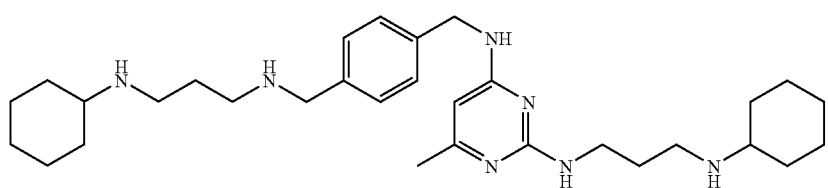

-continued
Compound 18
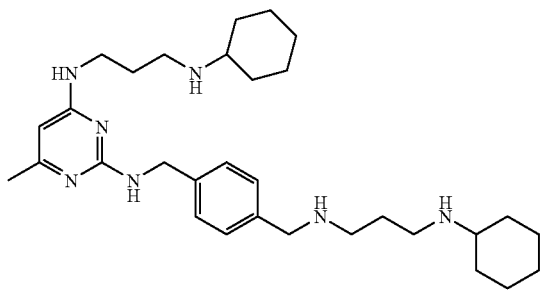
Compound 19
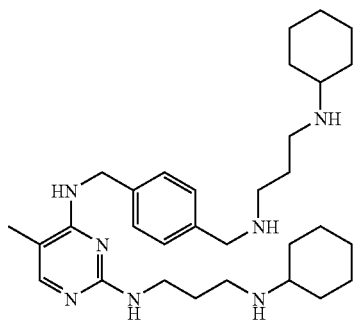
Compound 20
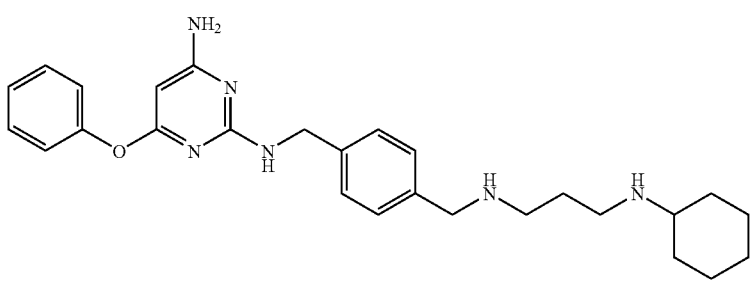
Compound 21
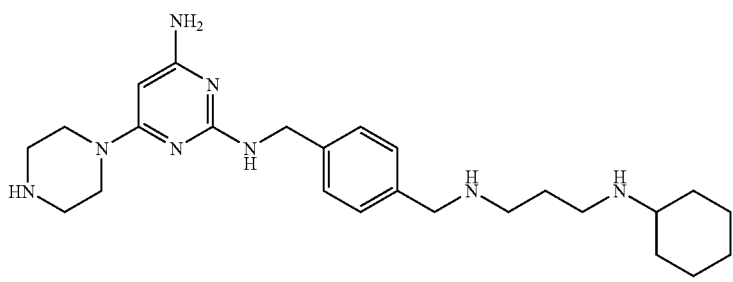
Compound 22
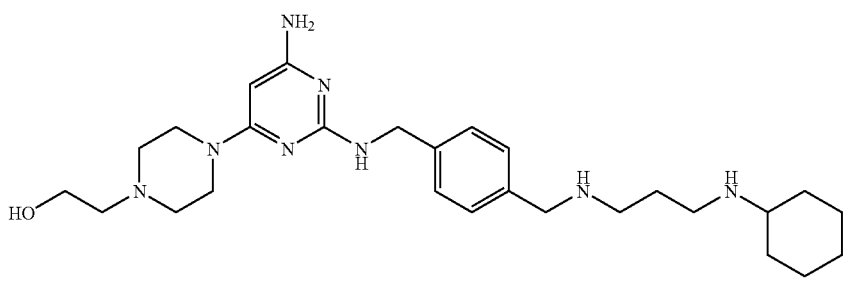
Compound 23
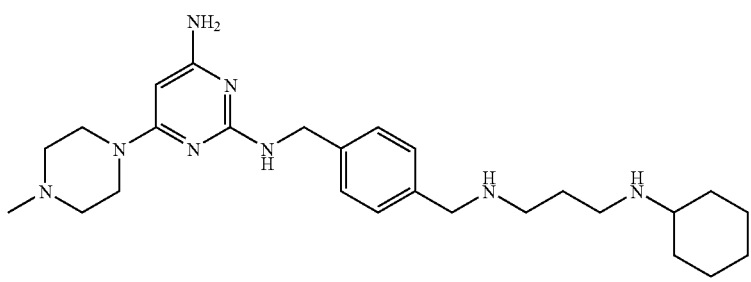

-continued
Compound 24
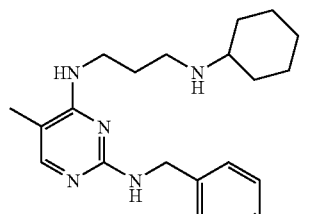
Compound 25
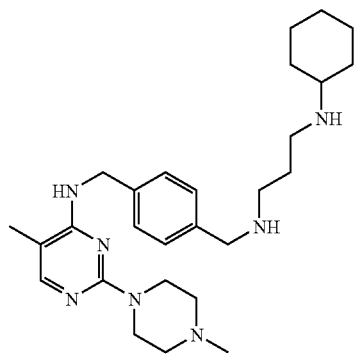
Compound 26
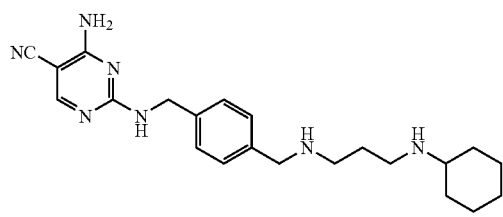
Compound 27
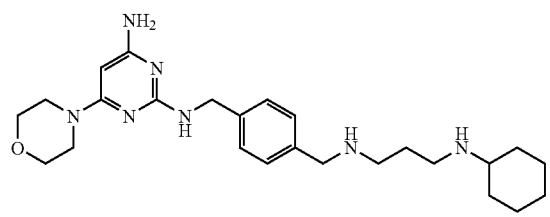
Compound 28
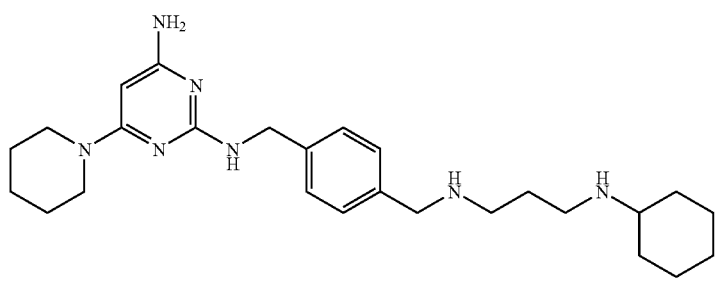
Compound 29
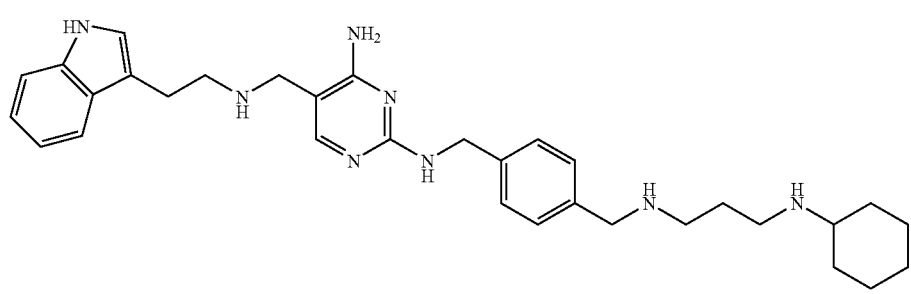
Compound 30
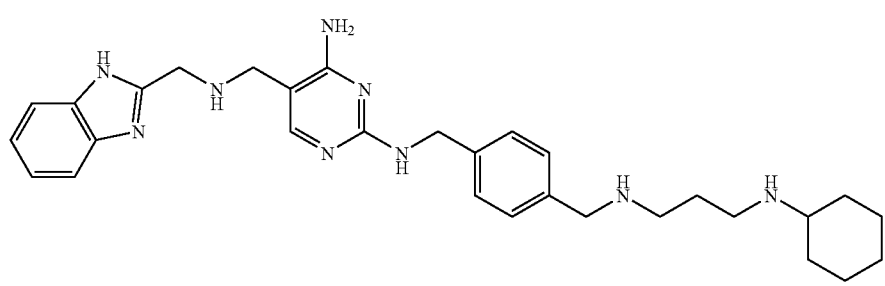

-continued
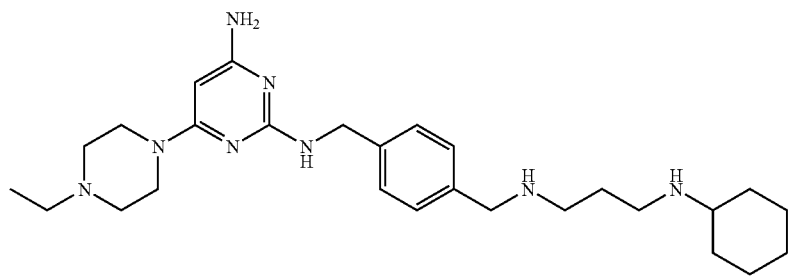
Compound 31
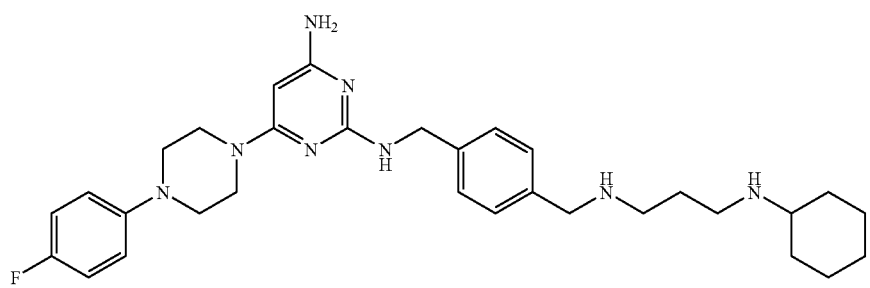
Compound 32
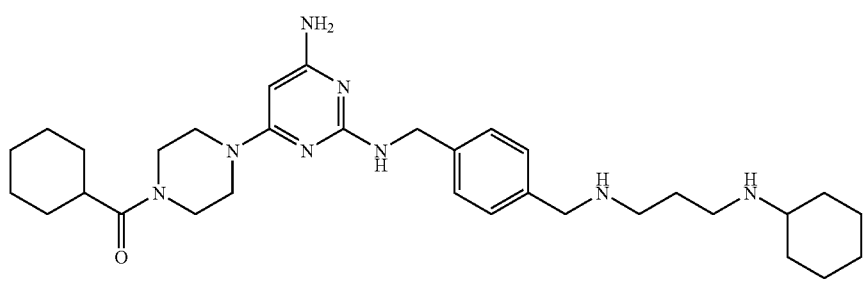
Compound 33
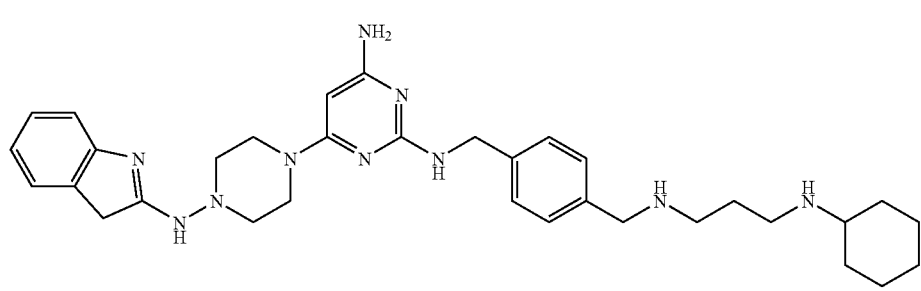
Compound 34
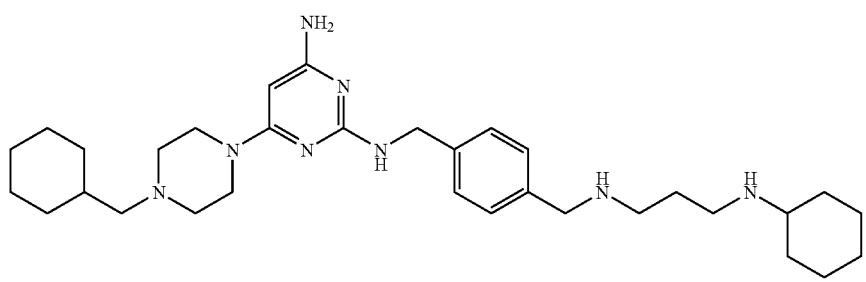
Compound 35

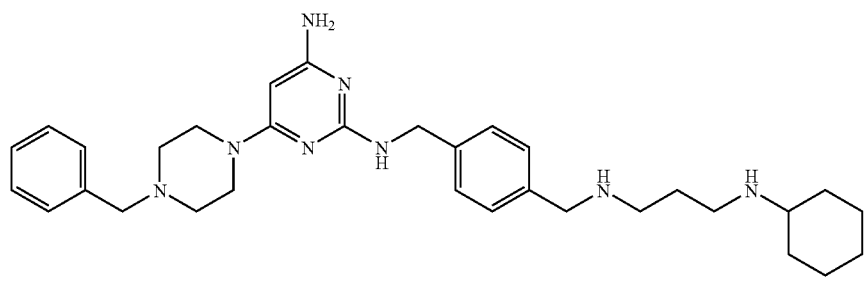
Compound 36
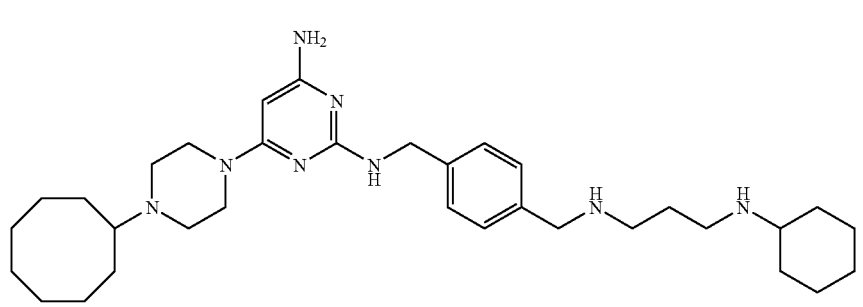
Compound 37
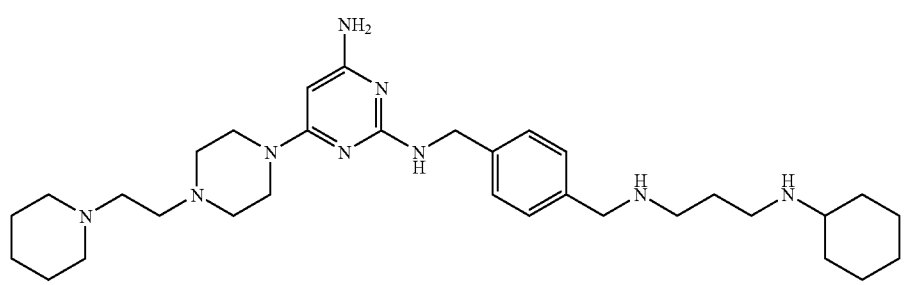
Compound 38
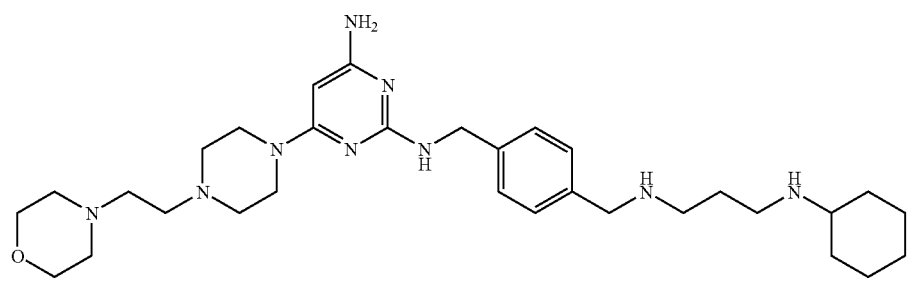
Compound 39
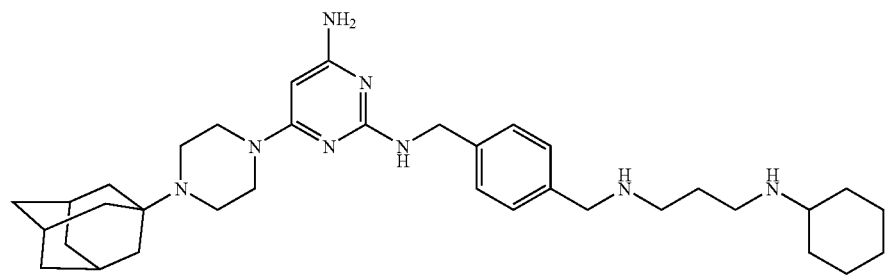
Compound 40

Compound 41
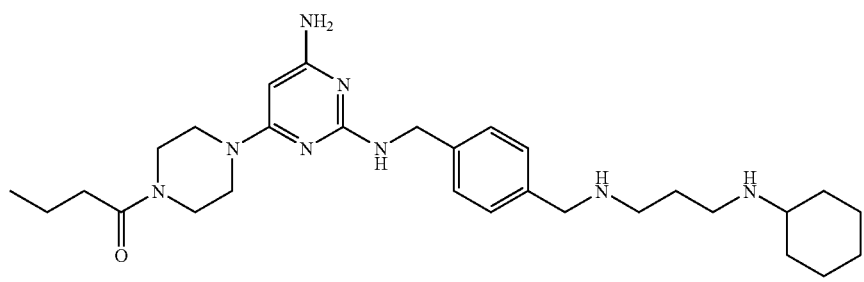
Compound 42
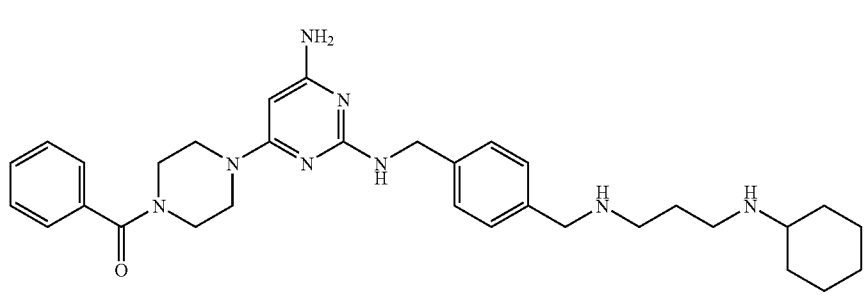
Compound 43
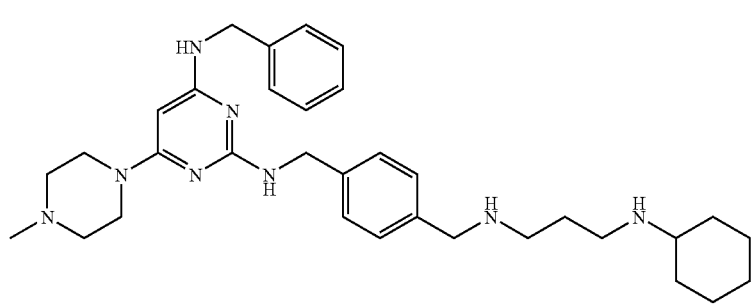
Compound 44
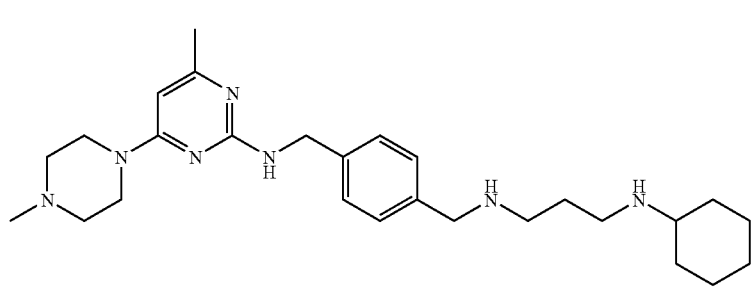
Compound 45
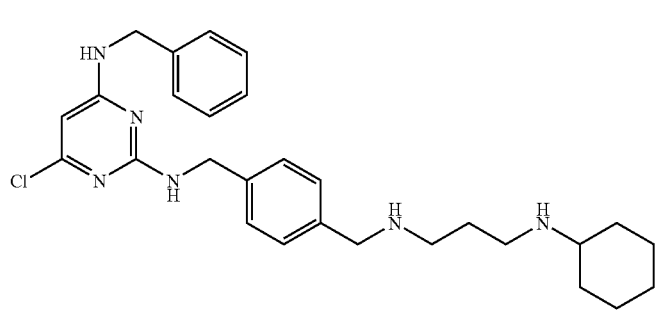

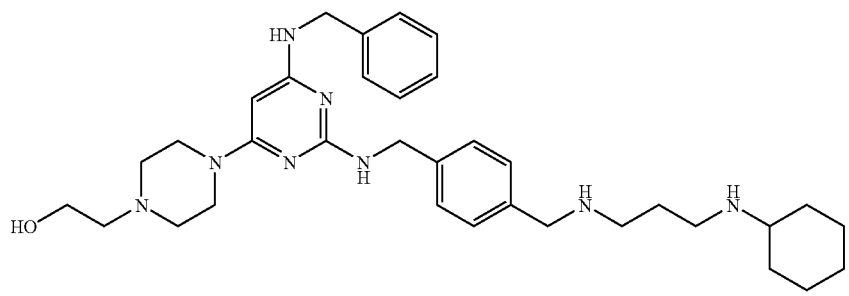
Compound 46
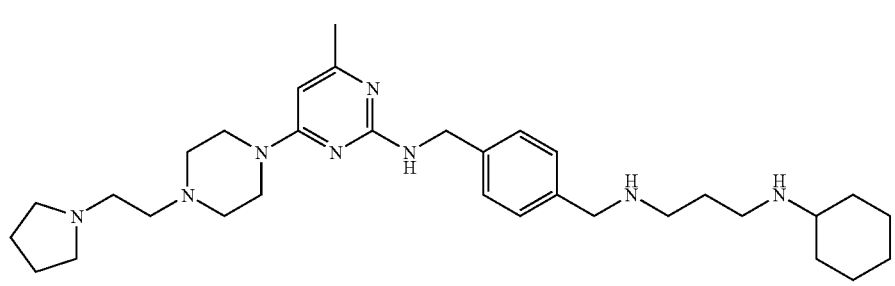
Compound 47
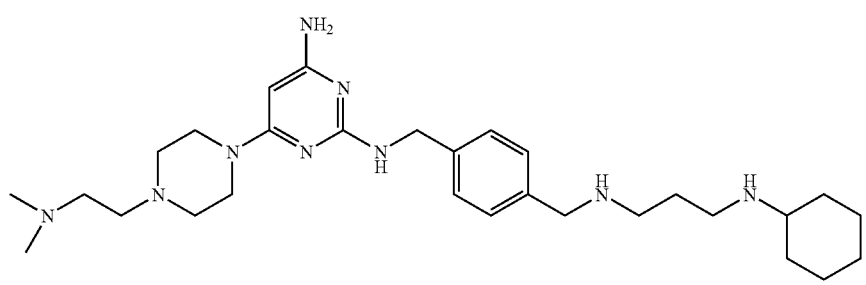
Compound 48
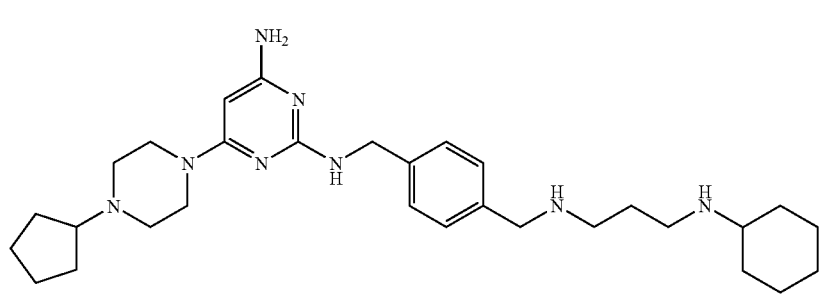
Compound 49
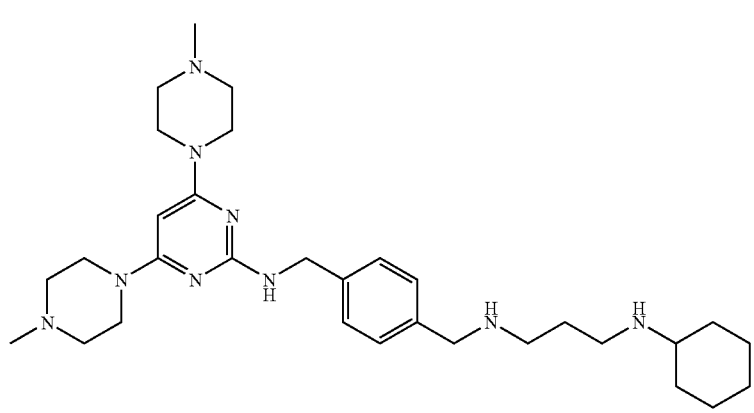
Compound 50

-continued
Compound 51
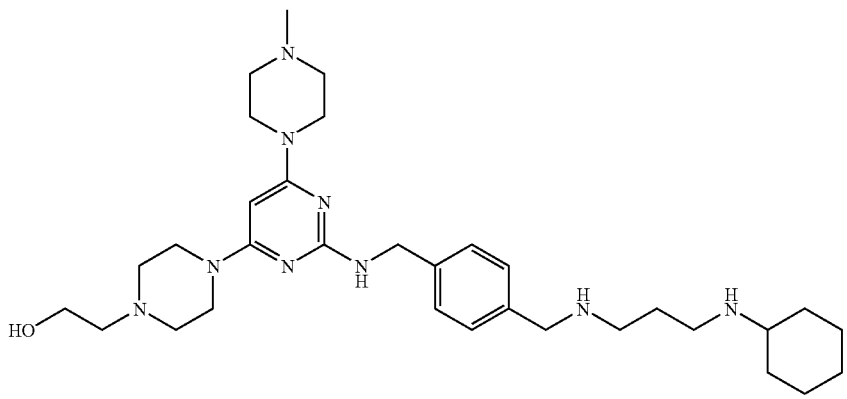
Compound 52
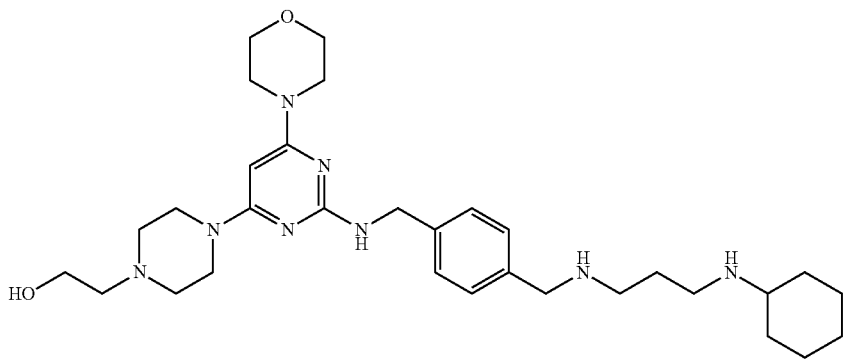
Compound 53
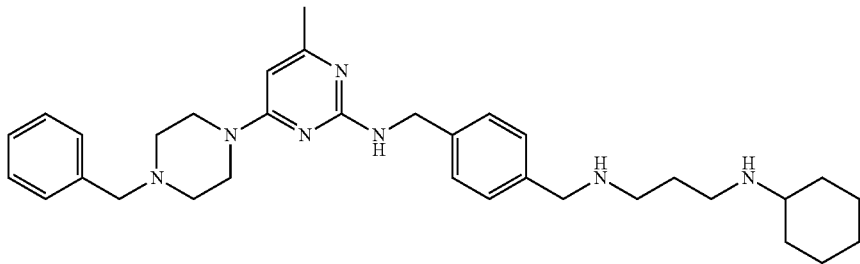
Compound 54
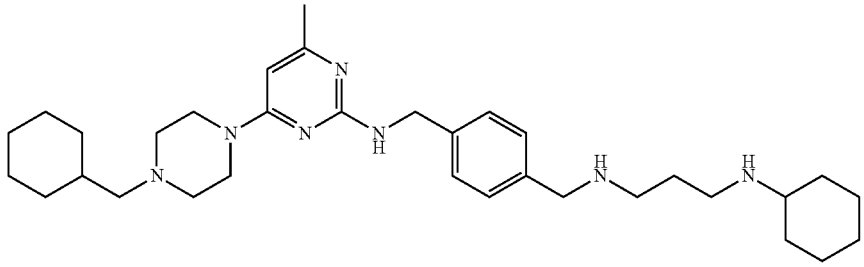
Compound 55
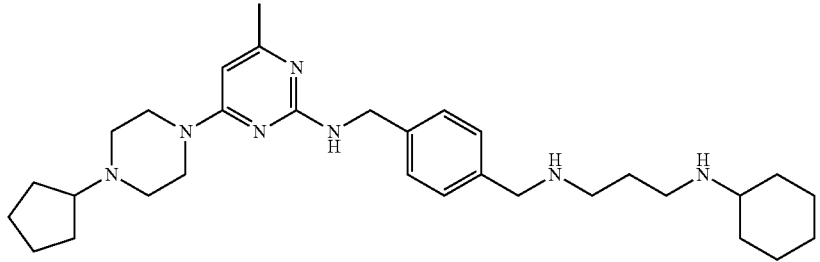

-continued
Compound 56
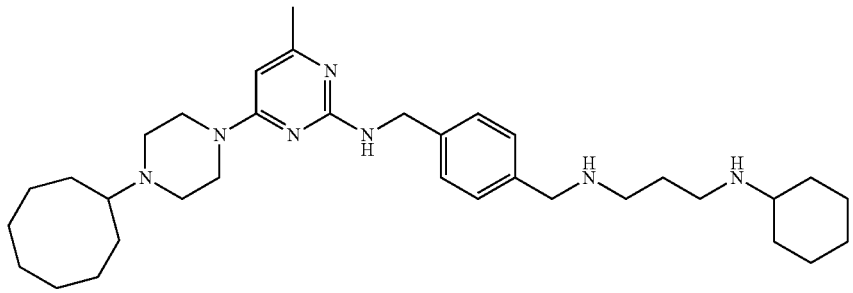
Compound 57
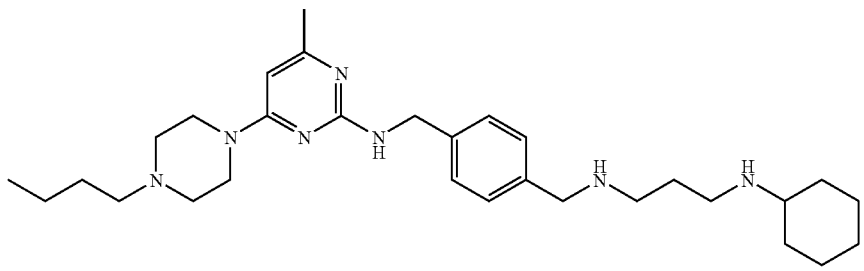
Compound 58
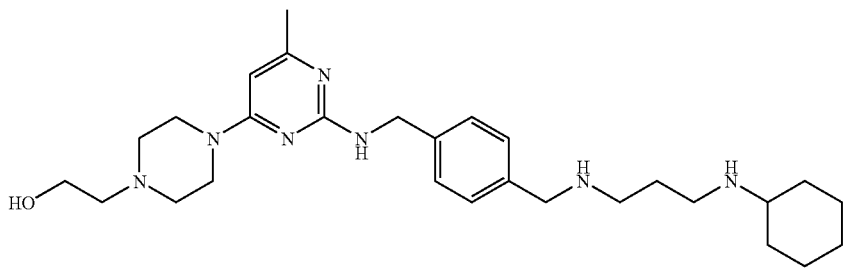
Compound 59
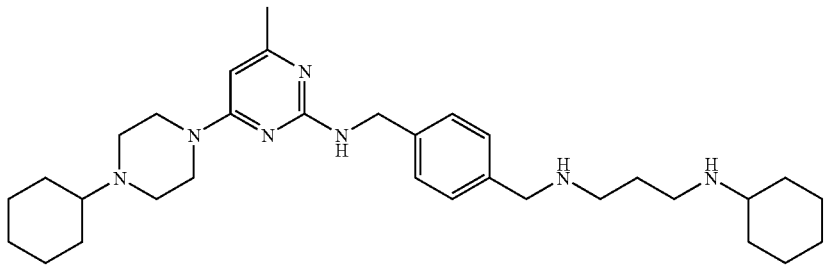
Compound 60
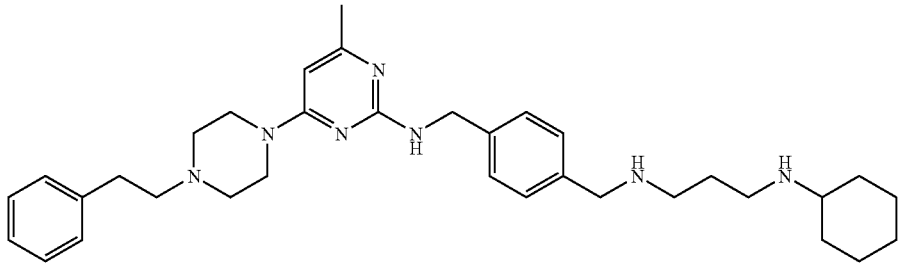
Compound 61
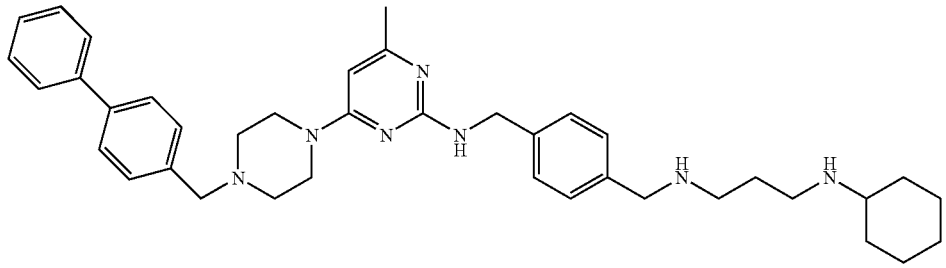

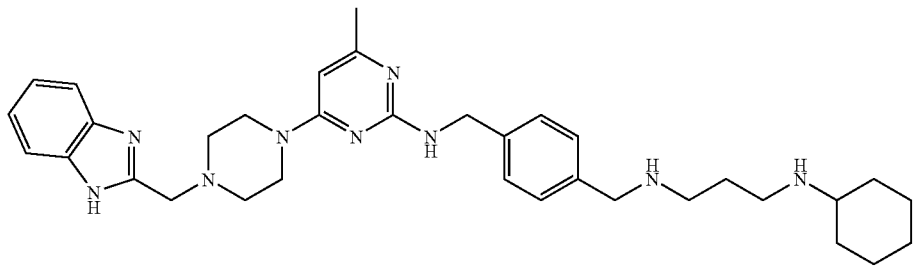
Compound 62
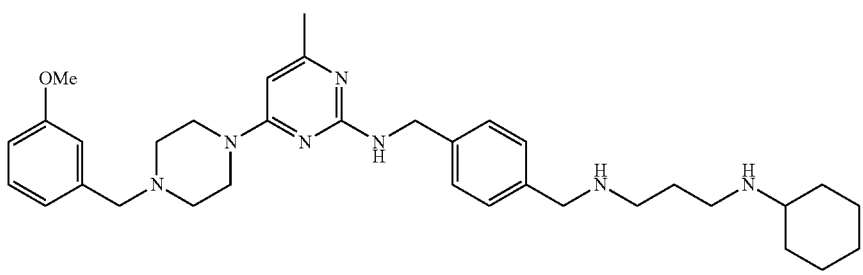
Compound 63
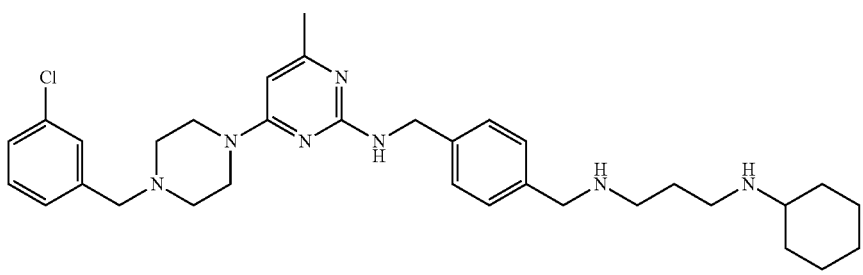
Compound 64
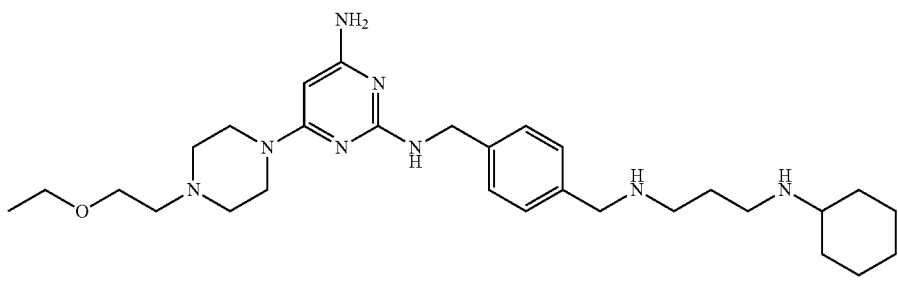
Compound 65
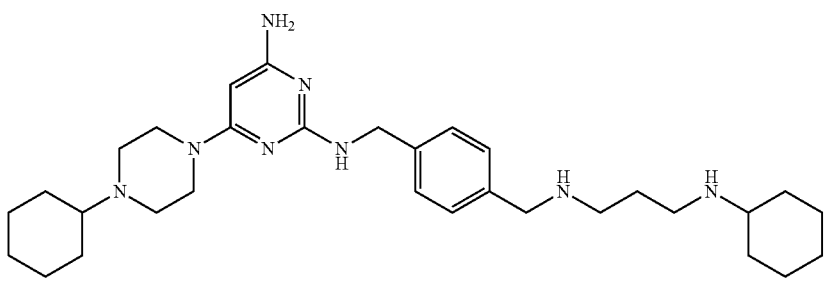
Compound 66

Compound 67
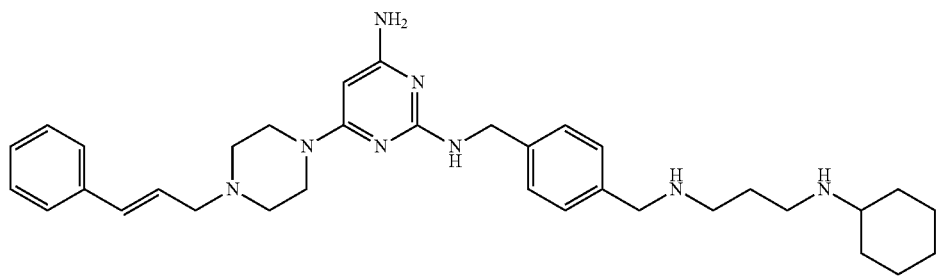
Compound 68
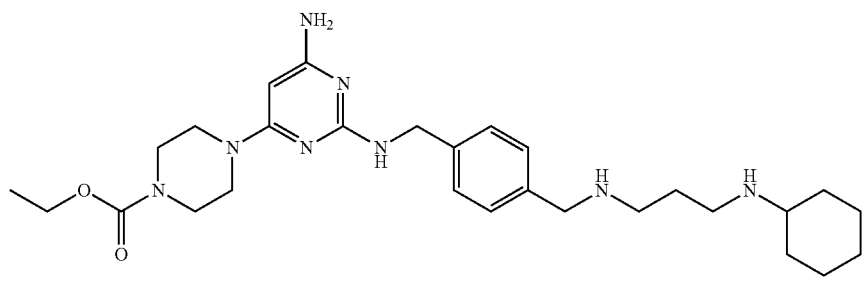
Compound 69
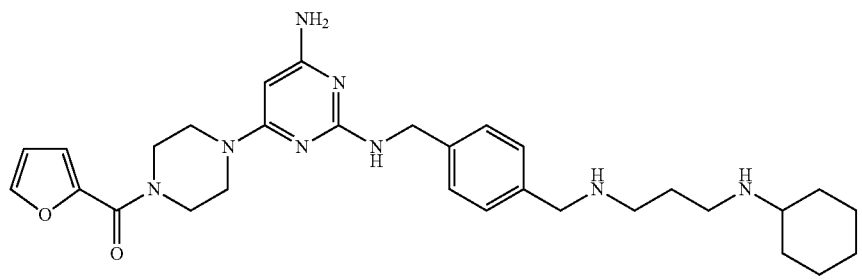
Compound 70
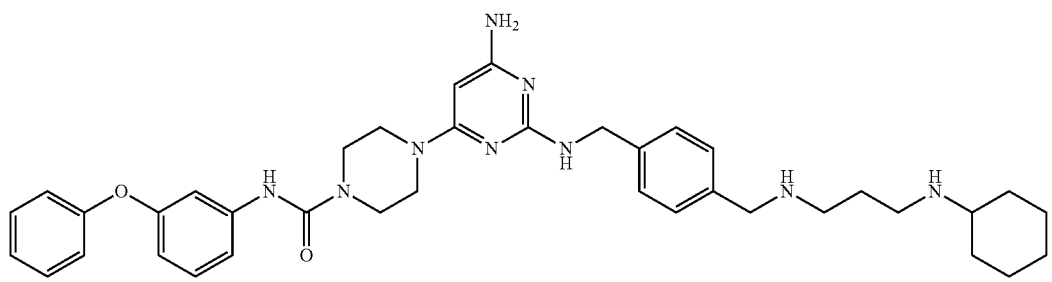
Compound 71
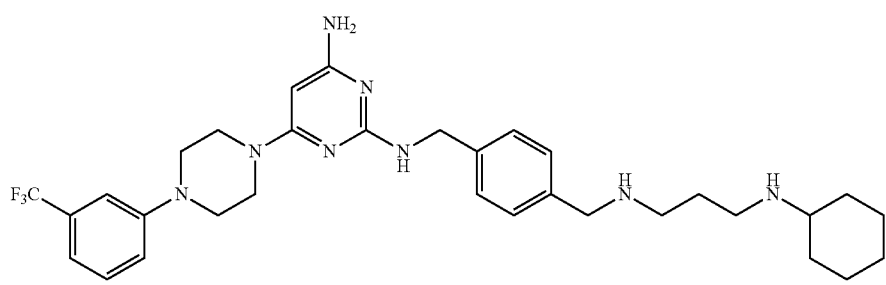

-continued
Compound 72
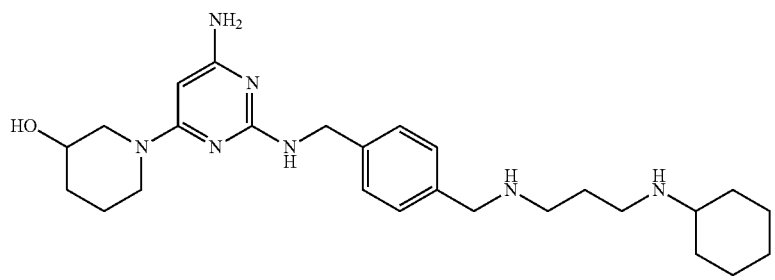
Compound 73
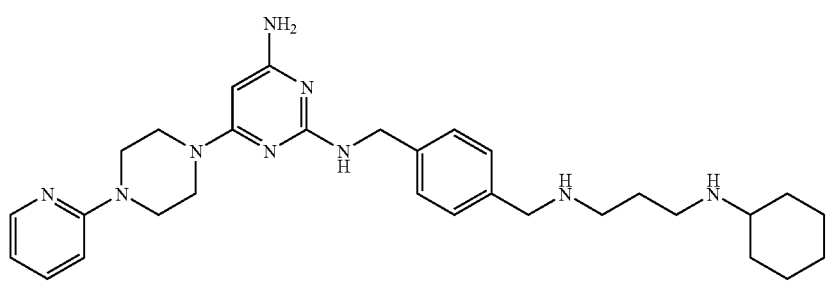
Compound 74
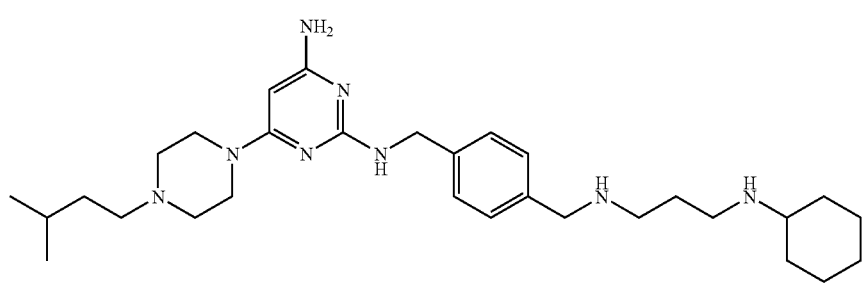
Compound 75
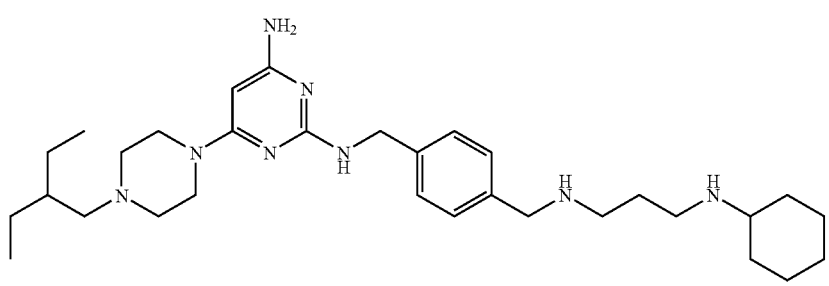
Compound 76
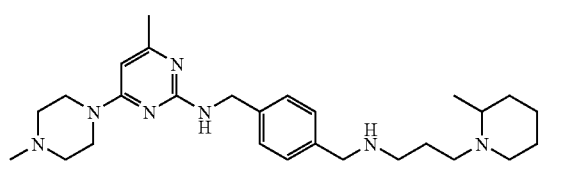
Compound 77
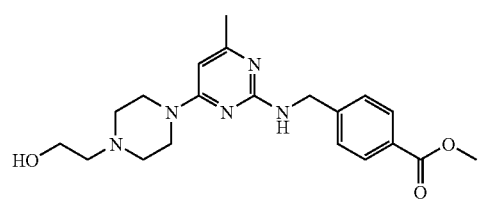
Compound 78
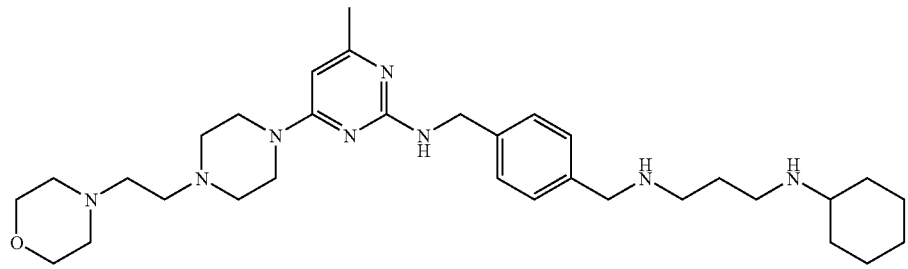

-continued
Compound 79
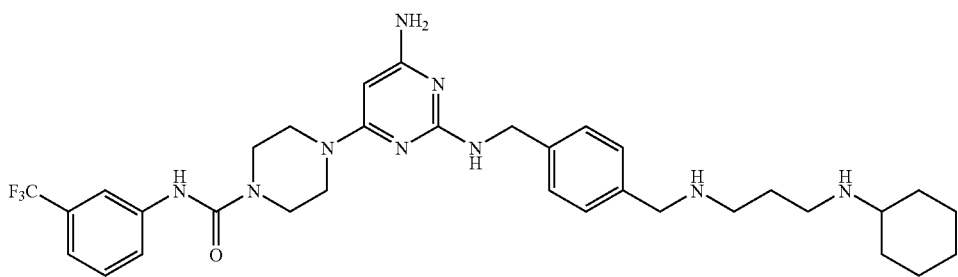
Compound 80
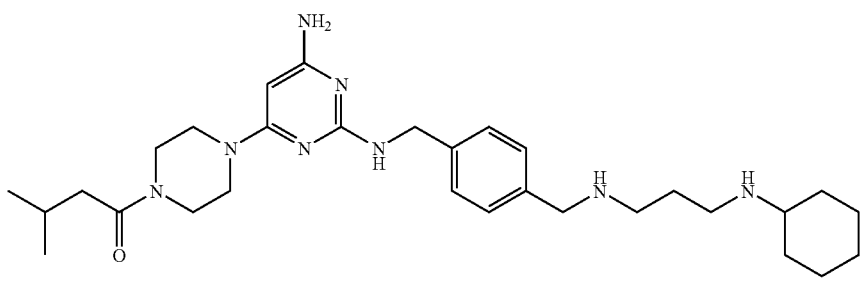
Compound 81
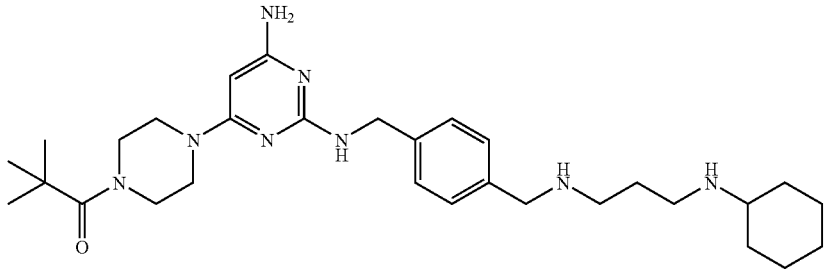
Compound 82
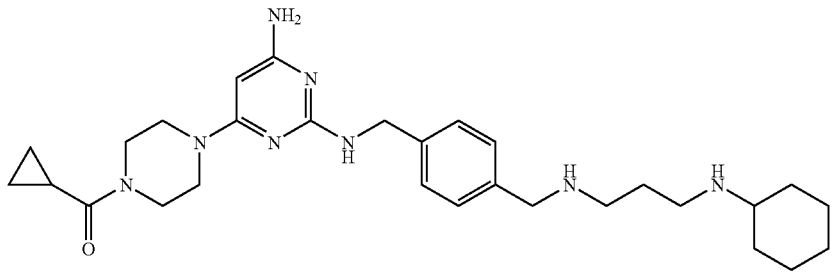
Compound 83
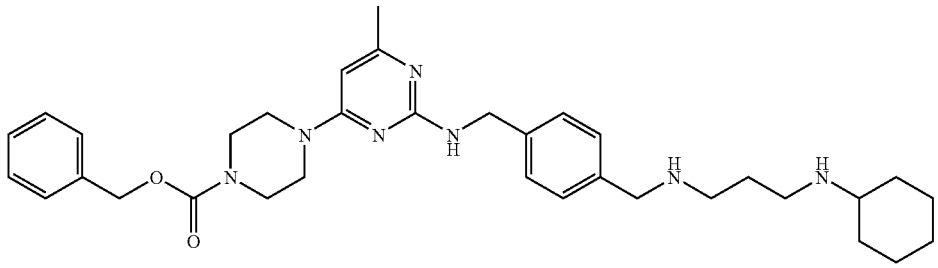
Compound 84
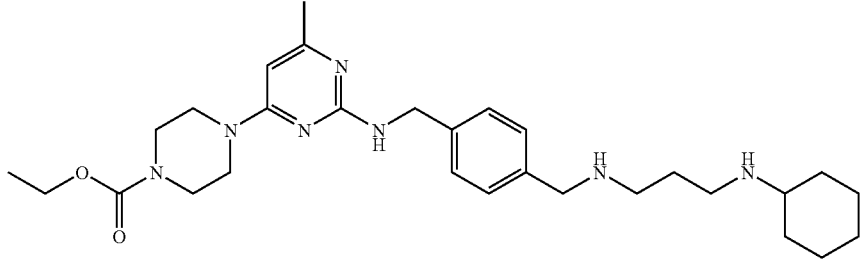

-continued
Compound 85
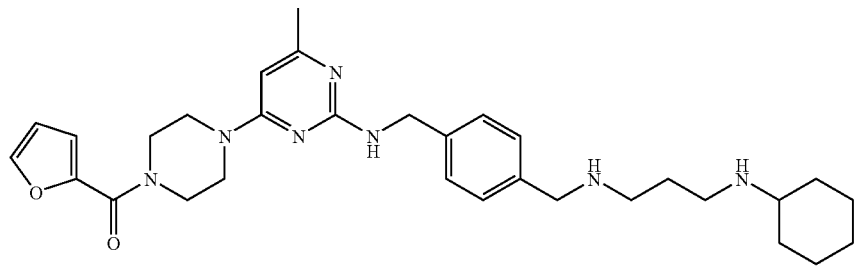
Compound 86
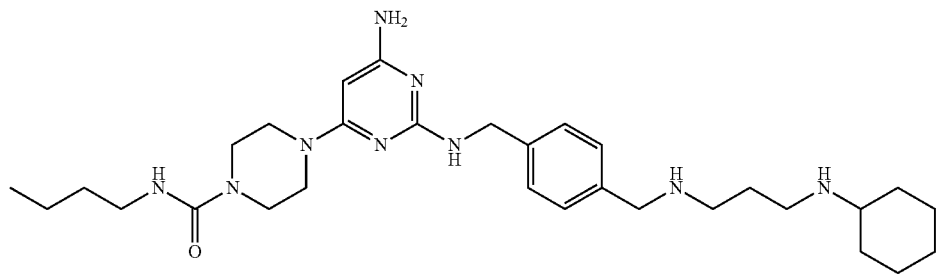
Compound 87
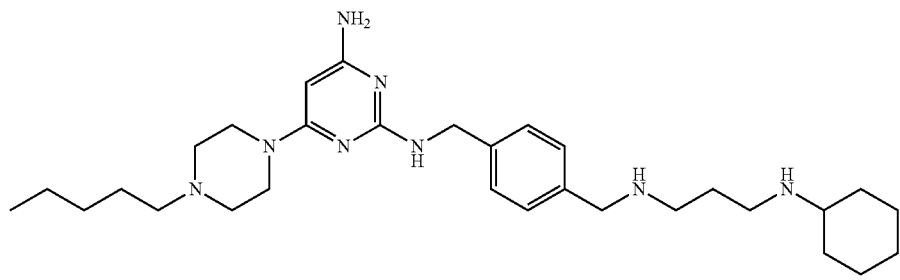
Compound 88
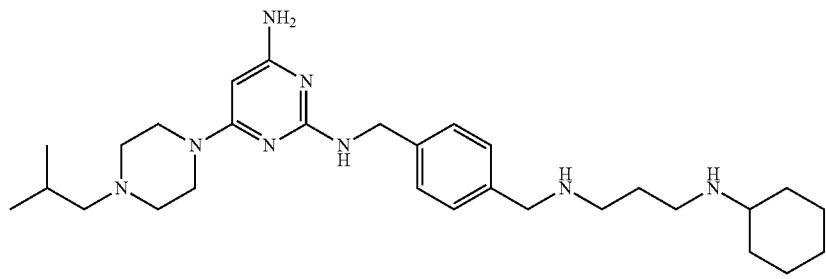
Compound 89
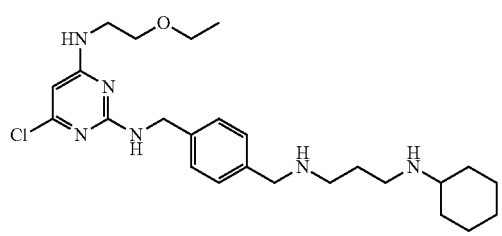
Compound 90
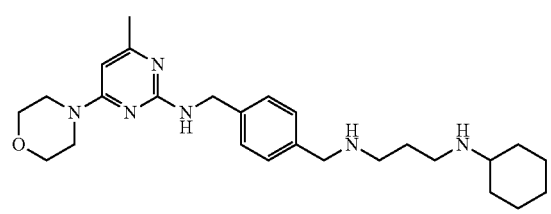
Compound 91
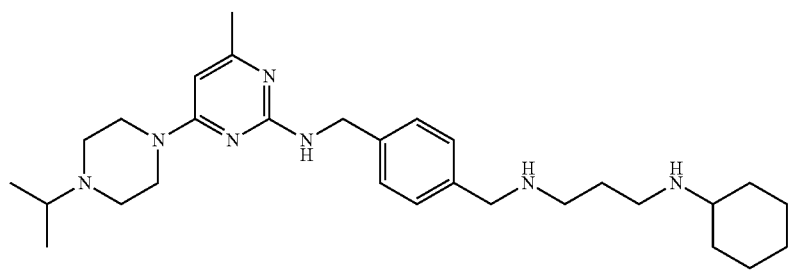

-continued
Compound 92
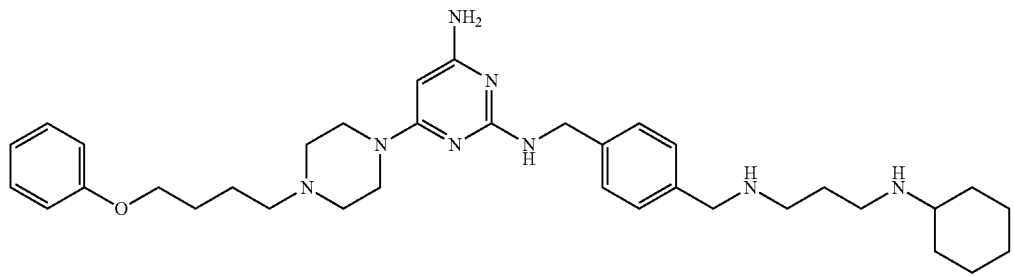
Compound 93
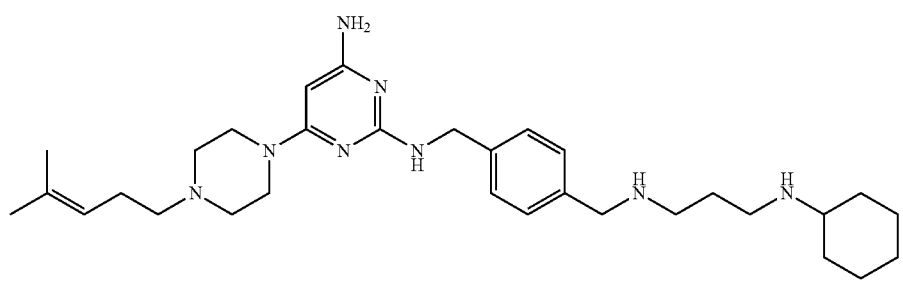
Compound 94
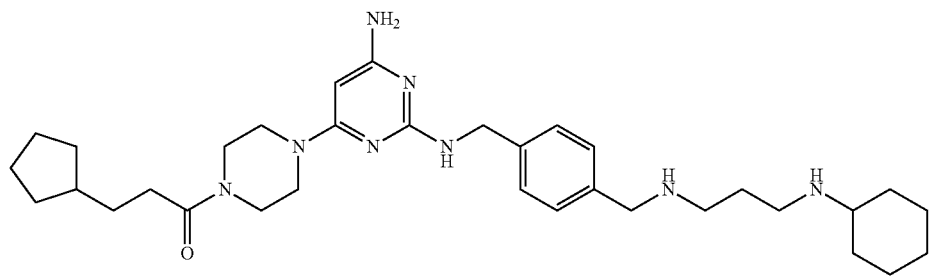
Compound 95
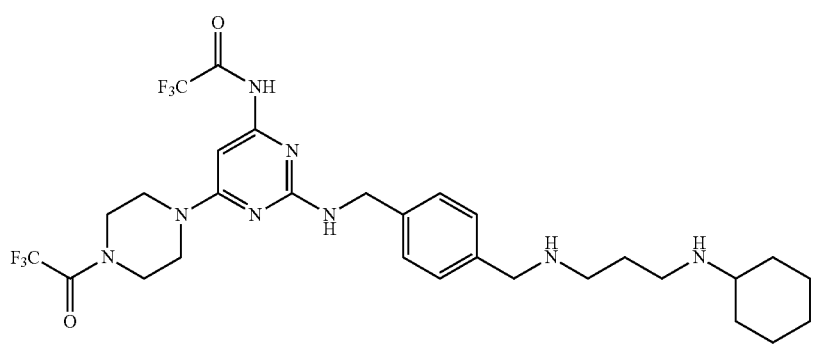
Compound 96
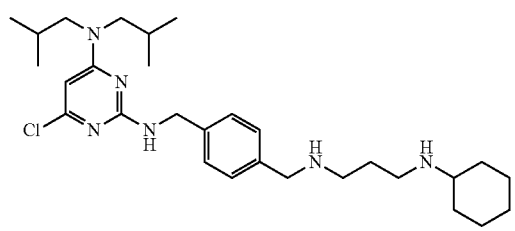
Compound 97
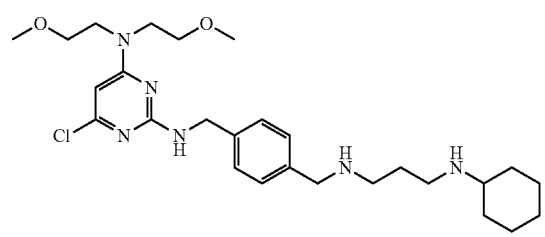

-continued
Compound 98
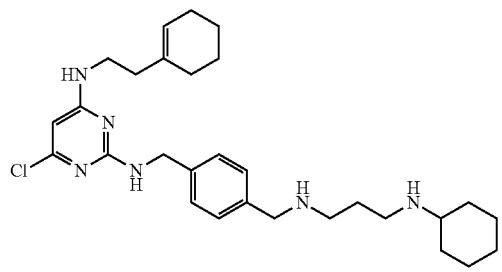
Compound 99
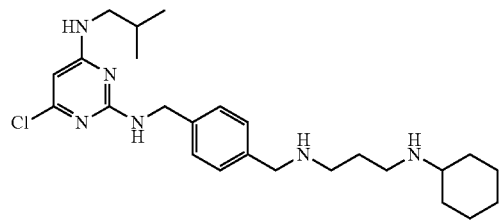
Compound 100
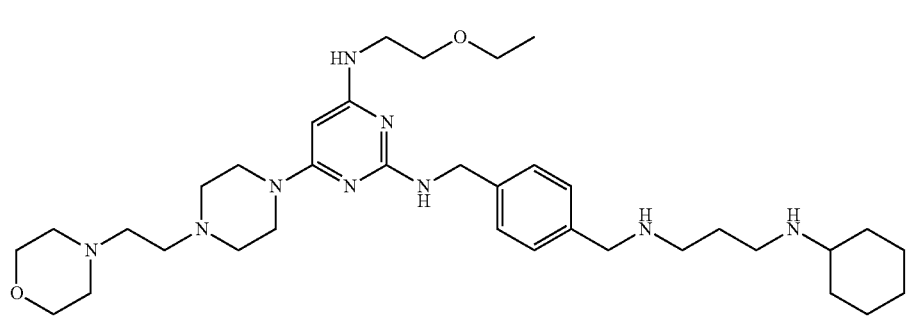
Compound 101
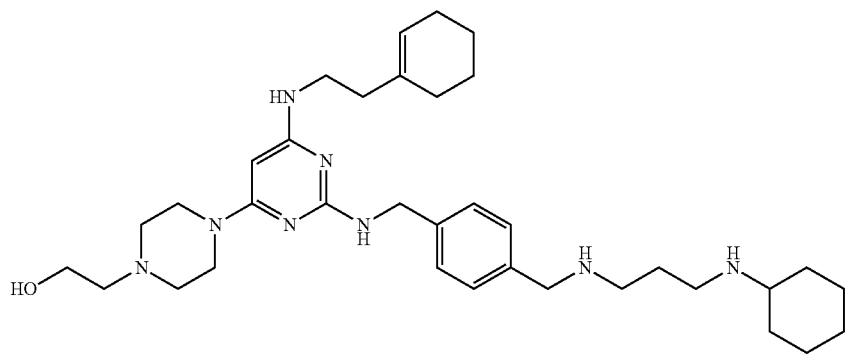
Compound 102
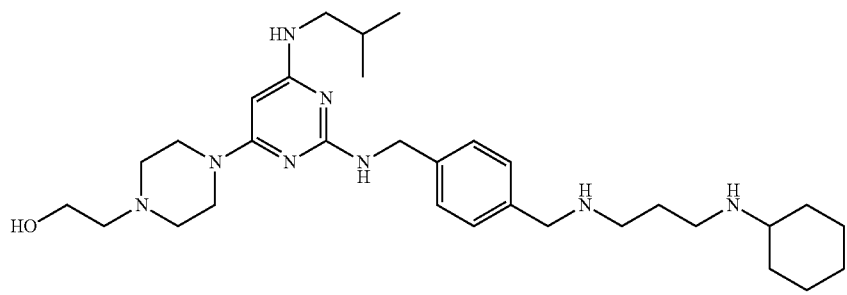
Compound 103
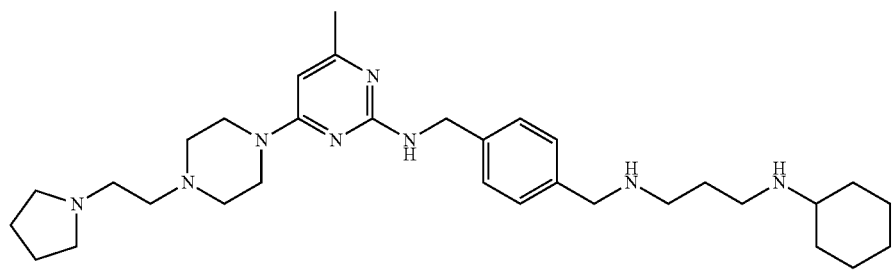

Compound 104
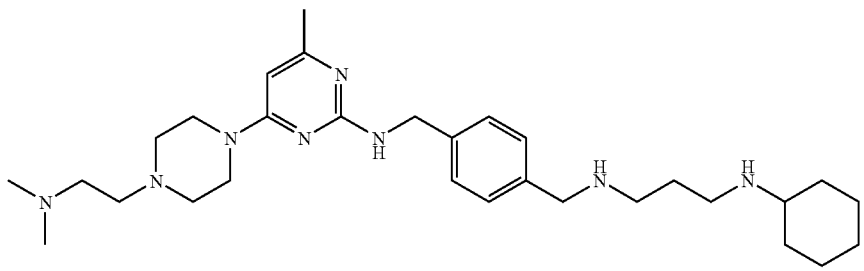
Compound 105
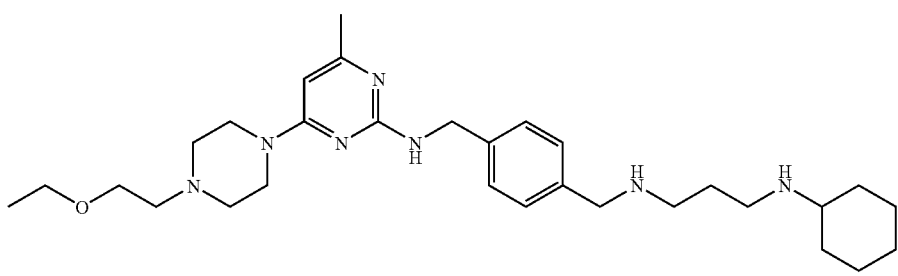
Compound 106
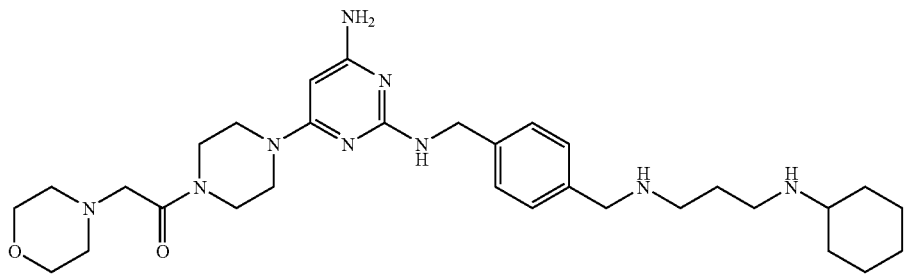
Compound 107
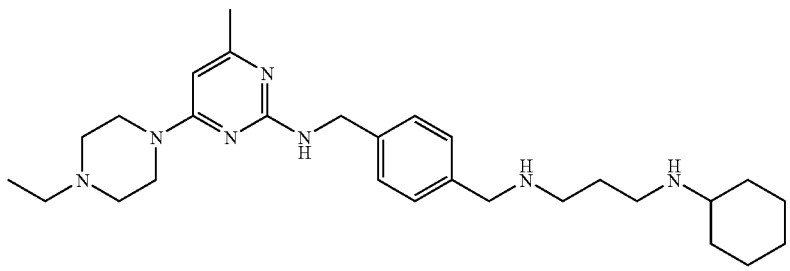
Compound 108
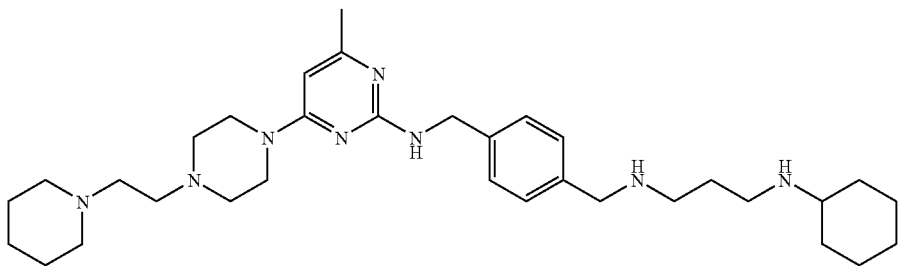
Compound 109
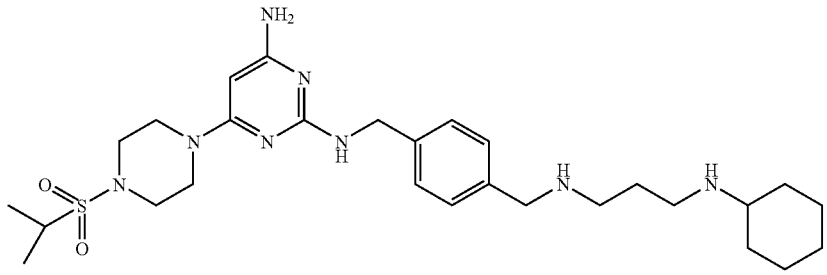

Compound 110
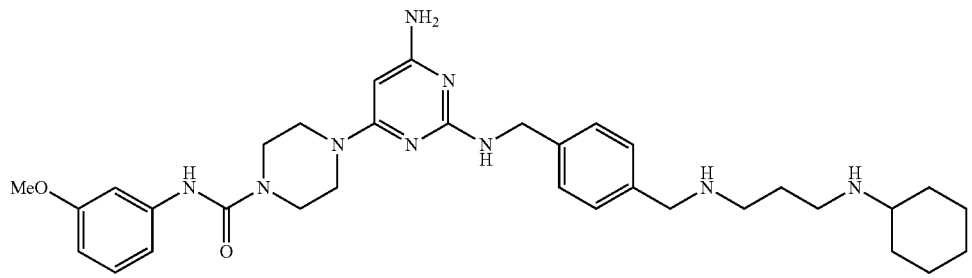
Compound 111
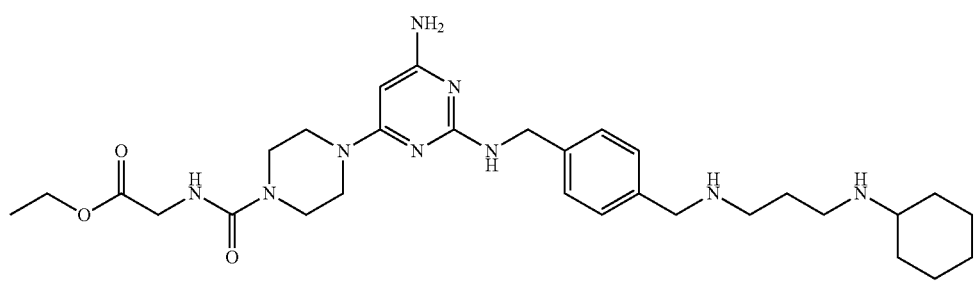
Compound 112
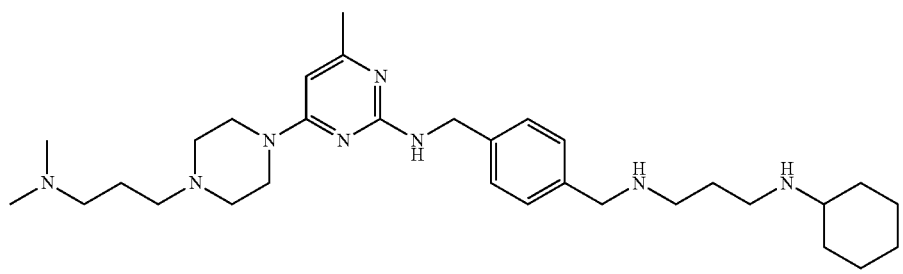
Compound 113
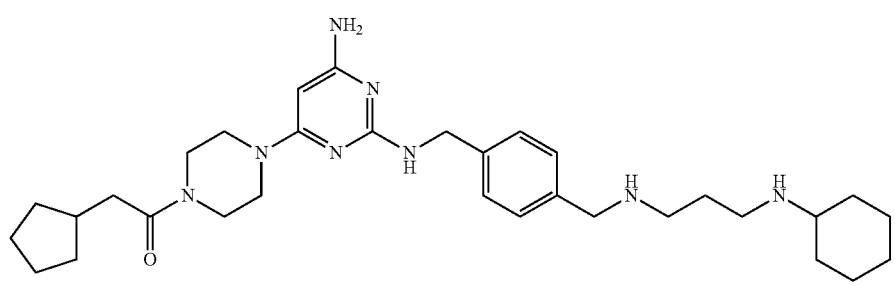
Compound 114
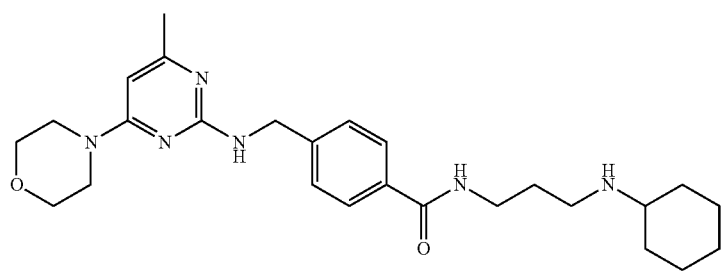

-continued
Compound 115
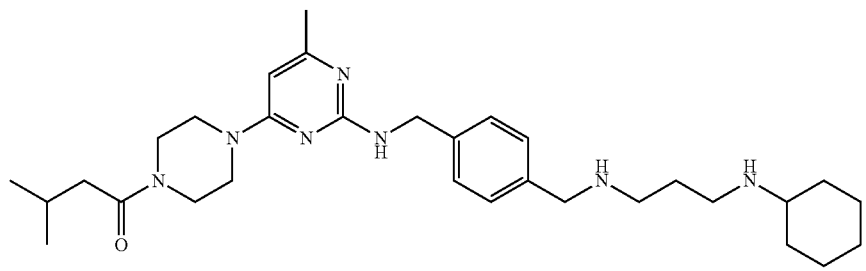
Compound 116
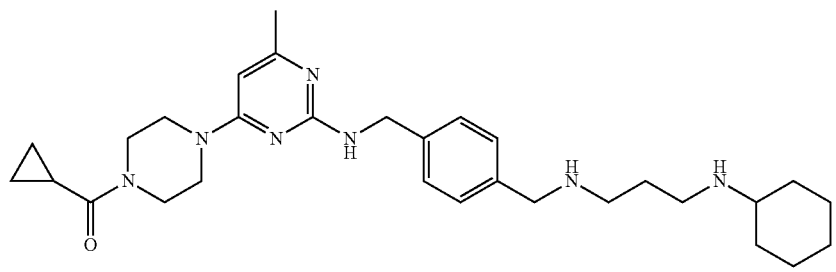
Compound 117
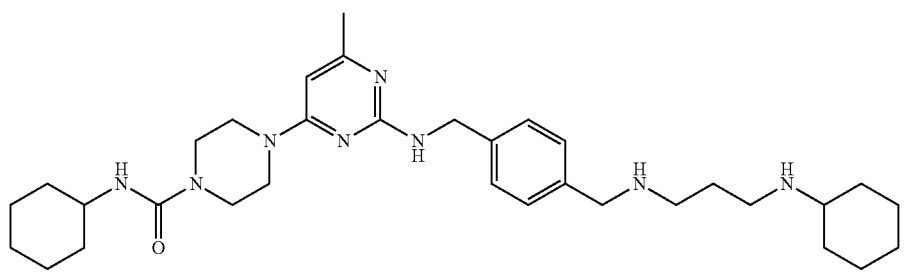
Compound 118
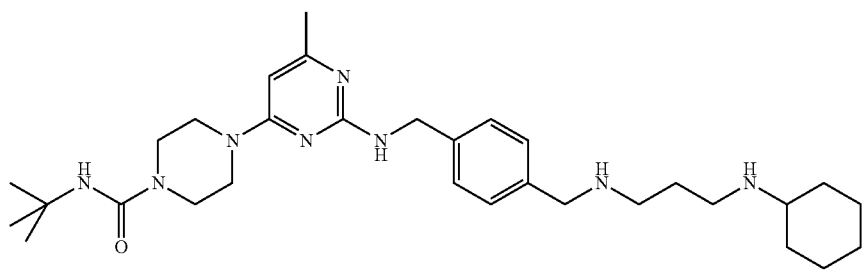
Compound 119
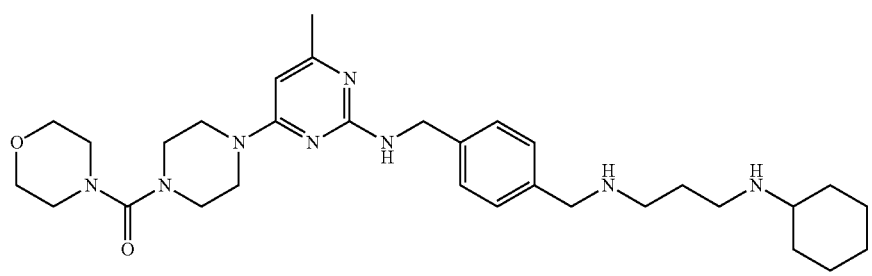
Compound 120
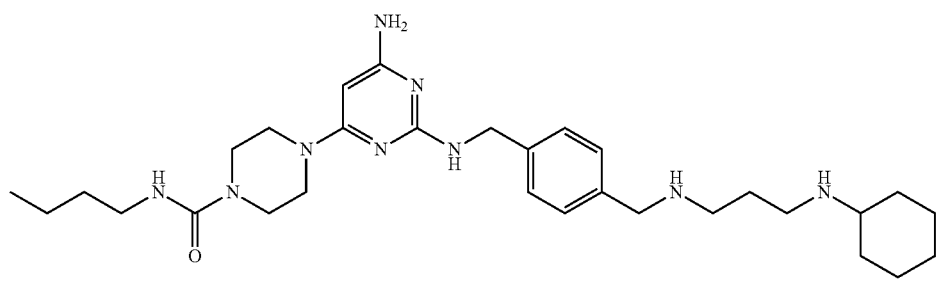

Compound 121
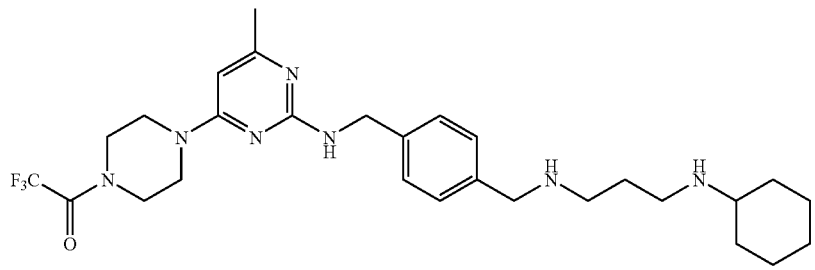
Compound 122
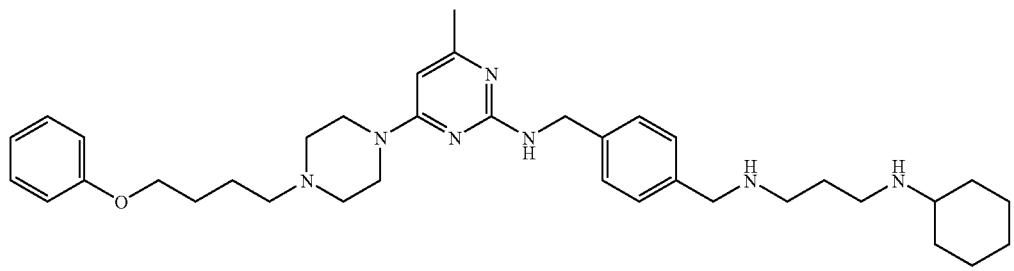
Compound 123
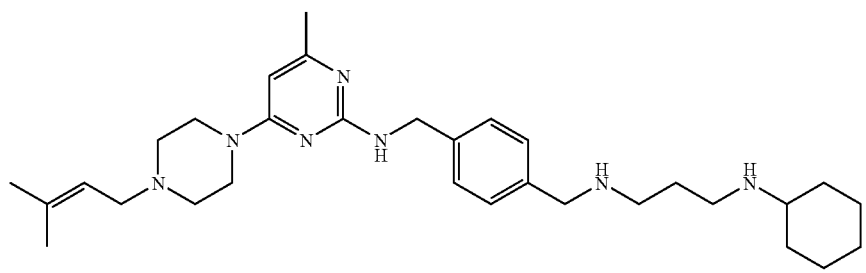
Compound 124
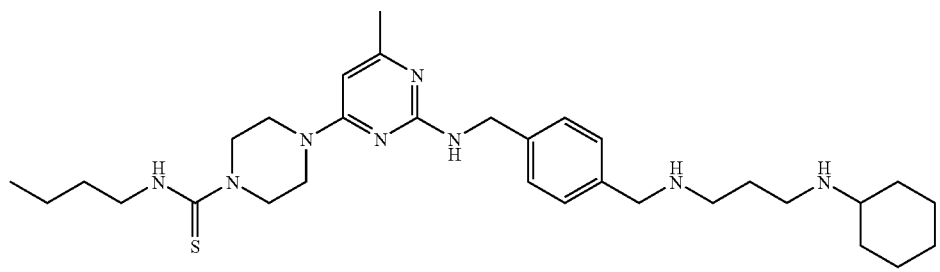
Compound 125
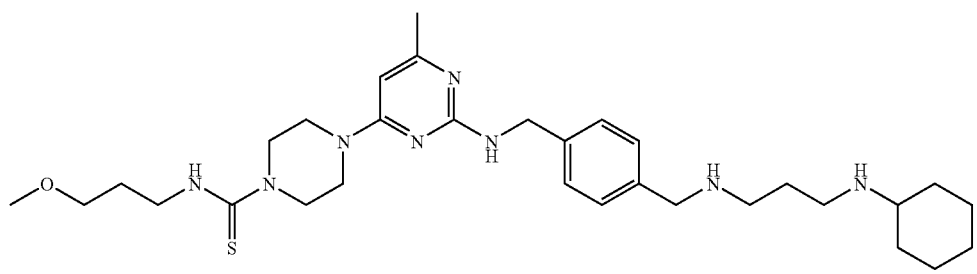
Compound 126
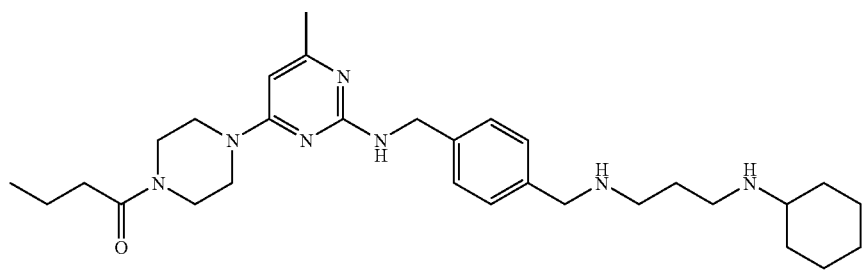

-continued
Compound 127
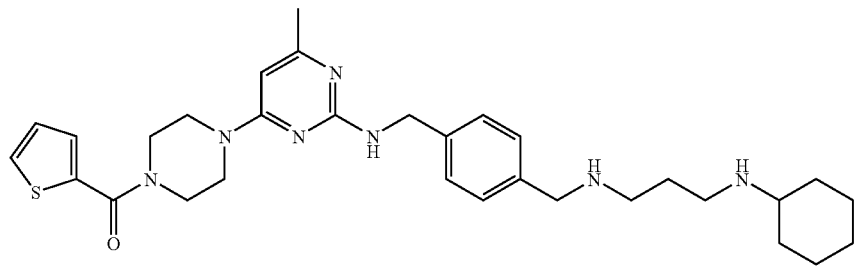
Compound 128
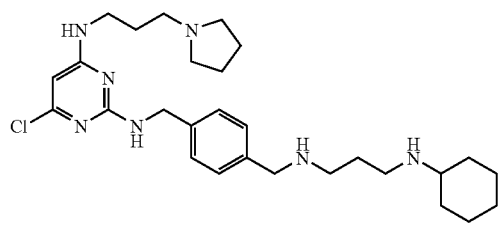
Compound 129
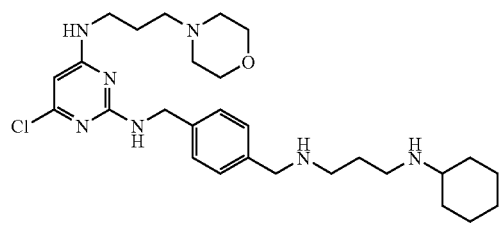
Compound 130
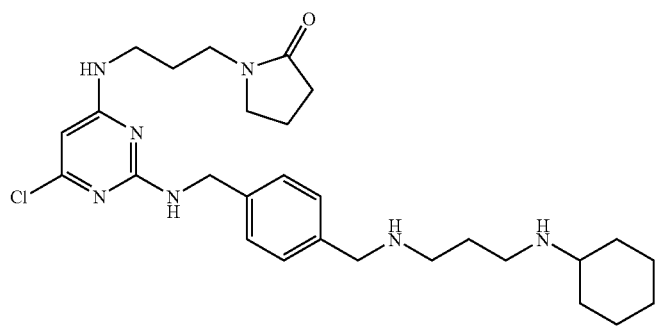
Compound 131
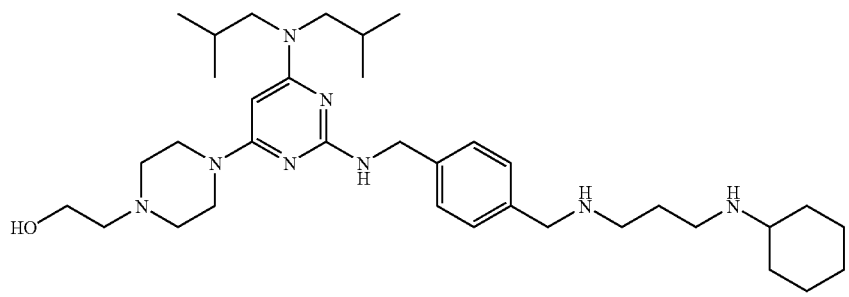
Compound 132
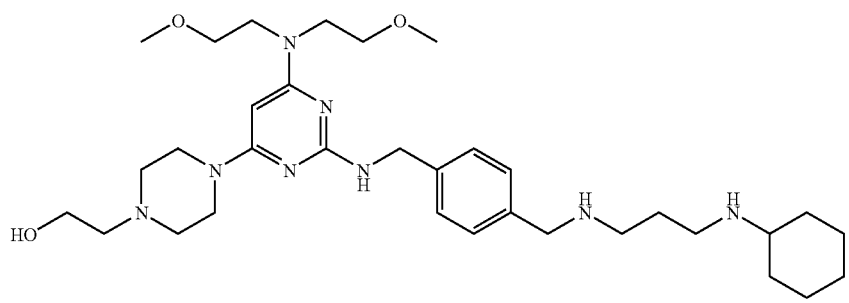

-continued
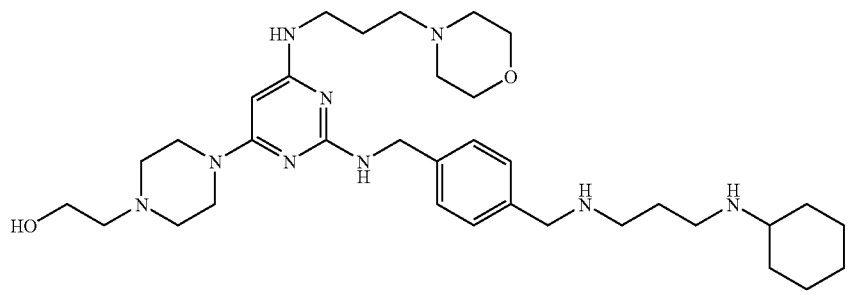
Compound 133
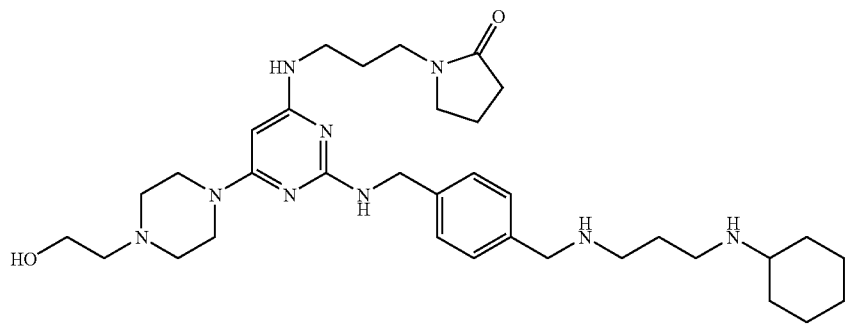
Compound 134
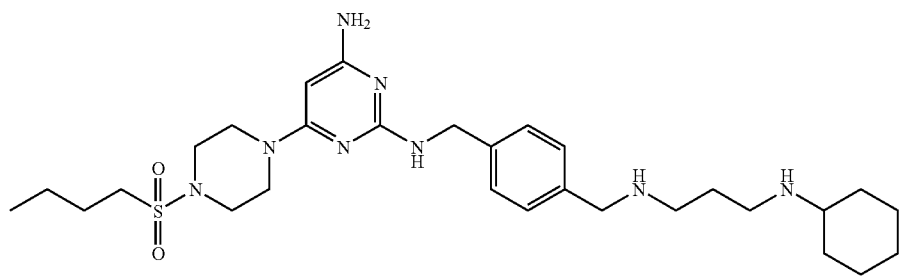
Compound 135
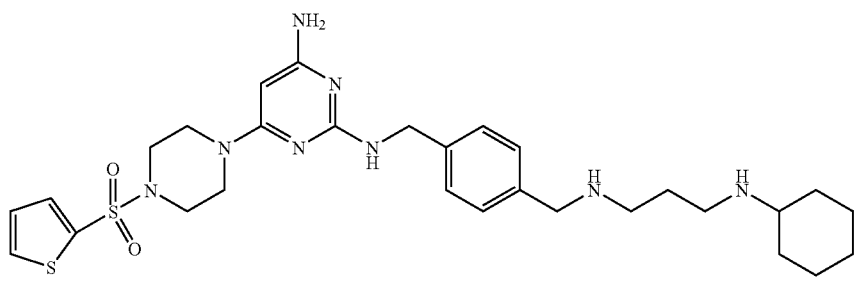
Compound 136
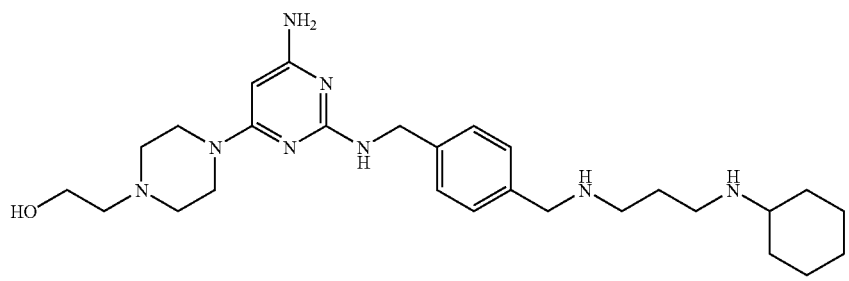
Compound 137

Compound 138
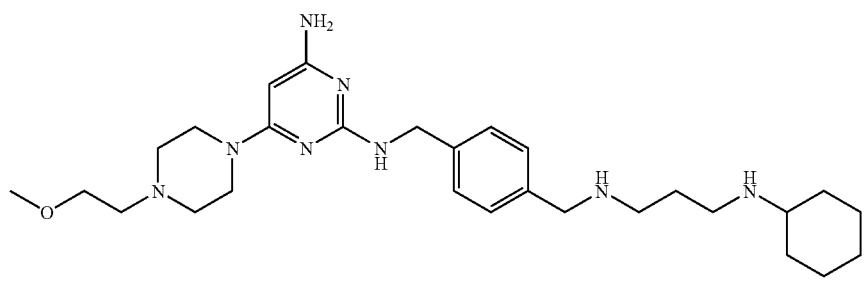
Compound 139
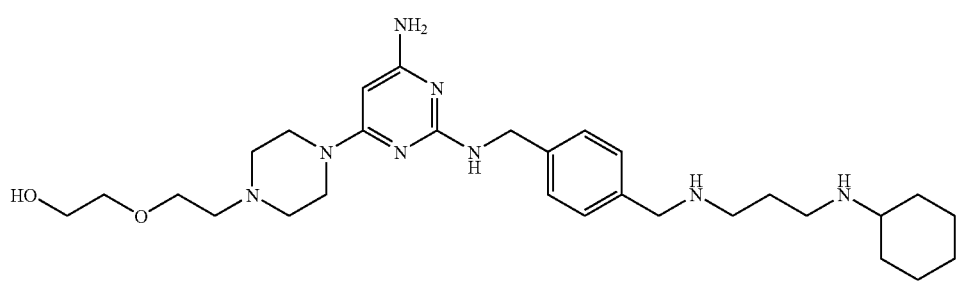
Compound 140
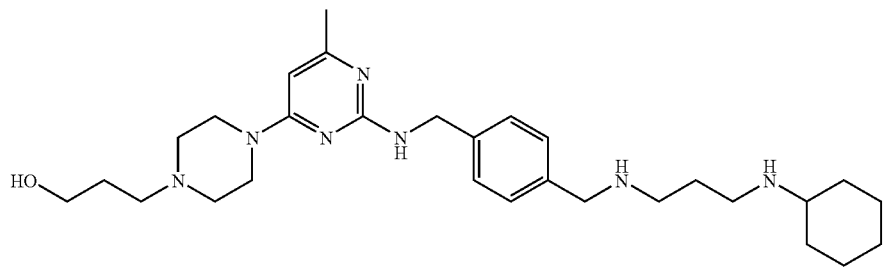
Compound 141
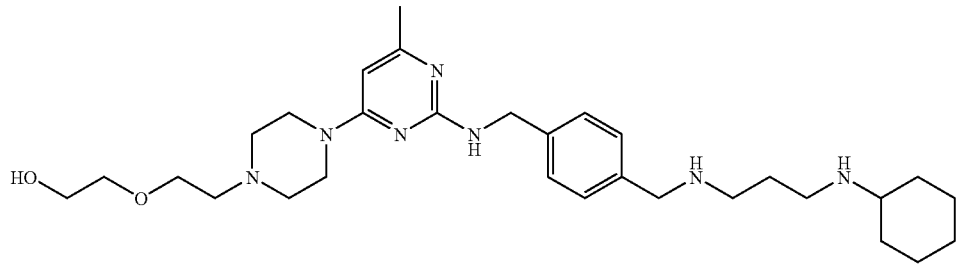
Compound 142
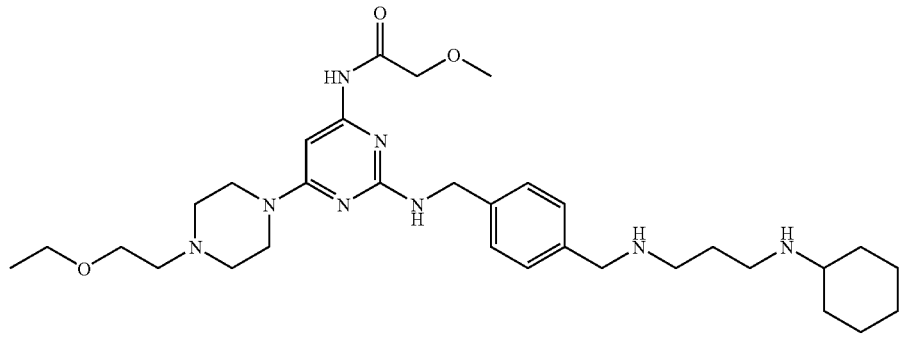

Compound 143
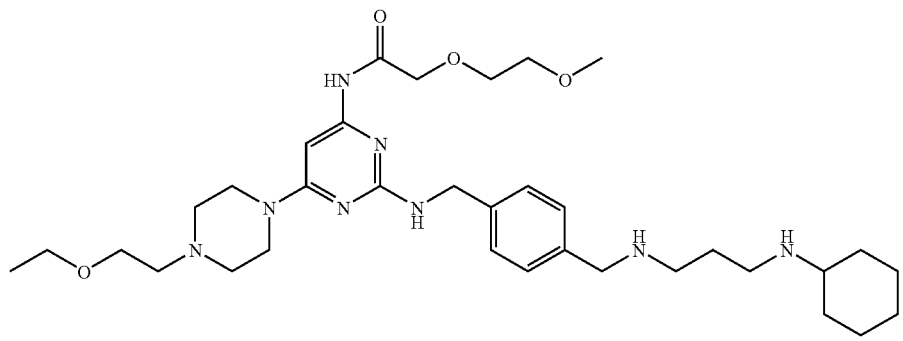
Compound 144
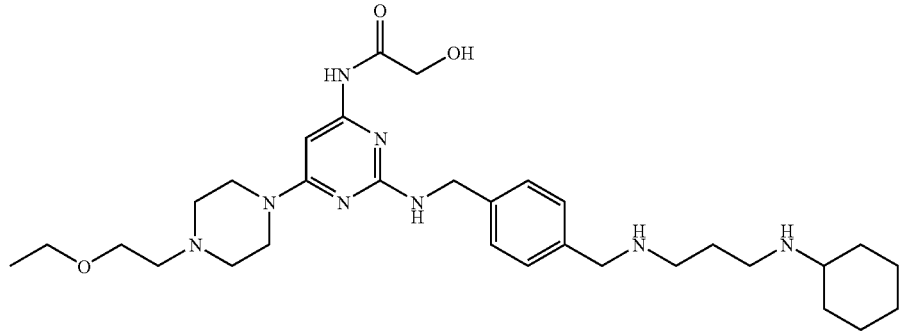
Compound 145
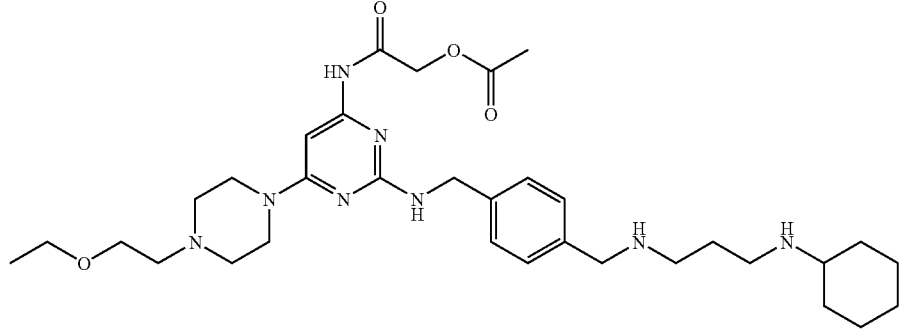
Compound 146
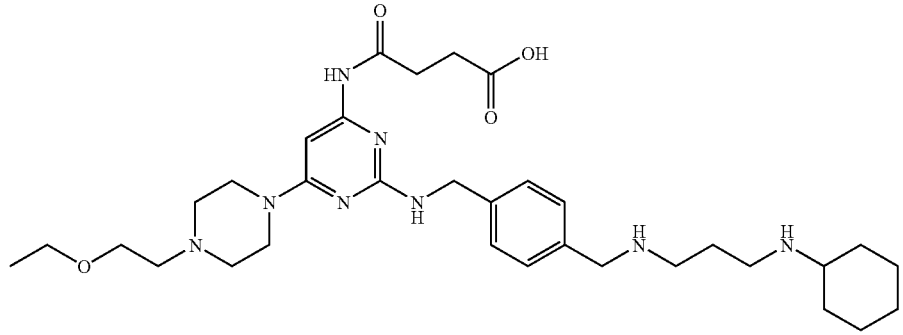
Compound 147
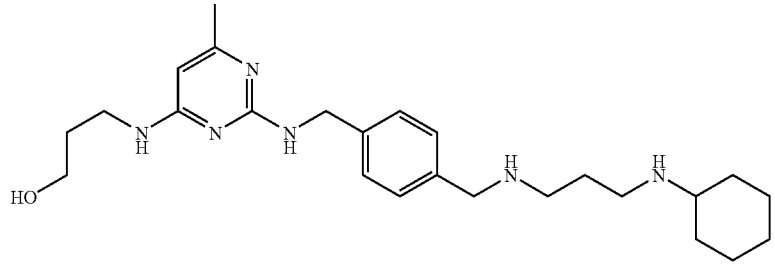

Compound 148
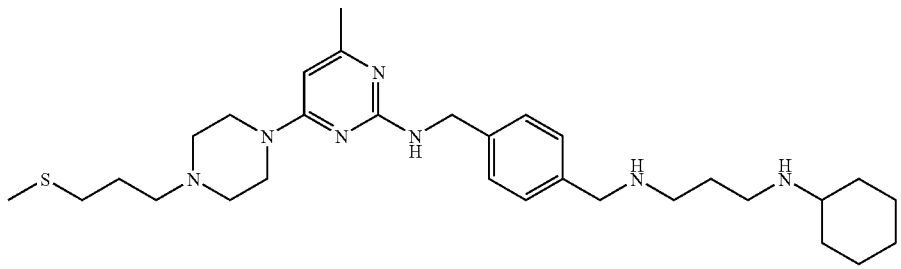
Compound 149
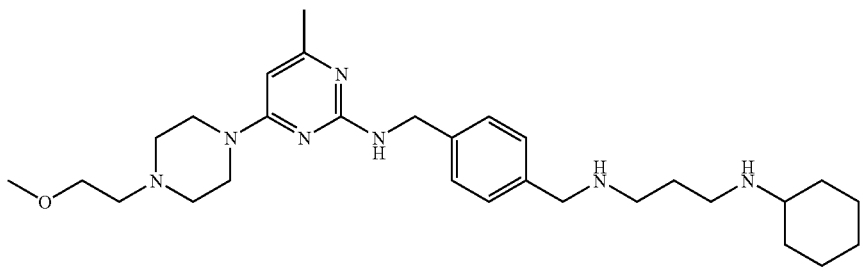
Compound 150
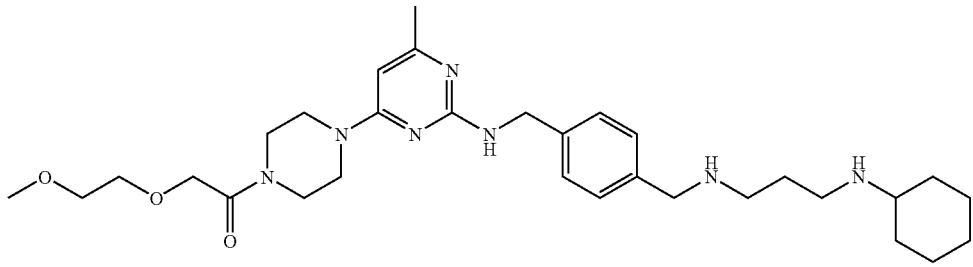
Compound 151
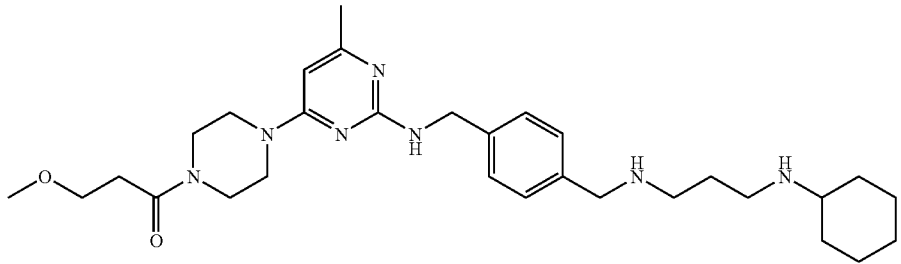
Compound 152
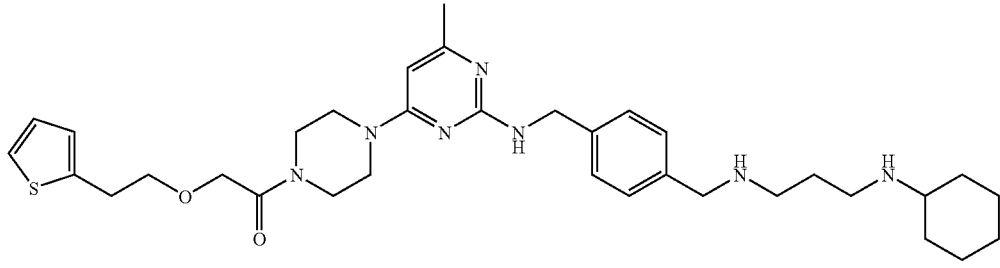
Compound 153
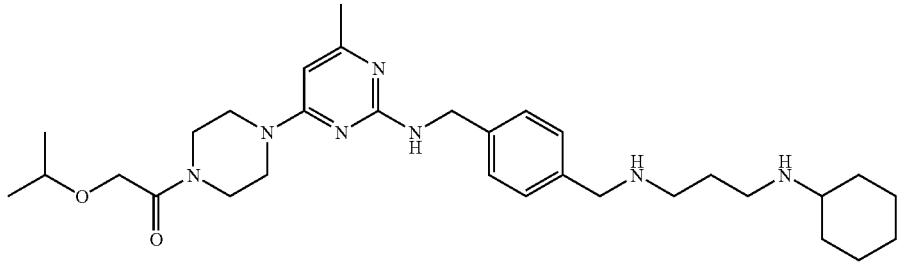

Compound 154
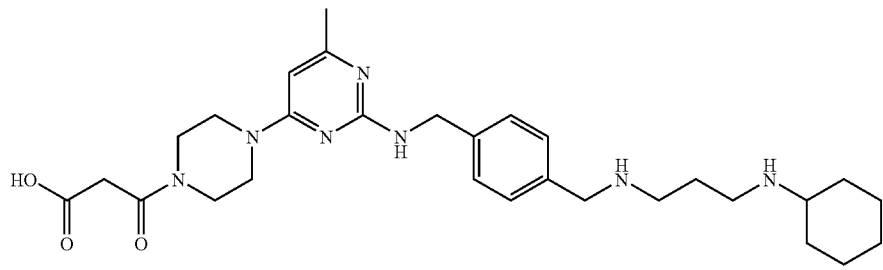
Compound 155
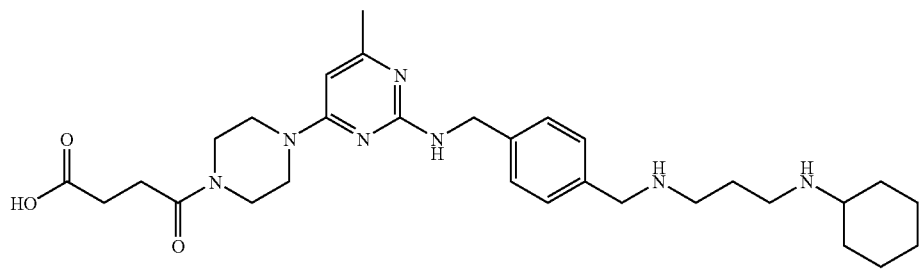
Compound 156
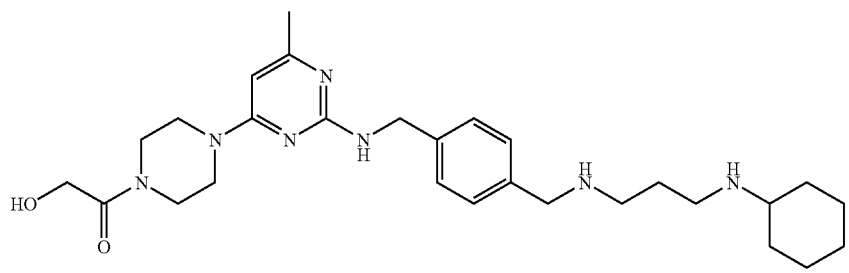
Compound 157
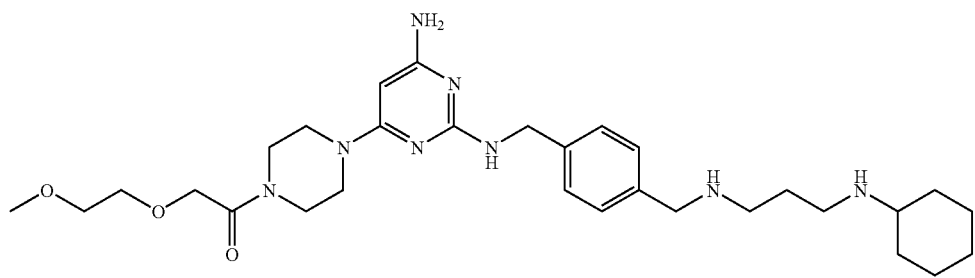
Compound 158
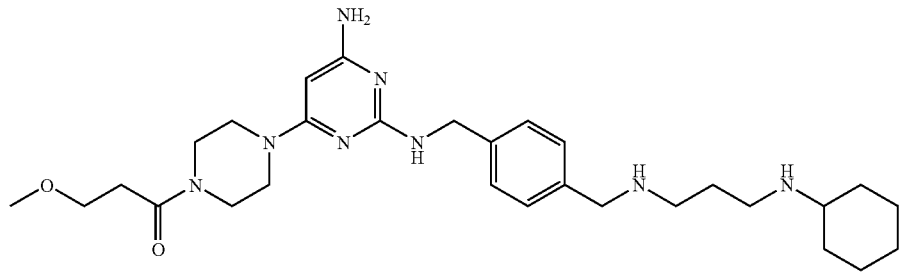
Compound 159
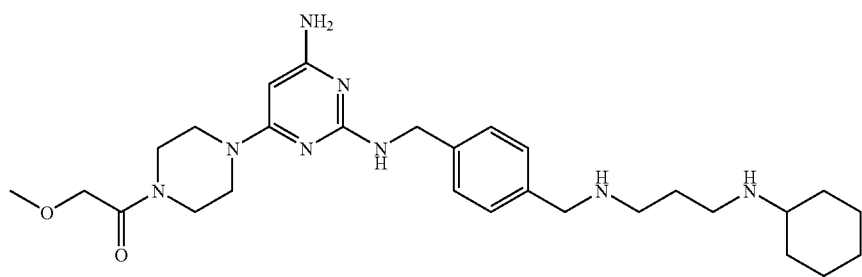

-continued
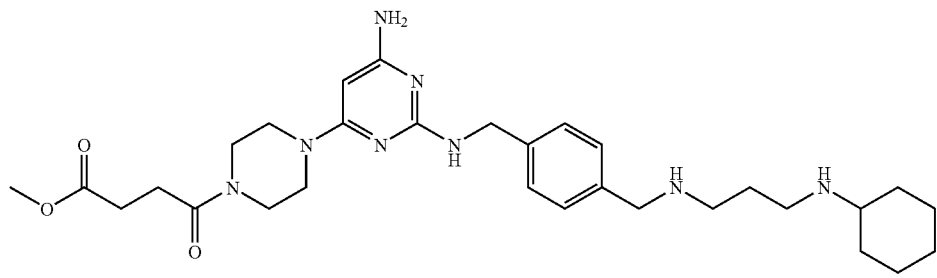
Compound 160
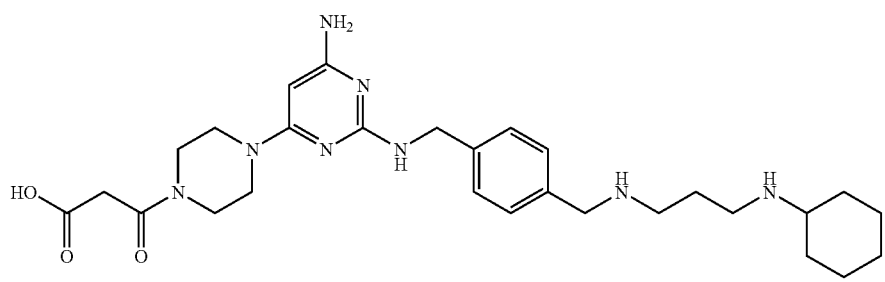
Compound 161
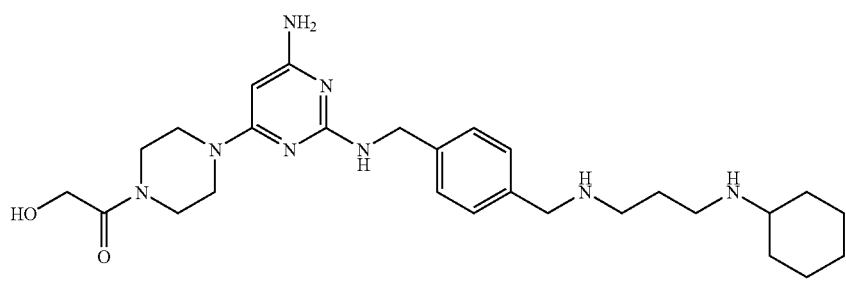
Compound 162
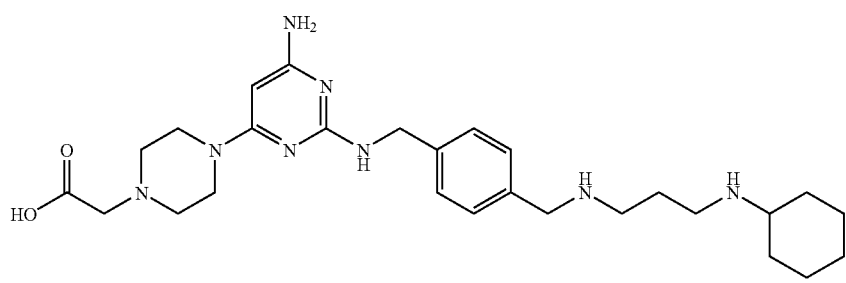
Compound 163
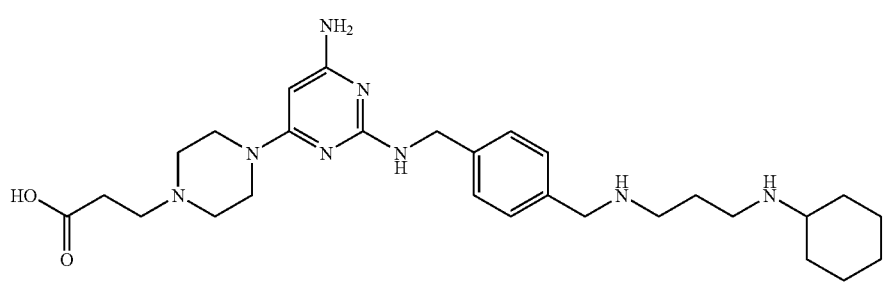
Compound 164

Compound 165
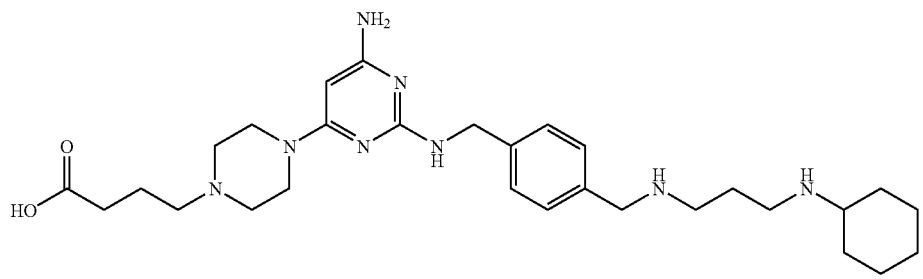
Compound 166
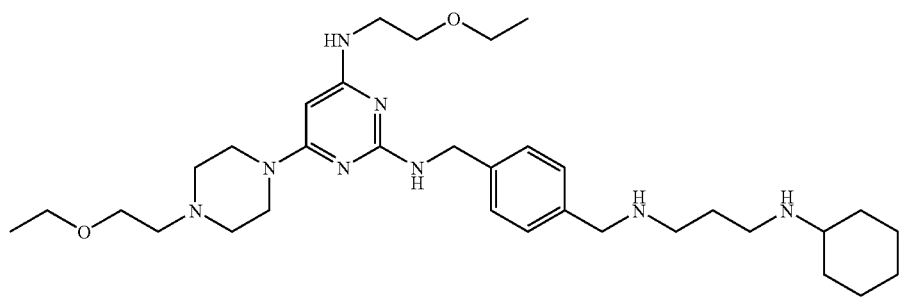
Compound 167
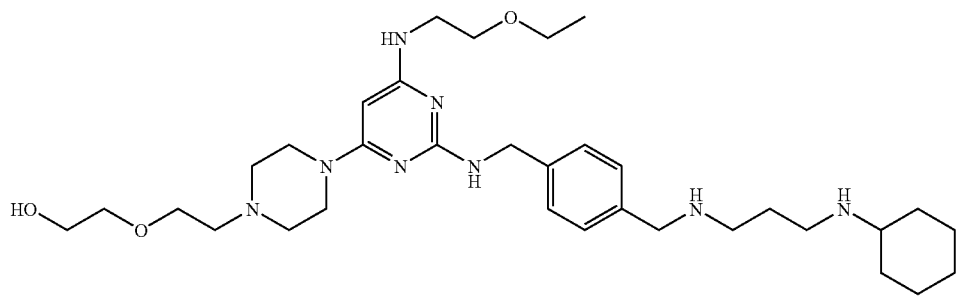
Compound 168
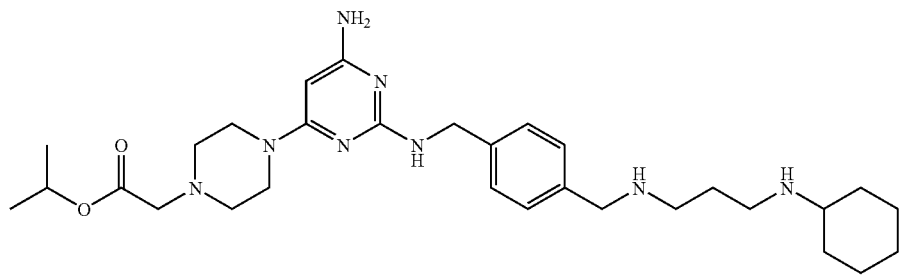
Compound 169
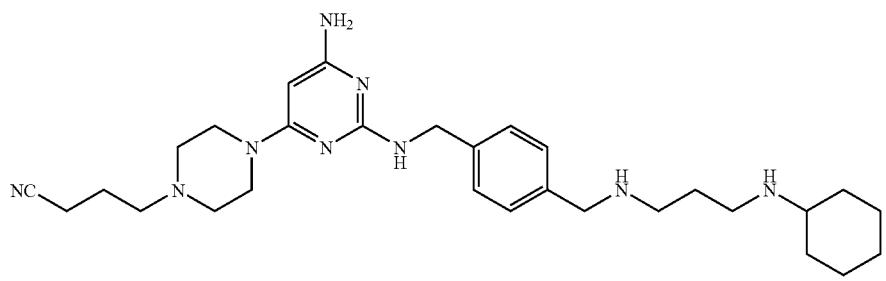

Compound 170
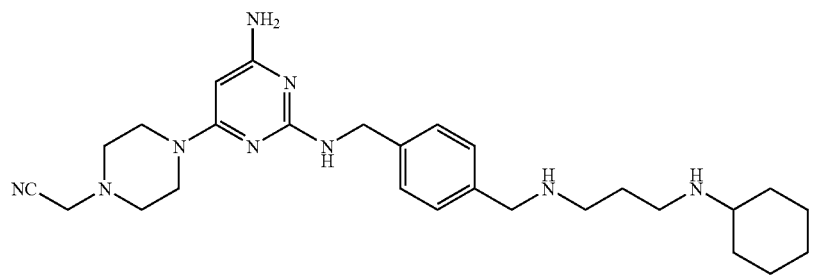
Compound 171
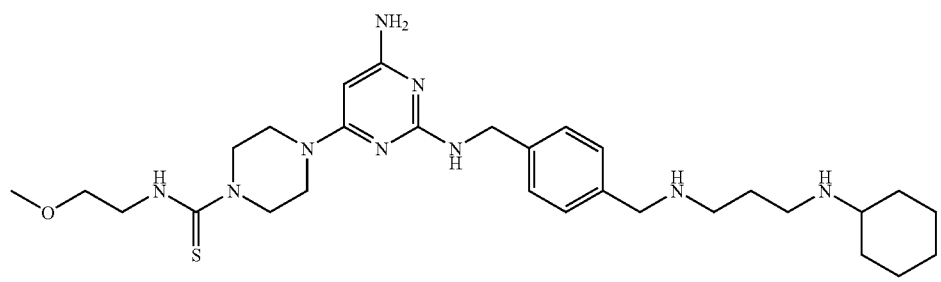
Compound 172
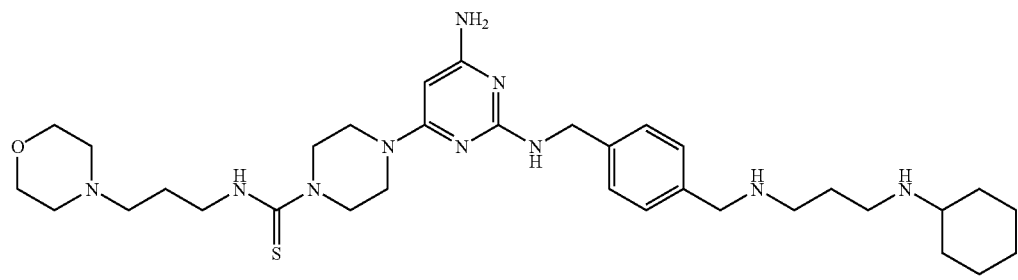
Compound 173
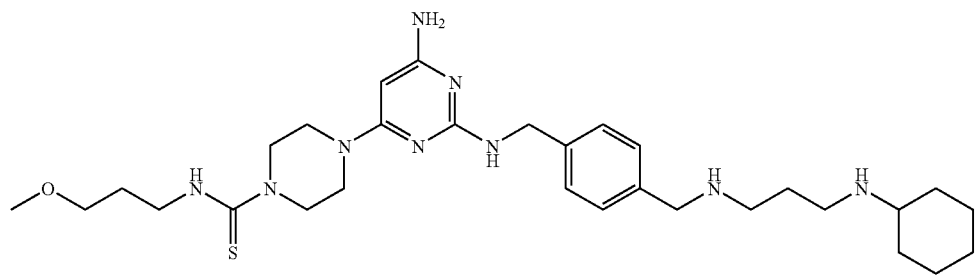
Compound 174
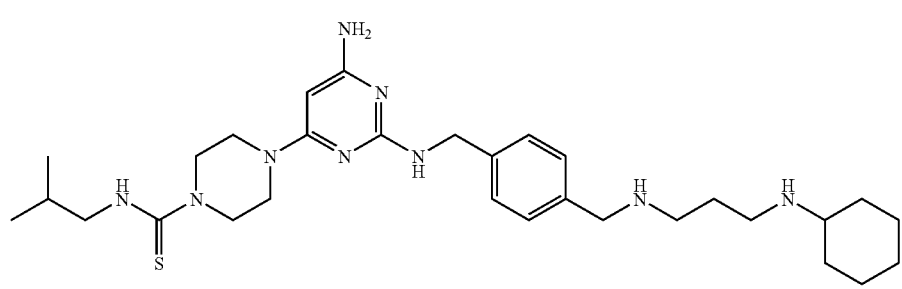

-continued
Compound 175
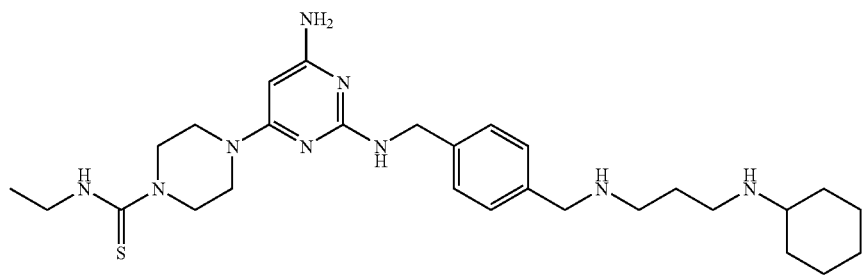
Compound 176
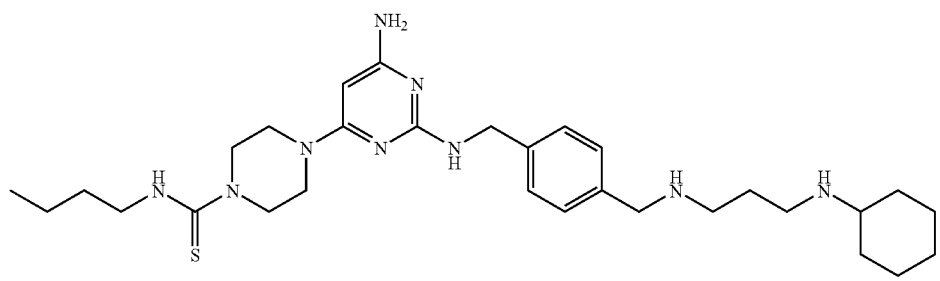
Compound 177
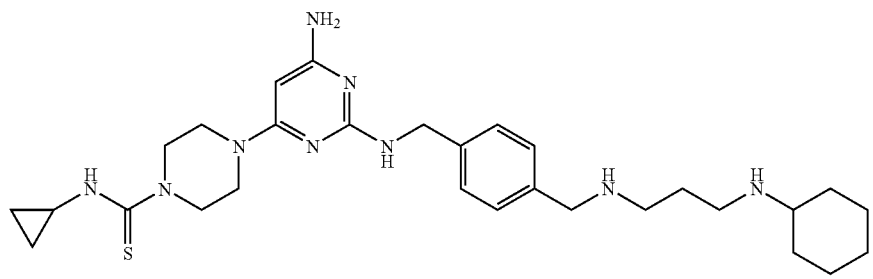
Compound 178
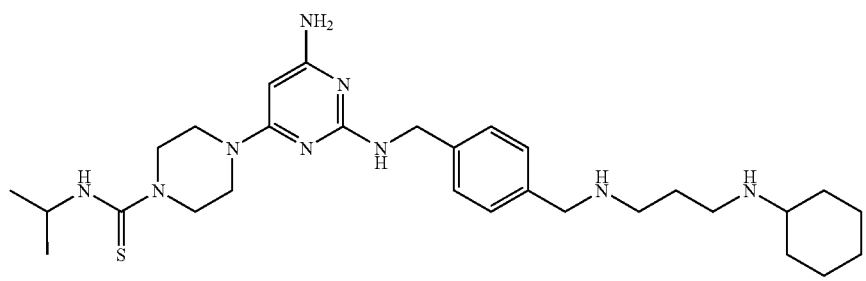
Compound 179
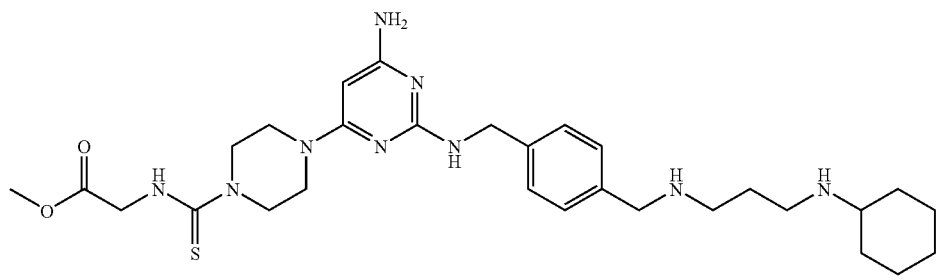

Compound 180
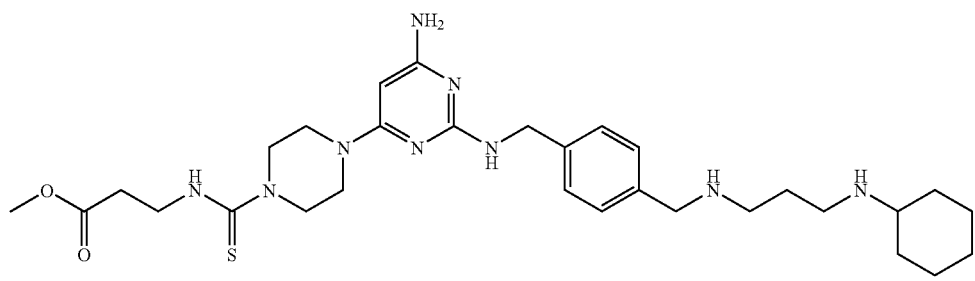
Compound 181
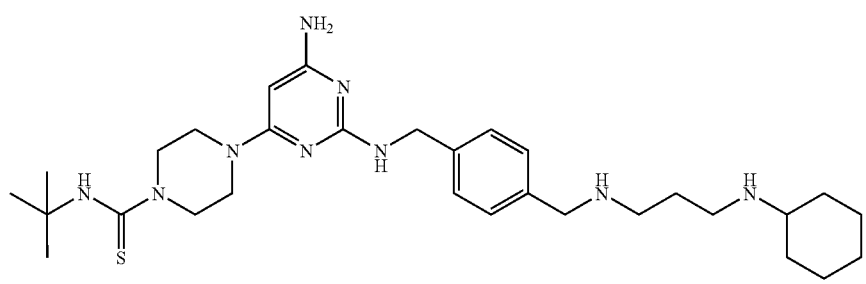
Compound 182
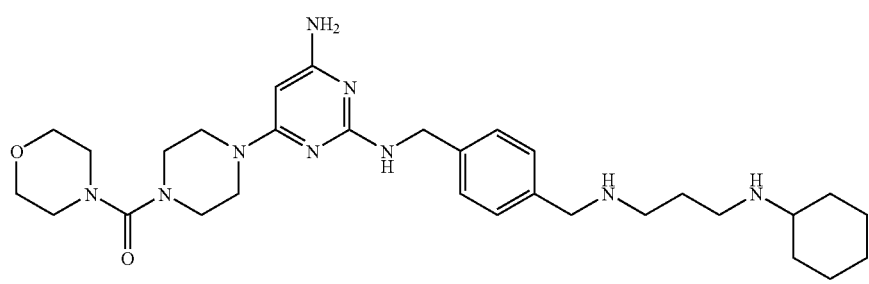
Compound 183
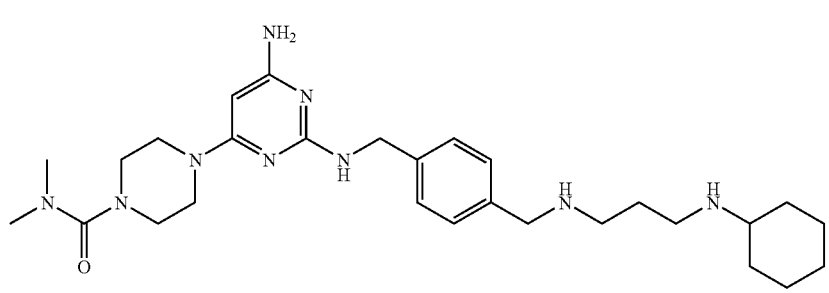
Compound 184
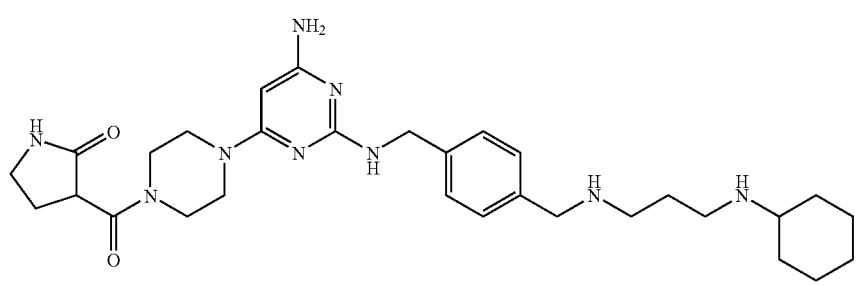

Compound 185
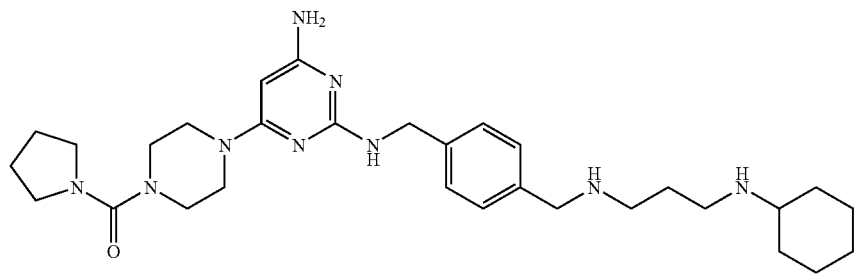
Compound 186
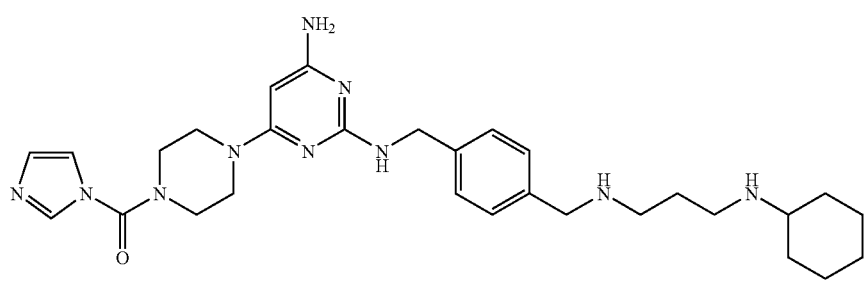
Compound 187
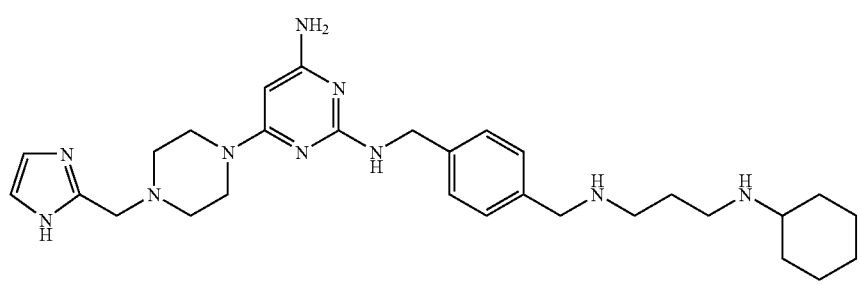
Compound 188
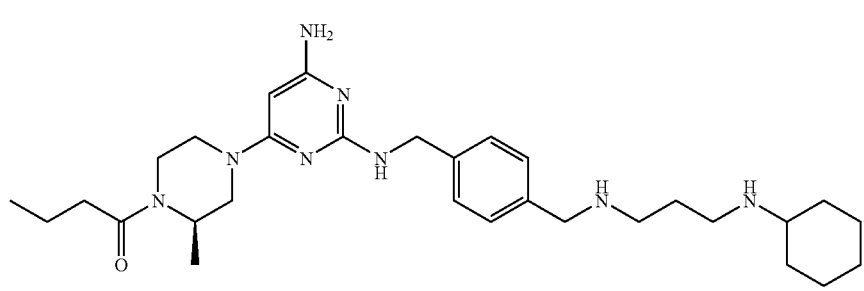
Compound 189
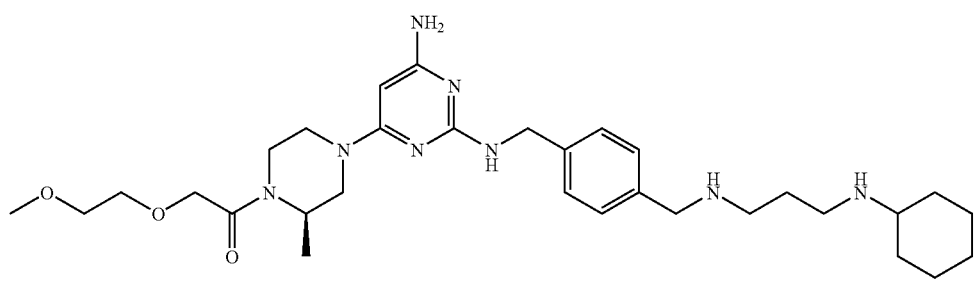

-continued
Compound 190
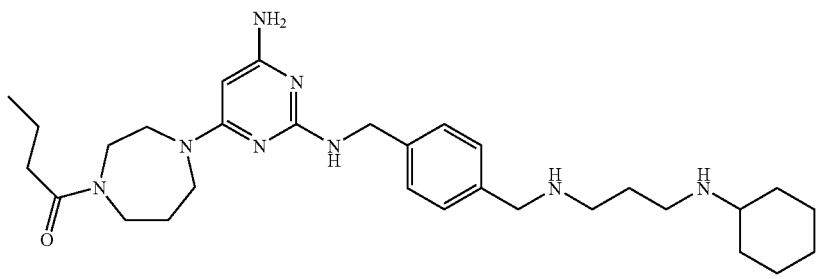
Compound 191
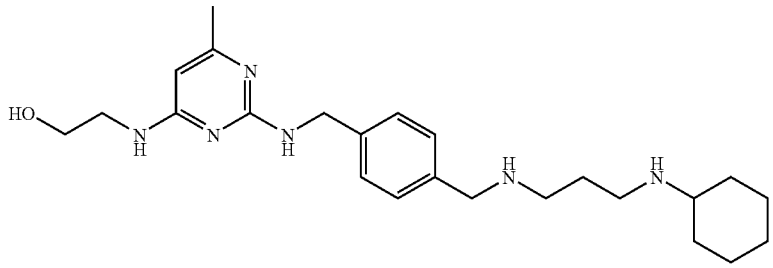
Compound 192
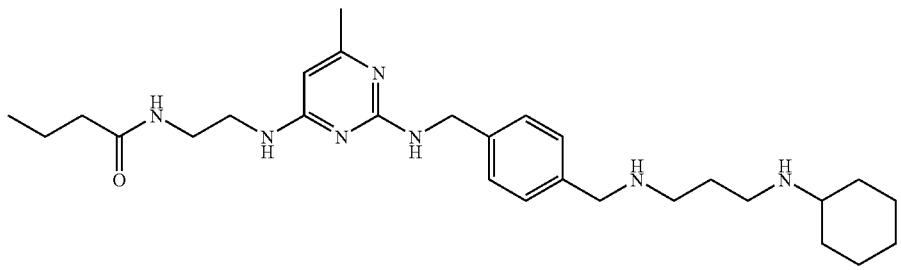
Compound 193
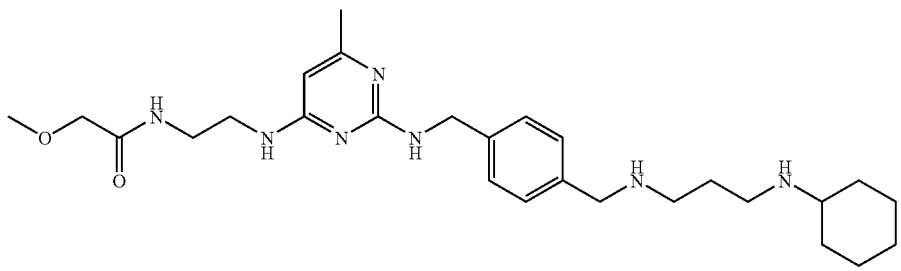
Compound 194
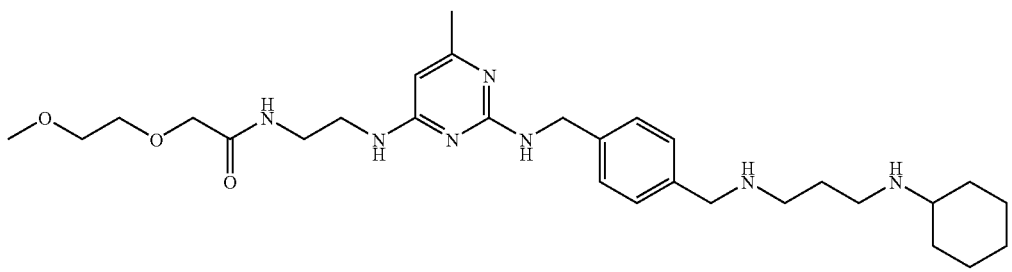
Compound 195
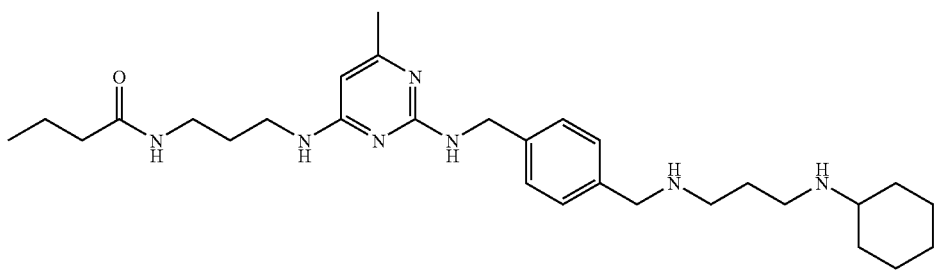

Compound 196
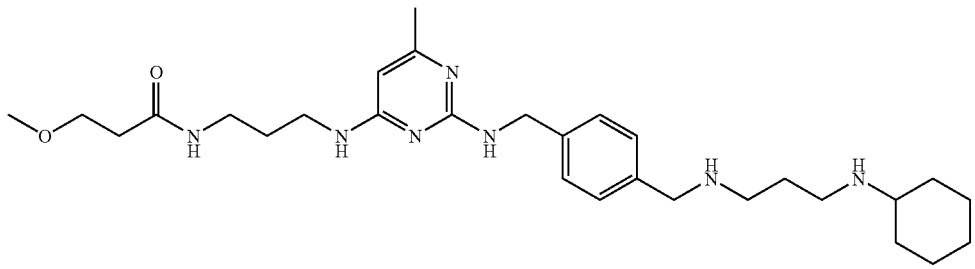
Compound 197
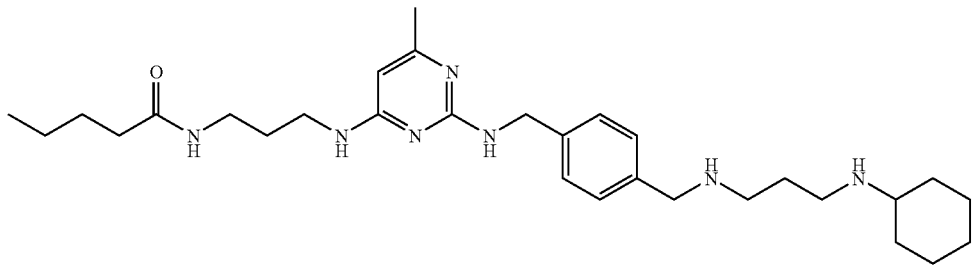
Compound 198
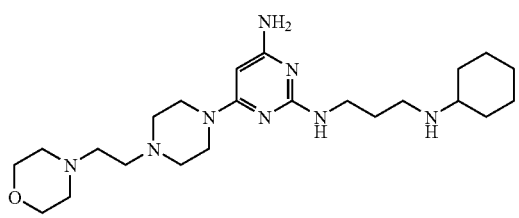
Compound 199
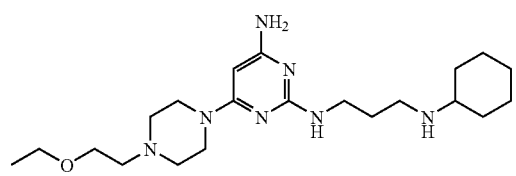
Compound 200
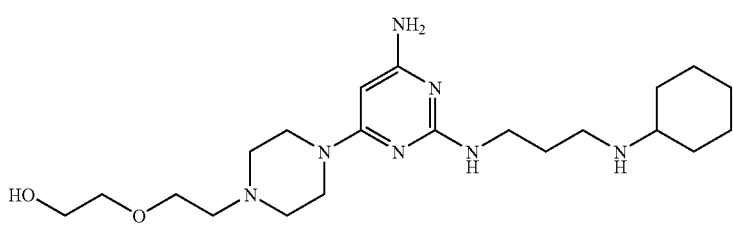
Compound 201
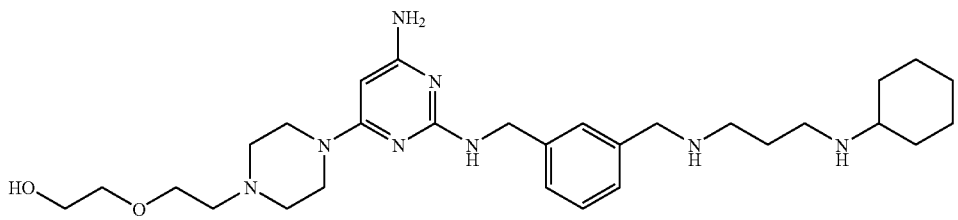
Compound 202
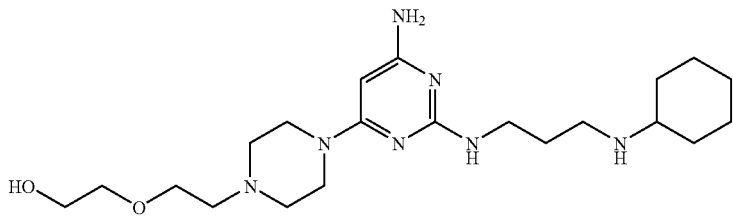

-continued
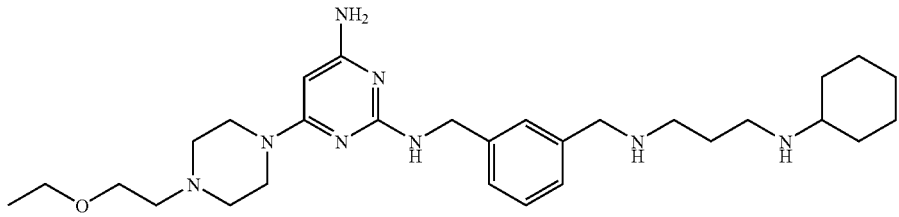
Compound 203
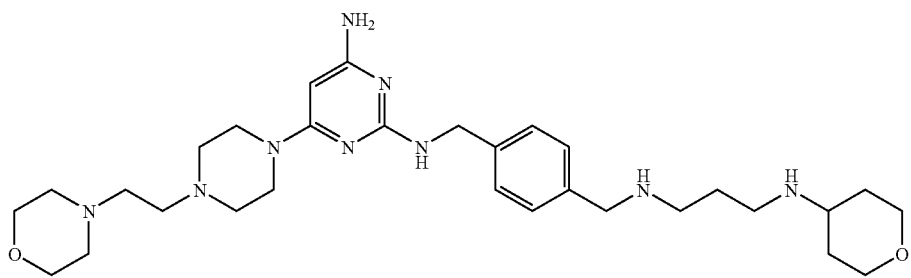
Compound 204
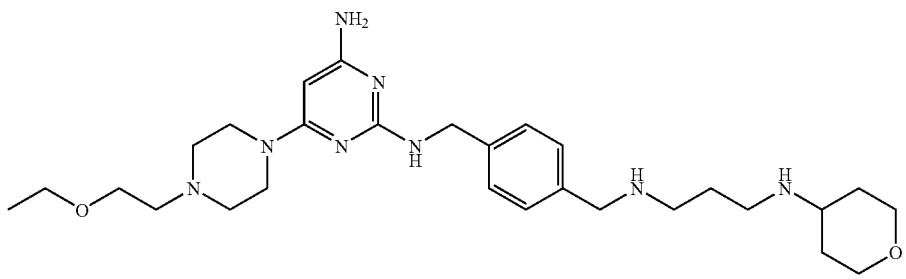
Compound 205
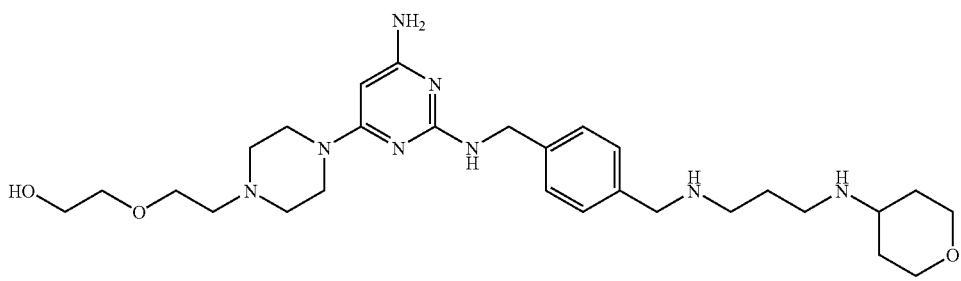
Compound 206
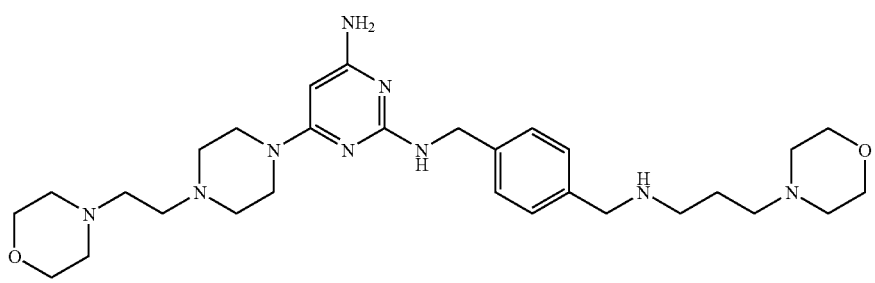
Compound 207
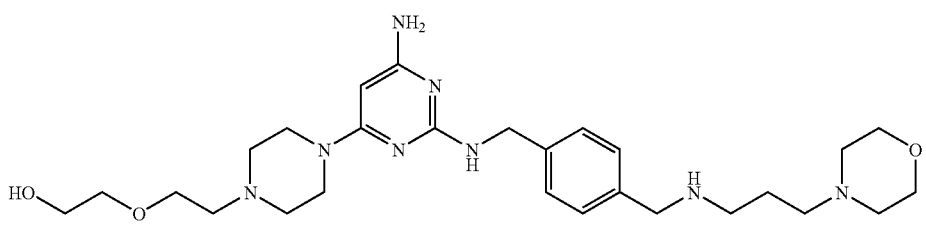
Compound 208

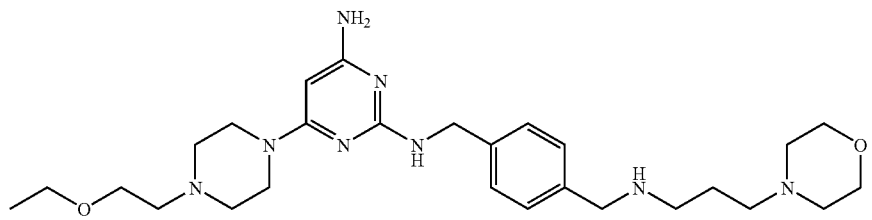
Compound 209
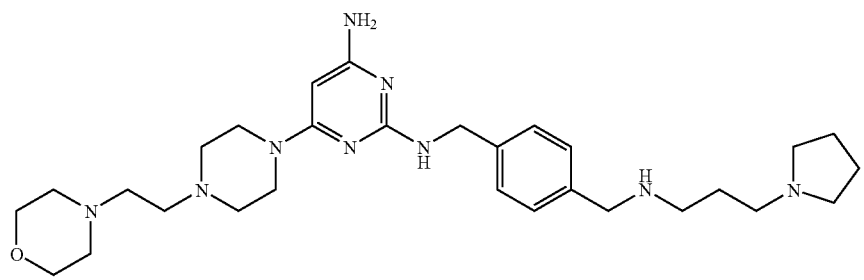
Compound 210
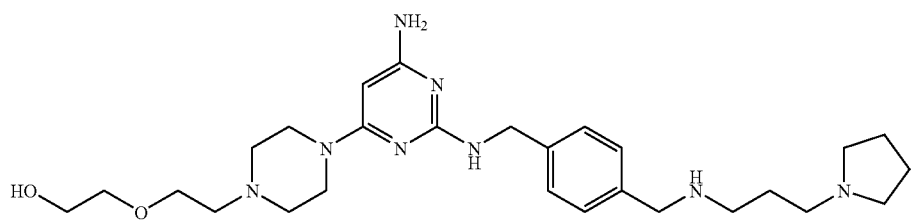
Compound 211
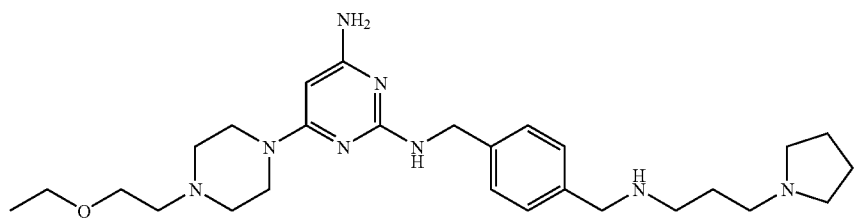
Compound 212
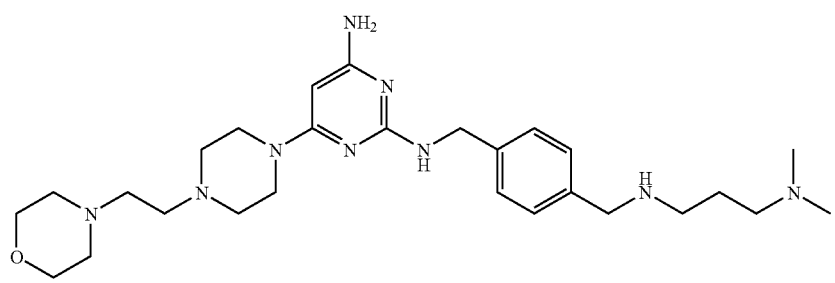
Compound 213
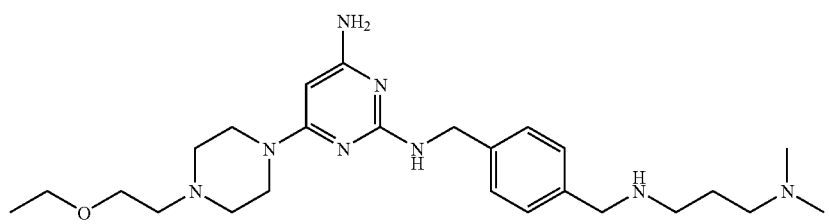
Compound 214

-continued
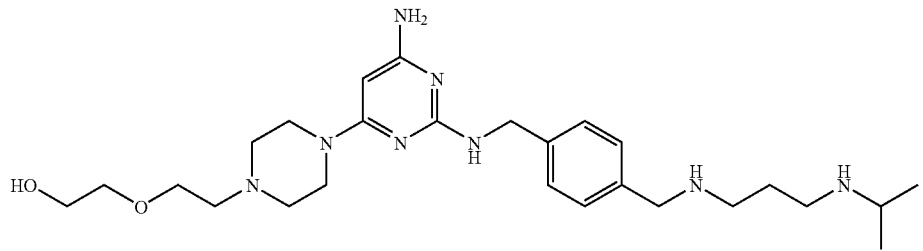
Compound 215
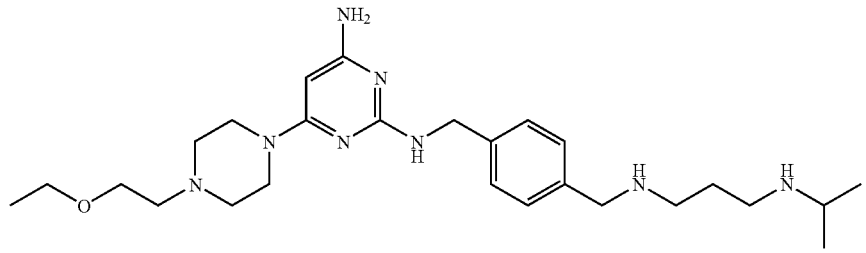
Compound 216
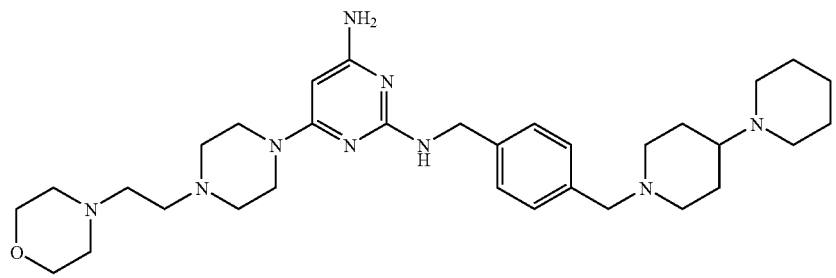
Compound 217
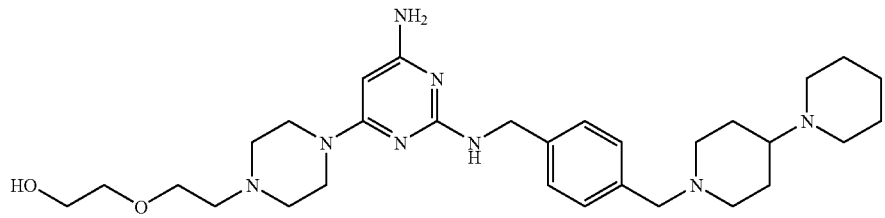
Compound 218
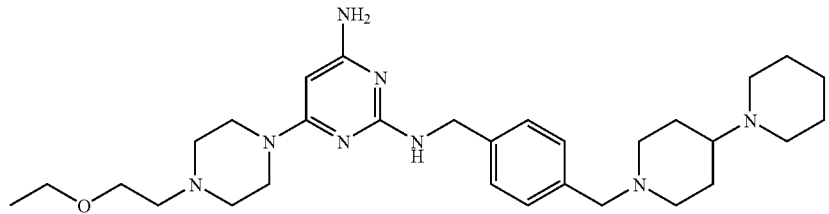
Compound 219
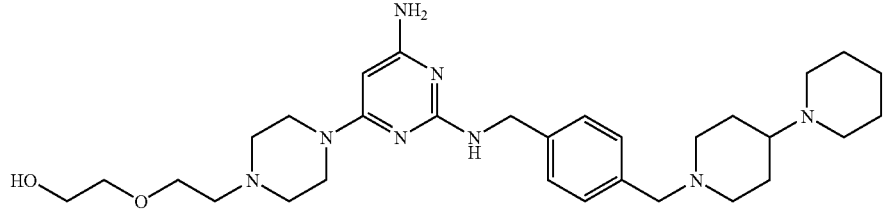
Compound 220

-continued
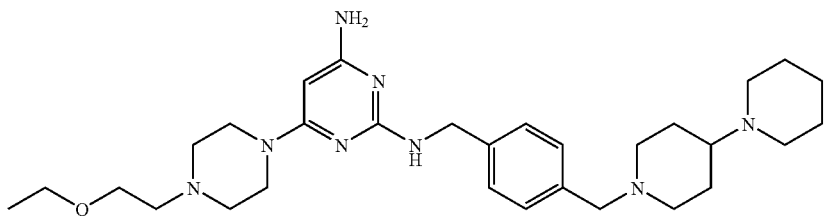
Compound 221
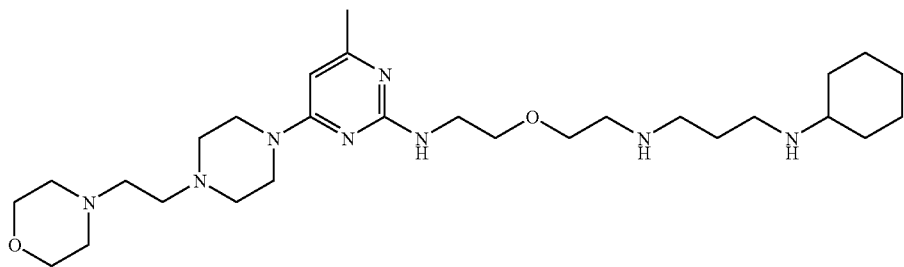
Compound 222
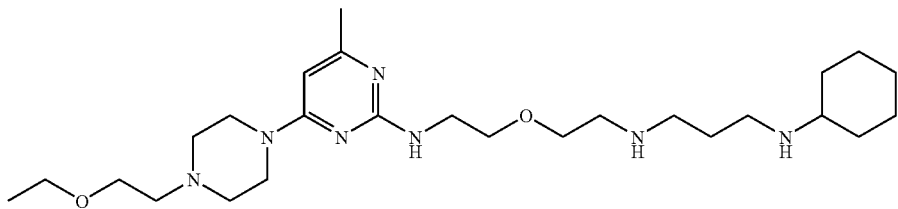
Compound 223
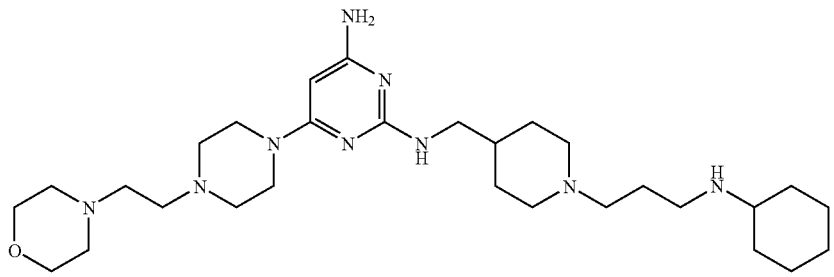
Compound 224
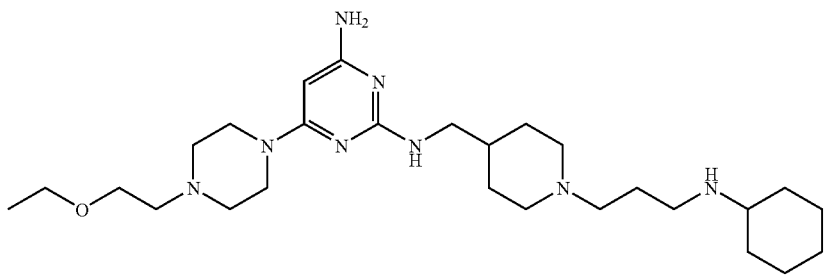
Compound 225
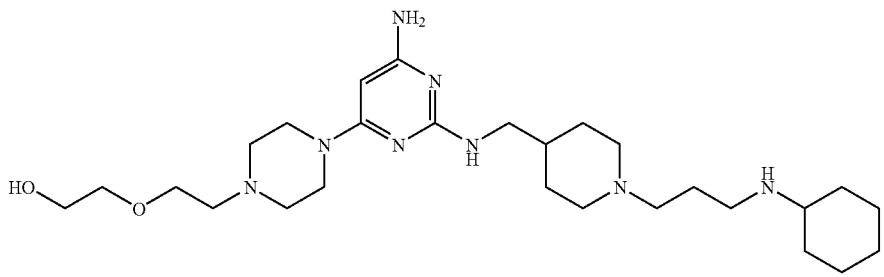
Compound 226

-continued
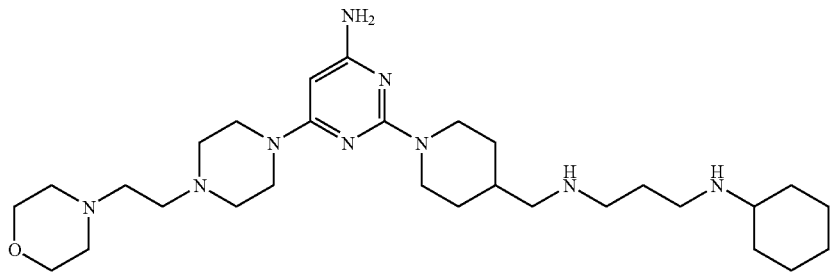
Compound 227
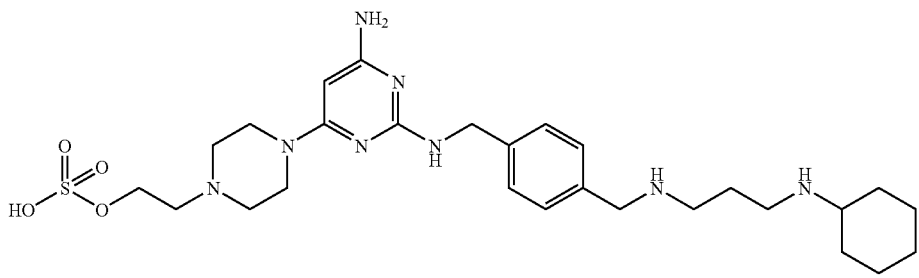
Compound 228
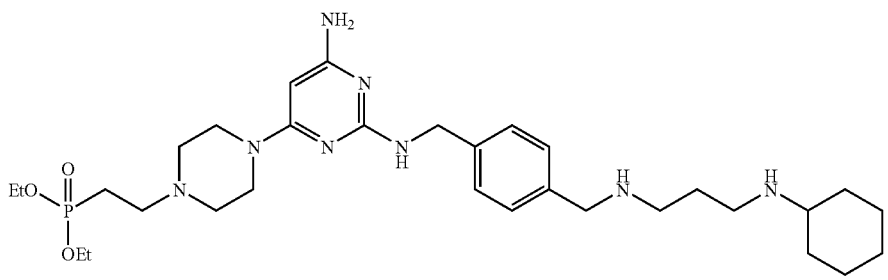
Compound 229
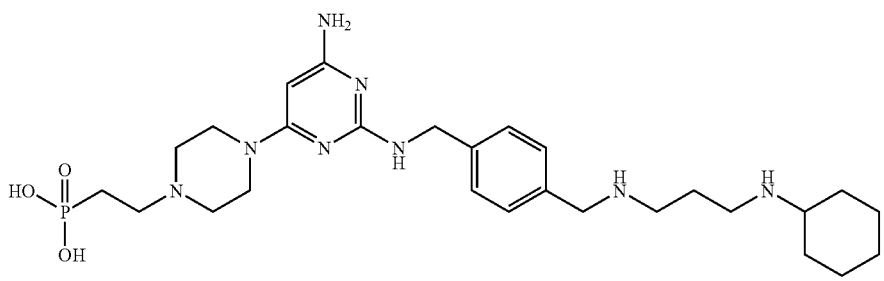
Compound 230
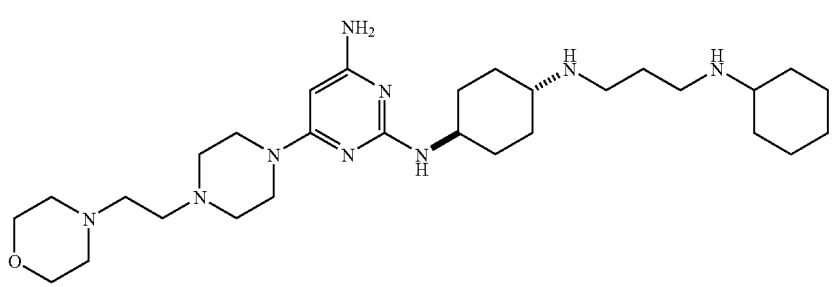
Compound 231
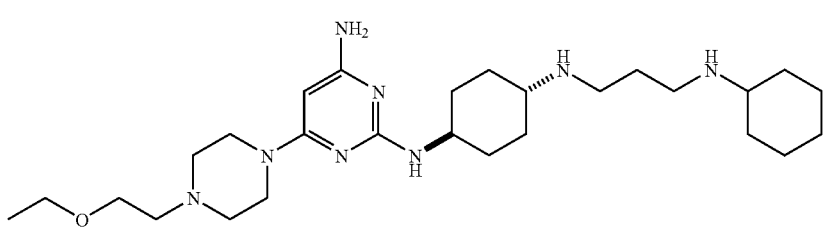
Compound 232

-continued
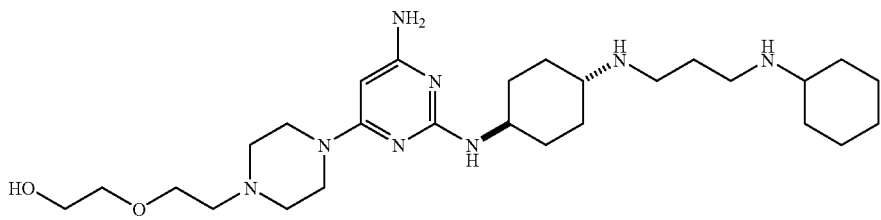
Compound 233
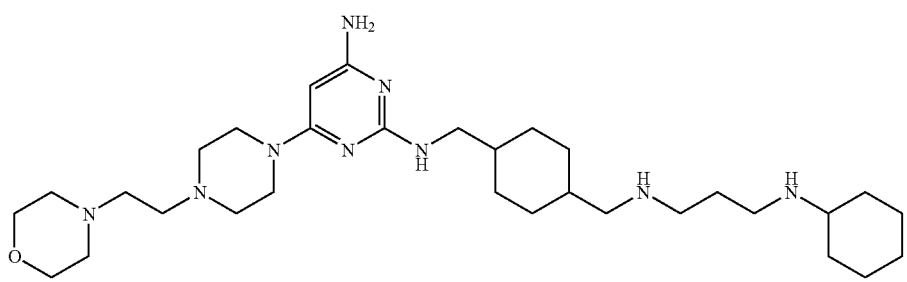
Compound 234
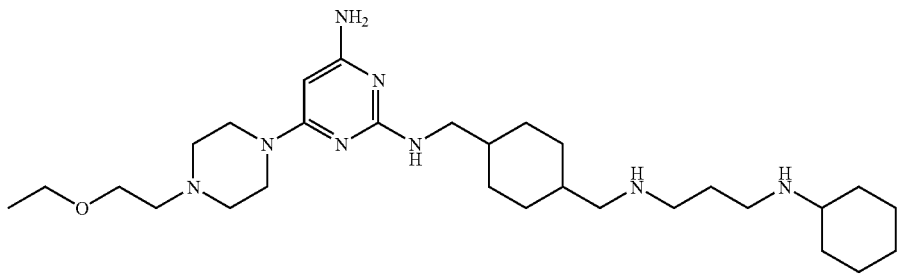
Compound 235
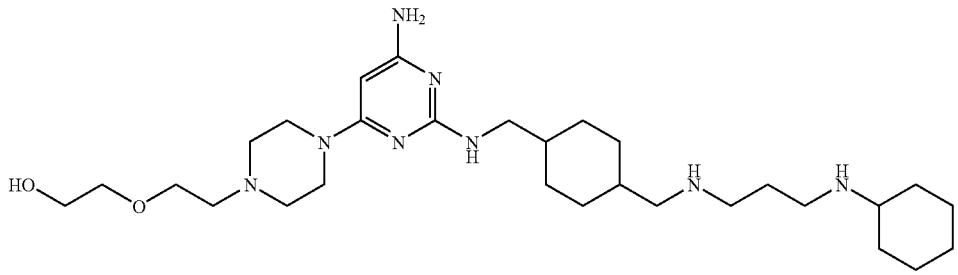
Compound 236
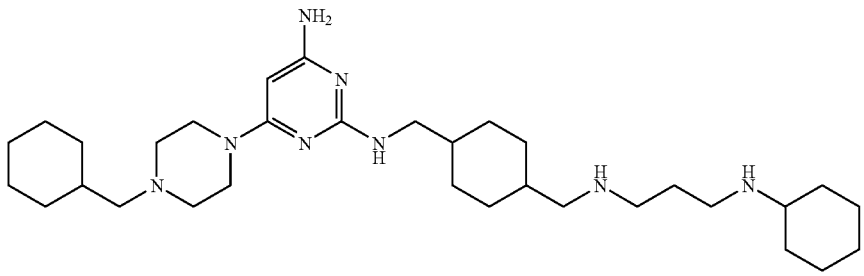
Compound 237
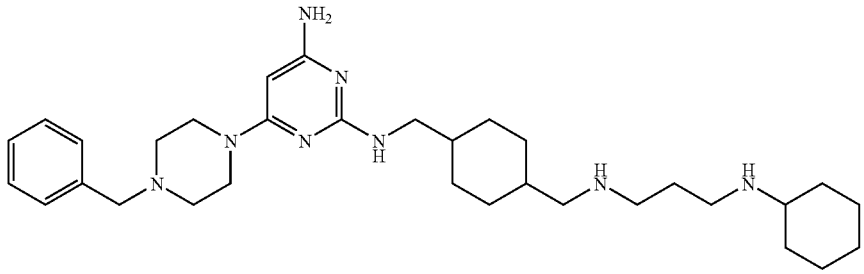
Compound 238

-continued
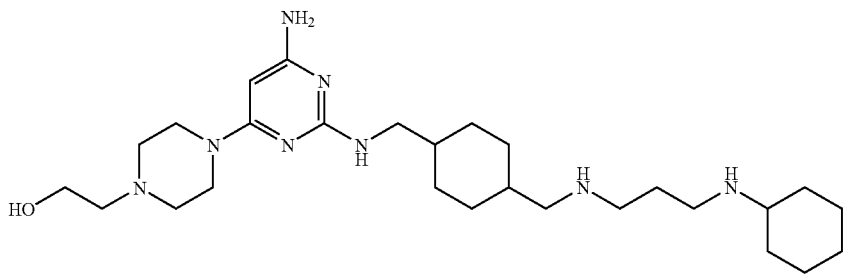
Compound 239
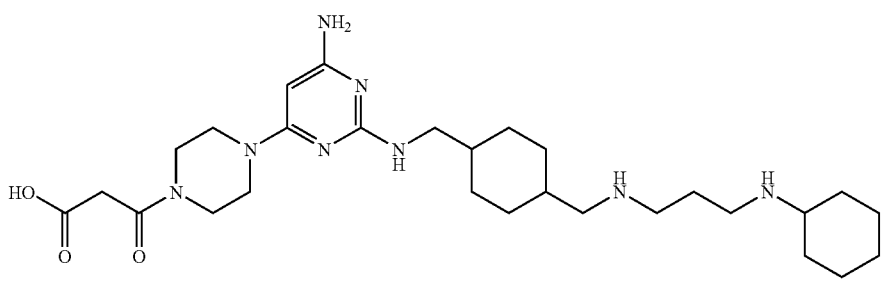
Compound 240
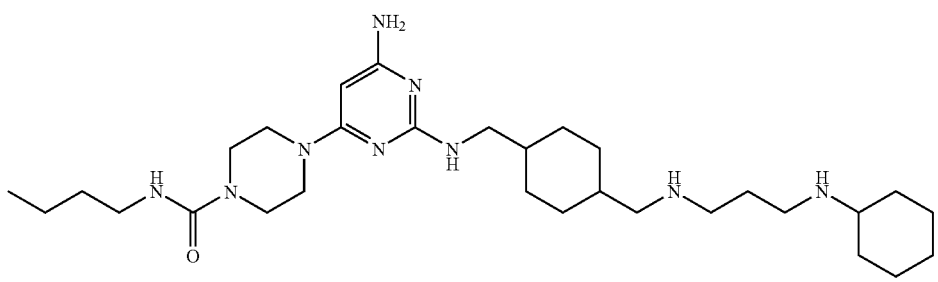
Compound 241
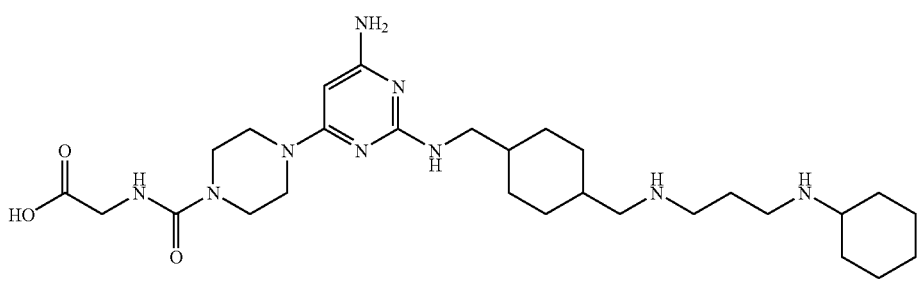
Compound 242
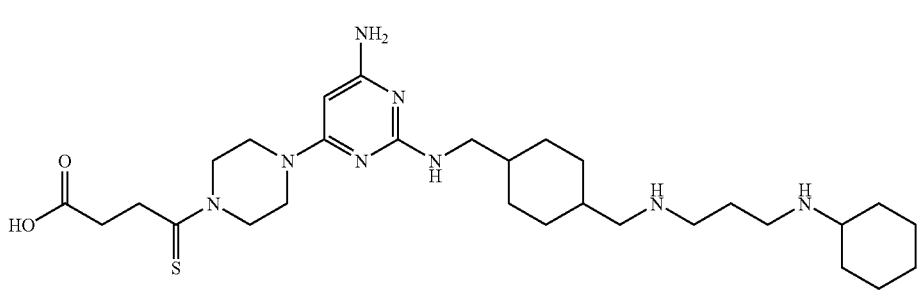
Compound 243

-continued
Compound 244
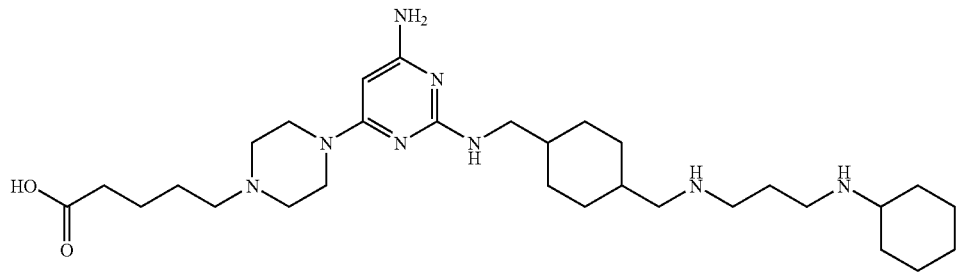
Compound 245
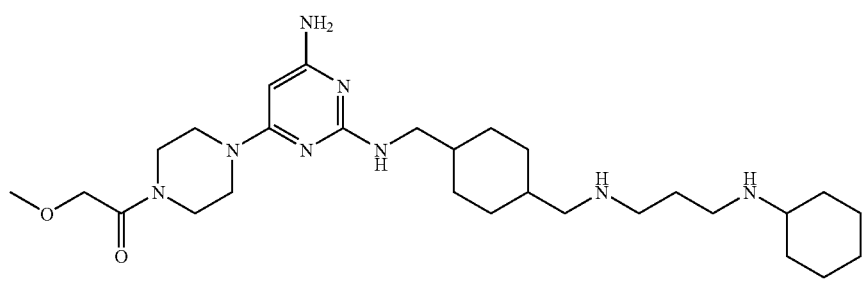
Compound 246
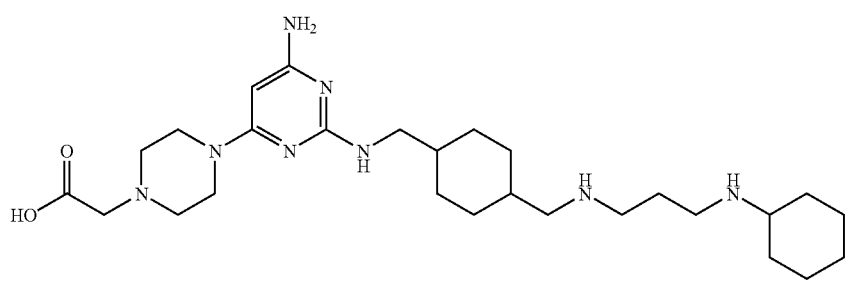
Compound 247
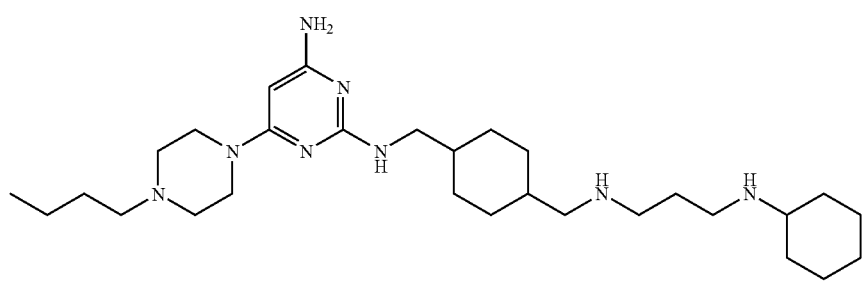
Compound 248
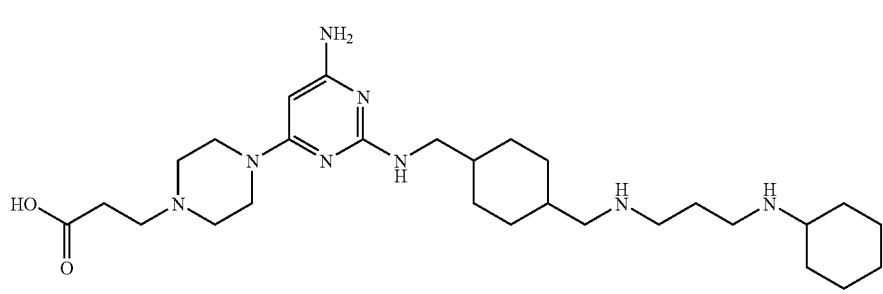

-continued
Compound 249
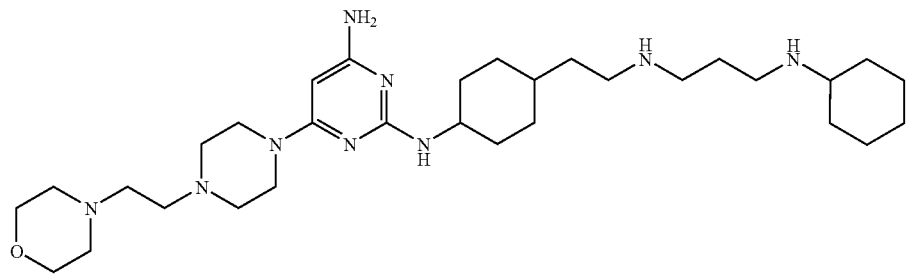
Compound 250
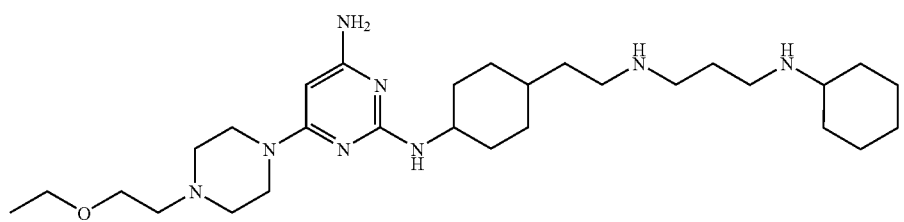
Compound 251
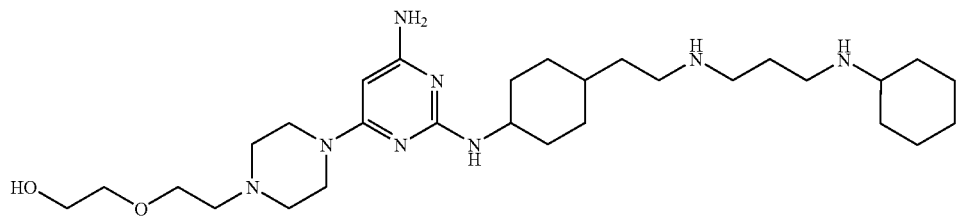
Compound 252
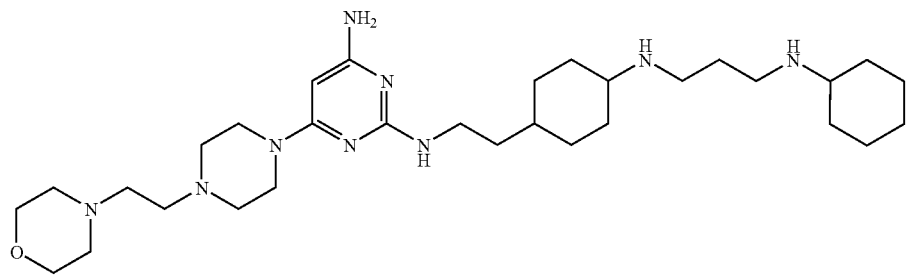
Compound 253
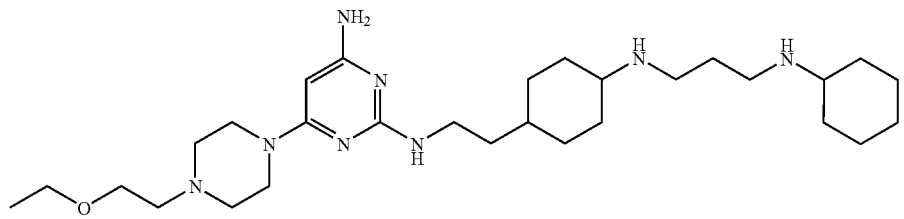
Compound 254
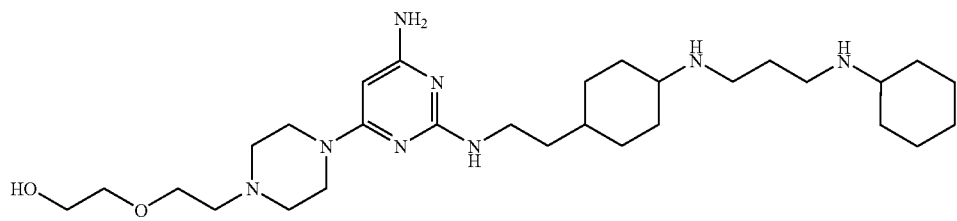

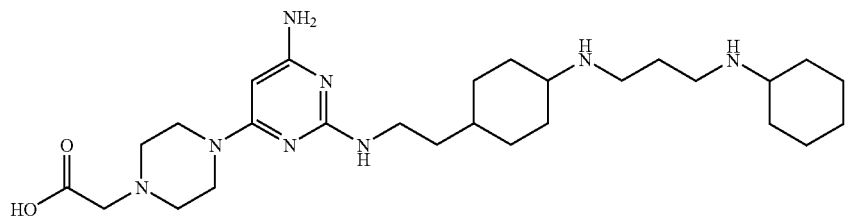
Compound 255
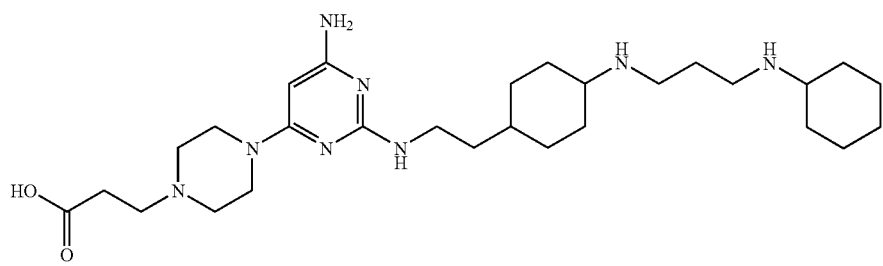
Compound 256
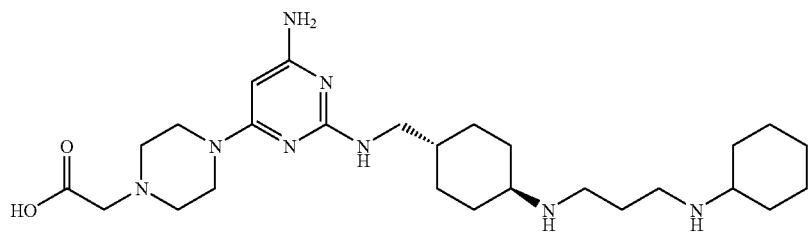
Compound 257
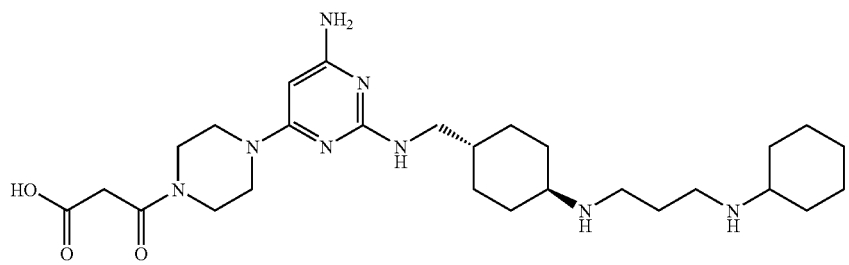
Compound 258
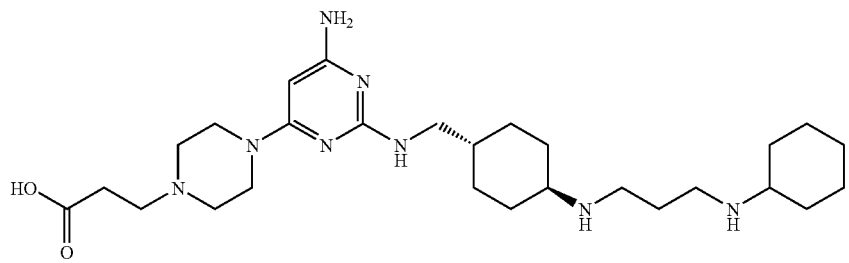
Compound 259
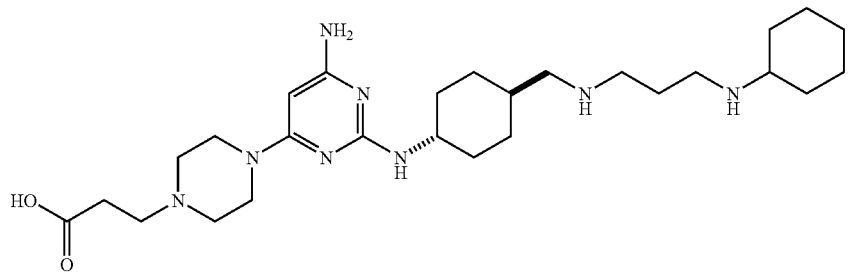
Compound 260

Compound 261
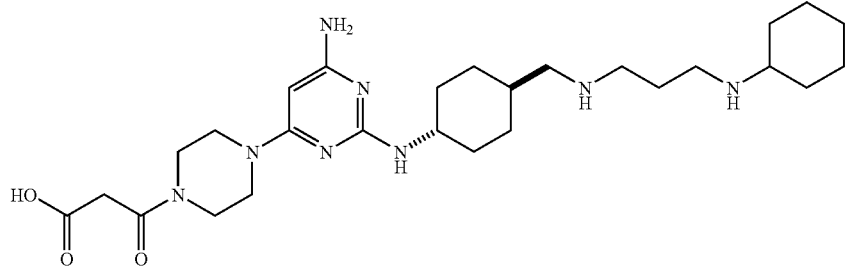
Compound 262
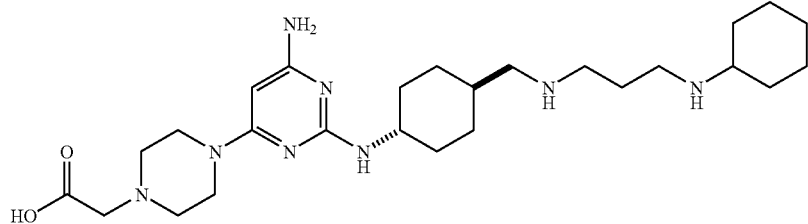
Compound 263
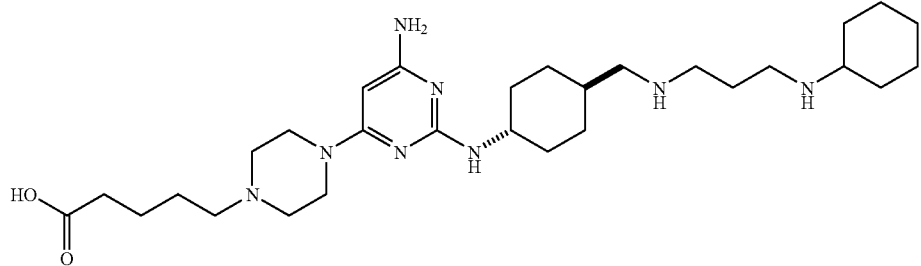
Compound 264
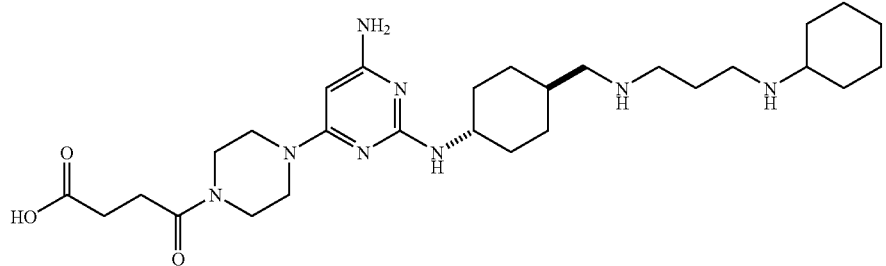
Compound 265
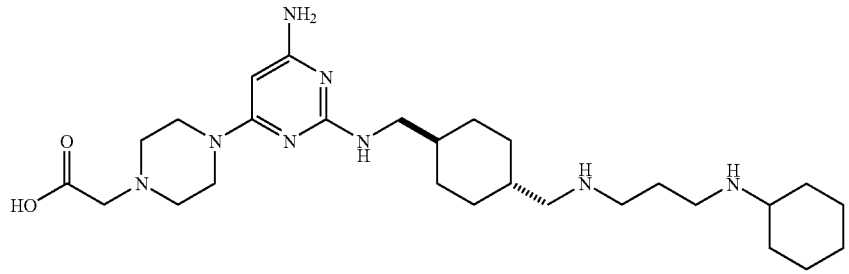
Compound 266
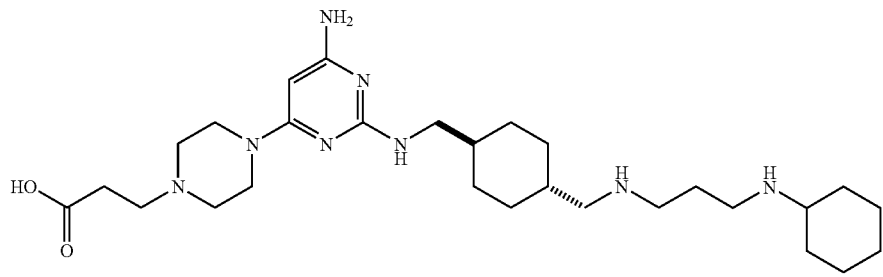

Compound 267

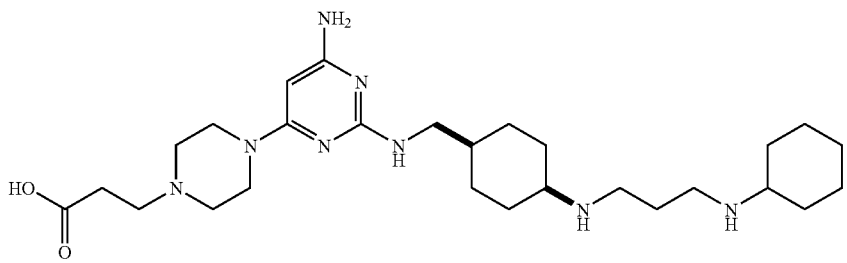

Compound 268

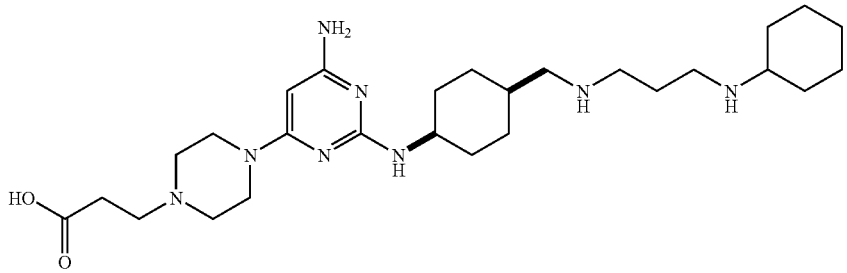

The pyrimidine compounds described above can be prepared by methods well known in the art. Examples 1-268 below provide detailed descriptions of the preparation of compounds 1-268 of this invention.

Scheme I shown below depicts a typical synthetic route for synthesizing certain exemplary compounds. In this scheme, $R_1$, $R_2$, $R_3$, $R_6$, and $R_7$ are as defined in the Summary section above. Specifically, a pyrimidine compound containing a halo group reacts with a compound containing two protected amino groups and an unprotected primary amino group to give a compound of formula (2), which is subsequently deprotected by removing the amino-protecting group to give a compound of formula (3). Exemplary amino-protecting groups include t-butoxycarbonyl, benzyloxycarbonyl, acetyl, phenylcarbonyl, and trialkylsilyl.

Scheme I

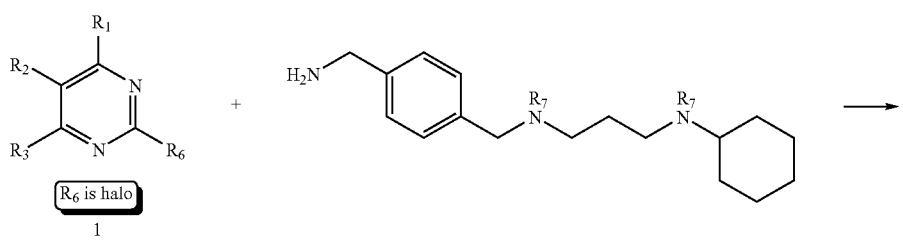

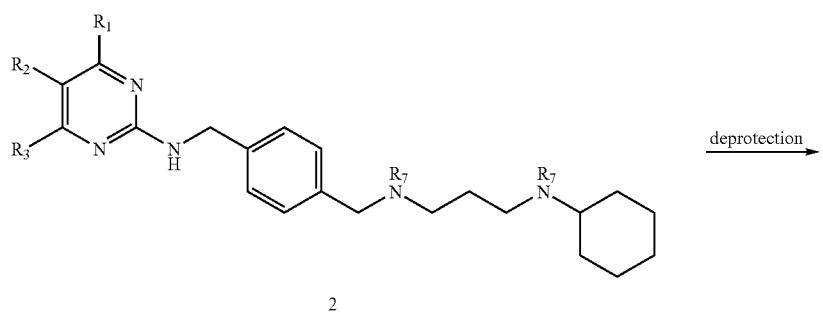

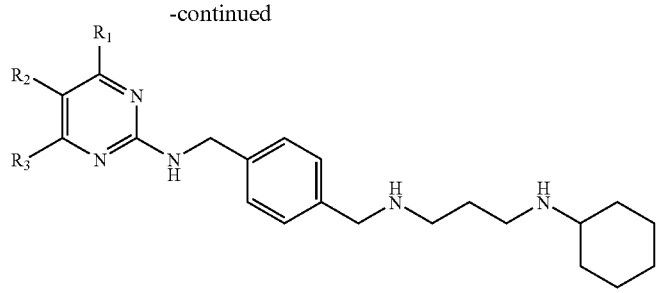

3

Compounds of formula (2) can be modified in various manners to afford other compounds of this invention. For example, as shown in Scheme II below, when $R_3$ is halo, a compound of formula (2) reacts with a heterocyclic compound containing a ring nitrogen atom to give a compound of formula (4), which is subsequently deprotected to give a compound of formula (5). As another example, when $R_3$ is also halo, a compound of formula (2) reacts with an alcohol to give a compound of formula (8), which is subsequently deprotected to give a compound of formula (9).

Scheme II

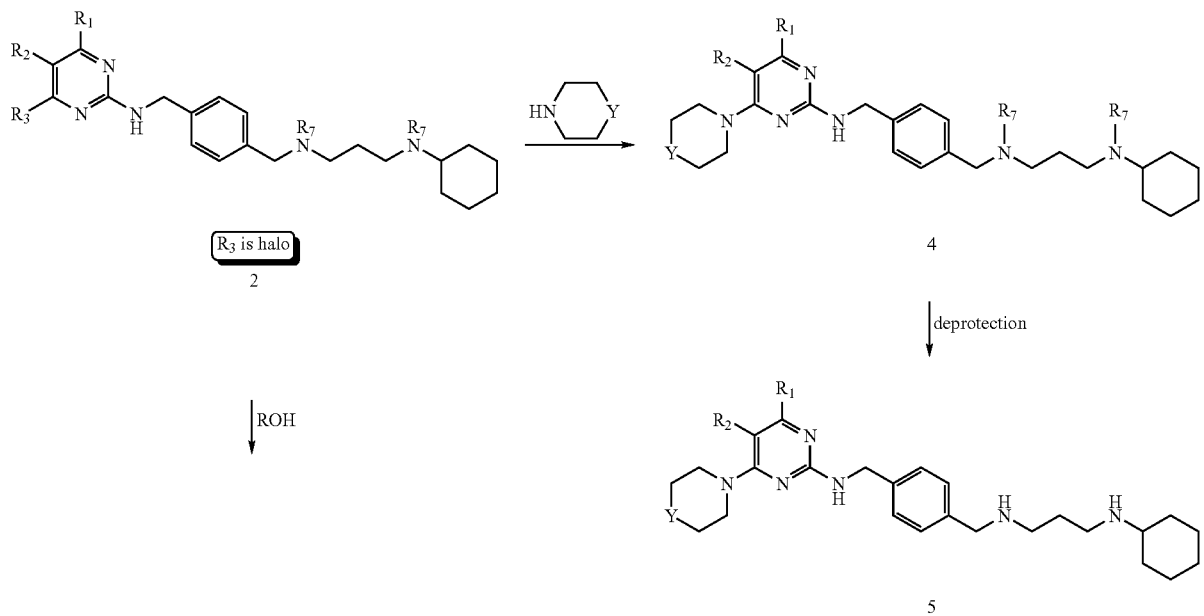

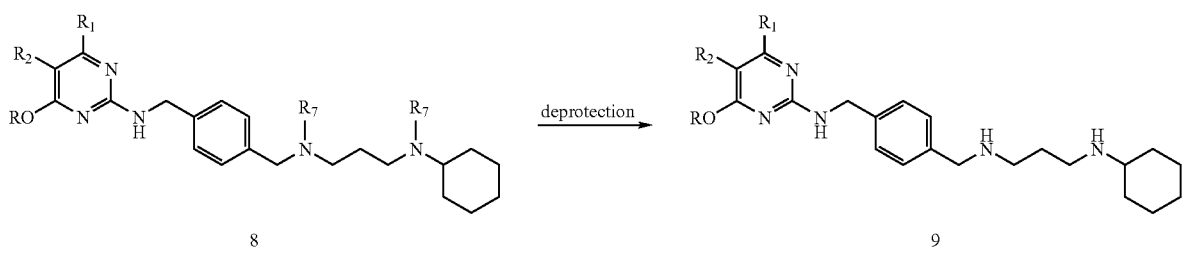

As shown in Scheme III below, when $R_2$ is CN, a compound of formula (2) can be first reduced to give a compound of formula (10), which contains an aldehyde group. The compound of formula (10) can then react with a primary amine to give a compound of formula (11), which can be subsequently deprotected to form a compound of formula (12).

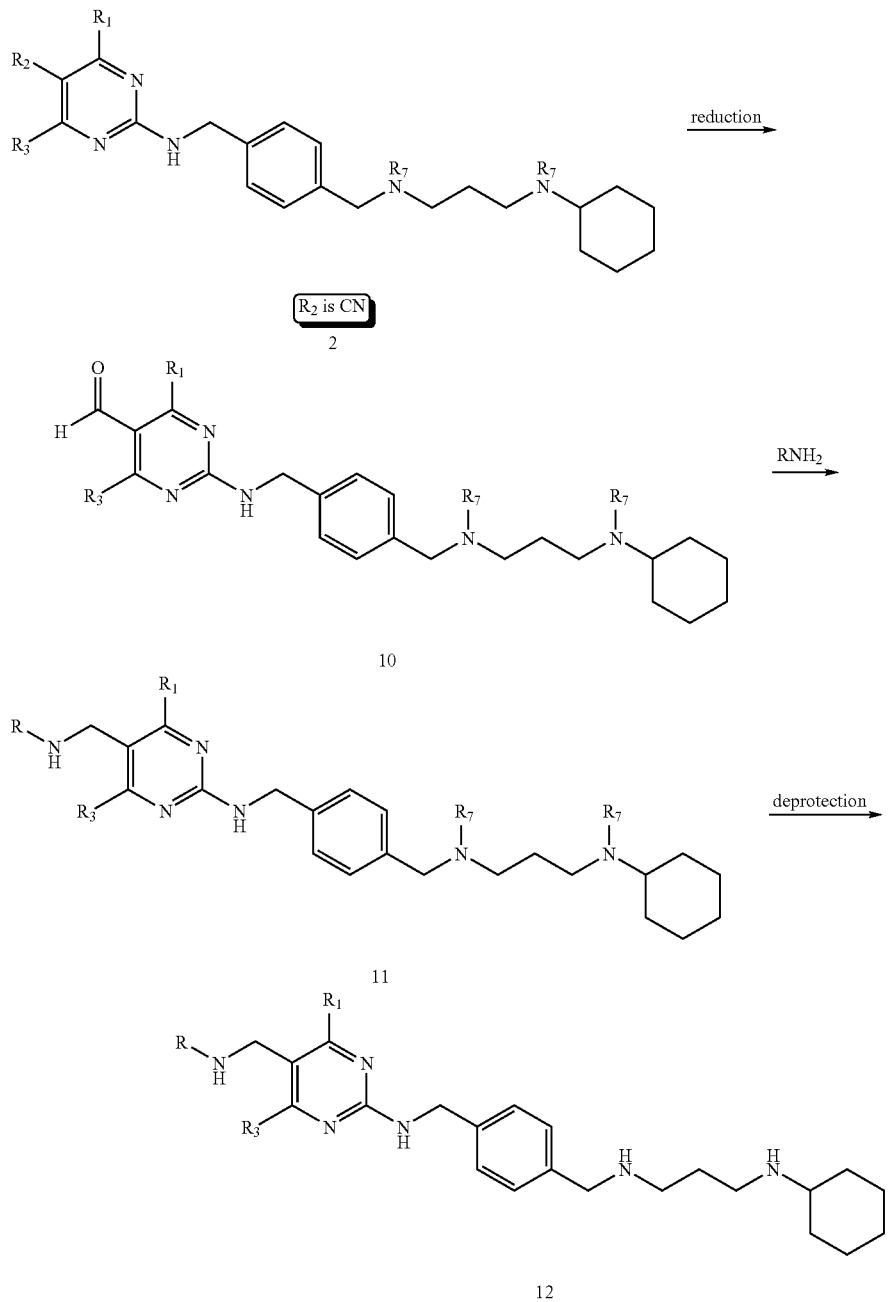

Compounds of formula (4) obtained above can be further modified in various manners to give other compounds of this invention. For example, as shown in Scheme IV below, when Y is NH, a compound of formula (4) reacts with a compound containing a halide group, an aldehyde group, or an acyl chloride group to give a compound of formula (6), which is subsequently deprotected to give a compound of formula (7). As another example, when Y is NH, a compound of formula (4) reacts with an α,β-unsaturated ester, followed by hydrolysis to give a compound of formula (13), which is subsequently deprotected to give a compound of formula (14). As another example, when Y is NH, a compound of formula (4) reacts with a vinyl phosphonate to give a compound of formula (15).

The compound of formula (15) is then deprotected and hydrolyzed to give a compound of formula (16).
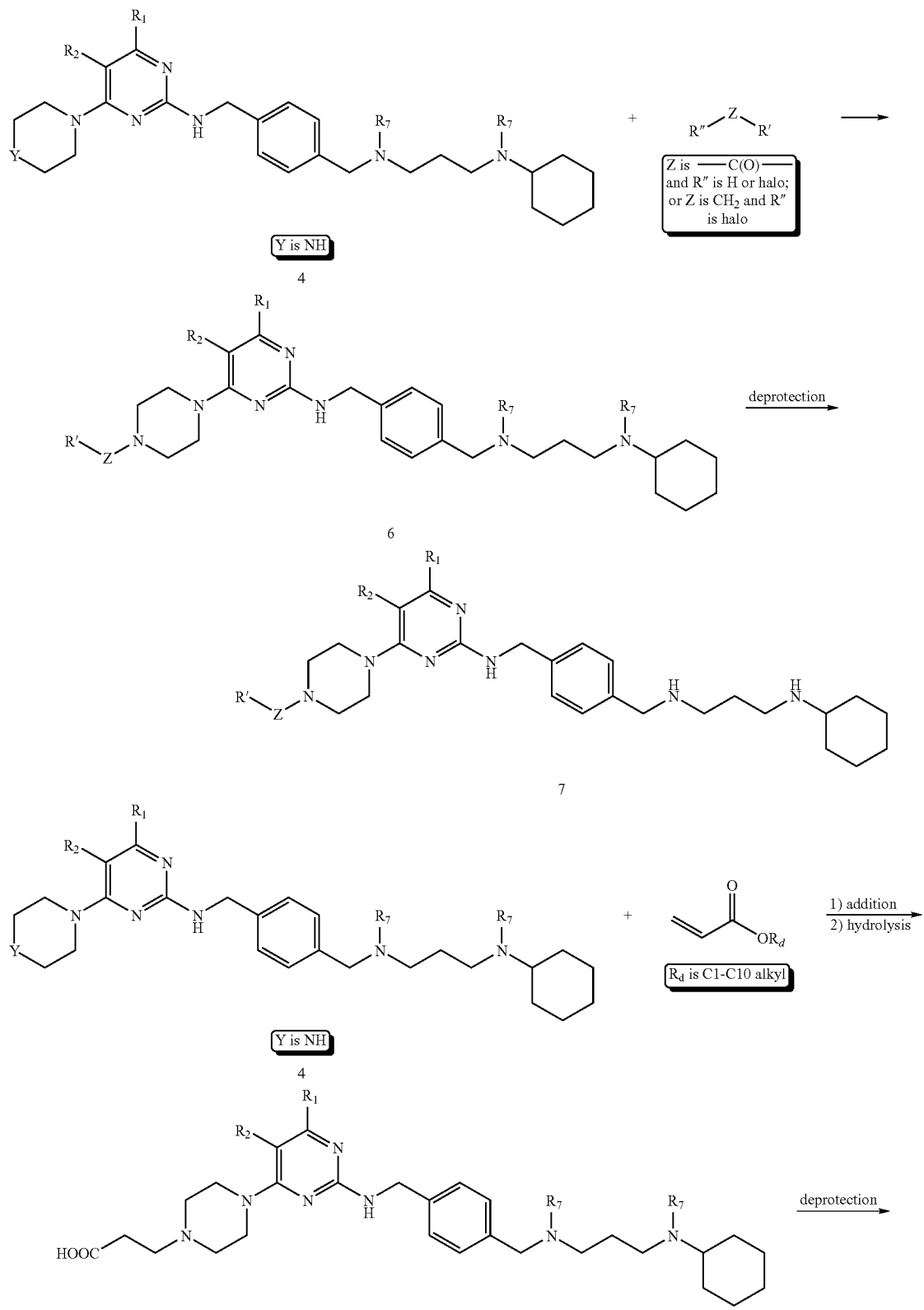
Scheme IV

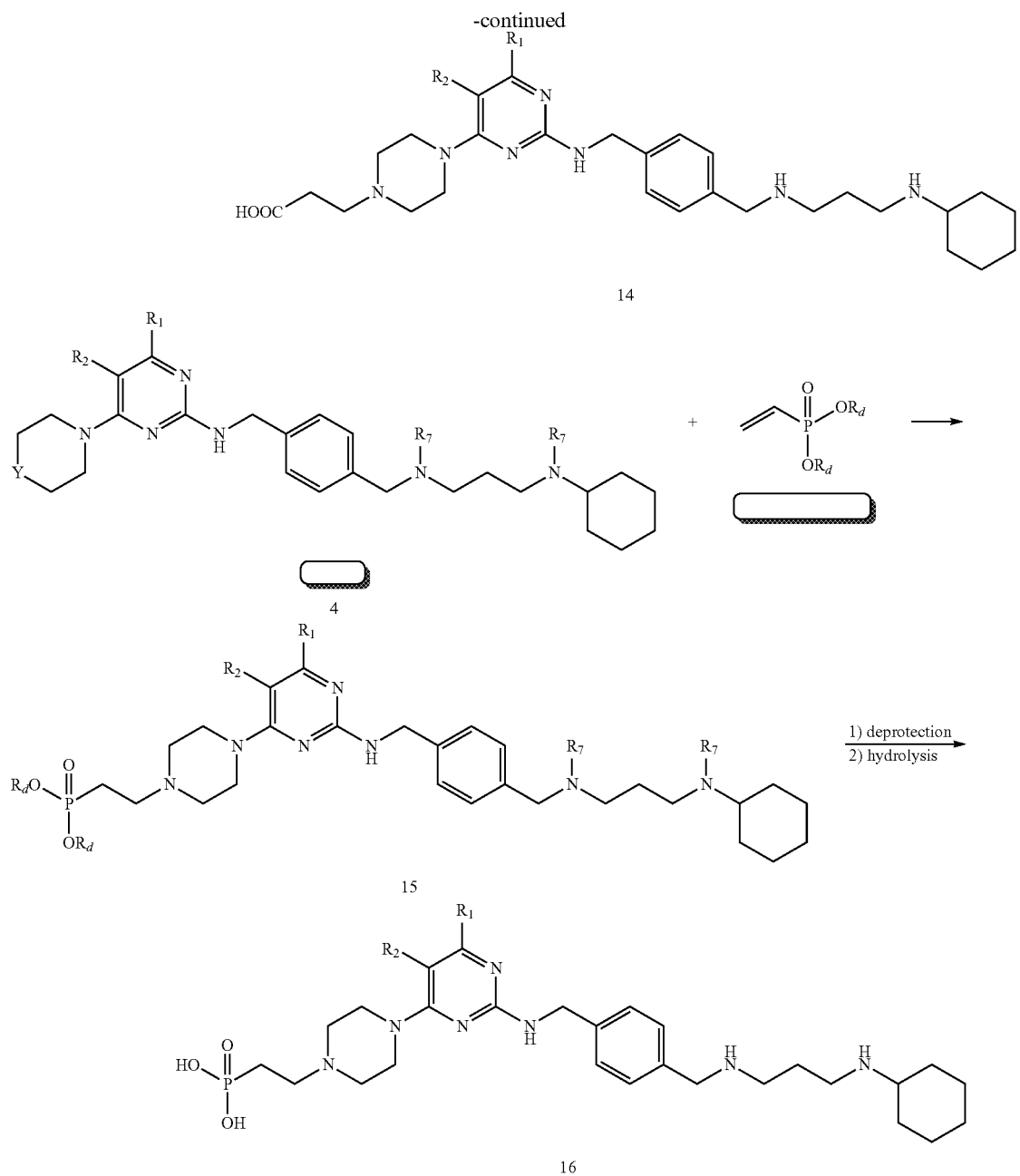

A pyrimidine compound thus synthesized can be purified by a method such as column chromatography, high-pressure liquid chromatography, or recrystallization.

Other pyrimidine compounds can be prepared using other suitable starting materials through the above synthetic routes and others known in the art. The methods described above may also additionally include steps, either before or after the steps described specifically herein, to add or remove suitable protecting groups in order to ultimately allow synthesis of the pyrimidine compounds. In addition, various synthetic steps may be performed in an alternate sequence or order to give the desired compounds. Synthetic chemistry transformations and protecting group methodologies (protection and deprotection) useful in synthesizing applicable pyrimidine compounds are known in the art and include, for example, those described in R. Larock, *Comprehensive Organic Transformations*, VCH Publishers (1989); T. W. Greene and P. G. M. Wuts, *Protective Groups in Organic Synthesis*, 2$^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The pyrimidine compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition containing an effective amount of at least one pyrimidine compound described above and a pharmaceutical acceptable carrier. Further, this invention covers a method of administering an effective amount of one or more of the pyrimidine compounds to a patient having a disease described in the summary section above. This invention also covers a method of administering an effective amount of one or more of the pyrimidine compounds for enhancing migration of bone marrow-derived cells to blood. "An effective amount" refers to the amount of an active pyrimidine compound that is required to confer a therapeutic effect on the treated subject. Effective doses will vary, as recognized by those skilled in the art, depending on the types of diseases treated, route of administration, excipient usage, and the possibility of co-usage with other therapeutic treatment.

To practice the method of the present invention, a composition having one or more pyrimidine compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active pyrimidine compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active pyrimidine compound. Examples of other carriers include colloidal silicon oxide, magnesium stearate, cellulose, sodium lauryl sulfate, and D&C Yellow #10.

The pyrimidine compounds described above can be preliminarily screened for their efficacy in treating above-described diseases by an in vitro assay (See Examples 269 and 270 below) and then confirmed by animal experiments and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Preparation of Compound 1

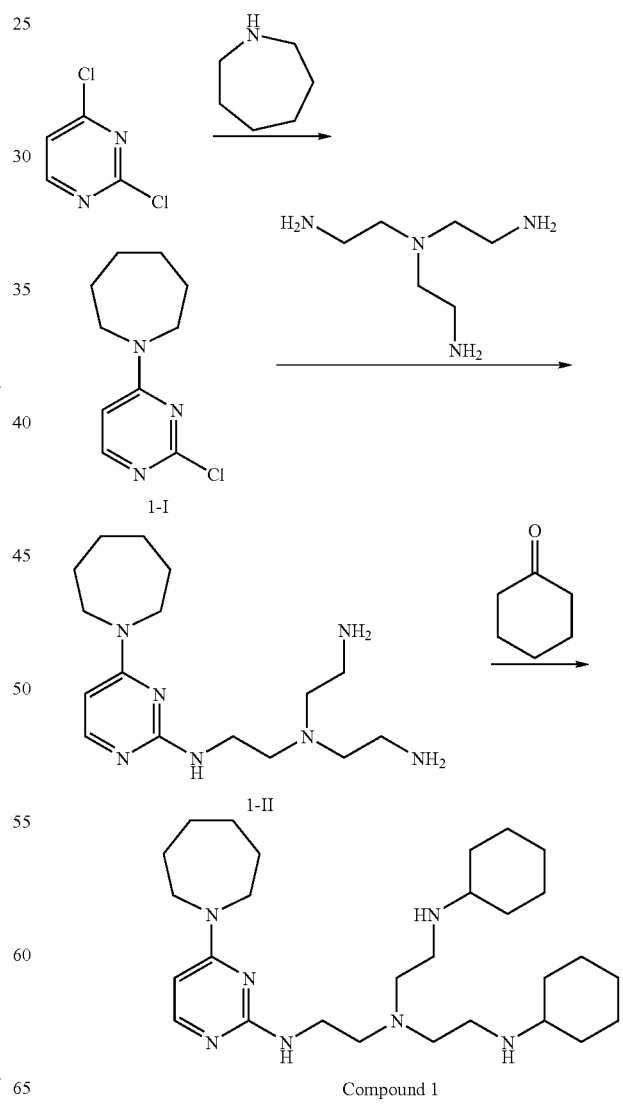

Hexamethyleneimine (0.673 g) was slowly added to a stirred solution of 2,4-dichloropyrimidine (1 g) in THF (50 mL) at 0° C. The reaction mixture was stirred at 0° C. for 2 hours and the reaction was allowed to warm-up to room temperature overnight. The solution was then concentrated to give a residue, which was purified by chromatography on silica gel (EtOAc/Hexane=1/5) to afford intermediate 1-I (1.234 g) in a 86% yield.

A solution of Intermediate 1-I (0.46 g) and tris-(2-aminoethyl)-amine (1.6 g) in DMSO (2 mL) was heated at 120° C. for 8 hours by microwave. The solution was partitioned between $CH_2Cl_2$ and $H_2O$. The organic layer was isolated and then concentrated. The residue was purified by chromatography on silica gel (21% $NH_3$(aq)/MeOH=1/3) to afford intermediate 1-II (0.454 g) in a 65% yield.

Cyclohexanone (488 mg) and $NaBH(OAc)_3$ (1320 mg) were added to a stirred solution of intermediate 1-II (200 mg) in $CH_2Cl_2$ (50 mL) at room temperature over a short period of time. The resulting solution was stirred at room temperature for 8 hours, and then quenched with a saturated aqueous $NaHCO_3$ solution. The aqueous layer was separated and extracted with $CH_2Cl_2$. The combined organic layers were subsequently washed with water, dried, filtered, and concentrated to give a crude residue, which was purified by chromatography on silica gel (21% $NH_3$(aq)/MeOH=1/10) to give compound 1 (217 mg) in a 72% yield.

CI-MS ($M^+$+1): 486.4.

1 M hydrochloric acid (6 mL) and $CH_2Cl_2$ (4 ml) were added to the compound 1 (217 mg). The mixture was stirred for 10 minutes at room temperature. After removing the supernatant, the solid was dried under vacuum to afford the hydrochloride salt of compound 1 (268 mg) in a 95% yield.

EXAMPLE 2

Preparation of Compound 2

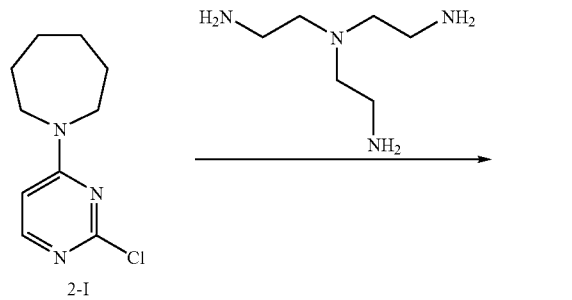

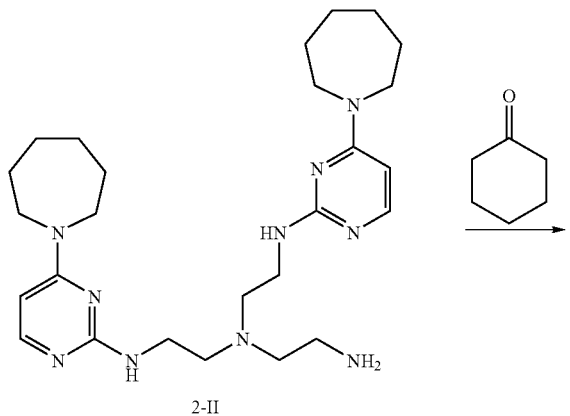

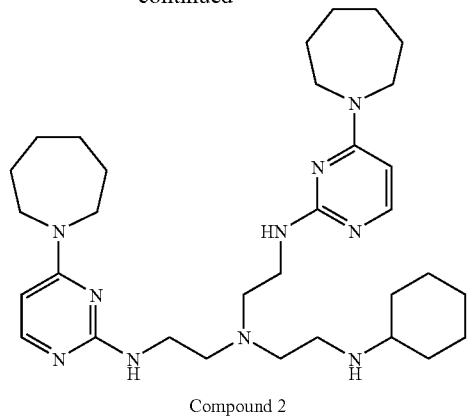

Compound 2

Intermediate 2-I was obtained during the preparation of compound 1.

A solution of Intermediate 2-I (200 mg) and tris-(2-aminoethyl)amine (70 mg) in DMSO (2 mL) was heated at 120° C. for 8 hours by microwave. The solution was partitioned between $CH_2Cl_2$ and $H_2O$. The organic layer was isolated and then concentrated. The residue was purified by chromatography on silica gel (21% $NH_3$(aq)/MeOH=1/5) to afford intermediate 2-II (296 mg) in a 63% yield.

Cyclohexanone (234 mg) and $NaBH(OAc)_3$ (506 mg) were added to a stirred solution of intermediate 2-II (296 mg) in $CH_2Cl_2$ (30 mL) at room temperature over a short period of time. The resulting solution was stirred at room temperature for 8 hours, and then quenched with a saturated aqueous $NaHCO_3$ solution. The aqueous layer was separated and extracted with $CH_2Cl_2$. The combined organic layers were subsequently washed with water, dried, filtered, and concentrated to give a crude residue, which was purified by chromatography on silica gel (21% $NH_3$(aq)/MeOH=1/15) to give compound 2 (266 mg) in a 77% yield.

CI-MS ($M^+$+1): 579.4.

1 M hydrochloric acid (6 mL) and $CH_2Cl_2$ (4 ml) were added to compound 2 (266 mg). The mixture was stirred for 10 minutes at room temperature. After removing the supernatant, the solid was dried under vacuum to afford the hydrochloride salt of compound 2 (302 mg) in a 91% yield.

EXAMPLE 3

Preparation of Compound 3

Compound 3 was prepared in a manner similar to that used to prepare compound 1.

CI-MS ($M^+$+1): 472.4.

EXAMPLE 4

Preparation of Compound 4

Compound 4 was prepared in a manner similar to that used to prepare compound 1.

CI-MS ($M^+$+1): 514.4.

EXAMPLE 5

Preparation of Compound 5

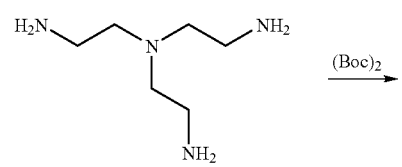

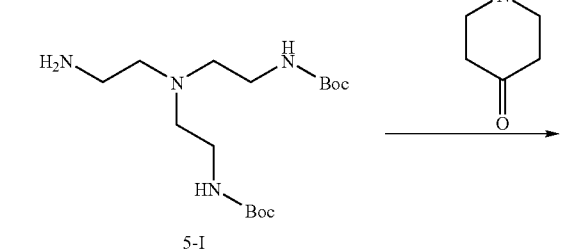

5-I

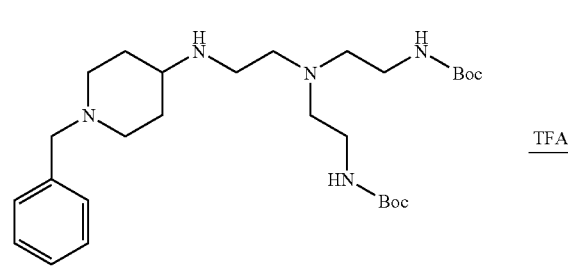

5-II

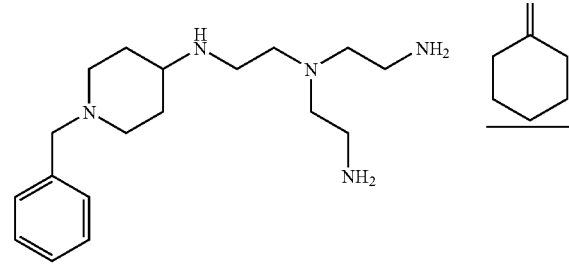

5-III

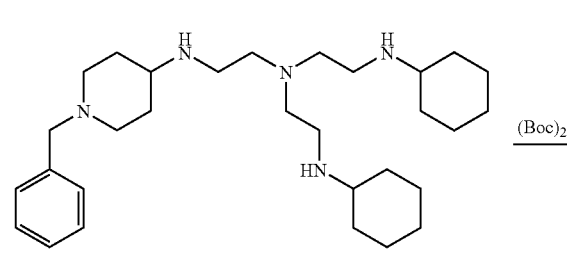

5-IV

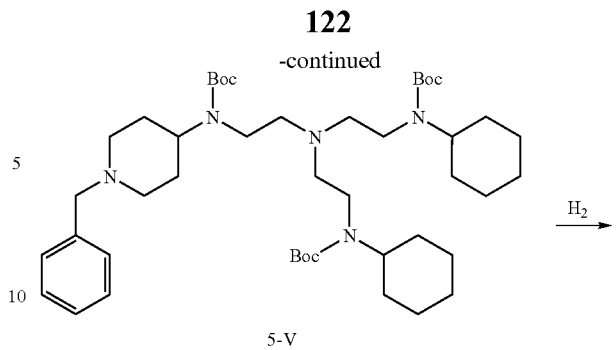

5-V

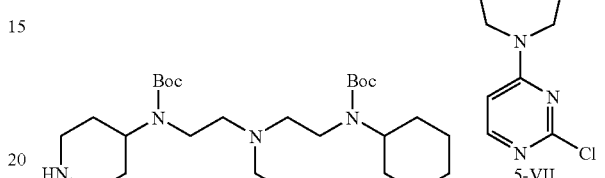

5-VI

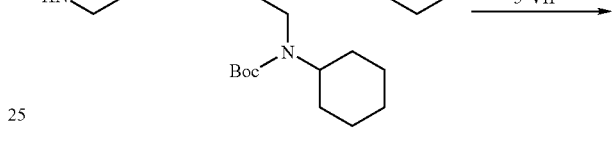

5-VIII

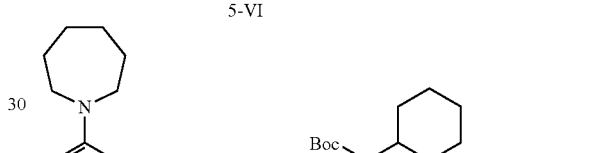

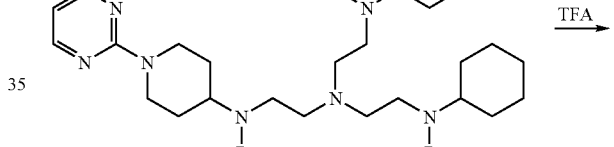

Compound 5

A solution of tris-(2-aminoethyl)-amine (2.0 g) and Boc$_2$O (1.0 g) in CH$_2$Cl$_2$ (280 mL) was stirred at 25° C. for 15 hours and then concentrated. The resultant residue was purified by chromatography on silica gel (EtOAc/MeOH=1/1) to afford intermediate 5-I (2.04 g) in a 43% yield.

1-Benzyl-4-piperidone (2.177 g) and NaBH(OAc)$_3$ (3.665 g) were added to a stirred solution of intermediate 5-I (2.0 g) in MeOH (30 mL) at room temperature over a short period of time. The resulting solution was stirred at room temperature for 8 hours, and then quenched with a saturated aqueous NaHCO$_3$ solution. The aqueous layer was separated and extracted with CH$_2$Cl$_2$. The combined organic layers were subsequently washed with water, dried, filtered, and concentrated to give a crude residue, which was purified by chromatography on silica gel (EtOAc/MeOH=9/1) to afford intermediate 5-II (2.488 g) in a 83% yield.

A solution of 20% TFA/CH$_2$Cl$_2$ (20 mL) was added to Intermediate 5-II (1.0 g) in CH$_2$Cl$_2$ (10 mL). The reaction mixture was stirred for 5 hours at room temperature and concentrated by removing the solvent. The residue was purified by chromatography on silica gel (21% NH$_3$(aq)/MeOH=1/4) to afford intermediate 5-III (0.54 g) in a 88% yield.

Cyclohexanone (1,323 mg) and NaBH(OAc)$_3$ (3,220 mg) were added to a stirred solution of intermediate 5-III (540 mg) in CH$_2$Cl$_2$ (30 mL) at room temperature over a short period of time. The resulting solution was stirred at room temperature for 8 hours and then quenched with a saturated aqueous NaHCO$_3$ solution. The aqueous layer was separated and extracted with CH$_2$Cl$_2$. The combined organic layers were subsequently washed with water, dried, filtered, and concentrated to give a crude residue, which was purified by chromatography on silica gel (21% NH$_3$(aq)/MeOH=1/10) to afford intermediate 5-IV (0.58 g) in a 71% yield.

A solution of intermediate 5-IV (580 mg), Boc$_2$O (863 mg) and Et$_3$N (485 mg) in CH$_2$Cl$_2$ (150 ml) was stirred at 25° C. for 15 hours and then concentrated. The resultant residue was purified by chromatography on silica gel (EtOAc/Hexane=1/5) to afford intermediate 5-V (865 mg) in a 92% yield.

A mixture of intermediate 5-V (865 mg) and Pd/C (90 mg) in MeOH (20 ml) was stirred under H$_2$ (balloon) at 25° C. for 15 hours and then filtered through a celite column and concentrated. The resultant residue was purified by chromatography on silica gel (EtOAc/MeOH=15/1) to afford intermediate 5-VI (681 mg) in a 89% yield.

Diisopropylethylamine (0.1 mL) was added to a solution of 5-VII (30 mg; obtained during preparation of compound 1) and intermediate 5-VI (100 mg) in 1-pentanol (2 mL). The reaction mixture was stirred overnight at 140° C. The solvent was then removed under vacuum and the resultant residue was purified by chromatography on silica gel (EtOAc/Hexane=1/1) to afford intermediate 5-VIII (76 mg) in a 61% yield.

A solution of 20% TFA/CH$_2$Cl$_2$ (2 mL) was added to intermediate 5-VIII (76 mg) in CH$_2$Cl$_2$ (1 mL). The reaction mixture was stirred for 5 hours at room temperature and concentrated by removing the solvent. 1 M hydrochloric acid (2 mL) and CH$_2$Cl$_2$ (1 mL) were added to the resultant residue. The mixture was stirred for 10 minutes at room temperature. After removal of the supernatant, the solid was dried under vacuum to afford the hydrochloride salt of compound 5 (81 mg) in a 85% yield.

CI-MS (M$^+$+1): 569.5.

EXAMPLE 6

Preparation of Compound 6

Compound 6 was prepared in a manner similar to that used to prepare compound 1.
CI-MS (M$^+$+1): 572.5.

EXAMPLE 7

Preparation of Compound 7

Compound 7 was prepared in a manner similar to that used to prepare compound 1
CI-MS (M$^+$+1): 458.4. .

EXAMPLE 8

Preparation of Compound 8

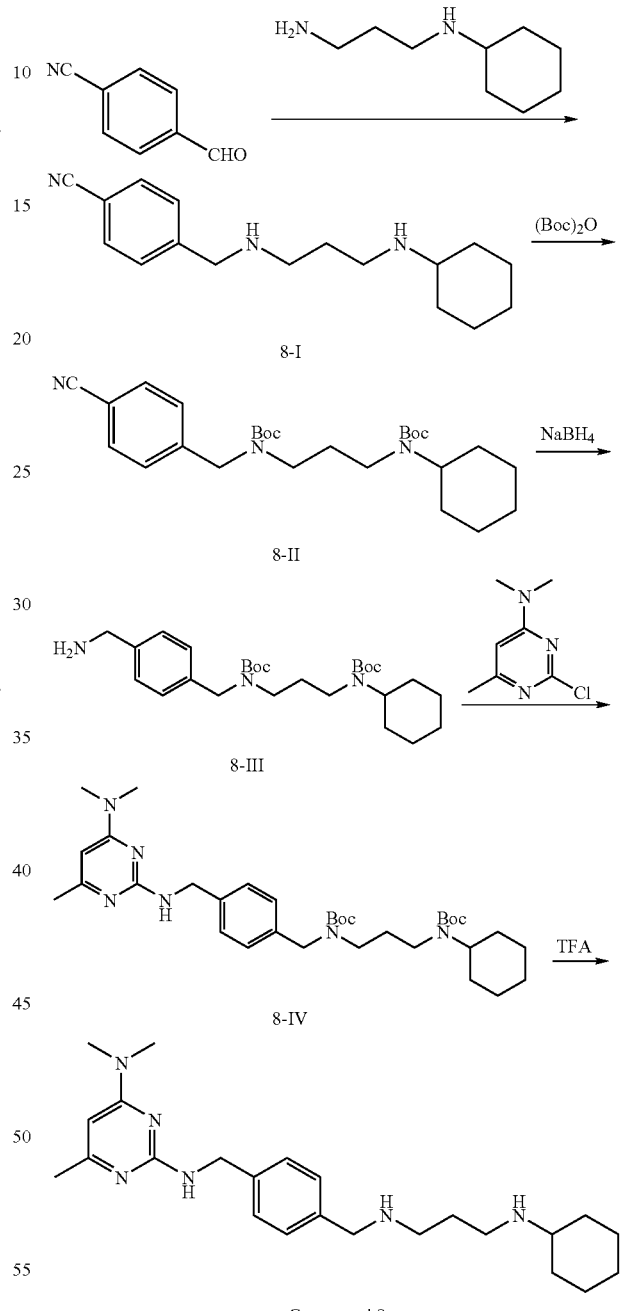

Compound 8

A solution of 4-cyanobenzylaldehyde (5 g) and N-cyclohexyl-1,3-propane-diamine (6 g) in CH$_3$OH (100 mL) was heated to 60° C. for 6 hours. After cooling to room temperature, NaBH$_4$ (2.5 g) was slowly added to the above solution. The mixture was stirred for another 30 minutes. The mixture was then concentrated, quenched with NH$_4$Cl (aq), and extracted with CH$_2$Cl$_2$. The organic layers were combined, dried with anhydrous MgSO$_4$, and concentrated to give a residue. The residue was purified by chromatography on silica gel (EtOAc/Et₃N=4/1) to afford Intermediate 8-I (7.2 g) in a 70% yield.

A solution of Intermediate 8-I (7.2 g) and Boc₂O (17.3 g) in CH₂Cl₂ (280 ml) was stirred at 25° C. for 15 hours and then concentrated. The resultant residue was purified by chromatography on silica gel (EtOAc/Hexane=1/1) to afford Intermediate 8-II as a yellow oil (10.6 g, yield: 85%).

A solution of Intermediate 8-II (4.7 g) and NiCl₂ (64 mg) in CH₃OH (100 ml) was first stirred at 25° C. After cooling to 0° C., NaBH₄ (1.83 g) was slowly added and the mixture was stirred for another 15 hours. The solution was concentrated, quenched with NH₄Cl (aq), and extracted with CH₂Cl₂. The combined organic layer was washed with water, filtered, dried with anhydrous MgSO₄, and concentrated to give a residue. The residue was purified by chromatography on silica gel (21% NH₃(aq)/MeOH=1/19) to afford Intermediate 8-III (2.36 g) in a 50% yield.

Diisopropylethylamine (0.1 mL) was added to a solution of 2-chloro-6-methyl-4-dimethylaminopyrimidine (110 mg) and Intermediate 8-III (150 mg) in 1-pentanol (2 mL). The reaction mixture was stirred overnight at 150° C. The solvent was removed under vacuum and the residue was purified by chromatography on silica gel (EtOAc/Hexane=1/1) to afford Intermediate 8-IV (88 mg) in a 47% yield.

A solution of 20% TFA/CH₂Cl₂ (2 mL) was added to Intermediate 8-IV (88 mg) in CH₂Cl₂ (1 mL). The reaction mixture was stirred for 5 hours at room temperature and concentrated by removing the solvent. 1 M hydrochloric acid (2 mL) and CH₂Cl₂ (1 mL) were added to the resultant residue. The mixture was stirred for 10 minutes at room temperature. After removal of the supernatant, the solid was dried under vacuum to afford the hydrochloride salt of compound 8 (60 mg) in an 80% yield.

CI-MS (M⁺+1): 411.3.

EXAMPLE 9

Preparation of Compound 9

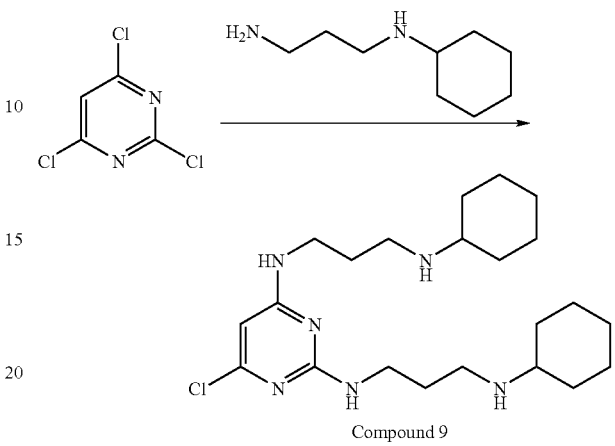

Compound 9

A solution of N-cyclohexyl-1,3-propanediamine (2.6 g), Et₃N (3.8 mL) and 2,4,6-trichloropyrimidine (1 g) in THF (50 mL) was stirred for overnight at 60° C. and concentrated by removing the solvent under vacuum. The residue was purified by chromatography on silica gel (21% NH₃ (aq)/MeOH=5/95) to afford compound 9 (1.7 g) in a 75% yield.

CI-MS (M⁺+1): 423.3.

1 M hydrochloric acid (3 mL) and CH₂Cl₂ (2 ml) were added to compound 9 (100 mg). The mixture was stirred for 10 minutes at room temperature. After removing the supernatant, the solid was dried under vacuum to afford the hydrochloride salt of compound 9 (130 mg) in a 97% yield.

EXAMPLE 10

Preparation of Compound 10

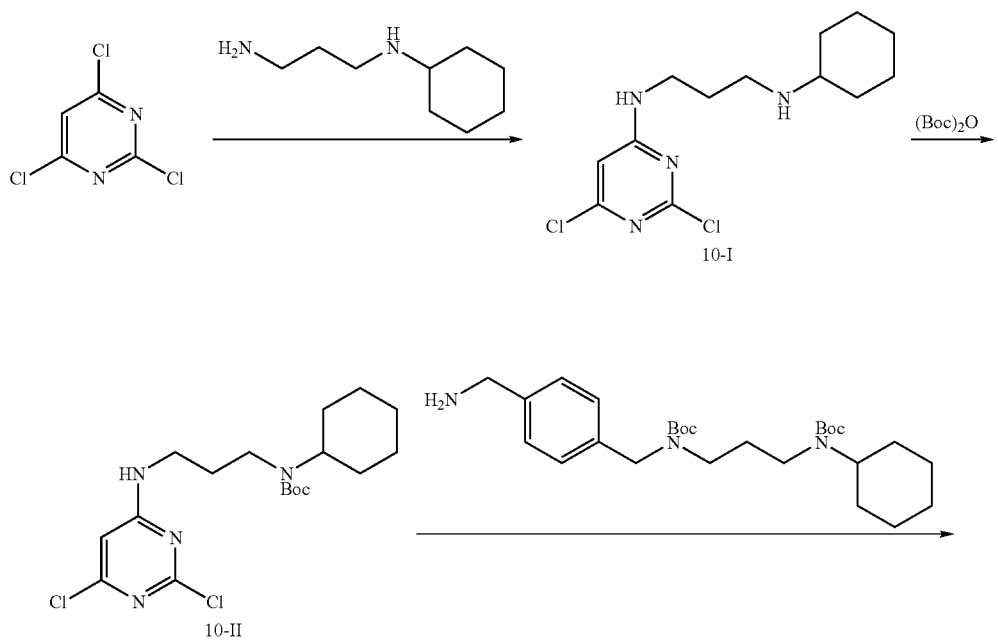

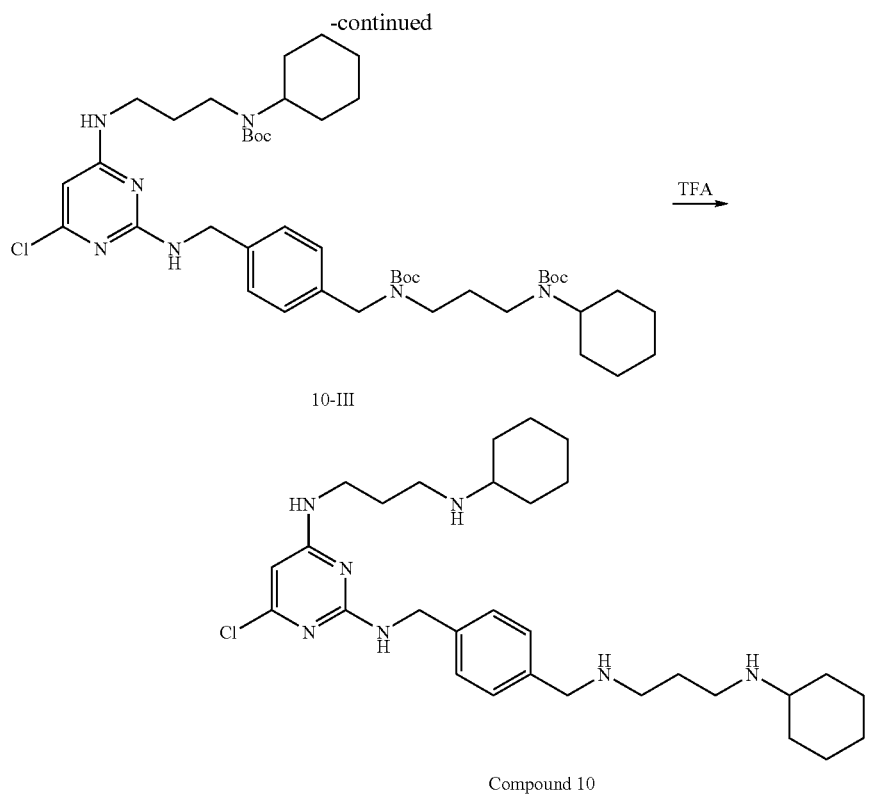

10-III

Compound 10

N-cyclohexyl-1,3-propanediamine (0.808 g) was slowly added to a stirred solution of 2,4,6-trichloropyrimidine (1 g) in THF (50 mL) at room temperature. The reaction mixture was stirred at 0° C. for 2 hours and the reaction was allowed to warm-up to room temperature overnight. The solution was then concentrated to give a residue, which was purified by chromatography on silica gel (EtOAc/Hexane=1/2) to afford Intermediate 10-I (1.386 g) in a 60% yield.

A solution of Intermediate 10-I (500 mg) and Boc$_2$O (770 mg) in CH$_2$Cl$_2$ (15 mL) was stirred at 25° C. overnight. The solution was then concentrated and the resultant residue was purified by chromatography on silica gel (EtOAc/Hexane=1/9) to afford Intermediate 10-II (590 mg) in an 80% yield.

Diisopropylethylamine (0.25 mL) was added to a solution of Intermediate 10-II (590 mg), Intermediate 8-III prepared in Example 8 (700 mg), and NaI (260 mg) in 1-pentanol (20 mL). The reaction mixture was stirred for 24 hours at 120° C. and then concentrated by removing the solvent under vacuum. The resultant residue was dissolved in CH$_2$Cl$_2$, washed with water, dried with anhydrous MgSO$_4$, and concentrated to give a residue. The residue was purified by chromatography on silica gel (EtOAc/Hexane=1/1) to afford Intermediate 10-III (865 mg) in a 70% yield.

A solution of 20% TFA/CH$_2$Cl$_2$ (3 mL) was added to a solution of Intermediate 10-III (150 mg) in CH$_2$Cl$_2$ (2 mL). The reaction mixture was stirred for 5 hours at room temperature and concentrated by removing the solvent. 1 M hydrochloric acid (3 mL) and CH$_2$Cl$_2$ (2 mL) were added to the residue. The mixture was stirred for another 10 minutes at room temperature. After removing the supernatant, the solid was dried under vacuum to afford the hydrochloride salt of compound 10 (107 mg) in an 80% yield.

CI-MS (M$^+$+1): 542.4.

EXAMPLE 11

Preparation of Compound 11

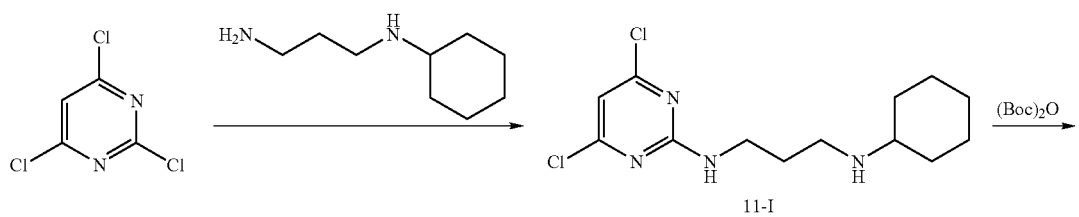

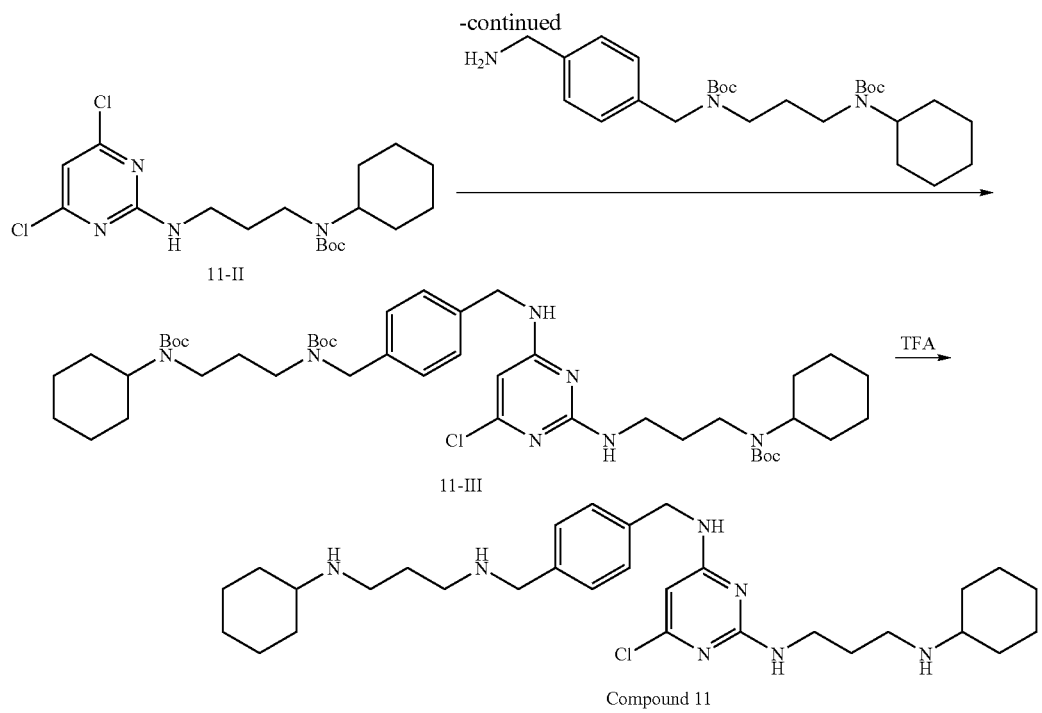

Compound 11

N-cyclohexyl-1,3-propanediamine (0.808 g) was slowly added to a stirred solution of 2,4,6-trichloropyrimidine (1 g) in THF (50 mL) at room temperature. The reaction mixture was stirred at 0° C. for 2 hours and the reaction was allowed to warm-up to room temperature overnight. The solution was then concentrated to give a residue, which was purified by chromatography on silica gel (EtOAc/Hexane=1/4) to afford intermediate 11-I (0.349 g) in a 21% yield.

A solution of intermediate 11-I (349 mg) and Boc$_2$O (540 mg) in CH$_2$Cl$_2$ (15 mL) was stirred at 25° C. overnight. The solution was then concentrated and the resultant residue was purified by chromatography on silica gel (EtOAc/Hexane=1/10) to afford intermediate 11-II (400 mg) in an 86% yield (CI-MS (M$^+$+1): 403.4).

Diisopropylethylamine (0.17 mL) was added to a solution of intermediate 11-II (400 mg), intermediate 8-III (prepared in Example 8) (475 mg), and NaI (176 mg) in 1-pentanol (20 mL). The reaction mixture was stirred for 24 hours at 120° C. and then concentrated by removing the solvent under vacuum. The resultant residue was dissolved in CH$_2$Cl$_2$, washed with water, dried with anhydrous MgSO$_4$, and concentrated to give a residue. The residue was purified by chromatography on silica gel (EtOAc/Hexane=1/1) to afford Intermediate 11-III (427 mg) in a 51% yield.

A solution of 20% TFA/CH$_2$Cl$_2$ (4 mL) was added to a solution of intermediate 11-III (200 mg) in CH$_2$Cl$_2$ (2 mL). The reaction mixture was stirred for 5 hours at room temperature and concentrated by removing the solvent. 1 M hydrochloric acid (5 mL) and CH$_2$Cl$_2$ (2 mL) were added to the residue. The mixture was stirred for another 10 minutes at room temperature. After removing the supernatant, the solid was dried under vacuum to afford the hydrochloride salt of compound 11 (117 mg) in a 91% yield.
CI-MS (M$^+$+1): 542.4.

EXAMPLE 12

Preparation of Compound 12

Compound 12 was prepared in a manner similar to that used to prepare compound 8.
CI-MS (M$^+$+1): 422.

EXAMPLE 13

Preparation of Compound 13

Compound 13 was prepared in a manner similar to that used to prepare compound 10.
CI-MS (M$^+$+1): 508.4.

EXAMPLE 14

Preparation of Compound 14

Compound 14 was prepared in a manner similar to that used to prepare compound 8.
CI-MS (M$^+$+1): 387.

EXAMPLE 15

Preparation of Compound 15

Compound 15 was prepared in a manner similar to that used to prepare compound 8.
CI-MS (M$^+$+1): 403.

EXAMPLE 16

Preparation of Compound 16

Compound 16 was prepared in a manner similar to that used to prepare compound 8.
CI-MS (M$^+$+1): 354.3.

EXAMPLE 17

Preparation of Compound 17

Compound 17 was prepared in a manner similar to that used to prepare compound 11.
CI-MS (M$^+$+1): 522.4.

EXAMPLE 18

Preparation of Compound 18

Compound 18 was prepared in a manner similar to that used to prepare compound 10.
CI-MS (M$^+$+1): 522.4.

EXAMPLE 19

Preparation of Compound 19

Compound 19 was prepared in a manner similar to that used to prepare compound 11.
CI-MS (M$^+$+1): 522.4.

EXAMPLE 20

Preparation of Compound 20

Intermediate 20-I was obtained as an intermediate during the preparation of compound 15.

NaH (110 mg) was added to a solution of the Intermediate 20-I (200 mg) and phenol (250 mg) in DMSO (3 mL). The reaction mixture was stirred at 25° C. for 1 hour. The mixture was then heated at 120° C. for 8 hours under microwave, cooled to room temperature, and concentrated by removing the solvent. The resultant residue was dissolved in $CH_2Cl_2$, washed with saturated aqueous $NaHCO_3$, dried with anhydrous $MgSO_4$, and concentrated to give a residue. The residue was purified by chromatography on silica gel (EtOAc/Hexane=1/1) to afford Intermediate 20-II (65 mg) in a 30% yield.

Intermediate 20-II (65 mg) in $CH_2Cl_2$ (1 mL) was added to a solution of 20% TFA/$CH_2Cl_2$ (2 mL). The reaction mixture was stirred for 5 hours at room temperature and concentrated by removing the solvent. 1 M hydrochloric acid (2 mL) and $CH_2Cl_2$ (1 mL) were subsequently added to the residue. The mixture was stirred for 10 minutes at room temperature. After removing the supernatant, the solid was dried under vacuum to afford the hydrochloride salt of compound 20 (45 mg) in an 80% yield.

CI-MS (M$^+$+1): 461.3.

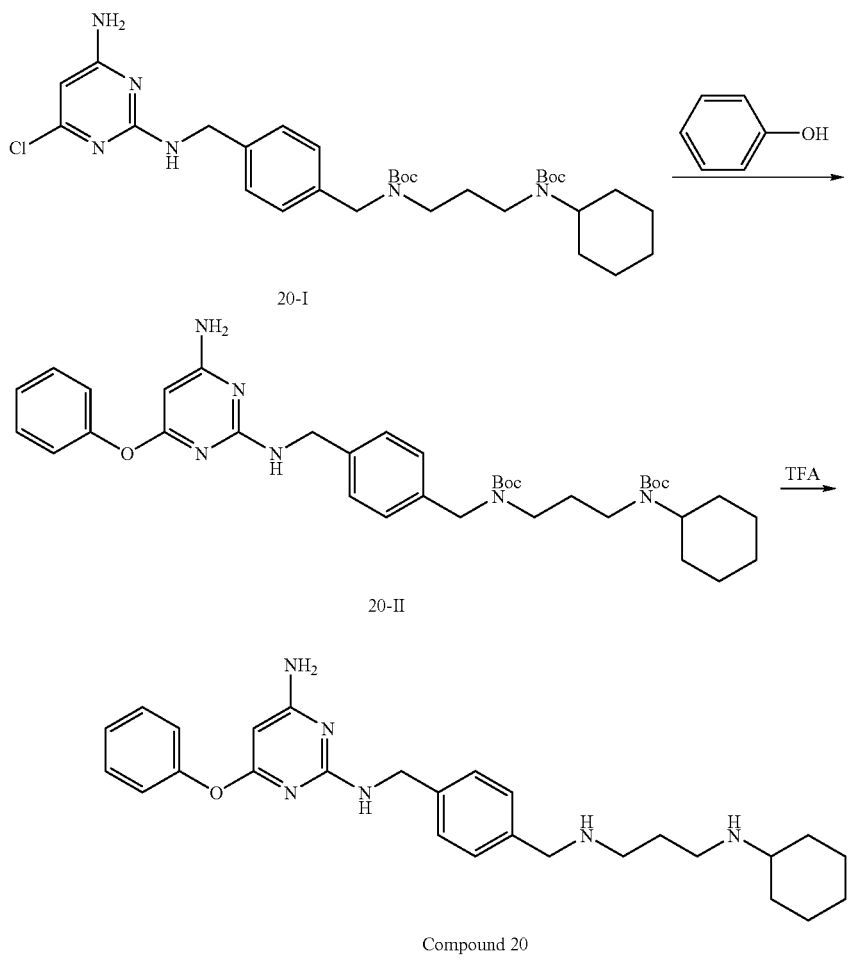

Compound 20

EXAMPLE 21

Preparation of Compound 21

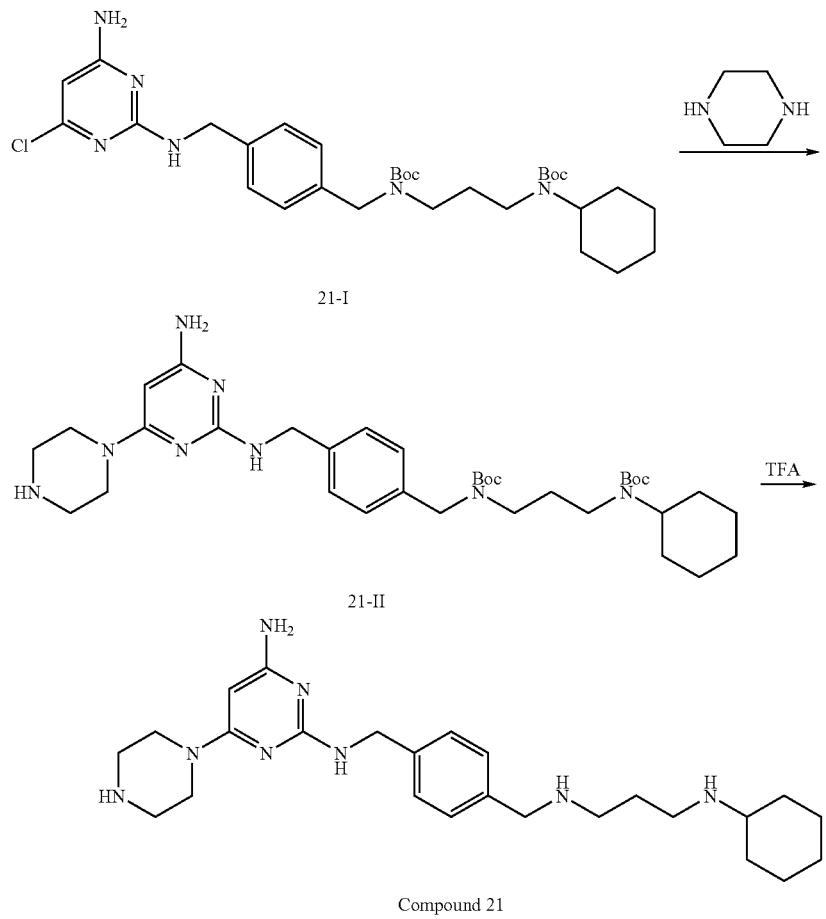

Intermediate 21-I was obtained as an intermediate during the preparation of compound 20.

A solution of 21-I (2 g) and piperazine (10 g) in 1-pentanol (3 mL) was stirred for 4 hours at 120° C. and concentrated by removing the solvent under vacuum. The resultant mixture was dissolved in CHCl$_3$, washed with water, dried with anhydrous MgSO$_4$, and concentrated to give a residue. The residue was purified by chromatography on silica gel (21% NH$_3$ (aq)/MeOH=1/99) to afford Intermediate 21-II (1.5 g) in a 60% yield.

A solution of 20% TFA/CH$_2$Cl$_2$ (3 mL) was added to a solution of Intermediate 20-II (130 mg) in CH$_2$Cl$_2$ (2 mL). The reaction mixture was stirred for 5 hours at room temperature and then concentrated by removing the solvent. 1 M hydrochloric acid (3 mL) and CH$_2$Cl$_2$ (2 ml) were added to the resultant residue. The mixture was stirred for another 10 minutes at room temperature. After removing the supernatant, the solid was dried under vacuum to afford the hydrochloride salt of compound 21 (90 mg) in an 80% yield.

CI-MS (M$^+$+1): 453.3.

EXAMPLE 22

Preparation of Compound 22

Compound 22 was prepared in a manner similar to that used to prepare compound 21.
CI-MS (M$^+$+1): 497.4

EXAMPLE 23

Preparation of Compound 23

Compound 23 was prepared in a manner similar to that used to prepare compound 21.
CI-MS (M$^+$+1): 467.4.

EXAMPLE 24

Preparation of Compound 24

Compound 24 was prepared in a manner similar to that used to prepare compound 10.
CI-MS (M$^+$+1): 522.4.

EXAMPLE 25

Preparation of Compound 25

Compound 25 was prepared in a manner similar to that used to prepare compound 11.
CI-MS (M$^+$+1): 466.4.

EXAMPLE 26

Preparation of Compound 26

Compound 26 was prepared in a manner similar to that used to prepare compound 8.
CI-MS (M$^+$+1): 394.3.

EXAMPLE 27

Preparation of Compound 27

Compound 27 was prepared in a manner similar to that used to prepare compound 21.
CI-MS (M$^+$+1): 454.3.

EXAMPLE 28

Preparation of Compound 28

Compound 28 was prepared in a manner similar to that used to prepare compound 21.
CI-MS (M$^+$+1): 452.3.

EXAMPLE 29

Preparation of Compound 29

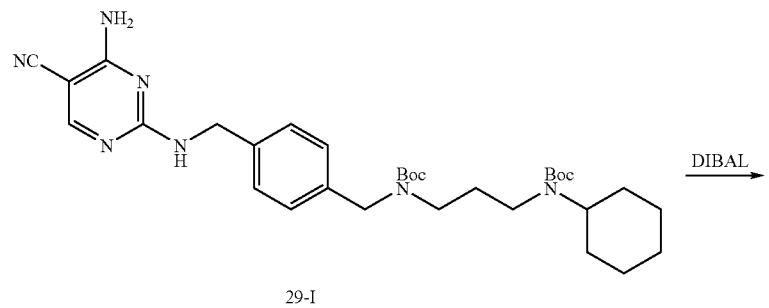

29-I

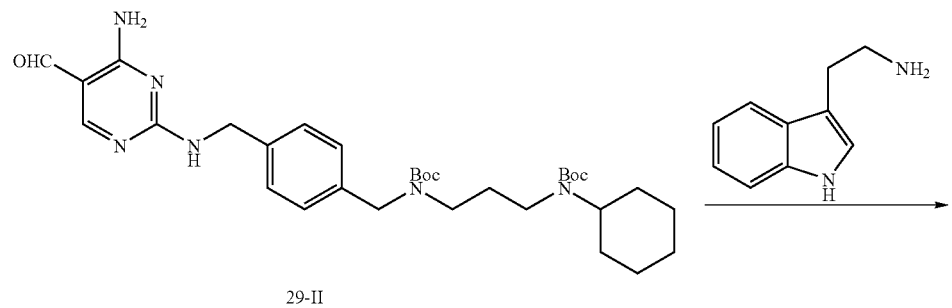

29-II

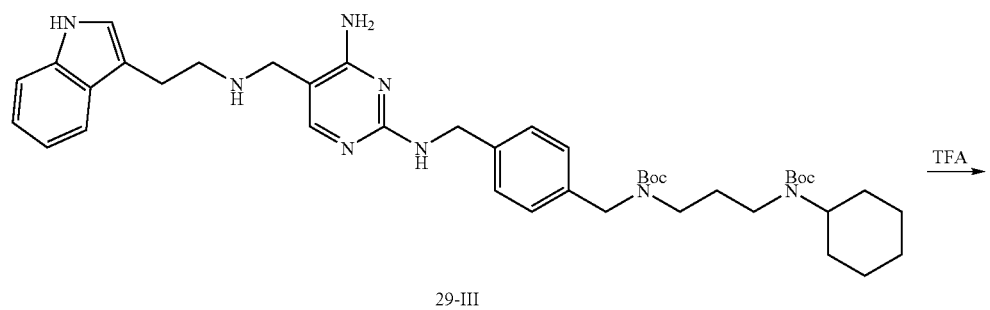

29-III

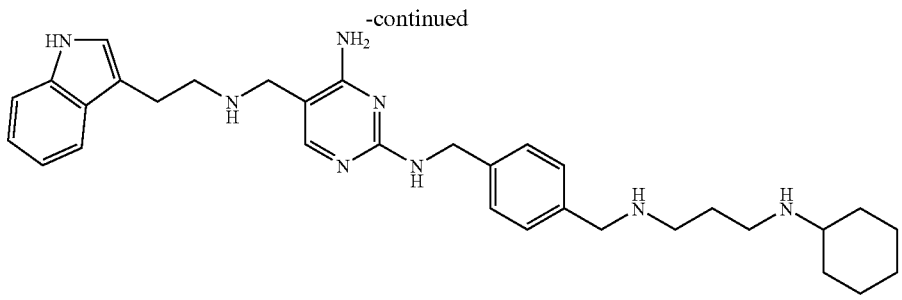

Compound 29

Intermediate 29-I was obtained as an intermediate during the preparation of compound 26.

1 M DIBAL/ether (8.35 mL) was added to a stirred solution of Intermediate 29-I (1.24 g) in dry toluene (100 mL) at −70~−78° C. under $N_2$ (g). The reaction mixture was stirred for 2 hours at this temperature. 5% HCl (aq) (9 mL) was then added to the solution at −60~−70° C. and the mixture was stirred for another 0.5 hour after the reaction temperature was increased to 25° C. To the solution was added $CH_2Cl_2$ (100 mL) and $H_2O$. The aqueous layer was extracted with $CH_2Cl_2$ twice. The organic layers were combined, dried with anhydrous $MgSO_4$, and concentrated by removing the solvent under vacuum. The resultant residue was purified by chromatography on silica gel (EtOAc/Hexane=1/2) to afford Intermediate 29-II (620 mg) in a 50% yield.

A solution of tryptamine (99 mg) and Intermediate 29-II (170 mg) in $CH_3OH$ (6 mL) was heated at 60° C. for 6 hours. After cooling to room temperature, $NaBH_4$ (20 mg) was slowly added to the solution and the mixture was stirred for another 30 minutes. The mixture was concentrated, quenched with $NH_4Cl$ (aq), extracted with $CH_2Cl_2$. The organic layer was dried with anhydrous $MgSO_4$ and concentrated to give a residue. The residue was purified by chromatography on silica gel (EtOAc/MeOH=9/1) to afford Intermediate 29-III (150 mg) in a 70% yield.

Intermediate 29-III (150 mg) in $CH_2Cl_2$ (2 mL) was added to a solution of 20% TFA/$CH_2Cl_2$ (3 mL). The reaction mixture was stirred for 5 hours at room temperature and concentrated by removing the solvent. 1 M hydrochloric acid (3 mL) and $CH_2Cl_2$ (2 mL) were added to the residue obtained above. The mixture was stirred for another 10 minutes at room temperature. After removal of the supernatant, the solid was dried under vacuum to afford the hydrochloride salt of compound 29 (92 mg) in a 70% yield.

CI-MS ($M^+$+1): 541.4.

EXAMPLE 30

Preparation of Compound 30

Compound 30 was prepared in a manner similar to that used to prepare compound 29.

CI-MS ($M^+$+1): 528.3.

EXAMPLE 31

Preparation of Compound 31

Compound 31 was prepared in a manner similar to that used to prepare compound 21.

CI-MS ($M^+$+1): 481.4.

EXAMPLE 32

Preparation of Compound 32

Compound 32 was prepared in a manner similar to that used to prepare compound 21.

CI-MS ($M^+$+1): 547.4.

EXAMPLE 33

Preparation of Compound 33

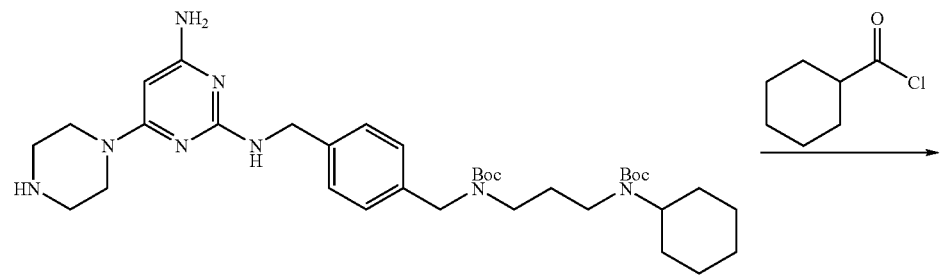

33-I

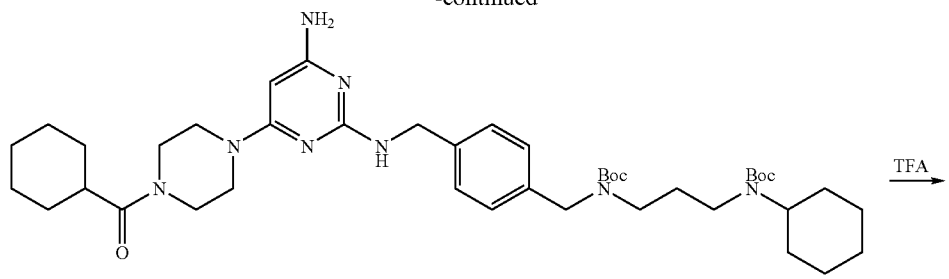

33-II

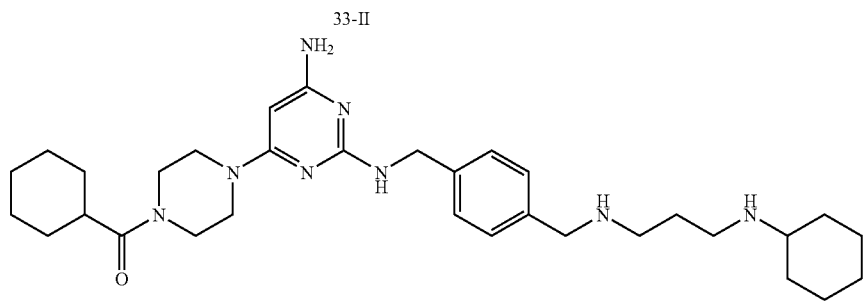

Compound 33

Intermediate 33-I was obtained as an intermediate during the preparation of compound 21.

Diisopropylethylamine (0.1 mL) and cyclohexanecarbonyl chloride (55 mg) were added to a solution of Intermediate 33-I (200 mg) in CH$_2$Cl$_2$ (10 mL). The reaction mixture was stirred overnight at room temperature and then concentrated by removing the solvent. The resultant mixture was dissolved in CHCl$_3$, washed with water, dried with anhydrous MgSO$_4$, and concentrated to give a residue. The residue was purified by chromatography on silica gel (EtOAc/Hexane=1/1) to afford Intermediate 33-II (140 mg) in a 60% yield.

A solution of 20% TFA/CH$_2$Cl$_2$ (3 mL) was added to a solution of Intermediate 33-II (140 mg) in CH$_2$Cl$_2$ (2 mL). The reaction mixture was stirred for 5 hours at room temperature and concentrated by removing the solvent. 1 M hydrochloric acid (3 mL) and CH$_2$Cl$_2$ (2 mL) were added to the residue. The resultant mixture was stirred for another 10 minutes at room temperature. After removal of the supernatant, the solid was dried under vacuum to afford the hydrochloride salt of compound 33 (100 mg) in an 80% yield.

CI-MS (M$^+$+1): 563.4.

EXAMPLE 34

Preparation of Compound 34

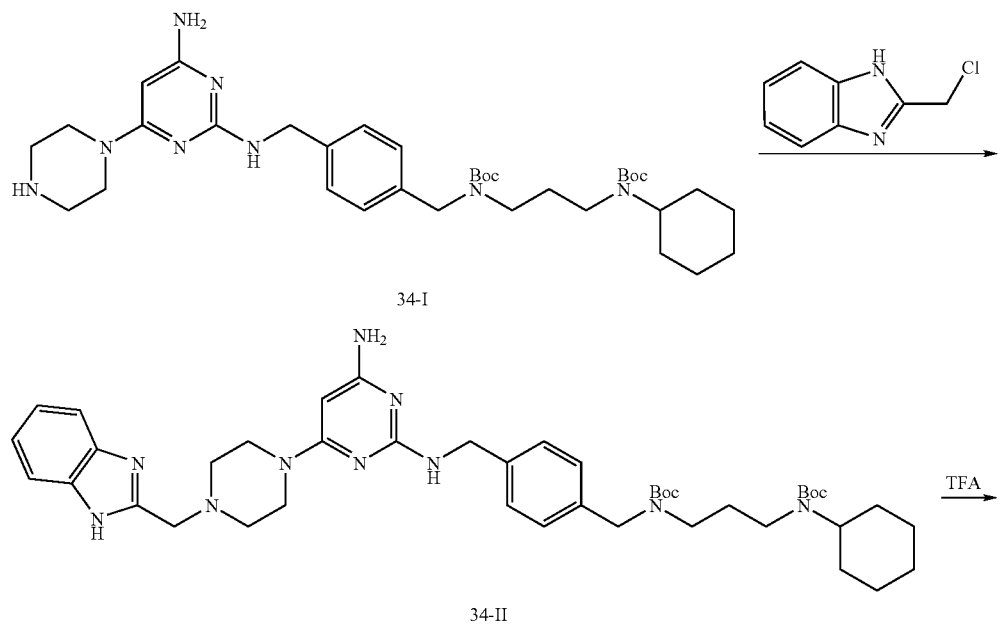

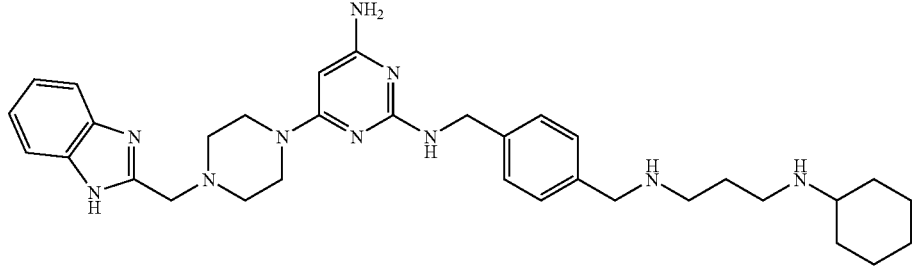

Compound 34

Intermediate 34-I was obtained as an intermediate during the preparation of compound 21. Intermediate 34-I (166 mg) was first dissolved in CH₃CN (10 mL). 2-chloromethylbenzimidazole (42 mg) and K₂CO₃ (79 mg) were then added to the above solution. After the mixture was stirred for 48 hours at room temperature, it was filtered and concentrated. The resultant residue was purified by chromatography on silica gel (EtOAc/MeOH=10/1) to afford Intermediate 34-II (70 mg) in a 35% yield.

A solution of 20% TFA/CH₂Cl₂ (2 mL) was added to a solution of Intermediate 34-II (70 mg) in CH₂Cl₂ (1 mL). The reaction mixture was stirred for 5 hours at room temperature and concentrated by removing the solvent. 1 M hydrochloric acid (2 mL) and CH₂Cl₂ (1 mL) were added to the resultant residue. The mixture was stirred for another 10 minutes at room temperature. After removal of the supernatant, the solid was dried under vacuum to afford the hydrochloride salt of compound 34 (50 mg) in an 80% yield.

CI-MS (M$^+$+1): 583.4.

EXAMPLE 35

Preparation of Compound 35

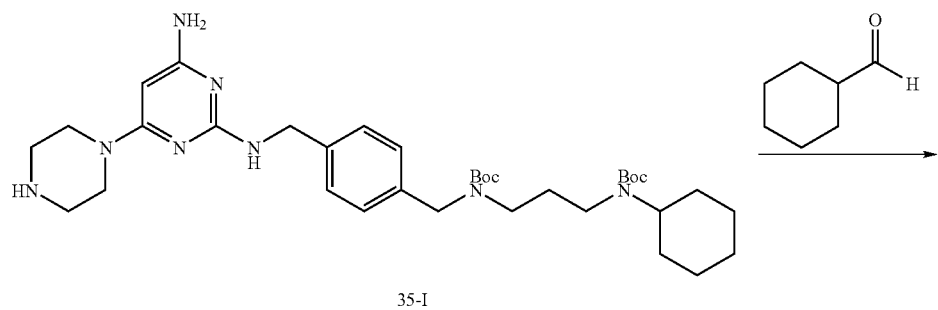

35-I

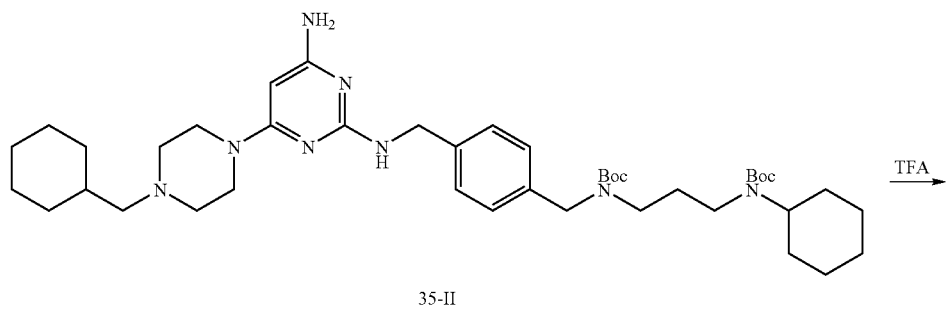

35-II

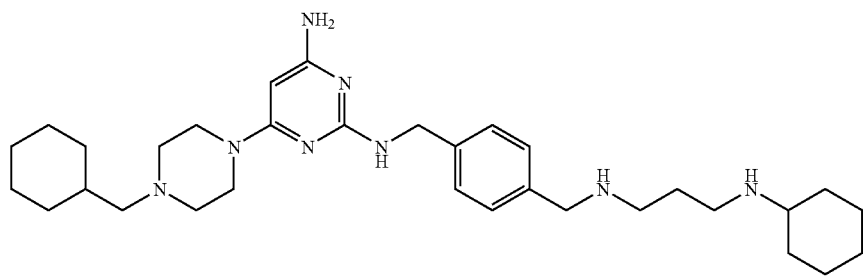

Compound 35

Intermediate 35-I was obtained as an intermediate during the preparation of compound 21.

NaBH(OAc)$_3$ (215 mg) was added to a solution of Intermediate 35-I (166 mg) in MeOH (10 mL) and cyclohexanecarbaldehyde (57 mg). A few drops of acetic acid was then added. The reaction mixture was stirred for 48 hours at room temperature and concentrated by removing the solvent through distillation. The resultant mixture was dissolved in CH$_2$Cl$_2$ and quenched with saturated aqueous NaHCO$_3$. The aqueous layer was separated and extracted with CH$_2$Cl$_2$. The combined organic layers were subsequently washed with water, dried with anhydrous MgSO$_4$, filtered, and concentrated to give a residue. The residue was purified by chromatography on silica gel (EtOAc/Hexane=2/1) to give Intermediate 35-II (120 mg) in a 65% yield.

A solution of 20% TFA/CH$_2$Cl$_2$ (3 mL) was added to a solution of Intermediate 35-II (120 mg) in CH$_2$Cl$_2$ (2 mL). The reaction mixture was stirred for 5 hours at room temperature and concentrated by removing the solvent. 1 M hydrochloric acid (3 mL) and CH$_2$Cl$_2$ (2 mL) were added to the residue. The mixture was stirred for another 10 minutes at room temperature. After removal of the supernatant, the solid was dried under vacuum to afford the hydrochloride salt of compound 35 (85 mg) in an 80% yield.

CI-MS (M$^+$+1): 549.4.

EXAMPLE 36

Preparation of Compound 36

Compound 36 was prepared in a manner similar to that used to prepare compound 35.
CI-MS (M$^+$+1): 543.4.

EXAMPLE 37

Preparation of Compound 37

Compound 37 was prepared in a manner similar to that used to prepare compound 21.
CI-MS (M$^+$+1): 563.4.

EXAMPLE 38

Preparation of Compound 38

Compound 38 was prepared in a manner similar to that used to prepare compound 21
CI-MS (M$^+$+1): 564.4. .

EXAMPLE 39

Preparation of Compound 39

Compound 39 was prepared in a manner similar to that used to prepare compound 21.
CI-MS (M$^+$+1): 566.4.

EXAMPLE 40

Preparation of Compound 40

Compound 40 was prepared in a manner similar to that used to prepare compound 21.
CI-MS (M$^+$+1): 587.4.

EXAMPLE 41

Preparation of Compound 41

Compound 41 was prepared in a manner similar to that used to prepare compound 33.
CI-MS (M$^+$+1): 523.4.

EXAMPLE 42

Preparation of Compound 42

Compound 42 was prepared in a manner similar to that used to prepare compound 33.
CI-MS (M$^+$+1): 557.4.

EXAMPLE 43

Preparation of Compound 43

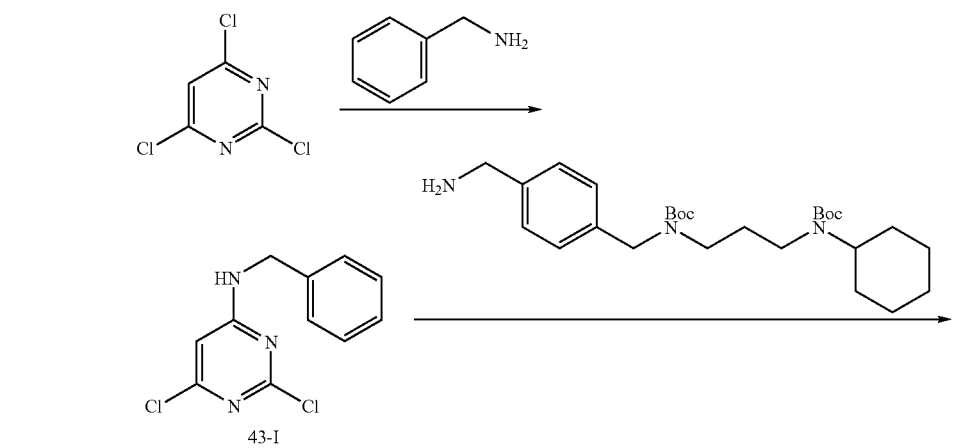

43-I

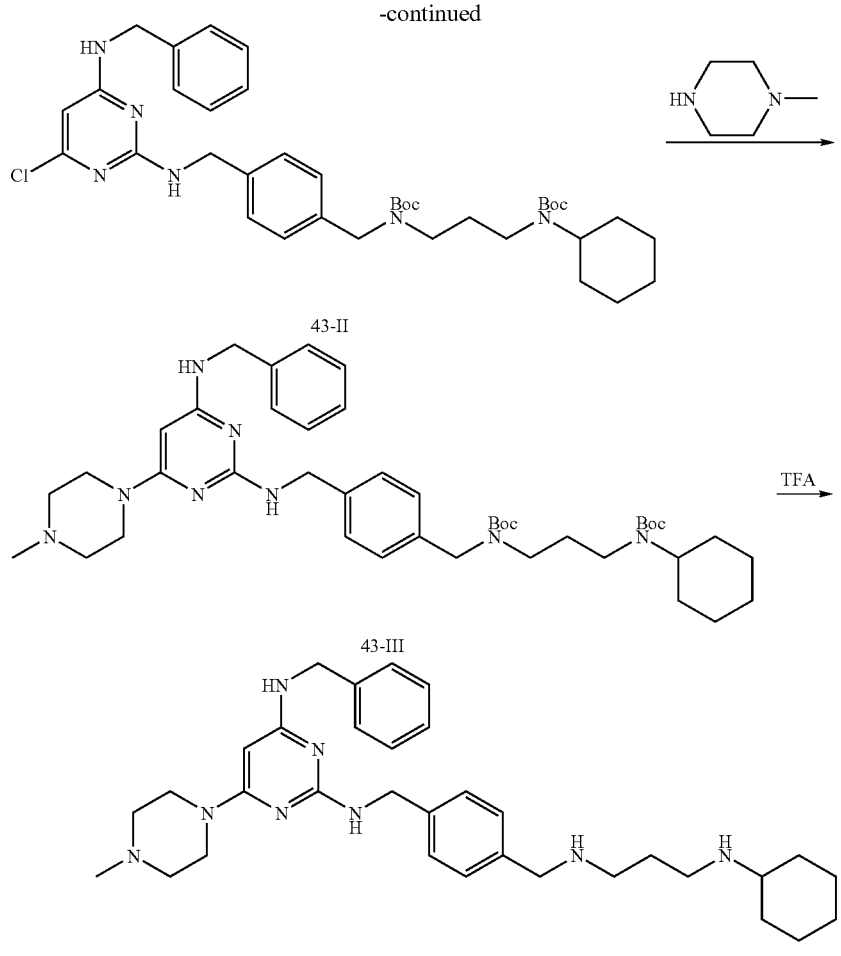

Compound 43

Intermediate 43-I was prepared in a 45% yield in a manner similar to that described in the first paragraph of Example 10 using benzylamine (645 mg) as a starting material.

Diisopropylethylamine (0.27 mL) was added to a solution of Intermediate 43-I (625 mg), Intermediate 8-III prepared in Example 8 (741 mg), and NaI (275 mg) in 1-pentanol (20 mL). The reaction mixture was stirred at 120° C. for 24 hours and concentrated by removing the solvent under vacuum. The resultant mixture was dissolved in $CH_2Cl_2$, washed with water, dried with anhydrous $MgSO_4$, and concentrated to give a residue. The residue was purified by chromatography on silica gel (EtOAc/Hexane=1/3) to afford Intermediate 43-II (1,100 mg) in a 65% yield.

A solution of Intermediate 43-II (200 mg) and N-methylpiperazine (2,000 mg) in 1-pentanol (1 mL) was stirred at 120° C. for 4 hours. The solvent was then removed under vacuum. The resultant mixture was dissolved in $CHCl_3$, washed with water, dried with anhydrous $MgSO_4$, and concentrated to give a residue. The residue was purified by chromatography on silica gel (EtOAc/MeOH=20/1) to afford Intermediate 43-III (215 mg) in a 70% yield.

A solution of 20% $TFA/CH_2Cl_2$ (4 mL) was added to a solution of Intermediate 43-III (215 mg) in $CH_2Cl_2$ (2 mL). The reaction mixture was stirred for 5 hours at room temperature and concentrated by removing the solvent. 1 M hydrochloric acid (4 mL) and $CH_2Cl_2$ (2 mL) were added to the residue. The mixture was stirred for another 10 minutes at room temperature. After removal of the supernatant, the solid was dried under vacuum to afford the hydrochloride salt of compound 43 (150 mg) in an 80% yield.

CI-MS ($M^+$+1): 557.4.

EXAMPLE 44

Preparation of Compound 44

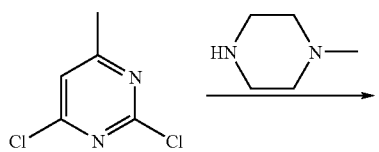

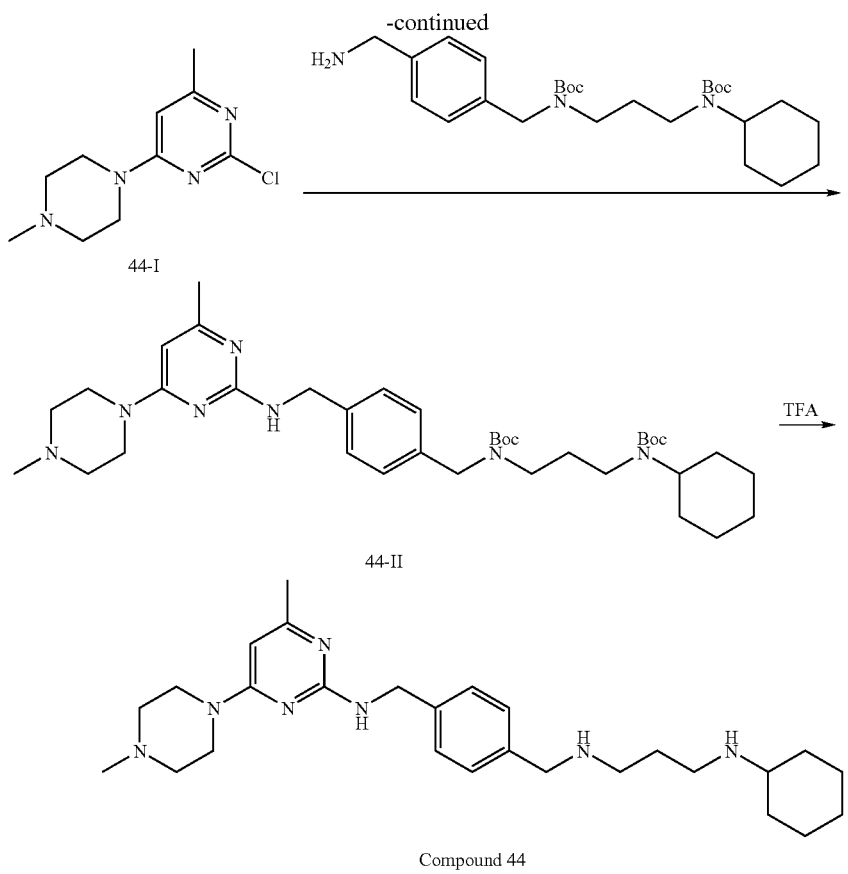

Compound 44

1-Methylpiperazine (0.76 g) and Et$_3$N (0.8 mL) were added to a solution of 2,4-dichloro-6-methylpyrimidine (1 g) in EtOH (60 mL). The reaction solution was stirred at 0° C. for 1 hour and then was allowed to warm-up to room temperature within 3 hours. The solution was then concentrated to give a residue, which was purified by chromatography on silica gel (EtOAc/MeOH=6/1) to afford Intermediate 44-I (0.76 g) in a 55% yield.

Diisopropylethylamine (0.25 mL) was added to a solution of Intermediate 44-I (300 mg), Intermediate 8-III prepared in Example 8 (689 mg), and NaI (260 mg) in 1-pentanol (20 mL). The reaction mixture was stirred for 24 hours at 120° C. and concentrated by removing the solvent under vacuum. The resultant mixture was dissolved in CH$_2$Cl$_2$, washed with water, dried with anhydrous MgSO$_4$, and concentrated to give a residue. The residue was purified by chromatography on silica gel (EtOAc/MeOH=5/1) to afford Intermediate 44-II (530 mg) in a 60% yield.

A solution of 20% TFA/CH$_2$Cl$_2$ (3 mL) was added to a solution of compound Intermediate 44-II (150 mg) in CH$_2$Cl$_2$ (2 mL). The reaction mixture was stirred for 5 hours at room temperature and concentrated by removing the solvent. 1 M hydrochloric acid (3 mL) and CH$_2$Cl$_2$ (2 mL) were added to the residue. The mixture was stirred for another 10 minutes at room temperature. After removal of the supernatant, the solid was dried under vacuum to afford the hydrochloride salt of compound 44 (100 mg) in an 80% yield.

CI-MS (M$^+$+1): 466.4.

EXAMPLE 45

Preparation of Compound 45

Compound 45 was prepared in a manner similar to that used to prepare compound 43.

CI-MS (M$^+$+1): 493.3.

EXAMPLE 46

Preparation of Compound 46

Compound 46 was prepared in a manner similar to that used to prepare compound 43.

CI-MS (M$^+$+1): 587.4.

EXAMPLE 47

Preparation of Compound 47

Compound 47 was prepared in a manner similar to that used to prepare compound 21.

CI-MS (M$^+$+1): 549.4.

EXAMPLE 48

Preparation of Compound 48

Compound 48 was prepared in a manner similar to that used to prepare compound 21.

CI-MS (M$^+$+1): 524.4.

EXAMPLE 49

Preparation of Compound 49

Compound 49 was prepared in a manner similar to that used to prepare compound 21.
CI-MS (M$^+$+1): 521.4.

EXAMPLE 50

Preparation of Compound 50

Compound 50 was prepared in a manner similar to that used to prepare compound 43.
CI-MS (M$^+$+1): 550.4.

EXAMPLE 51

Preparation of Compound 51

Compound 51 was prepared in a manner similar to that used to prepare compound 43.
CI-MS (M$^+$+1): 580.4.

EXAMPLE 52

Preparation of Compound 52

Compound 52 was prepared in a manner similar to that used to prepare compound 43.
CI-MS (M$^+$+1): 567.4.

EXAMPLE 53

Preparation of Compound 53

Compound 53 was prepared in a manner similar to that used to prepare compound 44.
CI-MS (M$^+$+1): 542.4.

EXAMPLE 54

Preparation of Compound 54

Compound 54 was prepared in a manner similar to that used to prepare compound 44.
CI-MS (M$^+$+1): 548.4.

EXAMPLE 55

Preparation of Compound 55

Compound 55 was prepared in a manner similar to that used to prepare compound 44. CI-MS (M$^+$+1): 520.4.

EXAMPLE 56

Preparation of Compound 56

Compound 56 was prepared in a manner similar to that used to prepare compound 44.
CI-MS (M$^+$+1): 562.5.

EXAMPLE 57

Preparation of Compound 57

Compound 57 was prepared in a manner similar to that used to prepare compound 44.
CI-MS (M$^+$+1): 508.4.

EXAMPLE 58

Preparation of Compound 58

Compound 58 was prepared in a manner similar to that used to prepare compound 44.
CI-MS (M$^+$+1): 496.4.

EXAMPLE 59

Preparation of Compound 59

Compound 59 was prepared in a manner similar to that used to prepare compound 44.
CI-MS (M$^+$+1): 534.4.

EXAMPLE 60

Preparation of Compound 60

Compound 60 was prepared in a manner similar to that used to prepare compound 44.
CI-MS (M$^+$+1): 556.4.

EXAMPLE 61

Preparation of Compound 61

Compound 61 was prepared in a manner similar to that used to prepare compound 44.
CI-MS (M$^+$+1): 618.4.

EXAMPLE 62

Preparation of Compound 62

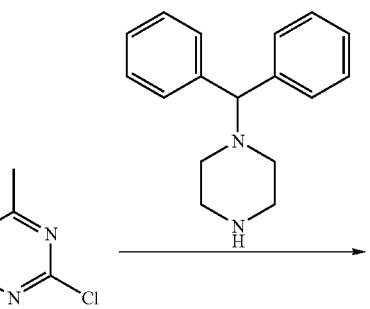

-continued
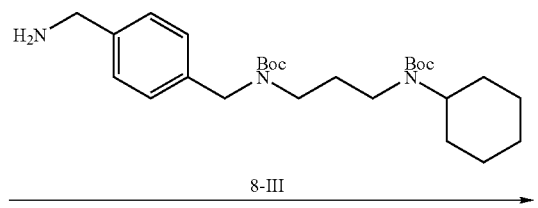
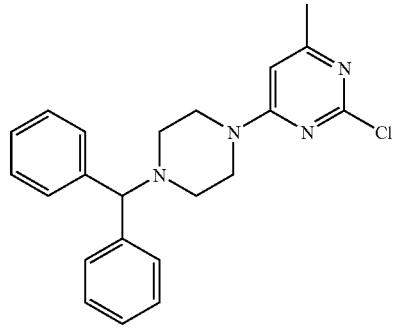
62-I
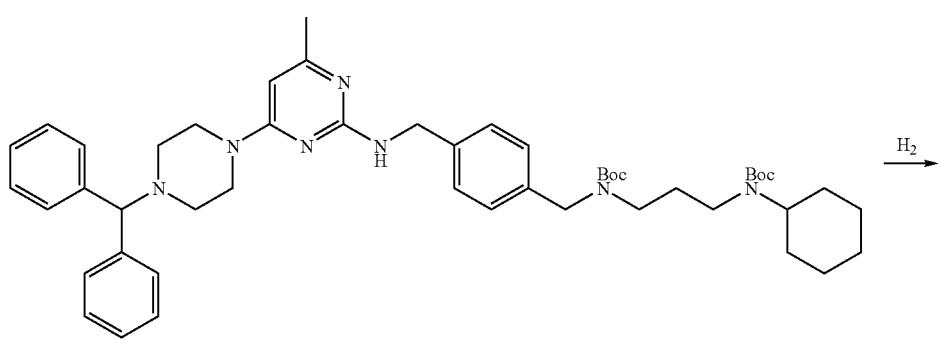
62-II
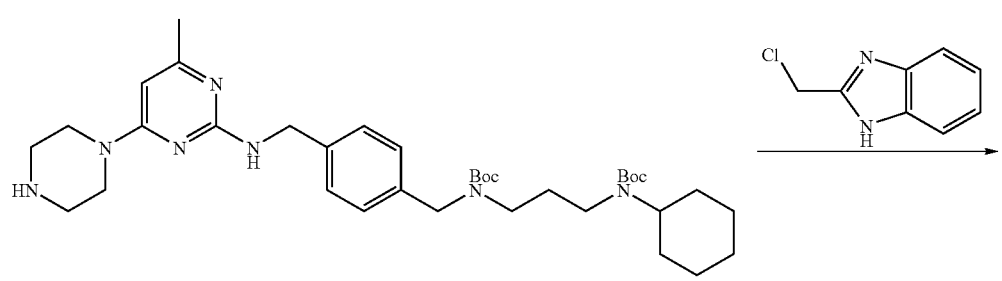
62-III
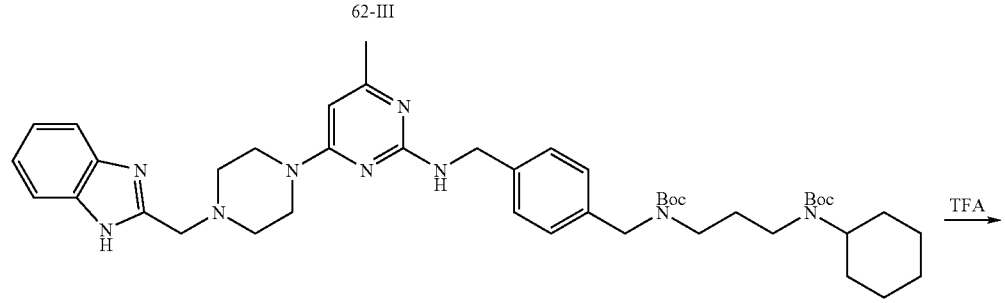
62-IV
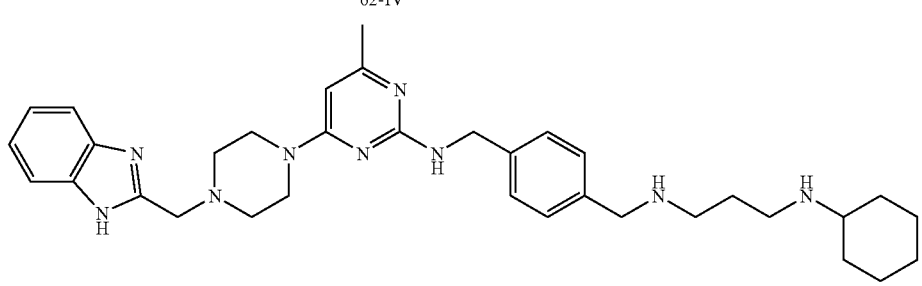
Compound 62

1-(Diphenylmethyl)piperazine (3.78 g) and Et$_3$N (2.3 mL) were added to a solution of 2,4-dichloro-6-methylpyrimidine (2.43 g) in EtOH (200 mL). The reaction mixture was stirred at 0° C. for 1 hour and then was allowed to warm-up to room temperature within 15 hours. The solution was then concentrated to give a residue, which was purified by chromatography on silica gel (EtOAc/Hexane=1/5) to afford intermediate 62-I (4.0 g) in a 70% yield.

Diisopropylethylamine (4.09 g) was added to a solution of intermediate 92-I (4.0 g), intermediate 8-III prepared in Example 8 (5.29 g), and NaI (2.38 g) in 1-pentanol (10 mL). The reaction mixture was stirred for 15 hours at 140° C. and concentrated by removing the solvent under vacuum. The resultant mixture was dissolved in CH$_2$Cl$_2$, washed with water, dried with anhydrous MgSO$_4$, and concentrated to give a residue. The residue was purified by chromatography on silica gel (EtOAc/Hexane=1/1) to afford intermediate 62-II (2.7 g) in a 31% yield.

A solution of intermediate 62-II (2.7 g) and Pd/C (2.0 g) in isopropanol (30 ml) was stirred under H$_2$ (balloon) at 60° C. for 3 hours and then filtered through a celite column and concentrated. The resultant residue was purified by chromatography on silica gel (EtOAc/MeOH=10/1) to afford intermediate 62-III (1.1 g) in a 50% yield.

Intermediate 62-III (200 mg) was first dissolved in CH$_3$CN (10 mL). 2-chloromethylbenzimidazole (51 mg) and K$_2$CO$_3$ (86 mg) were then added to the above solution. After the mixture was stirred for 48 hours at room temperature, it was filtered and concentrated. The resultant residue was purified by chromatography on silica gel (EtOAc/MeOH=10/1) to afford intermediate 62-IV (100 mg) in a 42% yield.

A solution of 20% TFA/CH$_2$Cl$_2$ (3 mL) was added to a solution of intermediate 62-IV (100 mg) in CH$_2$Cl$_2$ (2 mL). The reaction mixture was stirred for 5 hours at room temperature and concentrated by removing the solvent. 1 M hydrochloric acid (3 mL) and CH$_2$Cl$_2$ (2 mL) were added to the residue. The mixture was stirred for another 10 minutes at room temperature. After removal of the supernatant, the solid was dried under vacuum to afford the hydrochloride salt of compound 62 (100 mg) in a 84% yield.
CI-MS (M$^+$+1): 582.4.

EXAMPLE 63

Preparation of Compound 63

Compound 63 was prepared in a manner similar to that used to prepare compound 44.
CI-MS (M$^+$+1): 572.4.

EXAMPLE 64

Preparation of Compound 64

Compound 64 was prepared in a manner similar to that used to prepare compound 44.
CI-MS (M$^+$+1): 576.4.

EXAMPLE 65

Preparation of Compound 65

Compound 65 was prepared in a manner similar to that used to prepare compound 21.
CI-MS (M$^+$+1): 525.4.

EXAMPLE 66

Preparation of Compound 66

Compound 66 was prepared in a manner similar to that used to prepare compound 21.
CI-MS (M$^+$+1): 535.4.

EXAMPLE 67

Preparation of Compound 67

Compound 67 was prepared in a manner similar to that used to prepare compound 21.
CI-MS (M$^+$+1): 569.4.

EXAMPLE 68

Preparation of Compound 68

Compound 68 was prepared in a manner similar to that used to prepare compound 21.
CI-MS (M$^+$+1): 525.4.

EXAMPLE 69

Preparation of Compound 69

Compound 69 was prepared in a manner similar to that used to prepare compound 21.
CI-MS (M$^+$+1): 547.3.

EXAMPLE 70

Preparation of Compound 70

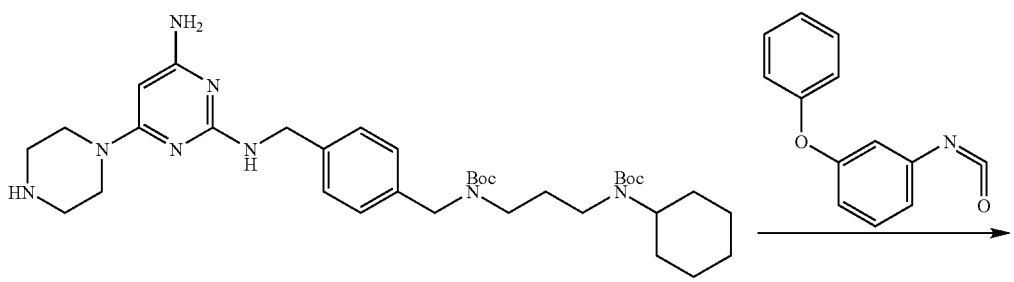

70-I

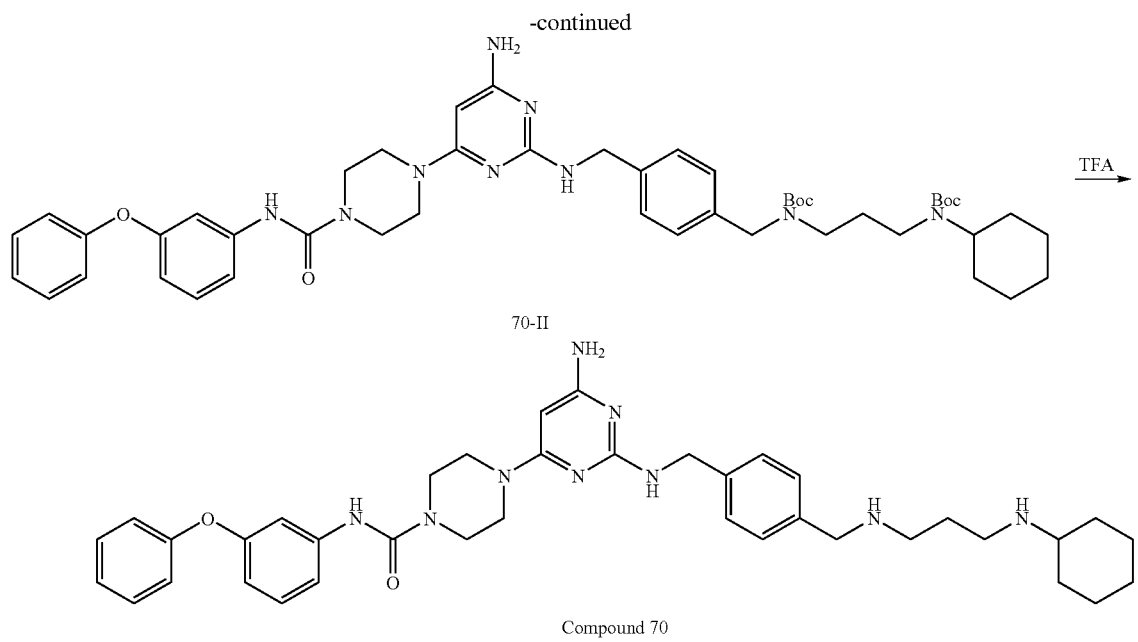

Compound 70

Intermediate 70-I was obtained during the preparation of compound 21.

A solution of intermediate 70-I (150 mg), 3-phenoxyphenyl isocyanate (48 mg) and Et$_3$N (46 mg) in CH$_2$Cl$_2$ (15 ml) was stirred at 25° C. overnight and then concentrated. The resultant residue was purified by chromatography on silica gel (EtOAc/MeOH=20/1) to afford Intermediate 70-II (163 mg) in a 82% yield.

A solution of 20% TFA/CH$_2$Cl$_2$ (3 mL) was added to a solution of intermediate 70-II (163 mg) in CH$_2$Cl$_2$ (2 mL). The reaction mixture was stirred for 5 hours at room temperature and concentrated by removing the solvent. 1 M hydrochloric acid (3 mL) and CH$_2$Cl$_2$ (2 mL) were added to the residue. The mixture was stirred for another 10 minutes at room temperature. After removal of the supernatant, the solid was dried under vacuum to afford the hydrochloride salt of compound 70 (164 mg) in a 86% yield.

CI-MS (M$^+$+1): 664.4.

EXAMPLE 71

Preparation of Compound 71

Compound 71 was prepared in a manner similar to that used to prepare compound 21.
CI-MS (M$^+$+1): 597.4.

EXAMPLE 72

Preparation of Compound 72

Compound 72 was prepared in a manner similar to that used to prepare compound 21.
CI-MS (M$^+$+1): 468.3.

EXAMPLE 73

Preparation of Compound 73

Compound 73 was prepared in a manner similar to that used to prepare compound 21
CI-MS (M$^+$+1): 530.4. .

EXAMPLE 74

Preparation of Compound 74

Compound 74 was prepared in a manner similar to that used to prepare compound 35.
CI-MS (M$^+$+1): 523.4.

EXAMPLE 75

Preparation of Compound 75

Compound 75 was prepared in a manner similar to that used to prepare compound 35.
CI-MS (M$^+$+1): 537.4.

EXAMPLE 76

Preparation of Compound 76

Compound 76 was prepared in a manner similar to that used to prepare compound 44.
CI-MS (M$^+$+1): 566.4.

EXAMPLE 77

Preparation of Compound 77

Compound 77 was prepared in a manner similar to that used to prepare compound 44.
CI-MS (M$^+$+1): 386.

EXAMPLE 78

Preparation of Compound 78

Compound 78 was prepared in a manner similar to that used to prepare compound 44.
CI-MS (M$^+$+1): 565.4.

EXAMPLE 79

Preparation of Compound 79

Compound 79 was prepared in a manner similar to that used to prepare compound 70.
CI-MS (M$^+$+1): 640.4.

EXAMPLE 80

Preparation of Compound 80

Compound 80 was prepared in a manner similar to that used to prepare compound 33.
CI-MS (M$^+$+1): 537.4.

EXAMPLE 81

Preparation of Compound 81

Compound 81 was prepared in a manner similar to that used to prepare compound 33.
CI-MS (M$^+$+1): 537.4.

EXAMPLE 82

Preparation of Compound 82

Compound 82 was prepared in a manner similar to that used to prepare compound 33.
CI-MS (M$^+$+1): 521.4.

EXAMPLE 83

Preparation of Compound 83

Compound 83 was prepared in a manner similar to that used to prepare compound 33.
CI-MS (M$^+$+1): 586.4.

EXAMPLE 84

Preparation of Compound 84

Compound 84 was prepared in a manner similar to that used to prepare compound 44.
CI-MS (M$^+$+1): 524.4.

EXAMPLE 85

Preparation of Compound 85

Compound 85 was prepared in a manner similar to that used to prepare compound 44.
CI-MS (M$^+$+1): 546.3.

EXAMPLE 86

Preparation of Compound 86

Compound 86 was prepared in a manner similar to that used to prepare compound 70.
CI-MS (M$^+$+1): 552.4.

EXAMPLE 87

Preparation of Compound 87

Compound 87 was prepared in a manner similar to that used to prepare compound 35.
CI-MS (M$^+$+1): 523.4.

EXAMPLE 88

Preparation of Compound 88

Compound 88 was prepared in a manner similar to that used to prepare compound 35.
CI-MS (M$^+$+1): 509.4.

EXAMPLE 89

Preparation of Compound 89

Compound 89 was prepared in a manner similar to that used to prepare compound 43.
CI-MS (M$^+$+1): 475.3.

EXAMPLE 90

Preparation of Compound 90

Compound 90 was prepared in a manner similar to that used to prepare compound 44.
CI-MS (M$^+$+1): 453.4.

EXAMPLE 91

Preparation of Compound 91

Compound 91 was prepared in a manner similar to that used to prepare compound 44.
CI-MS (M$^+$+1): 494.4.

EXAMPLE 92

Preparation of Compound 92

Compound 92 was prepared in a manner similar to that used to prepare compound 34.
CI-MS (M$^+$+1): 601.4.

EXAMPLE 93

Preparation of Compound 93

Compound 93 was prepared in a manner similar to that used to prepare compound 34.
CI-MS (M$^+$+1): 535.4.

EXAMPLE 94

Preparation of Compound 94

Compound 94 was prepared in a manner similar to that used to prepare compound 33.
CI-MS (M$^+$+1): 577.4.

EXAMPLE 95

Preparation of Compound 95

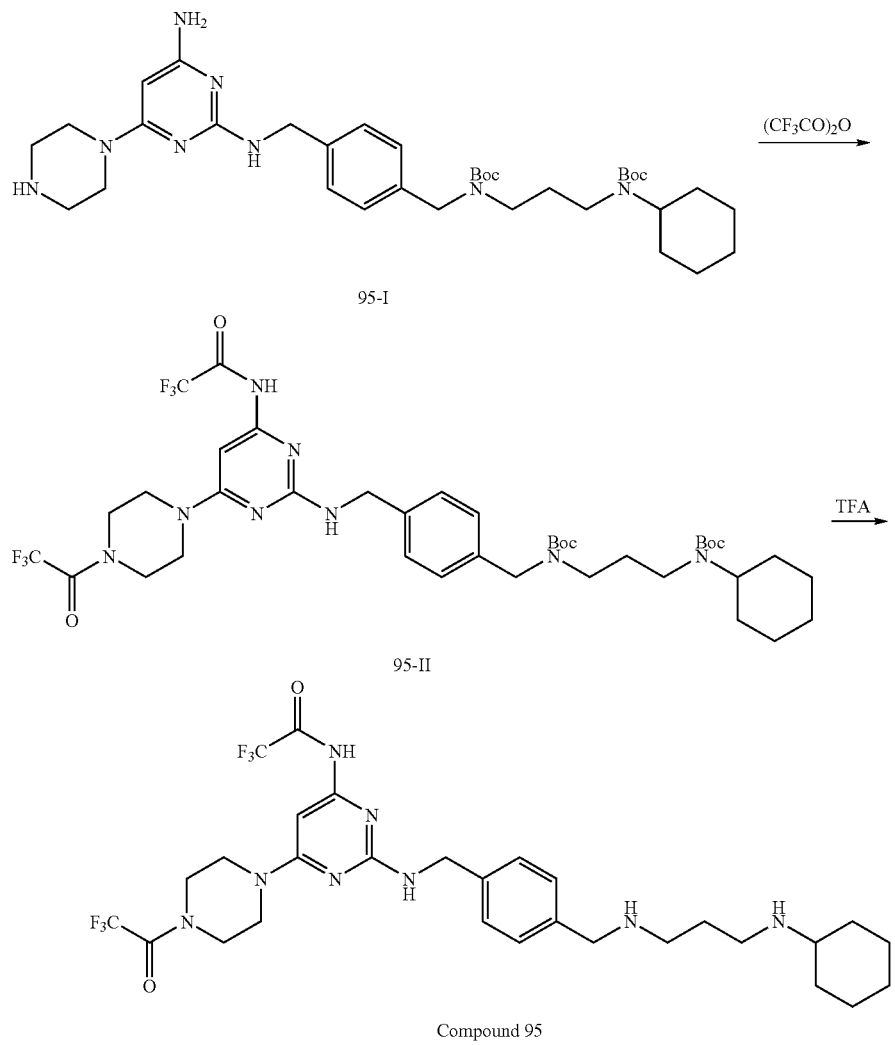

Intermediate 95-I was obtained during the preparation of compound 21.

A solution of intermediate 95-I (150 mg), trifluoroacetic anhydride (240 mg), and $Et_3N$ (230 mg) in $CH_2Cl_2$ (10 ml) was stirred at 25° C. overnight and then concentrated. The resultant residue was purified by chromatography on silica gel (EtOAc/MeOH=20/1) to afford Intermediate 95-II (148 mg) in a 76% yield.

A solution of 20% $TFA/CH_2Cl_2$ (3 mL) was added to a solution of compound 95-II (148 mg) in $CH_2Cl_2$ (2 mL). The reaction mixture was stirred for 5 hours at room temperature and concentrated by removing the solvent. 1 M hydrochloric acid (3 mL) and $CH_2Cl_2$ (2 mL) were added to the residue. The mixture was stirred for another 10 minutes at room temperature. After removal of the supernatant, the solid was dried under vacuum to afford the hydrochloride salt of compound 95 (127 mg) in a 92% yield.

CI-MS ($M^+$+1): 645.3.

EXAMPLE 96

Preparation of Compound 96

Compound 96 was prepared in a manner similar to that used to prepare compound 43.

CI-MS ($M^+$+1): 515.4.

EXAMPLE 97

Preparation of Compound 97

Compound 97 was prepared in a manner similar to that used to prepare compound 43.

CI-MS ($M^+$+1): 519.3.

EXAMPLE 98

Preparation of Compound 98

Compound 98 was prepared in a manner similar to that used to prepare compound 43

CI-MS ($M^+$+1): 511.3. .

EXAMPLE 99

Preparation of Compound 99

Compound 99 was prepared in a manner similar to that used to prepare compound 43.
CI-MS (M$^+$+1): 459.3.

EXAMPLE 100

Preparation of Compound 100

Compound 100 was prepared in a manner similar to that used to prepare compound 43.
CI-MS (M$^+$+1): 638.5.

EXAMPLE 101

Preparation of Compound 101

Compound 101 was prepared in a manner similar to that used to prepare compound 43.
CI-MS (M$^+$+1): 605.5.

EXAMPLE 102

Preparation of Compound 102

Compound 102 was prepared in a manner similar to that used to prepare compound 43.
CI-MS (M$^+$+1): 553.4.

EXAMPLE 103

Preparation of Compound 103

Compound 103 was prepared in a manner similar to that used to prepare compound 44.
CI-MS (M$^+$+1): 549.4.

EXAMPLE 104

Preparation of Compound 104

Compound 104 was prepared in a manner similar to that used to prepare compound 44.
CI-MS (M$^+$+1): 523.4.

EXAMPLE 105

Preparation of Compound 105

Compound 105 was prepared in a manner similar to that used to prepare compound 44.
CI-MS (M$^+$+1): 524.4.

EXAMPLE 106

Preparation of Compound 106

Compound 106 was prepared in a manner similar to that used to prepare compound 33.
CI-MS (M$^+$+1): 580.4.

EXAMPLE 107

Preparation of Compound 107

Compound 107 was prepared in a manner similar to that used to prepare compound 44.
CI-MS (M$^+$+1): 580.4.

EXAMPLE 108

Preparation of Compound 108

Compound 108 was prepared in a manner similar to that used to prepare compound 44.
CI-MS (M$^+$+1): 563.4.

EXAMPLE 109

Preparation of Compound 109

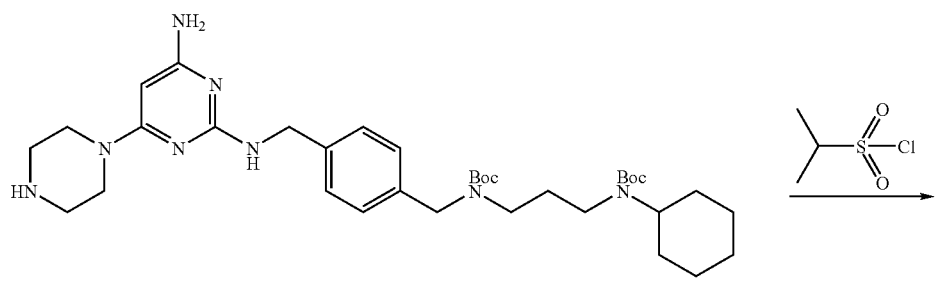

109-I

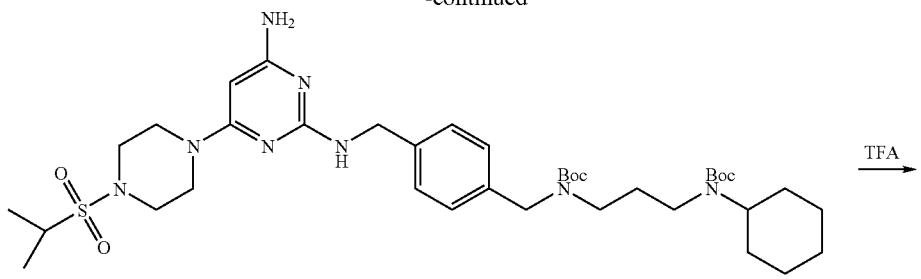

109-II

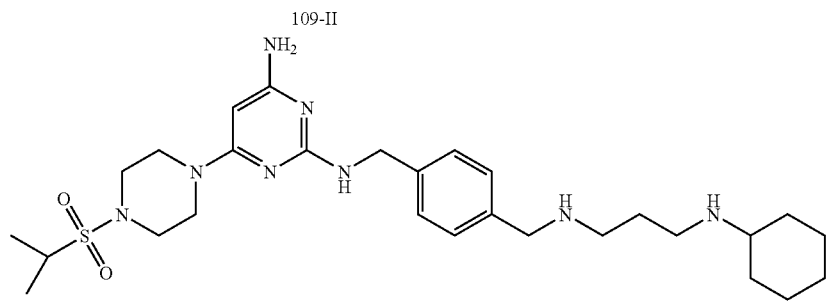

Compound 109

Intermediate 109-I was obtained during the preparation of compound 21.

A solution of intermediate 109-I (100 mg), isopropylsulfonyl chloride (35 mg), and Et₃N (30 mg) in CH₂Cl₂ (10 ml) was stirred at 25° C. for overnight and then concentrated. The resultant residue was purified by chromatography on silica gel (EtOAc/MeOH=20/1) to afford intermediate 109-II (100 mg) in a 86% yield.

A solution of 20% TFA/CH₂Cl₂ (3 mL) was added to a solution of compound 109-II (100 mg) in CH₂Cl₂ (2 mL). The reaction mixture was stirred for 5 hours at room temperature and concentrated by removing the solvent. 1 M hydrochloric acid (3 mL) and CH₂Cl₂ (2 mL) were added to the residue. The mixture was stirred for another 10 minutes at room temperature. After removal of the supernatant, the solid was dried under vacuum to afford the hydrochloride salt of compound 109 (80 mg) in a 87% yield.

CI-MS (M$^+$+1): 559.3.

EXAMPLE 110

Preparation of Compound 110

Compound 110 was prepared in a manner similar to that used to prepare compound 70.
CI-MS (M$^+$+1): 602.4.

EXAMPLE 111

Preparation of Compound 111

Compound 111 was prepared in a manner similar to that used to prepare compound 70.
CI-MS (M$^+$+1): 582.4.

EXAMPLE 112

Preparation of Compound 112

Compound 112 was prepared in a manner similar to that used to prepare compound 44.
CI-MS (M$^+$+1): 537.4.

EXAMPLE 113

Preparation of Compound 113

Compound 113 was prepared in a manner similar to that used to prepare compound 33.
CI-MS (M$^+$+1): 563.4.

EXAMPLE 114

Preparation of Compound 114

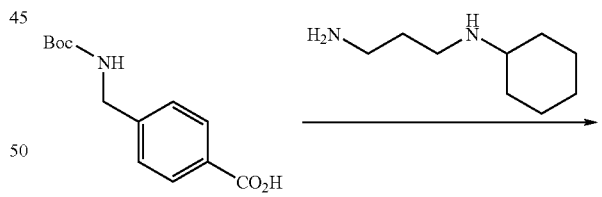

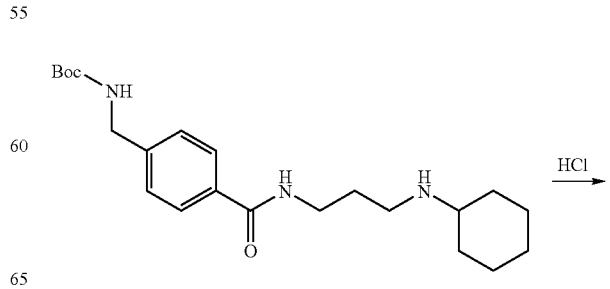

114-I

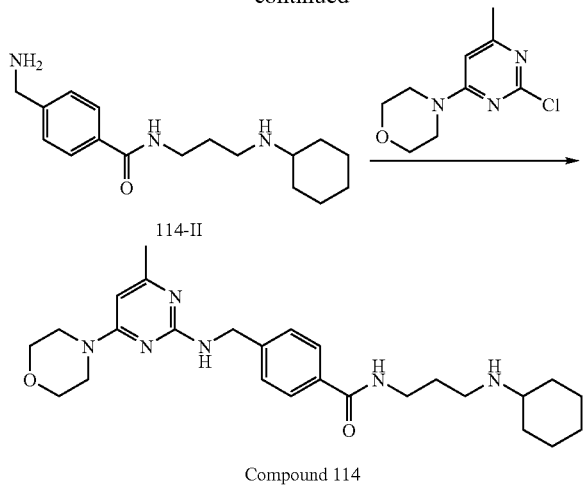

Compound 114

4-(tert-butoxycarbonylamino-methyl)benzoic acid (1,000 mg) was dissolved in CH$_2$Cl$_2$ (50 mL). N-cyclohexyl-1,3-propanediamine (745 mg), 1-hydroxybenzo-triazole hydrate (HOBt, 645 mg), 4-methylmorpholine (1,607 mg), and 1-(3-(dimethyl-amino)propyl)-3-ethylcarbodiimide hydrochloride (EDC, 740 mg) were added to the above solution sequentially. The reaction mixture was stirred at 25° C. for 18 hours and then was partitioned between water (150 mL) and EtOAc (2×150 mL). The combined organic layers were dried over Na$_2$SO$_4$ and were concentrated. The resultant residue was purified by chromatography on silica gel (EtOAc/MeOH=20/1) to afford intermediate 114-I (1,000 mg) in a 65% yield.

A solution of HCl in ether (1.0 M, 20 mL) was added to a solution of 114-I (1,000 mg) in MeOH (10 mL) at 25° C. The mixture was stirred for 12 hours at room temperature. After removal of the supernatant, the solid was dried under vacuum to afford the hydrochloride salt of intermediate 114-II (743 mg) in a 73% yield.

Diisopropylethylamine (134 mg) was added to a solution of intermediate 114-I (250 mg), intermediate 90-I prepared in Example 90 (184 mg), and NaI (22 mg) in 1-pentanol (5 mL). The reaction mixture was stirred for 15 hours at 140° C. and concentrated by removing the solvent under vacuum. The resultant mixture was dissolved in CH$_2$Cl$_2$, washed with water, dried with anhydrous MgSO$_4$, and concentrated to give a residue. The residue was purified by chromatography on silica gel (21% NH$_3$(aq)/MeOH=1/15) to give compound 114 (213 mg) in a 53% yield.
CI-MS (M$^+$+1): 467.3.

EXAMPLE 115

Preparation of Compound 115

Compound 115 was prepared in a manner similar to that used to prepare compound 44.
CI-MS (M$^+$+1): 536.4.

EXAMPLE 116

Preparation of Compound 116

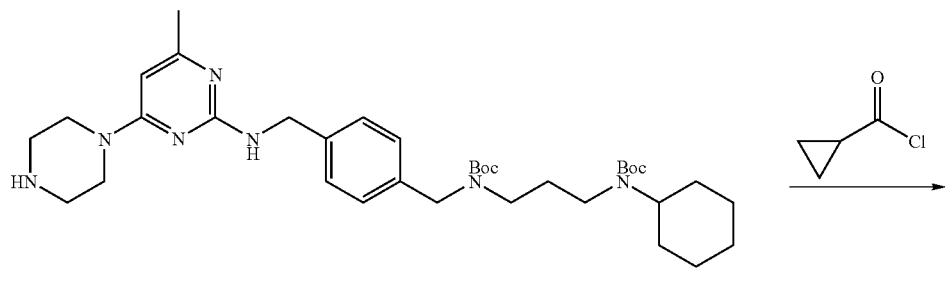

116-I

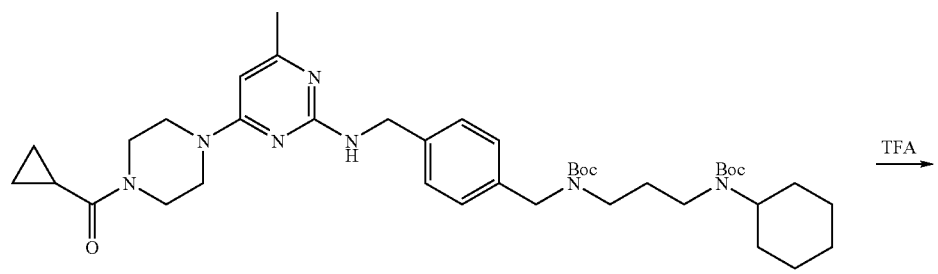

116-II

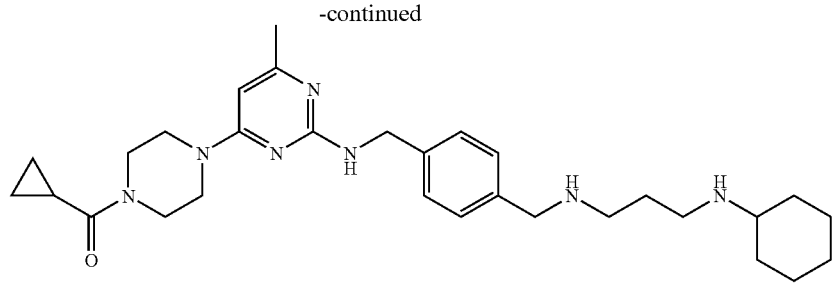

Compound 116

Intermediate 116-I was obtained during the preparation of compound 62.

Et₃N (0.18 mL) and cyclopropylcarbonyl chloride (96 mg) were added to a solution of intermediate 116-I (200 mg) in CH₂Cl₂ (10 mL). The reaction mixture was stirred overnight at room temperature and then concentrated by removing the solvent. The resultant mixture was dissolved in CHCl₃, washed with water, dried with anhydrous MgSO₄, and concentrated to give a residue. The residue was purified by chromatography on silica gel (EtOAc/Hexane=1/1) to afford intermediate 116-II (126 mg) in a 57% yield.

A solution of 20% TFA/CH₂Cl₂ (3 mL) was added to a solution of intermediate 116-II (126 mg) in CH₂Cl₂ (2 mL). The reaction mixture was stirred for 5 hours at room temperature and concentrated by removing the solvent. 1 M hydrochloric acid (3 mL) and CH₂Cl₂ (2 mL) were added to the residue. The resultant mixture was stirred for another 10 minutes at room temperature. After removal of the supernatant, the solid was dried under vacuum to afford the hydrochloride salt of compound 116 (93 mg) in an 80% yield.

CI-MS (M⁺+1): 520.4.

EXAMPLE 117

Preparation of Compound 117

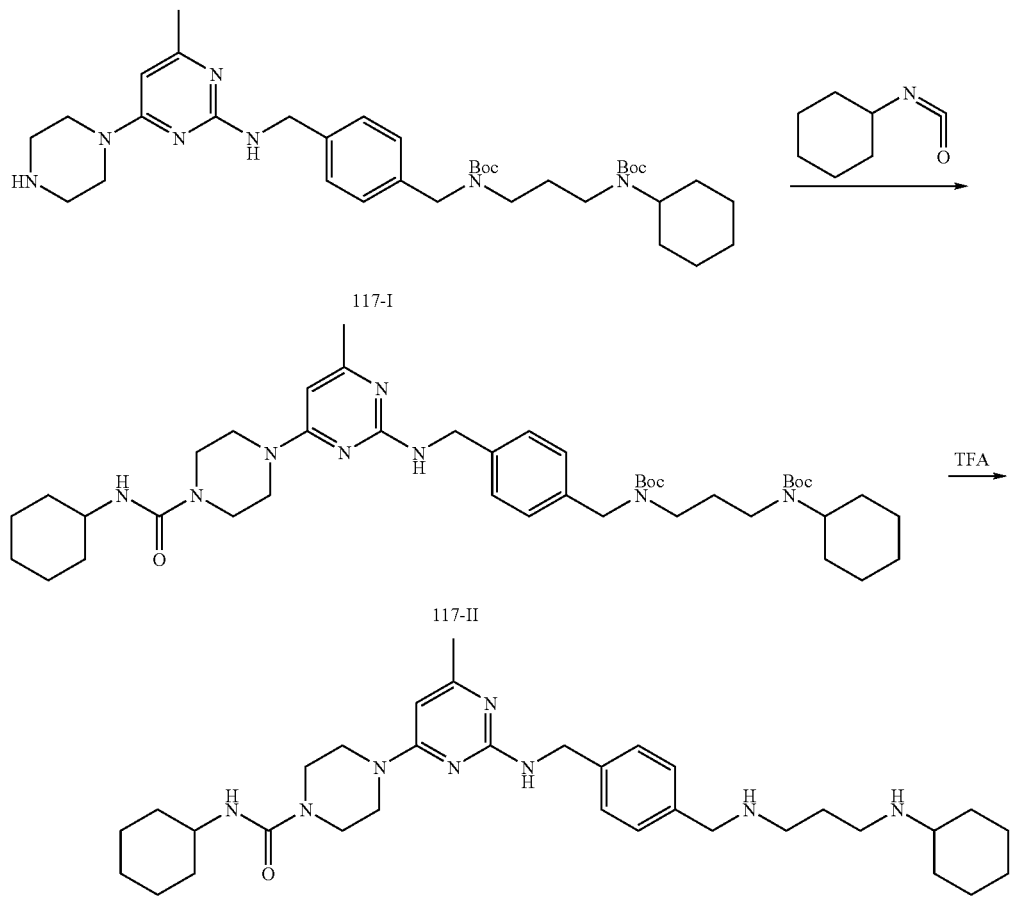

Compound 117

Intermediate 117-I was obtained during the preparation of compound 62.

A solution of Intermediate 117-I (200 mg), cyclohexyl isocyanate (42 mg), and Et$_3$N (62 mg) in CH$_2$Cl$_2$ (10 ml) was stirred at 25° C. for overnight and then concentrated. The resultant residue was purified by chromatography on silica gel (EtOAc/MeOH=20/1) to afford intermediate 117-II (172 mg) in a 72% yield.

A solution of 20% TFA/CH$_2$Cl$_2$ (3 mL) was added to a solution of compound 117-II (172 mg) in CH$_2$Cl$_2$ (2 mL). The reaction mixture was stirred for 5 hours at room temperature and concentrated by removing the solvent. 1 M hydrochloric acid (3 mL) and CH$_2$Cl$_2$ (2 mL) were added to the residue. The mixture was stirred for another 10 minutes at room temperature. After removal of the supernatant, the solid was dried under vacuum to afford the hydrochloride salt of compound 117 (145 mg) in a 91% yield.

CI-MS (M$^+$+1): 577.4.

EXAMPLE 118

Preparation of Compound 118

Compound 118 was prepared in a manner similar to that used to prepare compound 117.
CI-MS (M$^+$+1): 551.4.

EXAMPLE 119

Preparation of Compound 119

Compound 119 was prepared in a manner similar to that used to prepare compound 116.
CI-MS (M$^+$+1): 565.4.

EXAMPLE 120

Preparation of Compound 120

Compound 120 was prepared in a manner similar to that used to prepare compound 117.
CI-MS (M$^+$+1): 551.4.

EXAMPLE 121

Preparation of Compound 121

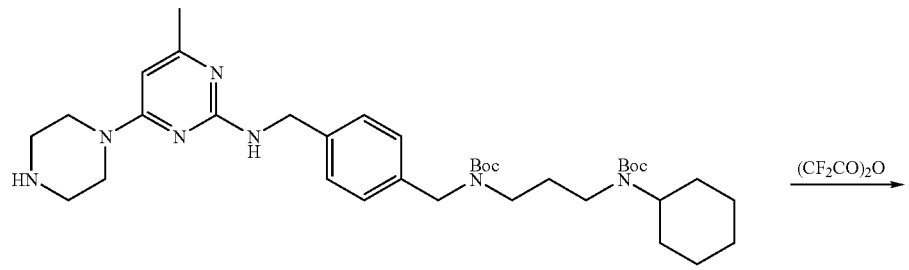

121-I

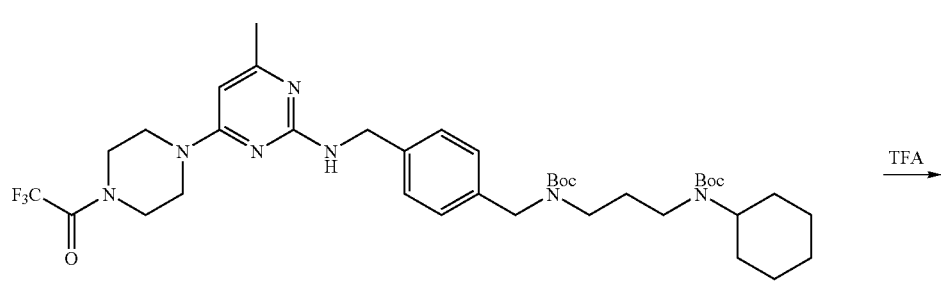

121-II

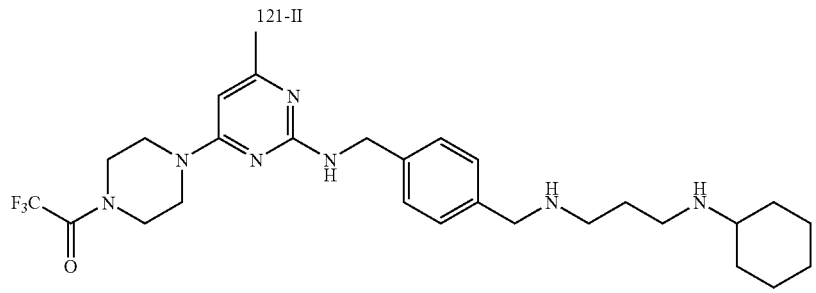

Compound 121

Intermediate 121-I was obtained during the preparation of compound 62.

A solution of intermediate 121-I (200 mg), trifluoroacetic anhydride (257 mg), and $Et_3N$ (155 mg) in $CH_2Cl_2$ (10 ml) was stirred at 25° C. for overnight and then concentrated. The resultant residue was purified by chromatography on silica gel (EtOAc/MeOH=15/1) to afford intermediate 121-II (163 mg) in a 71% yield.

A solution of 20% $TFA/CH_2Cl_2$ (3 mL) was added to a solution of compound 121-II (163 mg) in $CH_2Cl_2$ (2 mL). The reaction mixture was stirred for 5 hours at room temperature and concentrated by removing the solvent. 1 M hydrochloric acid (3 mL) and $CH_2Cl_2$ (2 mL) were added to the residue. The mixture was stirred for another 10 minutes at room temperature. After removal of the supernatant, the solid was dried under vacuum to afford the hydrochloride salt of compound 121 (127 mg) in an 84% yield.

CI-MS ($M^+$+1): 548.3.

EXAMPLE 122

Preparation of Compound 122

Compound 122 was prepared in a manner similar to that used to prepare compound 62.

CI-MS ($M^+$+1): 600.4.

EXAMPLE 123

Preparation of Compound 123

Compound 123 was prepared in a manner similar to that used to prepare compound 62.

CI-MS ($M^+$+1): 520.4.

EXAMPLE 124

Preparation of Compound 124

Compound 124 was prepared in a manner similar to that used to prepare compound 117.

CI-MS ($M^+$+1): 567.4.

EXAMPLE 125

Preparation of Compound 125

Compound 125 was prepared in a manner similar to that used to prepare compound 117.

CI-MS ($M^+$+1): 583.4.

EXAMPLE 126

Preparation of Compound 126

Compound 126 was prepared in a manner similar to that used to prepare compound 116.

CI-MS ($M^+$+1): 522.4.

EXAMPLE 127

Preparation of Compound 127

Compound 127 was prepared in a manner similar to that used to prepare compound 116.

CI-MS ($M^+$+1): 562.3.

EXAMPLE 128

Preparation of Compound 128

Compound 128 was prepared in a manner similar to that used to prepare compound 43.

CI-MS ($M^+$+1): 514.3.

EXAMPLE 129

Preparation of Compound 129

Compound 129 was prepared in a manner similar to that used to prepare compound 43.

CI-MS ($M^+$+1): 530.3.

EXAMPLE 130

Preparation of Compound 130

Compound 130 was prepared in a manner similar to that used to prepare compound 43.

CI-MS ($M^+$+1): 528.3.

EXAMPLE 131

Preparation of Compound 131

Compound 131 was prepared in a manner similar to that used to prepare compound 43.

CI-MS ($M^+$+1): 609.5.

EXAMPLE 132

Preparation of Compound 132

Compound 132 was prepared in a manner similar to that used to prepare compound 43.

CI-MS ($M^+$+1): 613.4.

EXAMPLE 133

Preparation of Compound 133

Compound 133 was prepared in a manner similar to that used to prepare compound 43.

CI-MS ($M^+$+1): 624.5.

EXAMPLE 134

Preparation of Compound 134

Compound 134 was prepared in a manner similar to that used to prepare compound 43.

CI-MS ($M^+$+1): 622.4.

EXAMPLE 135

Preparation of Compound 135

Compound 135 was prepared in a manner similar to that used to prepare compound 109.

CI-MS ($M^+$+1): 573.4.

EXAMPLE 136

Preparation of Compound 136

Compound 136 was prepared in a manner similar to that used to prepare compound 109.
CI-MS (M$^+$+1): 599.3.

EXAMPLE 137

Preparation of Compound 137

Compound 137 was prepared in a manner similar to that used to prepare compound 21.
CI-MS (M$^+$+1): 496.4.

EXAMPLE 138

Preparation of Compound 138

Compound 138 was prepared in a manner similar to that used to prepare compound 21.
CI-MS (M$^+$+1): 511.4.

EXAMPLE 139

Preparation of Compound 139

Compound 139 was prepared in a manner similar to that used to prepare compound 21.
CI-MS (M$^+$+1): 541.4.

EXAMPLE 140

Preparation of Compound 140

Compound 140 was prepared in a manner similar to that used to prepare compound 21.
CI-MS (M$^+$+1): 510.4.

EXAMPLE 141

Preparation of Compound 141

Compound 141 was prepared in a manner similar to that used to prepare compound 44.
CI-MS (M$^+$+1): 540.4.

EXAMPLE 142

Preparation of Compound 142

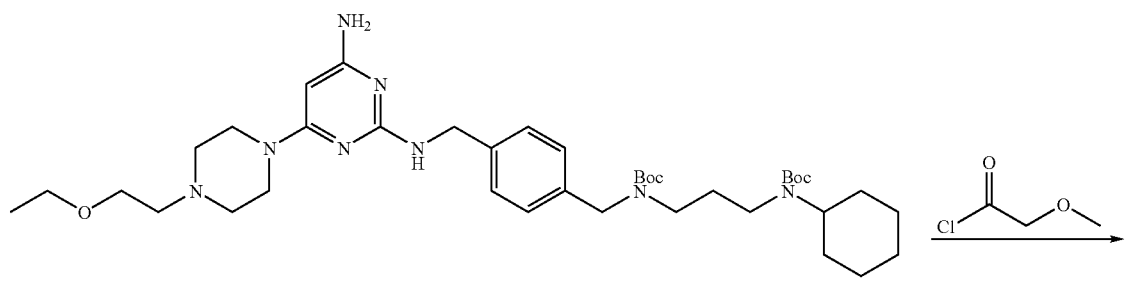

142-I

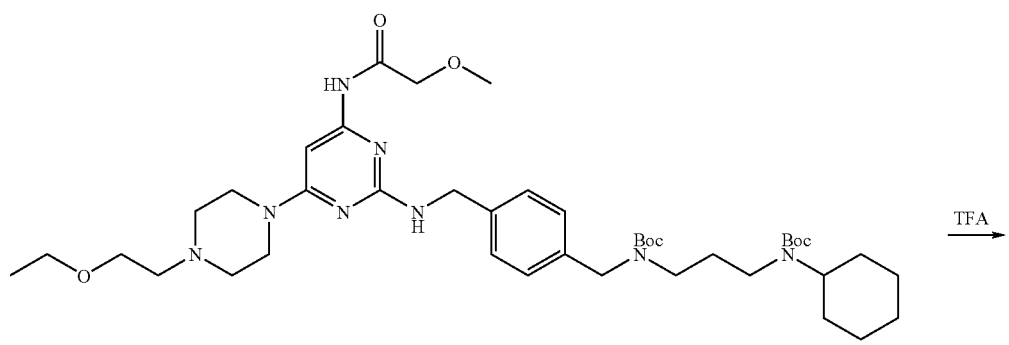

142-II

-continued

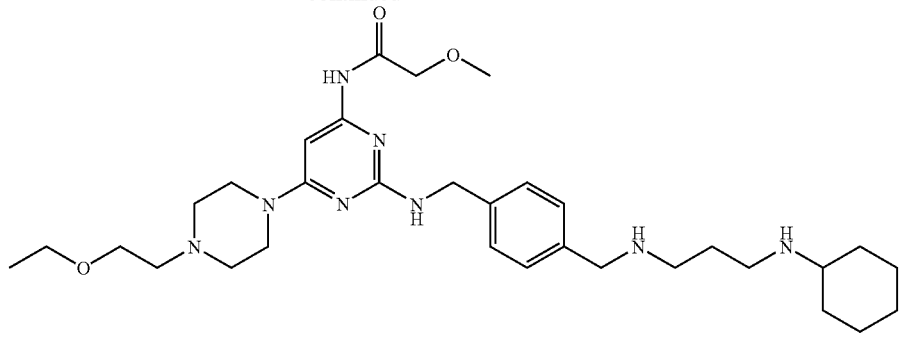

Compound 142

Intermediate 142-I was obtained during the preparation of compound 65.

A solution of intermediate 142-I (200 mg), methoxyacetyl chloride (60 mg), and Et$_3$N (60 mg) in CH$_2$Cl$_2$ (10 ml) was stirred at 0° C. for 1 hour and then was allowed to warm-up to room temperature within 3 hours. The solution was then concentrated to give a residue, which was purified by chromatography on silica gel (EtOAc/Hexane=1/1) to afford intermediate 142-II (107 g) in a 48% yield.

A solution of 20% TFA/CH$_2$Cl$_2$ (3 mL) was added to a solution of compound 142-II (107 mg) in CH$_2$Cl$_2$ (2 mL). The reaction mixture was stirred for 5 hours at room temperature and concentrated by removing the solvent. 1 M hydrochloric acid (3 mL) and CH$_2$Cl$_2$ (2 mL) were added to the residue. The mixture was stirred for another 10 minutes at room temperature. After removal of the supernatant, the solid was dried under vacuum to afford the hydrochloride salt of compound 142 (92 mg) in a 93% yield.

CI-MS (M$^+$+1): 597.4.

EXAMPLE 143

Preparation of Compound 143

Compound 143 was prepared in a manner similar to that used to prepare compound 142.

CI-MS (M$^+$+1): 641.4.

EXAMPLE 144

Preparation of Compound 144

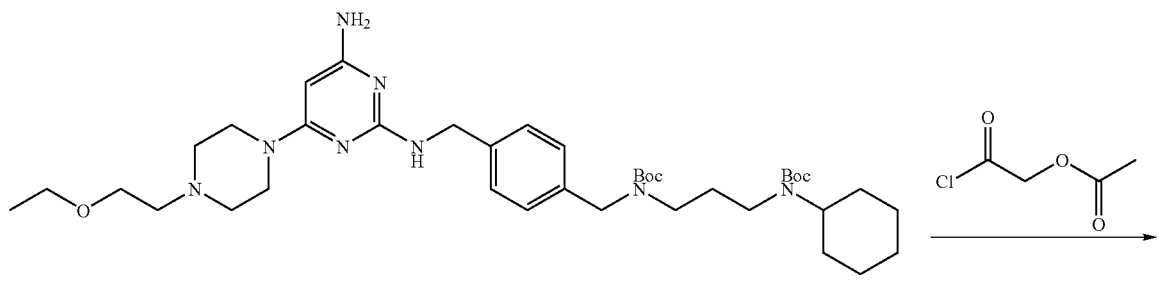

142-I

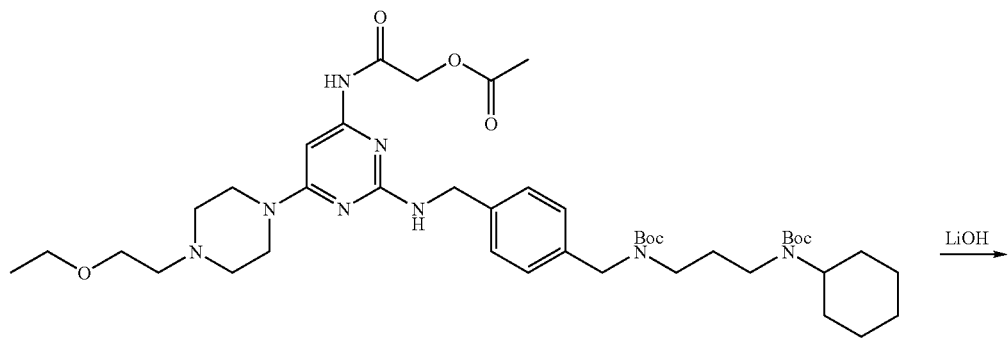

144-II

-continued

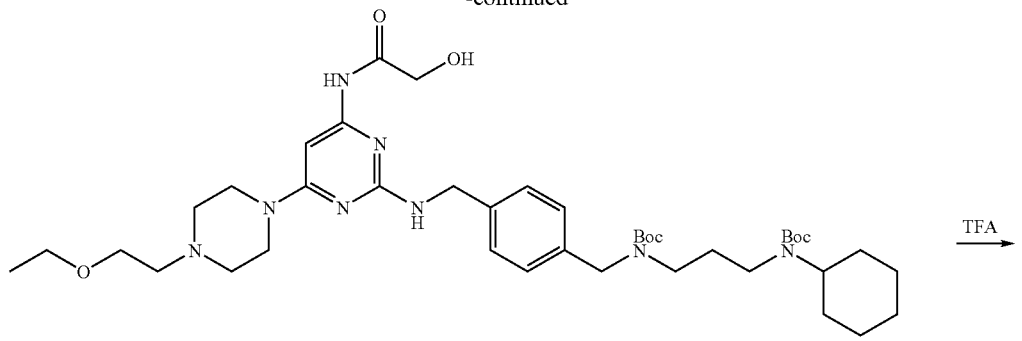

144-III

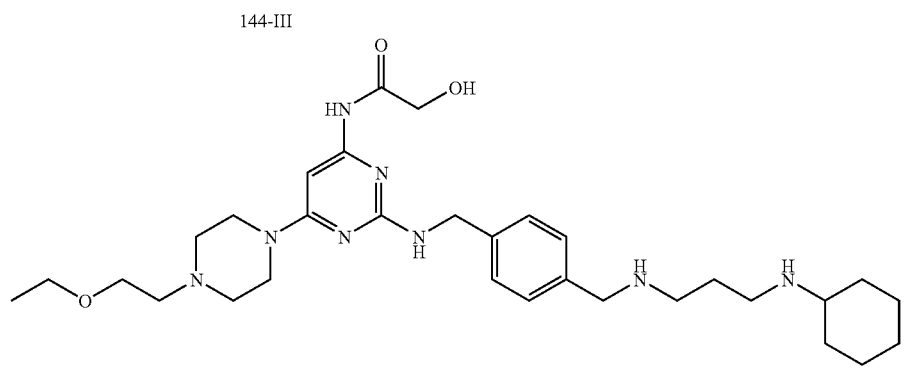

Compound 144

Acetyloxyacetyl chloride (304 mg) was added dropwise to a stirred solution of compound 142-I (200 mg) and Et$_3$N (0.3 mL) in CH$_2$Cl$_2$ (10 mL) at 0° C. for 2 hours to afford a residue. The resultant residue was purified by chromatography on silica gel (EtOAc/Hexane=1/1) to afford intermediate 144-II (200 mg) in a 90% yield.

An aqueous solution of 20% LiOH (4 mL) was added to 144-II (200 mg) in THF (5 mL). After stirring for 12 hour, the mixture was acidified with 2M HCl to obtain a crude product. The crude product was purified by chromatography on silica gel (EtOAc/MeOH=20/1) afforded intermediate 144-III (98 mg) in a 51% yield.

Compound 144-III (98 mg) was treated with 20% TFA/CH$_2$Cl$_2$ (2 mL) at room temperature for 12 hours and then concentrated. The resultant residue was purified by chromatography on silica gel (21% NH$_3$ (aq)/MeOH=1/19) to afford compound 144 (65 mg) in a 90% yield. Compound 144 was then treated with 1 M HCl (2 mL) in CH$_2$Cl$_2$ (2 mL) for 0.5 hour. The solvents were evaporated and the residue was treated with ether and filtered to afford the hydrochloride salt of compound 144.

CI-MS (M$^+$+1): 583.4.

EXAMPLE 145

Preparation of Compound 145

Compound 145 was prepared in the same manner as that used to prepare intermediate 144-II.
CI-MS (M$^+$+1): 625.5.

EXAMPLE 146

Preparation of Compound 146

Compound 146 was prepared in a manner similar to that used to prepare compound 144
CI-MS (M$^+$+1): 625.5..

EXAMPLE 147

Preparation of Compound 147

Compound 147 was prepared in a manner similar to that used to prepare compound 44.
CI-MS (M$^+$+1): 441.3.

EXAMPLE 148

Preparation of Compound 148

Compound 148 was prepared in a manner similar to that used to prepare compound 44.
CI-MS (M$^+$+1): 654.0.

EXAMPLE 149

Preparation of Compound 149

Compound 149 was prepared in a manner similar to that used to prepare compound 116.
CI-MS (M$^+$+1): 509.8.

EXAMPLE 150

Preparation of Compound 150

Compound 150 was prepared in a manner similar to that used to prepare compound 116.
CI-MS (M$^+$+1): 567.7.

EXAMPLE 151

Preparation of Compound 151

Compound 151 was prepared in a manner similar to that used to prepare compound 116.
CI-MS (M++1): 537.7.

EXAMPLE 152

Preparation of Compound 152

Compound 152 was prepared in a manner similar to that used to prepare compound 116.
CI-MS (M++1): 620.3.

EXAMPLE 153

Preparation of Compound 153

Compound 153 was prepared in a manner similar to that used to prepare compound 116.
CI-MS (M++1): 551.8.

EXAMPLE 154

Preparation of Compound 154

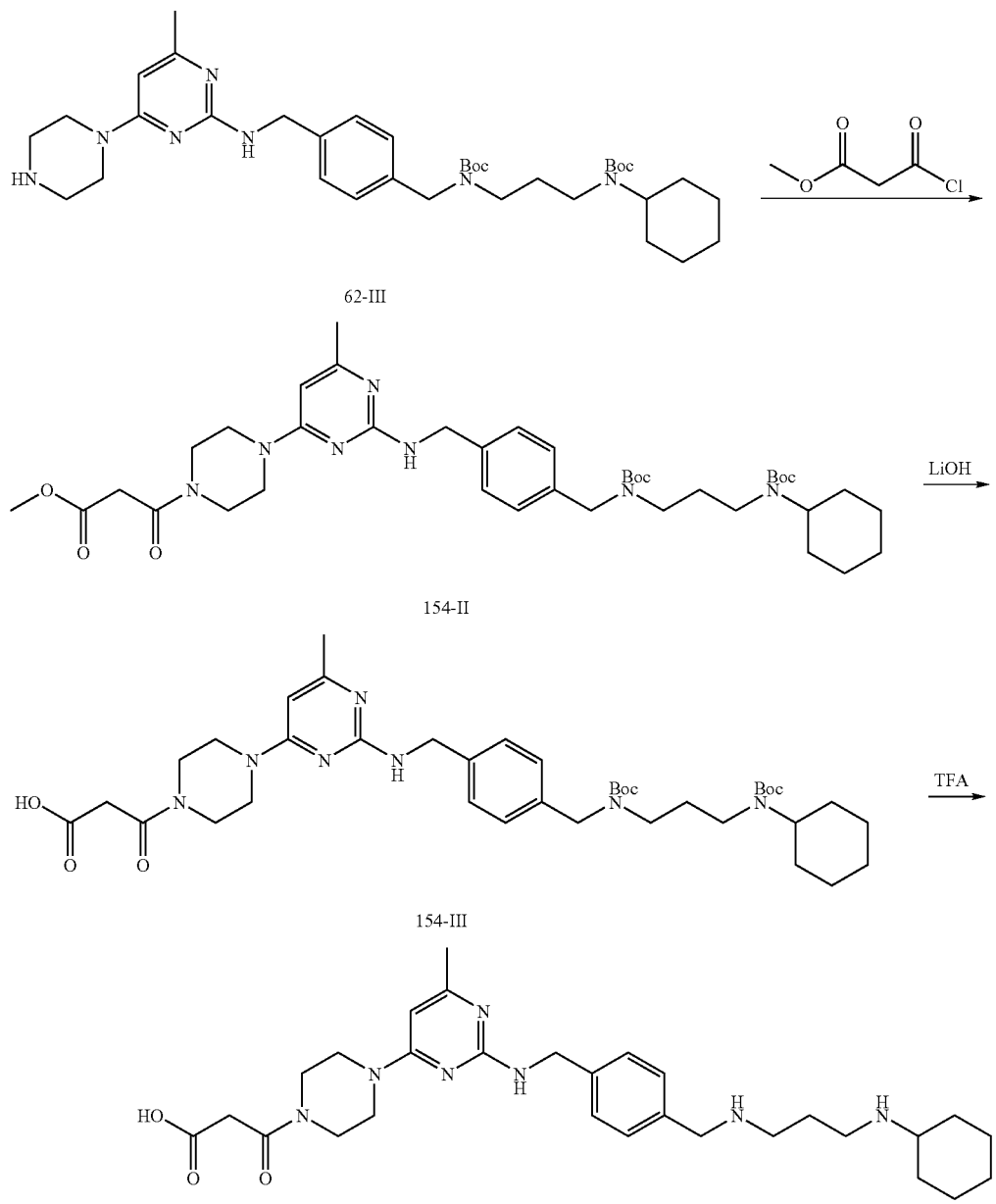

Compound 154 was prepared from compound 62-III in a manner similar to that used to prepare compound 144.
CI-MS (M$^+$+1): 538.4.

EXAMPLE 155

Preparation of Compound 155

Compound 155 was prepared from compound 62-III in a manner similar to that used to prepare compound 144.
CI-MS (M$^+$+1): 552.4.

EXAMPLE 156

Preparation of Compound 156

Compound 156 was prepared from compound 62-III in a manner similar to that used to prepare compound 144.
CI-MS (M$^+$+1): 510.3.

EXAMPLE 157

Preparation of Compound 157

Compound 157 was prepared from compound 109-I in a manner similar to that used to prepare compound 109.
CI-MS (M$^+$+1): 569.4.

EXAMPLE 158

Preparation of Compound 158

Compound 158 was prepared from compound 109-I in a manner similar to that used to prepare compound 109.
CI-MS (M$^+$+1): 539.4.

EXAMPLE 159

Preparation of Compound 159

Compound 159 was prepared from compound 109-I in a manner similar to that used to prepare compound 109.
CI-MS (M$^+$+1): 525.4.

EXAMPLE 160

Preparation of Compound 160

Compound 160 was prepared from compound 109-I in a manner similar to that used to prepare compound 109.
CI-MS (M$^+$+1): 567.4.

EXAMPLE 161

Preparation of Compound 161

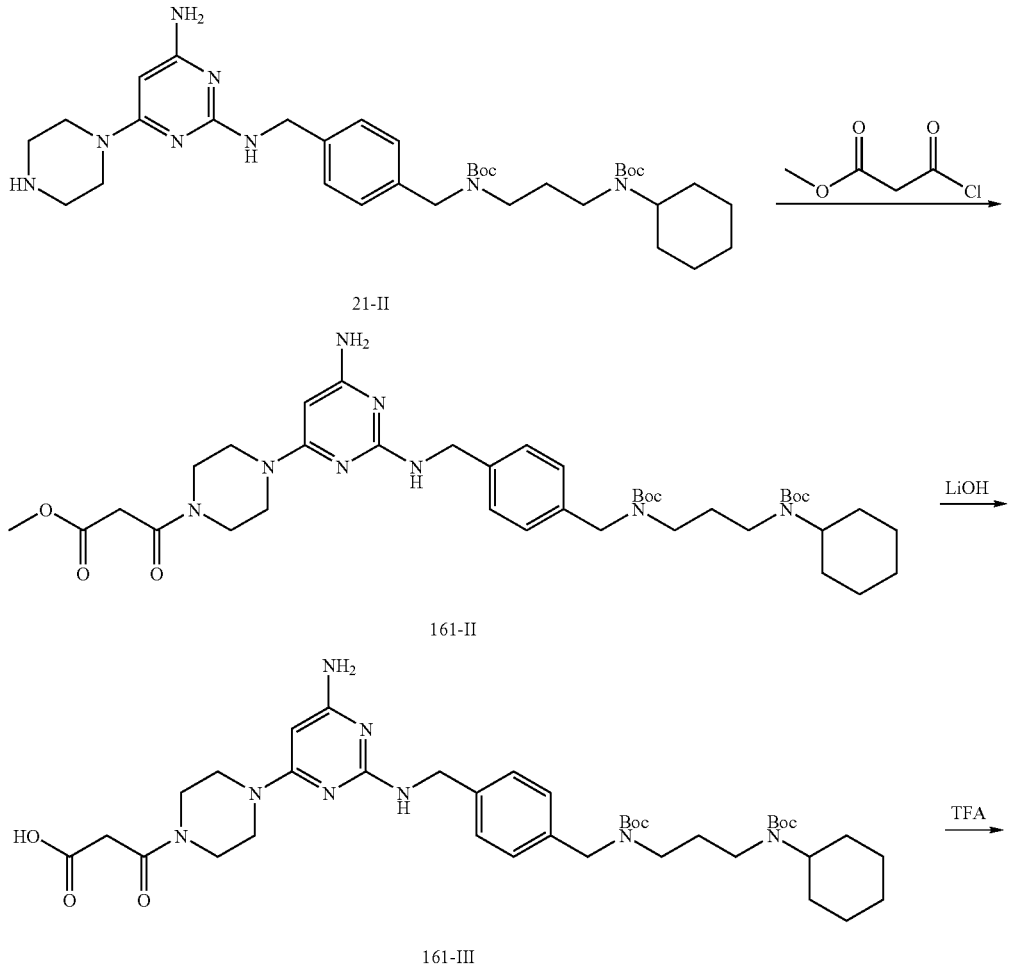

-continued

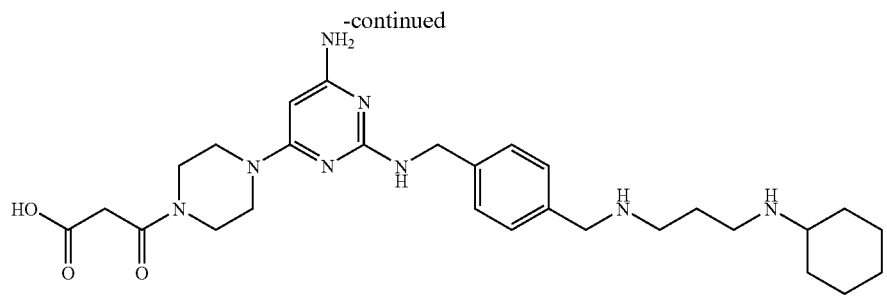

Compound 161

Compound 161 was prepared from compound 21-II in a manner similar to that used to prepare compound 154.
CI-MS (M$^+$+1): 539.3.

EXAMPLE 162

Preparation of Compound 162

Compound 162 was prepared from compound 21-II in a manner similar to that used to prepare compound 154.
CI-MS (M$^+$+1): 511.3.

EXAMPLE 163

Preparation of Compound 163

Compound 163 was prepared from compound 21-II in a manner similar to that used to prepare compound 154.
CI-MS (M$^+$+1): 511.1.

EXAMPLE 164

Preparation of Compound 164

Compound 164 was prepared from compound 21-II in a manner similar to that used to prepare compound 154.
CI-MS (M$^+$+1): 511.7.

EXAMPLE 165

Preparation of Compound 165

Compound 165 was prepared from compound 21-II in a manner similar to that used to prepare compound 154.
CI-MS (M$^+$+1): 539.4.

EXAMPLE 166

Preparation of Compound 166

Compound 166 was prepared in a manner similar to that used to prepare compound 43.
CI-MS (M$^+$+1): 597.4.

EXAMPLE 167

Preparation of Compound 167

Compound 167 was prepared in a manner similar to that used to prepare compound 43.
CI-MS (M$^+$+1): 613.4.

EXAMPLE 168

Preparation of Compound 168

Compound 168 was prepared in a manner similar to that used to prepare compound 109.
CI-MS (M$^+$+1): 553.4.

EXAMPLE 169

Preparation of Compound 169

Compound 169 was prepared from compound 34-I in a manner similar to that used to prepare compound 34.
CI-MS (M$^+$+1): 520.4.

EXAMPLE 170

Preparation of Compound 170

Compound 170 was prepared from compound 34-I in a manner similar to that used to prepare compound 34.
CI-MS (M$^+$+1): 492.3.

EXAMPLE 171

Preparation of Compound 171

Compound 171 was prepared from compound 70-I and the corresponding thioisocyanate in a manner similar to that used to prepare compound 70.
CI-MS (M$^+$+1): 570.3.

EXAMPLE 172

Preparation of Compound 172

Compound 172 was prepared from compound 70-I and the corresponding thioisocyanate in a manner similar to that used to prepare compound 70.
CI-MS (M$^+$+1): 539.4.

EXAMPLE 173

Preparation of Compound 173

Compound 173 was prepared from compound 70-I and the corresponding thioisocyanate in a manner similar to that used to prepare compound 70.
CI-MS (M$^+$+1): 574.3.

EXAMPLE 174

Preparation of Compound 174

Compound 174 was prepared from compound 70-I and the corresponding thioisocyanate in a manner similar to that used to prepare compound 70.
CI-MS ($M^+$+1): 568.3.

EXAMPLE 175

Preparation of Compound 175

Compound 175 was prepared from compound 70-I and the corresponding thioisocyanate in a manner similar to that used to prepare compound 70.
CI-MS ($M^+$+1): 553.4.

EXAMPLE 176

Preparation of Compound 176

Compound 176 was prepared from compound 70-I and the corresponding thioisocyanate in a manner similar to that used to prepare compound 70.
CI-MS ($M^+$+1): 568.3.

EXAMPLE 177

Preparation of Compound 177

Compound 177 was prepared from compound 70-I and the corresponding thioisocyanate in a manner similar to that used to prepare compound 70.
CI-MS ($M^+$+1): 552.2.

EXAMPLE 178

Preparation of Compound 178

Compound 178 was prepared from compound 70-I and the corresponding thioisocyanate in a manner similar to that used to prepare compound 70.
CI-MS ($M^+$+1): 554.2.

EXAMPLE 179

Preparation of Compound 179

Compound 179 was prepared from compound 70-I and the corresponding thioisocyanate in a manner similar to that used to prepare compound 70.
CI-MS ($M^+$+1): 584.3.

EXAMPLE 180

Preparation of Compound 180

Compound 180 was prepared from compound 70-I and the corresponding thioisocyanate in a manner similar to that used to prepare compound 70.
CI-MS ($M^+$+1): 598.5.

EXAMPLE 181

Preparation of Compound 181

Compound 181 was prepared from compound 70-I and the corresponding thioisocyanate in a manner similar to that used to prepare compound 70.
CI-MS ($M^+$+1): 553.4.

EXAMPLE 182

Preparation of Compound 182

Compound 182 was prepared from compound 109-I in a manner similar to that used to prepare compound 109.
CI-MS ($M^+$+1): 566.3.

EXAMPLE 183

Preparation of Compound 183

Compound 183 was prepared from compound 109-I in a manner similar to that used to prepare compound 109.
CI-MS ($M^+$+1): 524.3.

EXAMPLE 184

Preparation of Compound 184

Compound 184 was prepared from compound 109-I in a manner similar to that used to prepare compound 109.
CI-MS ($M^+$+1): 565.3.

EXAMPLE 185

Preparation of Compound 185

Compound 185 was prepared from compound 109-I in a manner similar to that used to prepare compound 109.
CI-MS ($M^+$+1): 550.3.

EXAMPLE 186

Preparation of Compound 186

Compound 186 was prepared from compound 109-I in a manner similar to that used to prepare compound 109.
CI-MS ($M^+$+1): 547.4.

EXAMPLE 187

Preparation of Compound 187

Compound 187 was prepared from compound 35-I in a manner similar to that used to prepare compound 35.
CI-MS ($M^+$+1): 533.4.

EXAMPLE 188

Preparation of Compound 188

Compound 188 was prepared from compound 33-I in a manner similar to that used to prepare compound 33.
CI-MS ($M^+$+1): 537.4.

EXAMPLE 189

Preparation of Compound 189

Compound 189 was prepared from compound 33-I in a manner similar to that used to prepare compound 33.
CI-MS (M$^+$+1): 583.4.

EXAMPLE 190

Preparation of Compound 190

Compound 190 was prepared from compound 33-I in a manner similar to that used to prepare compound 33.
CI-MS (M$^+$+1): 537.4.

EXAMPLE 191

Preparation of Compound 191

Compound 191 was prepared in a manner similar to that used to prepare compound 44.
CI-MS (M$^+$+1): 463.2.

EXAMPLE 192

Preparation of Compound 192

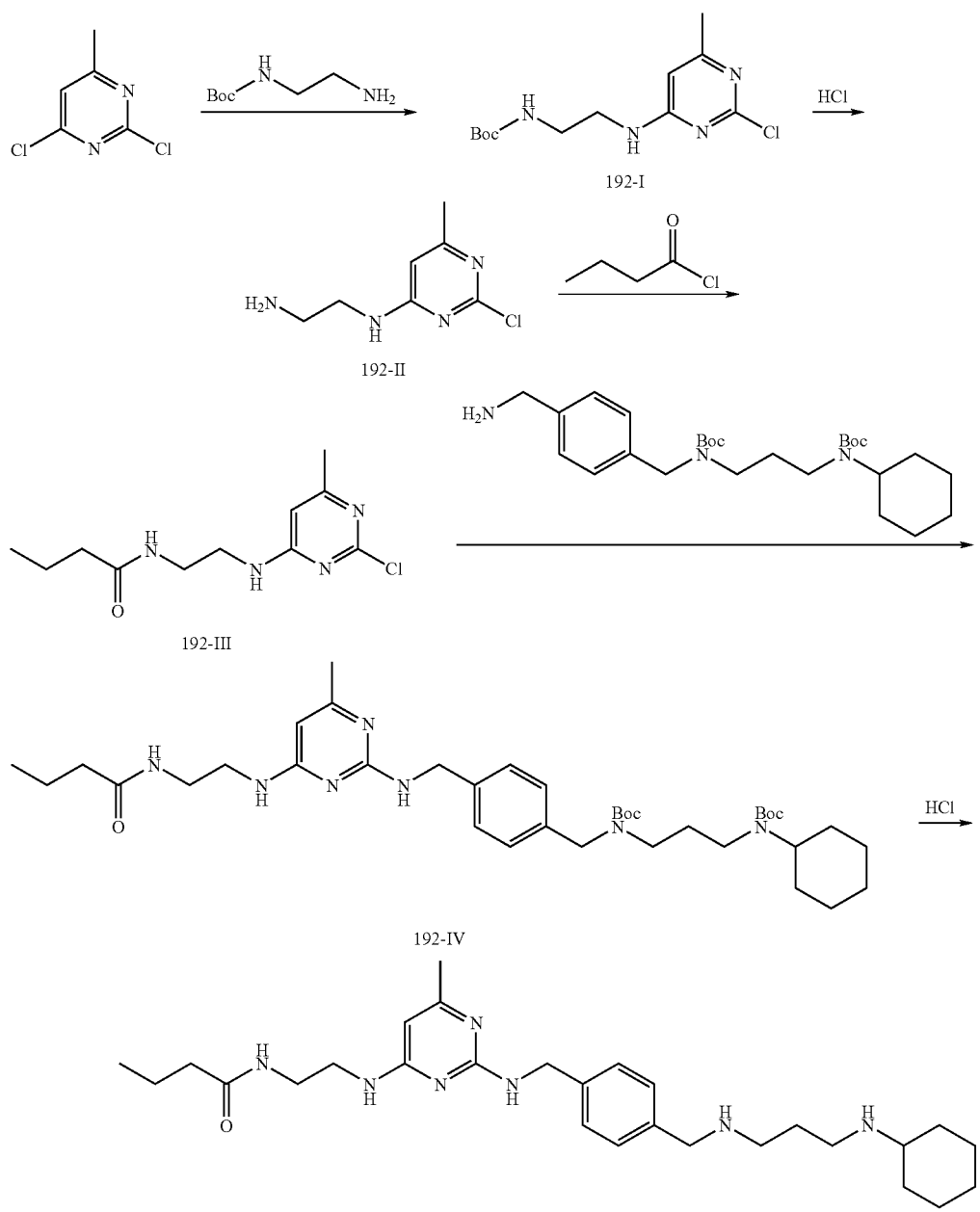

tert-Butoxycarbonylaminoethylamine (5.4 g) was added to a solution of 2,4-dichloro-6-methylpyrimidine (5 g) in THF (350 mL). The reaction mixture was stirred at 0° C. for 1 hour and then was allowed to warm-up to room temperature within 3 hours. After the solution was then concentrated and treated with 1 M HCl (40 mL) in MeOH (50 mL), it was stirred at room temperature for another 8 hours. The solution was then again concentrated. The resultant residue was then neutralization with $NH_4OH$ and extracted with $CH_2Cl_2$. The solution was concentrated and the residue was purified by chromatography on silica gel (MeOH as eluant) to afford intermediate 192-II (4.6 g) in a 90% yield.

Butyryl chloride (430 mg) was added to a solution of 192-II (680 mg) in $CH_2Cl_2$ (35 mL). After 1 hour of stirring at room temperature, the solution was concentrated and 1-pentanol (2 mL) was added. Diisopropylethylamine (0.2 mL), intermediate 8-III prepared in example 8 (150 mg), and NaI (110 mg) were also added to this solution, which was then stirred for 24 hours at 120° C. The resultant mixture was dissolved in $CH_2Cl_2$, washed with water, dried with anhydrous $MgSO_4$ and evaporated to afford 192-IV in a 50% yield after purification by chromatography on silica gel (EtOAc/MeOH=5/1).

192-IV (950 mg) was treated with 1 M HCl (20 mL) and stirred for overnight. After the supernatant was removed, compound 192 was collected by filtration.

CI-MS ($M^+$+1): 498.4.

EXAMPLE 193

Preparation of Compound 193

Compound 193 was prepared in a manner similar to that used to prepare compound 192.
CI-MS ($M^+$+1): 493.4.

EXAMPLE 194

Preparation of Compound 194

Compound 194 was prepared in a manner similar to that used to prepare compound 192.
CI-MS ($M^+$+1): 542.4.

EXAMPLE 195

Preparation of Compound 195

Compound 195 was prepared in a manner similar to that used to prepare compound 192.
CI-MS ($M^+$+1): 510.4.

EXAMPLE 196

Preparation of Compound 196

Compound 196 was prepared in a manner similar to that used to prepare compound 192.
CI-MS ($M^+$+1): 526.4.

EXAMPLE 197

Preparation of Compound 197

Compound 197 was prepared in a manner similar to that used to prepare compound 192.
CI-MS ($M^+$+1): 524.4.

EXAMPLE 198

Preparation of Compound 198

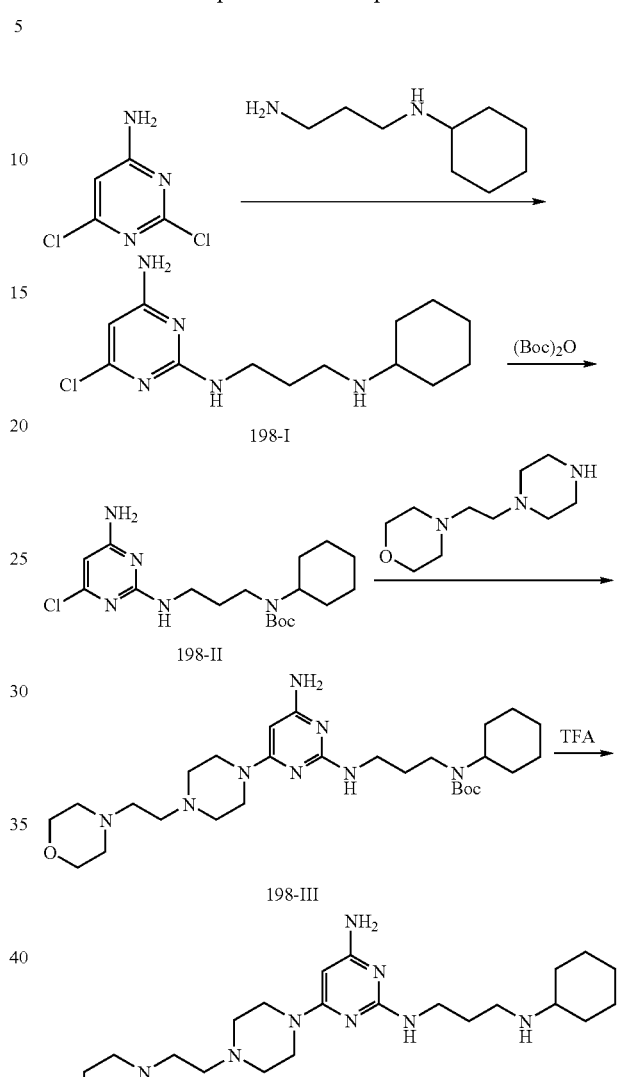

2,4-Dichloro-6-aminopyrimidine (2.0 g) was dissolved in 1-pentanol (10 mL). Cyclohexylaminopropylamine (1.92 g) was then added. The reaction mixture was stirred at 120° C. for 24 hours. The solution was concentrated and the residue was purified by column chromatography on silica gel (EtOAc/Hexane=1/3) to afford 198-I (1.8 mg) in a 52% yield.

A solution of intermediate 198-I (1.8 g) reacted with $(Boc)_2$ O in $CH_2Cl_2$ (120 mL) for 8 hours at 25° C. The solution was concentrated and the residue was purified by column chromatography on silica gel (EtOAc/Hexane=1/9) to give pure 198-II (1.06 g) in a 70% yield.

$N^1$-Morpholine-$N^1$-piperazine ethane (0.3 g) was added to 198-II (130 mg). The mixture was stirred at 120° C. for 8 hours. The solution was concentrated and the residue was treated with water and extracted with $CH_2Cl_2$. The organic layer was collected, concentrated to give a crude product, which was purified by column chromatography on silica gel (EtOAc/MeOH=10/1) to afford 198-III (100 mg) in a 72% yield.

Compound 198-III (100 mg) was treated with 20% TFA/CH$_2$Cl$_2$ (2 mL) for 8 hours and then concentrated. The resultant residue was purified by chromatography on silica gel (21% NH$_3$ (aq)/MeOH=1/19) to afford Compound 198 (69 mg) in a 85% yield. Compound 198 was then treated with 1 M HCl (2 mL) in CH$_2$Cl$_2$ (2 mL) for 0.5 hour. After the solvents were evaporated, the residue was treated with ether and filtered to give hydrochloride salt of 198.

CI-MS (M$^+$+1): 447.4.

EXAMPLE 199

Preparation of Compound 199

Compound 199 was prepared in a manner similar to that used to prepare compound 197.
CI-MS (M$^+$+1): 408.3.

EXAMPLE 200

Preparation of Compound 200

Compound 200 was prepared in a manner similar to that used to prepare compound 197.
CI-MS (M$^+$+1): 422.2.

EXAMPLE 201

Preparation of Compound 201

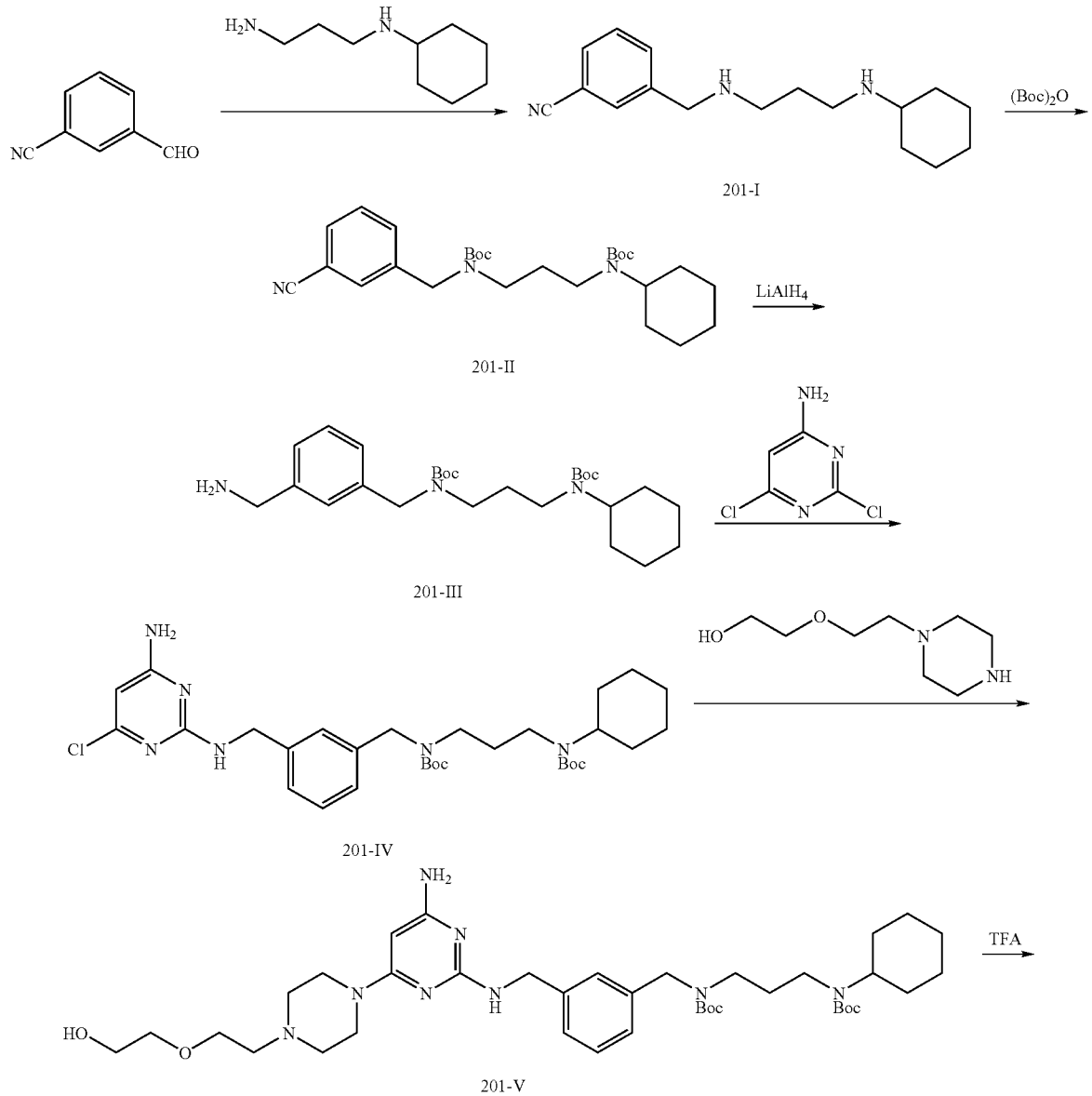

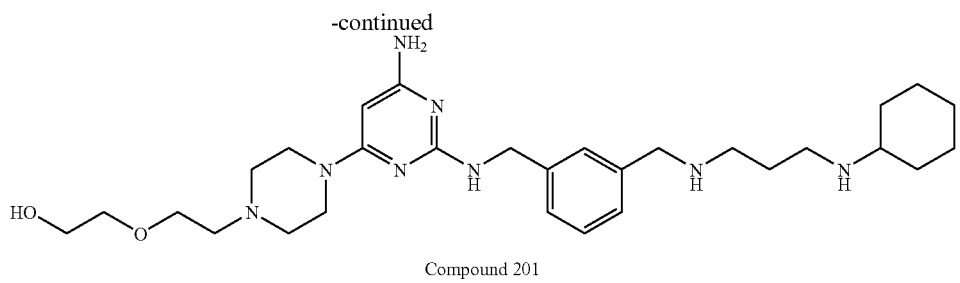

Compound 201

A solution of 3-cyanobenzylaldehyde (1.0 g) and N-cyclohexyl-1,3-propane-diamine (2.4 g) in CH₃OH (150 mL) was heated to 60° C. for 18 hours. After cooling to room temperature, NaBH₄ (1.5 g) was slowly added to the above solution. The mixture was stirred for another 30 minutes. The mixture was then concentrated, quenched with NH₄Cl (aq), and extracted with CH₂Cl₂. The organic layers were combined, dried with anhydrous MgSO₄, and concentrated to give a residue. The residue was purified by chromatography on silica gel (EtOAc/Et₃N=7/3) to afford Intermediate 201-I (1.6 g) in a 80% yield.

A solution of Intermediate 201-I (1.6 g) and Boc₂O (3.5 g) in CH₂Cl₂ (160 ml) was stirred at 25° C. for 15 hours and then concentrated. The resultant residue was purified by chromatography on silica gel (EtOAc/Hexane=1/1) to afford Intermediate 201-II as a yellow oil (2.36 g) in a 85% yield.

A solution of Intermediate 201-II and LiAlH₄ (2.3 g) in THF (230 mL) was stirred at 0° C. for 4 hours. After Na₂SO₄·10H₂O was added, the solution was stirred at room temperature for 0.5 hour. The solution was then filtered through a celite pad. The filtrate was dried over anhydrous MgSO₄ and concentrated to give a residue. The residue was purified by column chromatography on silica gel (using MeOH as an eluant) to afford Intermediate 201-III (1.1 g) in a 50% yield.

Diisopropylethylamine (1.1 mL) was added to a solution of 2,4-dichloro-6-aminopiperidine (0.41 g) and Intermediate 201-III (1.1 g) in 1-pentanol (10 mL). The reaction mixture was stirred overnight at 120° C. The solvent was removed under vacuum and the residue was purified by column chromatography on silica gel (EtOAc/Hexane=3/7) to afford 201-IV (1.0 g) in a 65% yield.

To a solution of Intermediate 201-IV (1.0 g) in 1-pentanol (1 mL) was added N¹-hydroxyethoxyethyl piperazine (0.25 g). After the solution was stirred at 120° C. for 8 hours, it was concentrated. The residue thus obtained was purified by column chromatography on silica gel (EtOAc/MeOH=4/1) to afford Intermediate 201-V (730 mg) in a 60% yield.

A solution of 20% TFA/CH₂Cl₂ (5 mL) was added to a solution of Intermediate 201-V (0.73 g) in CH₂Cl₂ (2 mL). The reaction mixture was stirred for 5 hours at room temperature and concentrated by removing the solvent. The resultant residue was purified by column chromatography on silica gel (21% NH₃ (aq)/MeOH=1/19) to afford Compound 201 (434 mg) in a 85% yield. Compound 201 was then treated with 1 M HCl (4 mL) in CH₂Cl₂ (2 mL) for 0.5 hour. After the solvents were removed, the residue was treated with ether and filtered to give hydrochloride salt of compound 201.

CI-MS (M⁺+1): 541.3.

EXAMPLE 202

Preparation of Compound 202

Compound 202 was prepared in a manner similar to that used to prepare compound 200.

CI-MS (M⁺+1): 566.4.

EXAMPLE 203

Preparation of Compound 203

Compound 203 was prepared in a manner similar to that used to prepare compound 200.

CI-MS (M⁺+1): 525.4.

EXAMPLE 204

Preparation of Compound 204

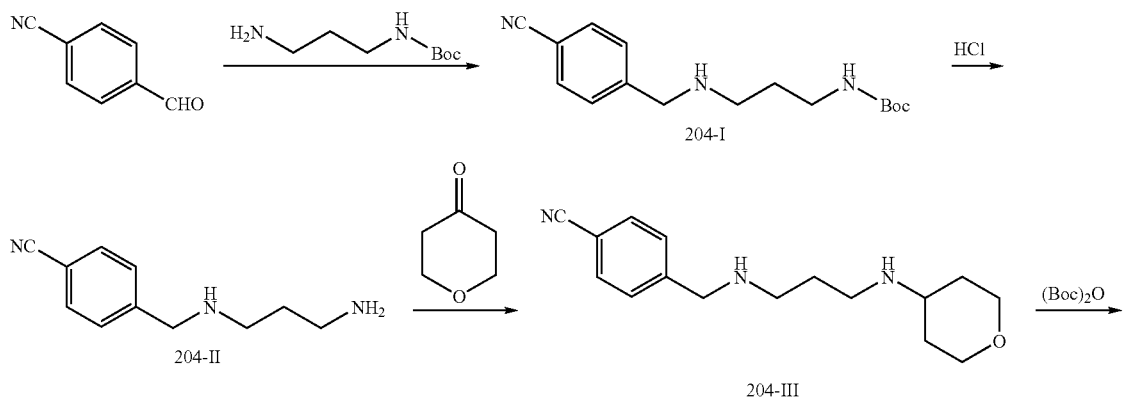

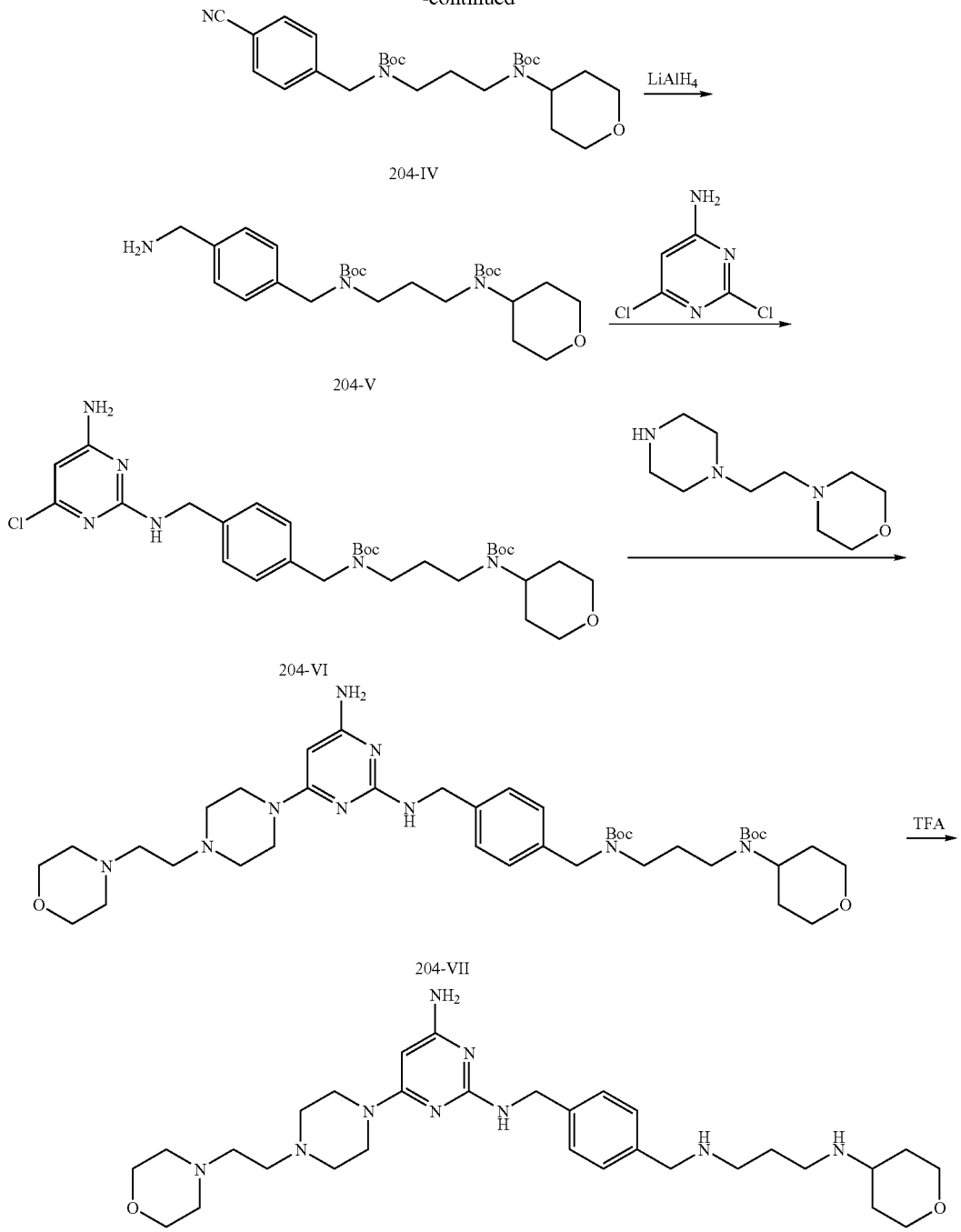

Compound 204

A solution of 4-cyanobenzaldehyde (3.0 g) and tert-butoxyaminopropylamine (3.9 g) in MeOH (60 mL) was heated at 60° C. for 6 hours. After the solution was cooled to room temperature, NaBH$_4$ (2.5 g) was slowly added. After the mixture was stirred for 30 minutes, it was concentrated, quenched with NH$_4$Cl (aq.), and extracted with CH$_2$Cl$_2$. The organic layer was separated and concentrated. The residue thus obtained was purified by column chromatography on silica gel (EtOAc/Hexane=1/3) to afford Intermediate 204-I (5.8 g) in a 88% yield.

A solution of intermediate 204-I (5.8 g) and 1 M HCl (40 mL) in MeOH (50 mL) was stirred at room temperature for 8 hours. The solution was then concentrated and the resultant residue was neutralization with NH$_4$OH, and extracted with CH$_2$Cl$_2$. The organic layer was separated and concentrated. The residue thus obtained was purified by column chromatography on silica gel (using MeOH as an eluant) to afford Intermediate 204-II (3.4 g) in a 90% yield.

To a solution of compound 204-II (3.5 g) in MeOH (50 mL) was added tetrahydro-4H-pyran-4-one (2 g). The solution was then heated at 60° C. for 6 hours. After the solution was cooled to room temperature, NaBH$_4$ (1.85 g) was slowly added. After the mixture was stirred 30 minutes, it was concentrated, quenched with NH$_4$Cl (aq.), and extracted with CH$_2$Cl$_2$. The organic layer was separated and concentrated. The residue thus obtained was purified by column chromatography on silica gel (EtOAc/MeOH=1/1) to afford Intermediate 204-III (3.5 g) in a 70% yield.

A solution of Intermediate 204-III (12.99 g) and Boc$_2$O (20.76 g) in 1,4-dioxane (200 ml) and H$_2$O (100 mL) was stirred at room temperature for 15 hours and then concentrated. The resultant residue was purified by column chromatography on silica gel (EtOAc/Hexane=1/3) to afford Intermediate 204-IV (21.5 g) in a 95% yield.

LiAlH4 (8.6 g) was added to a solution of Intermediate 204-IV (21.5 g) in THF (500 mL) and ether (500 mL). After the solution was stirred at 0° C. for 2 hours, it was treated with saturated aq. NH$_4$Cl solution, extracted with CH$_2$Cl$_2$, and concentrated. The residue thus obtained was purified by column chromatography on silica gel (using MeOH as an eluant) to afford Intermediate 204-V (13.0 g) in a 60% yield.

A solution of Intermediate 204-V (7.6 g) in 1-pentanol (50 mL) was reacted with 2,4-dichloro-6-aminopyrimidine (3.1 g) at 120° C. for 12 h. The solvent was then removed and the residue was purified by column chromatography on silica gel (EtOAc/MeOH=5/1) to afford Intermediate 204-VI (7.2 g) in a 75% yield.

Intermediate 204-VI (400 mg) was added to N$^1$-Morpholine-N$^1$-piperazine ethane (470 mg) in 1-pentanol (1 mL). The reaction mixture was heated at 120° C. for 12 hours. The solvent was then removed under vacuum and the residue was purified by column chromatography on silica gel (EtOAc/MeOH=1/1) to afford Intermediate 204-VII (386 mg) in a 76% yield.

A solution of 20% TFA/CH$_2$Cl$_2$ (3 mL) was added to a solution of Intermediate 204-VI (386 mg) in CH$_2$Cl$_2$ (2 mL). The reaction mixture was stirred for 8 hours at room temperature and concentrated by removing the solvent. The resultant residue was purified by column chromatography on silica gel (21% NH$_3$ (aq)/MeOH=1/19) to afford Compound 204 (256 mg) in a 85% yield. Compound 204 was then treated with 1 M HCl (3 mL) in CH$_2$Cl$_2$ (1 mL) for 0.5 hour. After the solvents were removed, the residue was treated with ether and filtered to give hydrochloride salt of 204.

CI-MS (M$^+$+1): 568.4.

EXAMPLE 205

Preparation of Compound 205

Compound 205 was prepared in a manner similar to that used to prepare compound 204.
CI-MS (M$^+$+1): 527.3.

EXAMPLE 206

Preparation of Compound 206

Compound 206 was prepared in a manner similar to that used to prepare compound 204.
CI-MS (M$^+$+1): 543.3.

EXAMPLE 207

Preparation of Compound 207

Compound 207 was prepared in a manner similar to that used to prepare compound 204.
CI-MS (M$^+$+1): 554.4.

EXAMPLE 208

Preparation of Compound 208

Compound 208 was prepared in a manner similar to that used to prepare compound 204.
CI-MS (M$^+$+1): 529.3.

EXAMPLE 209

Preparation of Compound 209

Compound 209 was prepared in a manner similar to that used to prepare compound 204.
CI-MS (M$^+$+1): 513.3.

EXAMPLE 210

Preparation of Compound 210

Compound 210 was prepared in a manner similar to that used to prepare compound 204.
CI-MS (M$^+$+1): 538.4.

EXAMPLE 211

Preparation of Compound 211

Compound 211 was prepared in a manner similar to that used to prepare compound 204.
CI-MS (M$^+$+1): 513.4.

EXAMPLE 212

Preparation of Compound 212

Compound 212 was prepared in a manner similar to that used to prepare compound 204.
CI-MS (M$^+$+1): 497.3.

EXAMPLE 213

Preparation of Compound 213

Compound 213 was prepared in a manner similar to that used to prepare compound 204.
CI-MS (M$^+$+1): 512.4.

EXAMPLE 214

Preparation of Compound 214

Compound 214 was prepared in a manner similar to that used to prepare compound 204.
CI-MS (M$^+$+1): 471.4.

EXAMPLE 215

Preparation of Compound 215

Compound 215 was prepared in a manner similar to that used to prepare compound 204.
CI-MS (M$^+$+1): 501.4.

EXAMPLE 216

Preparation of Compound 216

Compound 216 was prepared in a manner similar to that used to prepare compound 204.
CI-MS (M$^+$+1): 485.3.

EXAMPLE 217

Preparation of Compound 217

Compound 217 was prepared in a manner similar to that used to prepare compound 204.
CI-MS (M$^+$+1): 578.4.

EXAMPLE 218

Preparation of Compound 218

Compound 218 was prepared in a manner similar to that used to prepare compound 204.
CI-MS (M$^+$+1): 553.4.

EXAMPLE 219

Preparation of Compound 219

Compound 219 was prepared in a manner similar to that used to prepare compound 204.
CI-MS (M$^+$+1): 537.4.

EXAMPLE 220

Preparation of Compound 220

Compound 220 was prepared in a manner similar to that used to prepare compound 204.
CI-MS (M$^+$+1): 553.3.

EXAMPLE 221

Preparation of Compound 221

Compound 221 was prepared in a manner similar to that used to prepare compound 204.
CI-MS (M$^+$+1): 537.4.

EXAMPLE 222

Preparation of Compound 222

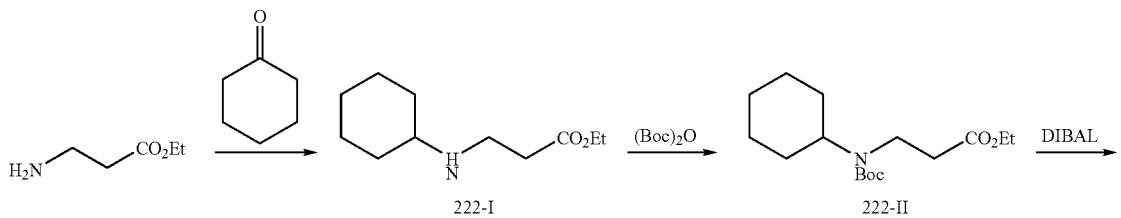

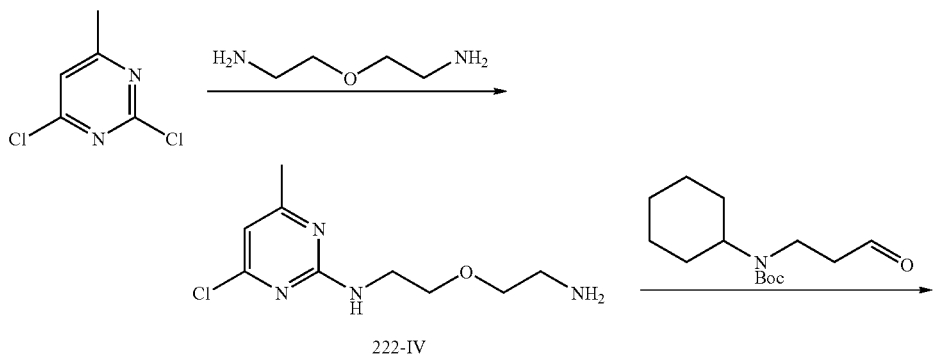

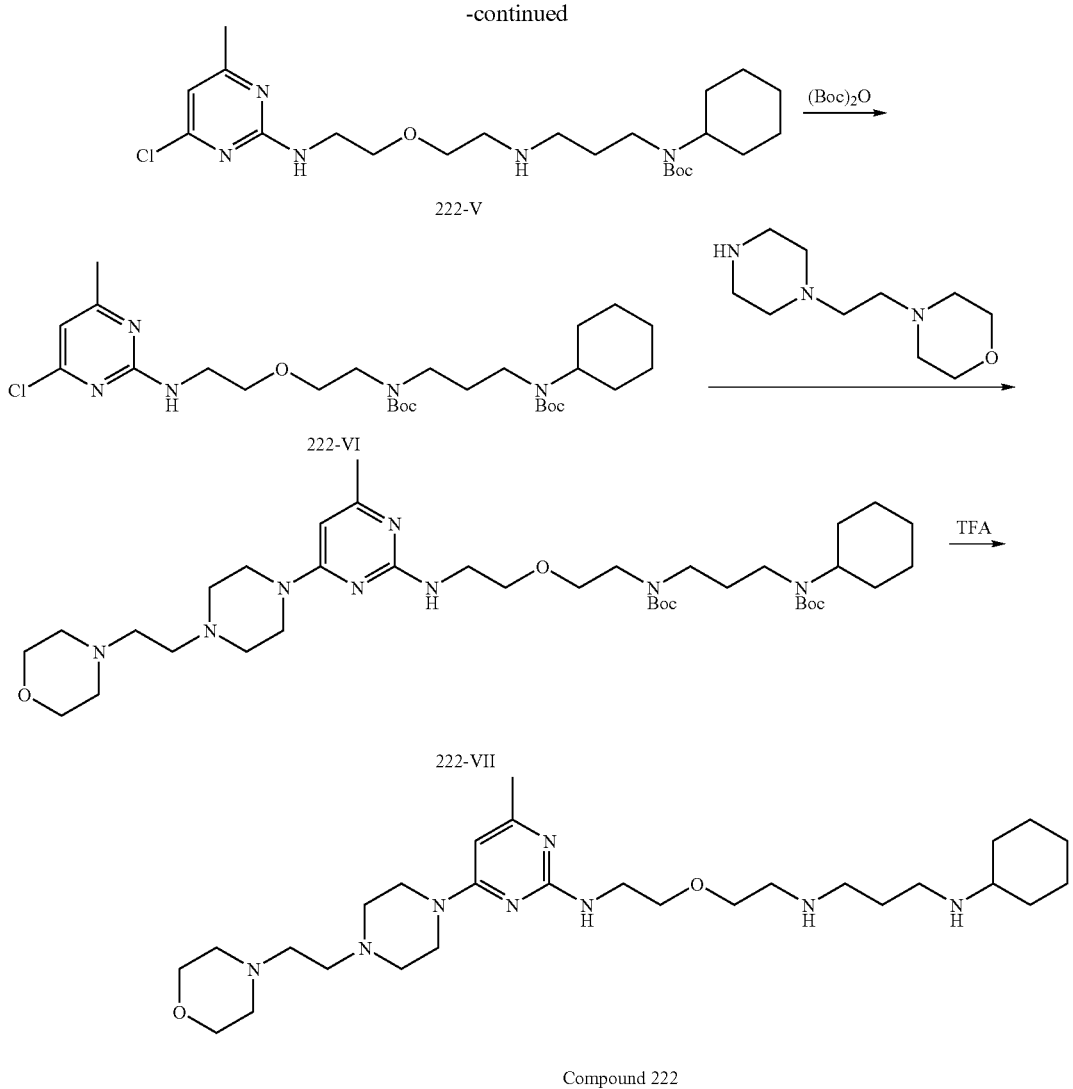

Compound 222

NaBH(OAc)$_3$ (52.68 g) was added to a solution of ethyl (2-aminomethyl)acetate (25.5 g) and cyclohexanone (24.45 g) in CH$_2$Cl$_2$ (200 mL) and MeOH (300 ml). The mixture was stirred at room temperature for 6 hours. After a saturated aq. NaHCO$_3$ solution was added, the mixture was extracted with EtOAc, dried over anhydrous MgSO$_4$, and filtered. The solvent was then removed and the residue was purified by column chromatography on silica gel (EtOAc/Hexane=1/1) to afford Intermediate 222-I (32.9 g) in a 76% yield.

A solution of Intermediate 222-I (32.9 g) and Boc$_2$O (36.0 g) in CH$_2$Cl$_2$ (300 mL) was stirred at 25° C. overnight. The solution was then concentrated and the resultant residue was purified by column chromatography on silica gel (EtOAc/Hexane=1/9) to give Intermediate 222-II (39.5 g) in a 80% yield.

1M DIBAL/ether (85 mL) was added to a stirred solution of Intermediate 222-I (15 g) in dry toluene (500 mL) at −70∼−78° C. under N$_2$ (g). The reaction mixture was stirred for 2 hours at this temperature. After 5% HCl (aq) (85 mL) was then added to the solution at −60∼−70° C., the mixture was stirred for another 0.5 hour after the reaction temperature was increased to 25° C. The aqueous layer was extracted with CH$_2$Cl$_2$ twice. The organic layers were combined, dried with anhydrous MgSO$_4$, and concentrated by removing the solvent under vacuum. The resultant residue was purified by column chromatography on silica gel (EtOAc/Hexane=1/5) to afford Intermediate 222-III (7.7 g) in a 60% yield.

Di-2-aminoethylether (1.0 g) was slowly added to a stirred solution of 2,4-dichloro-6-methylpyrimidine (2.0 g) in THF (15 mL) at room temperature. The mixture was stirred at 0° C. for 2 hours and the reaction was allowed to warm-up to room temperature overnight. The solution was then concentrated and the resultant residue was purified by column chromatography on silica gel (EtOAc/MeOH=1/1) to give Intermediate 222-IV (1.5 g) in a 53% yield.

A solution of Intermediate 222-IV (0.7 g) and Intermediate 222-III (0.77 g) in MeOH (60 mL) was stirred at 60° C. for 8 hours. NaBH$_4$ (0.17 g) was then added the solution at 0° C. After the solution was stirred for 0.5 hour, a saturated aq. NH$_4$Cl solution was added and the mixture was extracted with EtOAc, dried over anhydrous MgSO$_4$, and filtered. The solution was then concentrated and the resultant residue was purified by column chromatography on silica gel (EtOAc/MeOH=2/1) to afford Intermediate 222-V (356 mg) in a 25% yield.

A solution of Intermediate 222-V (356 mg) and Boc$_2$O (180 mg) in CH$_2$Cl$_2$ (10 mL) was stirred at 25° C. overnight.

The solution was then concentrated and the resultant residue was purified by column chromatography on silica gel (EtOAc/Hexane=1/5) to give Intermediate 222-VI (410 mg) in a 95% yield.

$N^1$-Morpholine-$N^1$-piperazine ethane (221 mg) was added to a solution of Intermediate 222-VI (210 mg) in 1-pentanol (1 mL). The mixture was stirred at 120° C. for 12 hours. It was then concentrated and the resultant residue was purified by column chromatography on silica gel (EtOAc/MeOH=10/1) to afford Intermediate 222-VII (100 mg) in a 37% yield.

A solution of 20% $TFA/CH_2Cl_2$ (2 mL) was added to a solution of Intermediate 222-VII (100 mg) in $CH_2Cl_2$ (1 mL). The reaction mixture was stirred for 8 hours at room temperature and concentrated by removing the solvent. The resultant residue was purified by column chromatography on silica gel (21% $NH_3$ (aq)/MeOH=1/19) to afford Compound 222 (65 mg) in 90% yield. Compound 222 was then treated with 1 M HCl (2 mL) in $CH_2Cl_2$ (1 mL) for 0.5 hour. After the solvents were removed, the residue was treated with ether and filtered to afford hydrochloride salt of 222.

CI-MS ($M^+$+1): 533.4.

EXAMPLE 223

Preparation of Compound 223

Compound 223 was prepared in a manner similar to that used to prepare compound 222.

CI-MS ($M^+$+1): 528.4.

EXAMPLE 224

Preparation of Compound 224

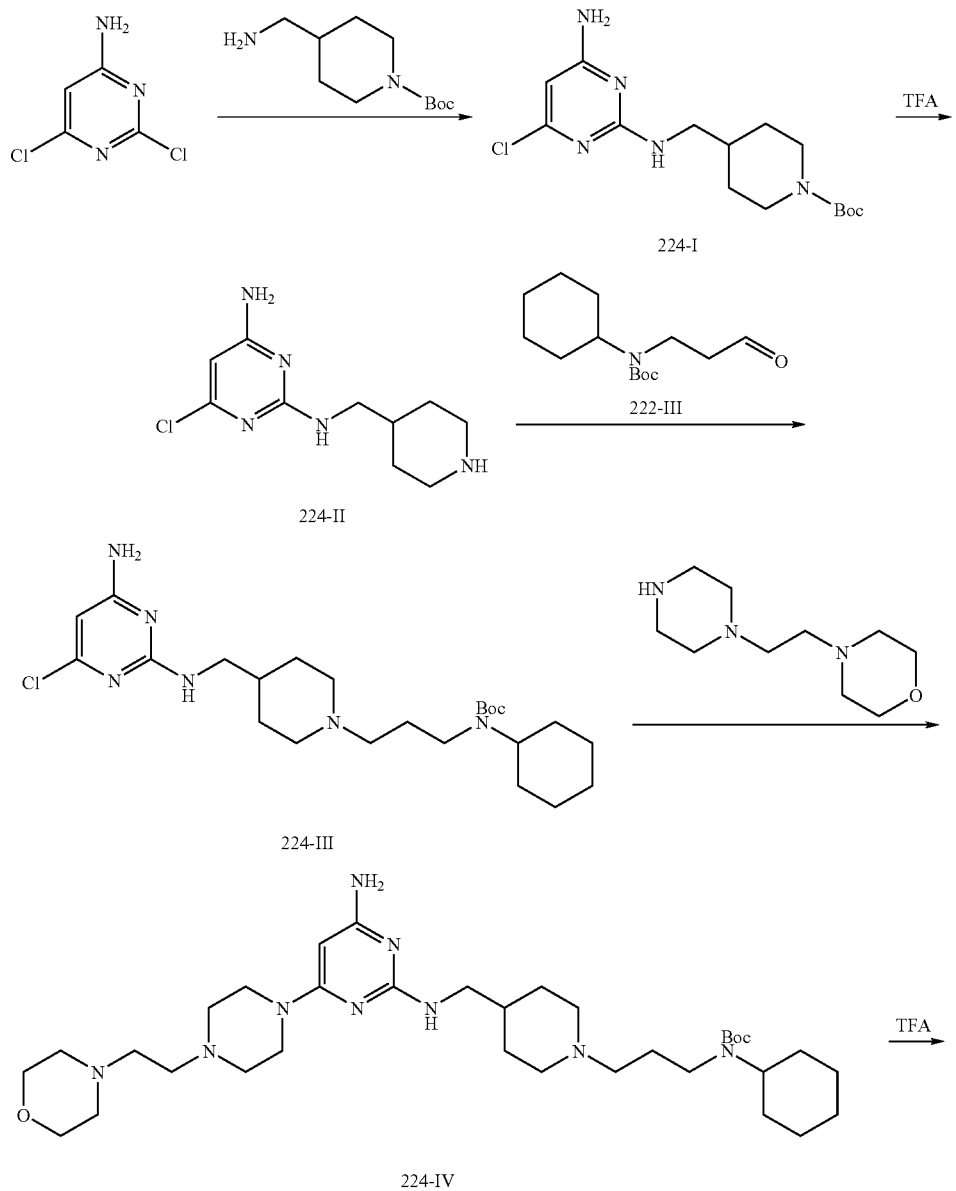

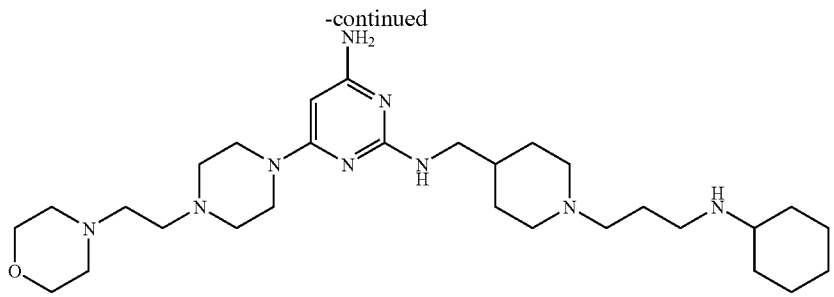

Compound 224

N-tert-Butoxycarbonylpiperidinyl-4-methylamine (5.0 g) was slowly added to a stirred solution of 2,4-dichloro-6-aminopyrimidine (5.7 g) in 1-pentanol (20 mL). The solution was stirred at 120° C. for 12 hours. The solution was then concentrated and the resultant residue was purified by column chromatography on silica gel (EtOAc/Hexane=1/9) to give Intermediate 224-I (3.6 g) in a 45% yield.

Intermediate 224-I (2.4 g) was then dissolved in $CH_2Cl_2$ (80 mL) and 20% TFA/$CH_2Cl_2$ (20 mL) was added. The solution was stirred at room temperature overnight. The solution was then concentrated and the resultant residue was purified by column chromatography on silica gel (21% $NH_3$ (aq)/MeOH=1/19) to afford Intermediate 224-I (1.5 g) in a 90% yield.

Intermediate 222-III (3.3 g) prepared in Example 222 was added to a solution of Intermediate 224-II (1.9 g) in MeOH (40 mL). The mixture was stirred at 60° C. for 12 hours. $NaBH_4$ (0.3 g) was then added at 0° C. After the mixture was stirred for 1 hour, an aqueous solution of $NH_4Cl$ (10%, 10 mL) was added. The mixture was extracted with EtOAc, dried over anhydrous $MgSO_4$, and filtered. The solution thus obtained was then concentrated. The resultant residue was purified by column chromatography on silica gel (EtOAc/Hexane=1/1) to afford Intermediate 224-III (1.5 g) in a 40% yield.

$N^1$-Morpholine-$N^1$-piperazine ethane (370 mg) was added to Intermediate 224-III (300 mg) in 1-pentanol (1 mL). The mixture was stirred at 120° C. for 12 hours. After the solution was concentrated, the residue was treated with water and extracted with $CH_2Cl_2$. The organic layer was separated and concentrated. The resultant residue was purified by column chromatography on silica gel (EtOAc/Hexane=1/9) to afford Intermediate 224-IV (281 mg) in a 70% yield.

A solution of 20% TFA/$CH_2Cl_2$ (3 mL) was added to a solution of Intermediate 224-IV (281 mg) in $CH_2Cl_2$ (2 mL). The reaction mixture was stirred for 8 hours at room temperature and concentrated by removing the solvent. The resultant residue was purified by column chromatography on silica gel (21% $NH_3$ (aq)/MeOH=1/19) to afford Compound 224 (200 mg) in a 85% yield. Compound 224 was then treated with 1 M HCl (4 mL) in $CH_2Cl_2$ (2 mL) for 0.5 hours. After the solvents were removed, the residue was treated with ether and filtered to give hydrochloride salt of Compound 224.

CI-MS ($M^+$+1): 544.4.

EXAMPLE 225

Preparation of Compound 225

Compound 225 was prepared in a manner similar to that used to prepare compound 224.

CI-MS ($M^+$+1): 503.4.

EXAMPLE 226

Preparation of Compound 226

Compound 226 was prepared in a manner similar to that used to prepare compound 224.

CI-MS ($M^+$+1): 519.4.

EXAMPLE 227

Preparation of Compound 227

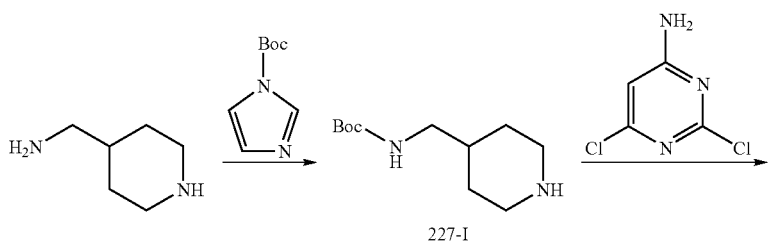

227-I

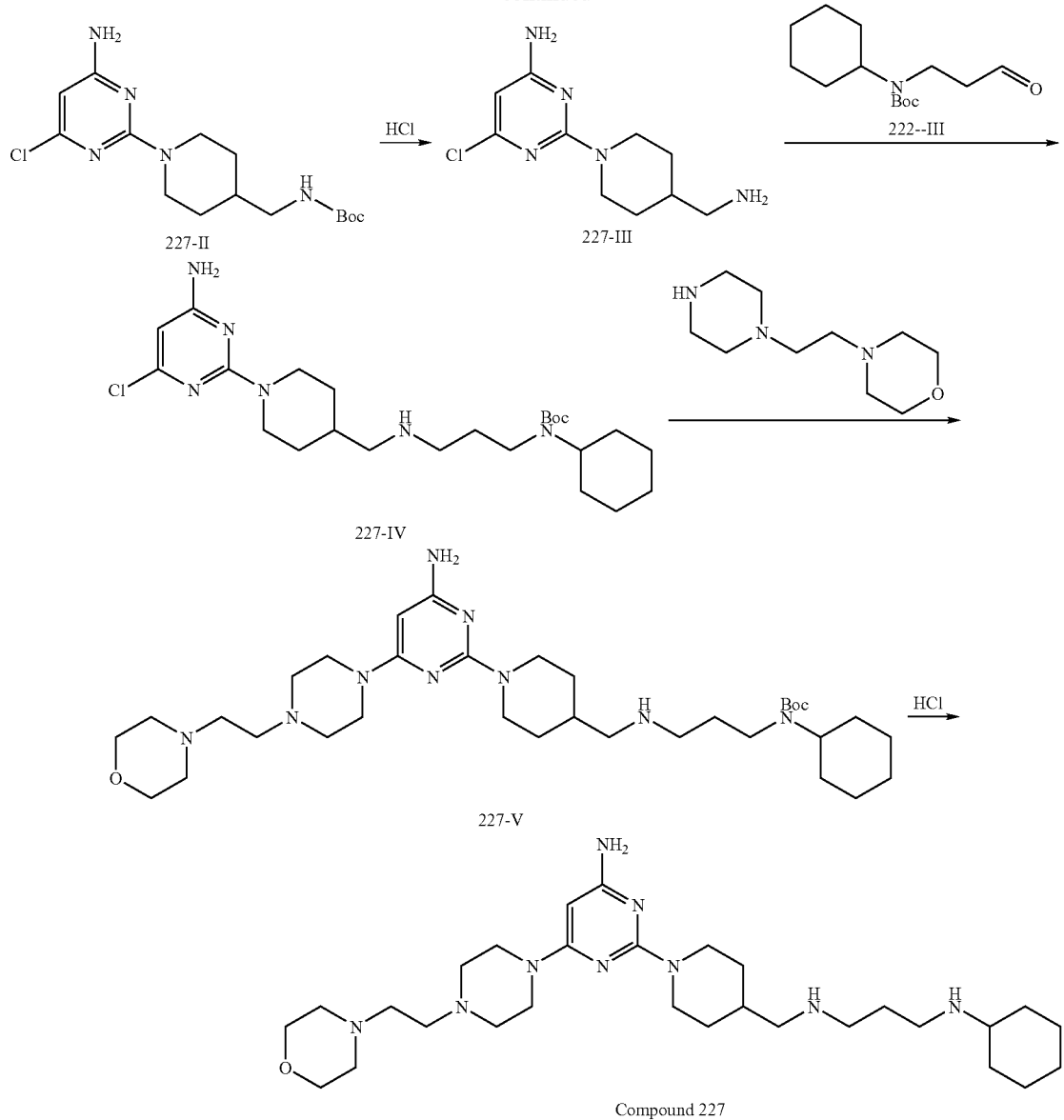

Compound 227

A solution of piperidinyl-4-methylamine (3.6 g) and N-tert-butoxycarbonylimidazole (5.3 g) in toluene (80 mL) was stirred at 25° C. overnight. The solution was then concentrated and the resultant residue was purified by column chromatography on silica gel (EtOAc/Hexane=1/2) to give Intermediate 227-I (4.7 g) in a 70% yield.

Intermediate 227-I (4.7 g) and Et$_3$N (2.7 mL) in 1-pentanol (20 mL) was reacted with 2,4-dichloro-6-aminopyrimidine (5.4 g) at 120° C. for 12 hours. After the solvent was removed, the residue was purified by column chromatography on silica gel (EtOAc/Hexane=1/9) to afford Intermediate 227-II (5.2 g) in a 70% yield.

A solution of Intermediate 227-II (1.0 g) treated with 1 M HCl (20 mL) in CH$_2$Cl$_2$ (10 mL) was stirred at room temperature for 8 hours. After the solution was concentrated, the resultant residue was neutralization with NH$_4$OH, and extracted with CH$_2$Cl$_2$. The organic layer was separated and concentrated. The residue thus obtained was purified by column chromatography on silica gel (using MeOH as an eluant) to afford Intermediate 227-III (636 mg) in a 90% yield.

Intermediate 222-III (790 mg) prepared from Example 222 was added to a solution of Intermediate 227-III (450 mg) in MeOH (20 mL). The mixture was stirred at 25° C. for 2 hours. NaBH(OAc)$_3$ (2.0 g) was then added at 25° C. for 12 hours. After the solution was concentrated, a saturated aq. NaHCO$_3$ solution was added to the resultant residue. The mixture was then extracted with CH$_2$Cl$_2$. The organic layer was separated and concentrated. The residue thus obtained was purified by column chromatography on silica gel (using MeOH as an eluant) to afford Intermediate 227-IV (539 mg) in a 60% yield.

N$^1$-Morpholine-N$^1$-piperazine ethane (240 mg) was added to a solution of Intermediate 227-IV (160 mg) in 1-pentanol (1 mL). The mixture was stirred at 120° C. for 8 hours. The solution was concentrated and the residue was purified by column chromatography on silica gel (EtOAc/MeOH=5/1) to afford Intermediate 227-V (85 mg) in a 40% yield.

A solution of 20% TFA/CH$_2$Cl$_2$ (1 mL) was added to a solution of Intermediate 227-V (85 mg) in CH$_2$Cl$_2$ (1 mL).

The reaction mixture was stirred for 8 hours at room temperature and concentrated by removing the solvent. The resultant residue was purified by column chromatography on silica gel (21% NH₃ (aq)/MeOH=1/19) to afford Compound 227 (65 mg) in a 90% yield. Compound 227 was then treated with 1 M HCl (1 mL) in CH₂Cl₂ (1 mL) for 0.5 hour. After the solvents were removed, the residue was treated with ether and filtered to give hydrochloride salt of Compound 227.

CI-MS (M⁺+1): 544.4.

EXAMPLE 228

Preparation of Compound 228

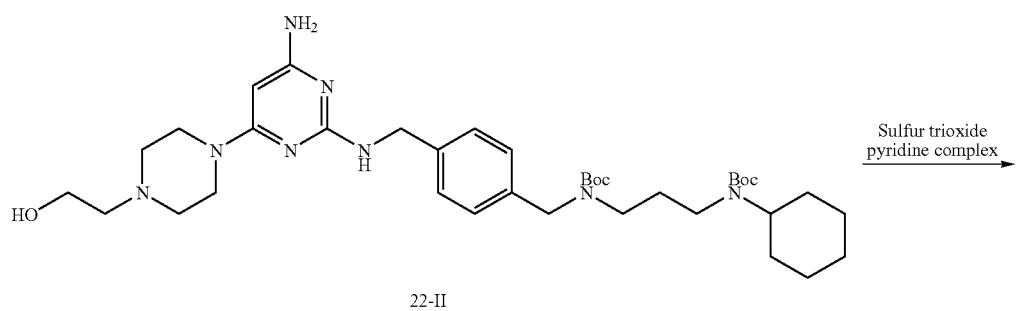

22-II

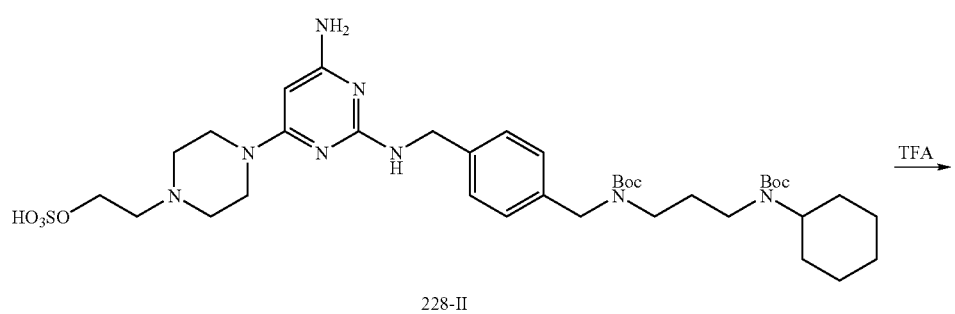

228-II

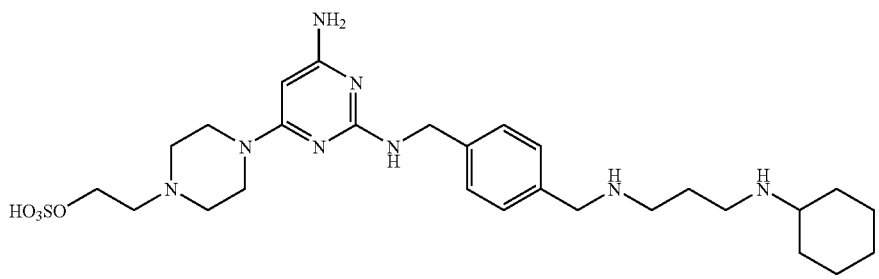

Compound 228

To a solution of 22-II (500 mg) in THF (10 mL) was added sulfur trioxide pyridine complex (457 mg). The mixture was stirred at 25° C. for 12 hours. The solution was filtered and concentrated. The resultant residue was purified by column chromatography on silica gel (EA/MeOH=10/1) to give Intermediate 228-II (82 mg) in a 10% yield.

A solution of 20% TFA/CH₂Cl₂ (1 mL) was added to a solution of Intermediate 228-II (82 mg) in CH₂Cl₂ (1 mL). The reaction mixture was stirred for 8 hours at room temperature and concentrated by removing the solvent. The resultant residue was purified by chromatography on silica gel (21% NH₃ (aq)/MeOH=1/19) to afford Compound 228 (54 mg) in 90% yield. Compound 228 was then treated with 1 M HCl (1 mL) in CH₂Cl₂ (1 mL) for 0.5 hour. After the solvents were removed, the residue was treated with ether and filtered to give hydrochloride salt of Compound 228.

CI-MS (M⁺+1): 577.2.

EXAMPLE 229

Preparation of Compound 229

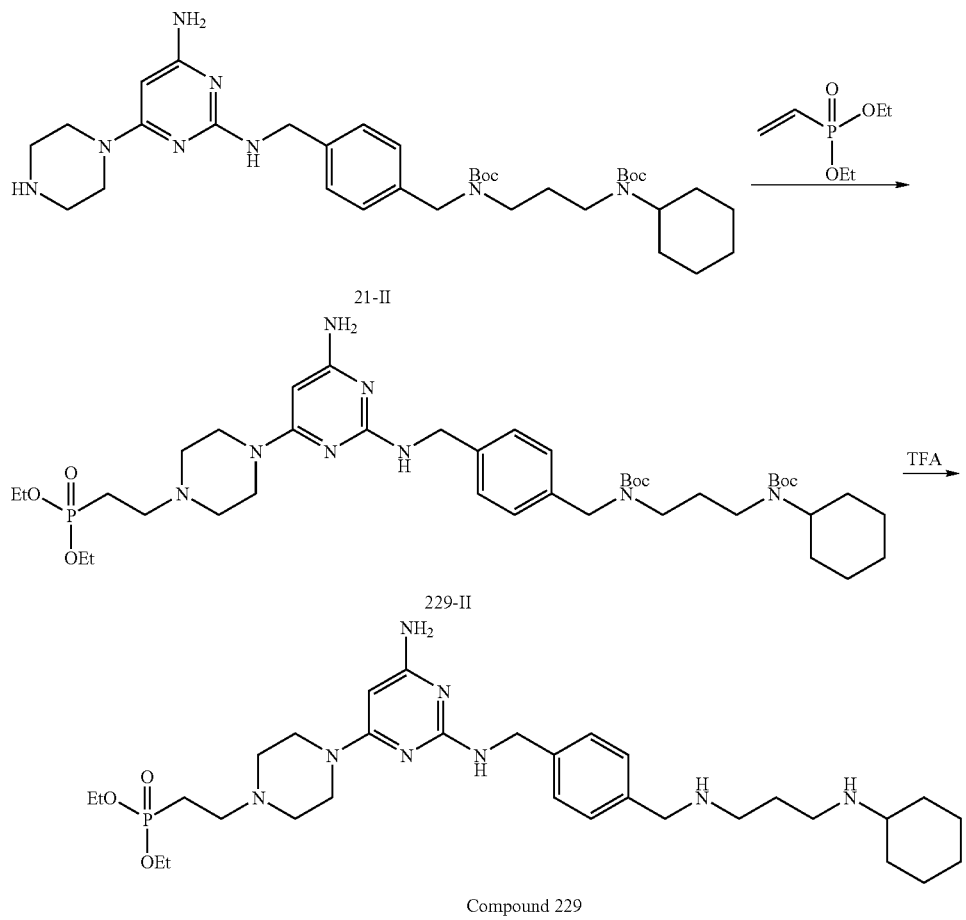

The reaction mixture was stirred for 8 hours at room temperature and concentrated by removing the solvent. The resultant residue was purified by column chromatography on silica gel (EA/MeOH=1/1) to afford Compound 229 (165 mg) in a 50% yield.

CI-MS (M+1): 617.4.

Diethyl vinylphosphonate (377 mg) was added to a solution of Intermediate 21-I (500 mg) prepared from Example 21 in MeOH (10 mL). The solution was stirred at 25° C. for 12 hours. The solution was concentrated and the residue was purified by column chromatography on silica gel (EA/MeOH=5/1) to afford Intermediate 229-II (438 mg) in a 70% yield.

A solution of 20% TFA/CH$_2$Cl$_2$ (5 mL) was added to a solution of Intermediate 229-II (438 mg) in CH$_2$Cl$_2$ (2 mL).

EXAMPLE 230

Preparation of Compound 230

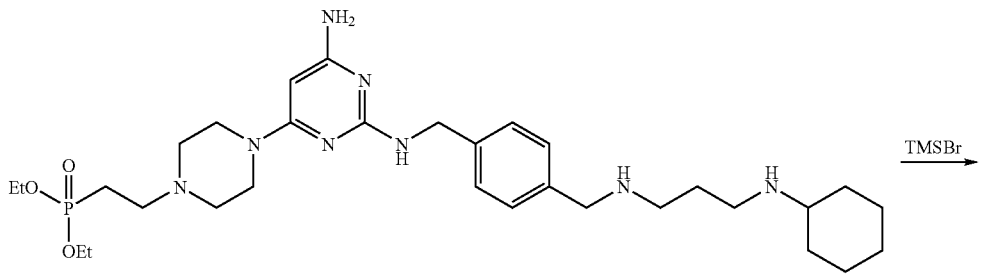

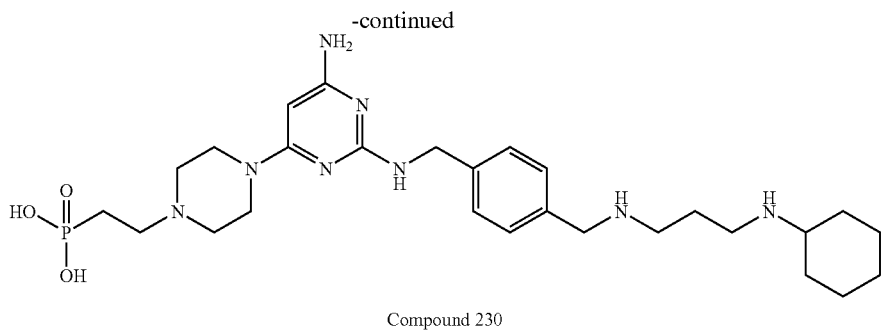

Compound 230

A solution of Compound 229 (600 mg) and trimethylsilyl bromide (1.19 g) in CH$_2$Cl$_2$ (30 mL) was stirred at 25° C. for 72 hours. The solution was then concentrated in vacuo to yield a yellow-orange foam, which was re-dissolved in water (50 mL). The solution was washed with ether (3×35 mL) and then concentrated in vacuo to yield a solid. The solid was purified through a column of cation exchange resin (Dowex AG50X8) by eluting the column first with water (ca. 500 mL), and then with 0.2 M aqueous ammonia to afford ammonium salt of Compound 230 (58 mg) in a 10% yield.

CI-MS (M$^+$+1): 561.1.

EXAMPLE 231

Preparation of Compound 231

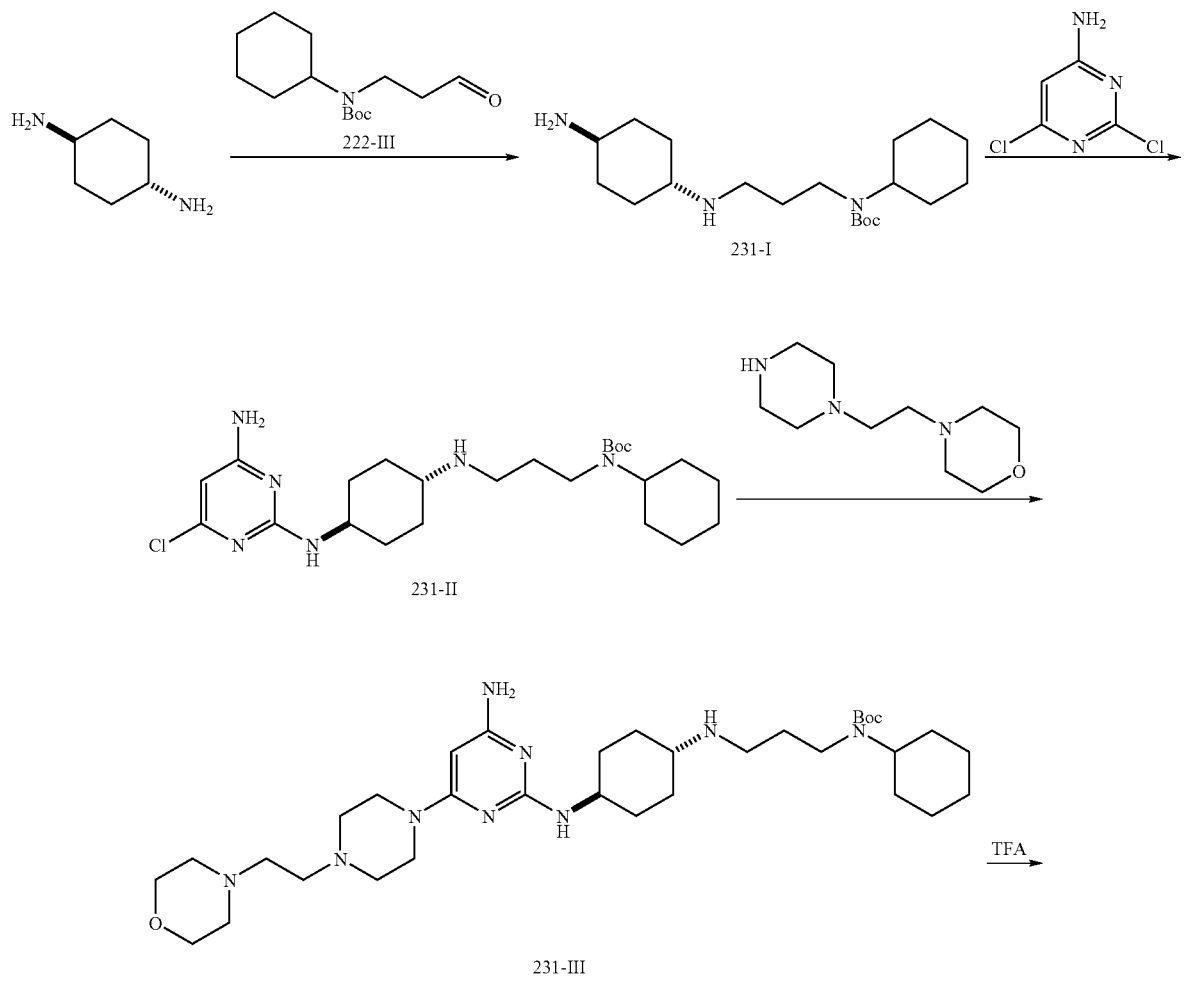

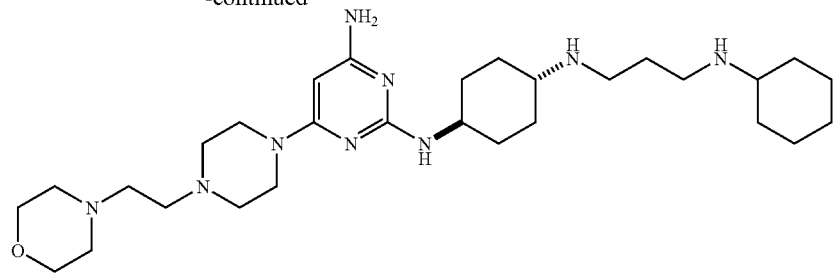

Compound 231

Intermediate 222-III (4.5 g) was added to a solution of trans-1,4-diaminocyclohexane (3 g) in MeOH (200 mL). The mixture was stirred at 60° C. for 8 hours. After NaBH$_4$ (0.7 g) was added at 0° C., the mixture was stirred for 0.5 hour and then concentrated by removing the solvent. An aqueous solution of NH$_4$Cl (10%, 10 mL) was added to the resultant residue. The mixture was extracted with CH$_2$Cl$_2$, dried over anhydrous MgSO$_4$, filtered, and concentrated. The residue was purified by column chromatography on silica gel (using MeOH as an eluant) to afford Intermediate 231-I (6.0 g) in a 65% yield.

Intermediate 231-I (6.0 g) and Et$_3$N (6.0 mL) in 1-pentanol (30 mL) was reacted with 2,4-dichloro-6-aminopyrimidine (2.7 g) at 120° C. for 12 hours. The solvent was then removed and the residue was purified by column chromatography on silica gel (EtOAc/Hexane=1/1) to afford Intermediate 231-II (5.7 g) in a 70% yield.

N$^1$-Morpholine-N$^1$-piperazine ethane (620 mg) was added to Intermediate 231-II (500 mg) in 1-pentanol (5 mL). The mixture was stirred at 120° C. for 8 hours and then concentrated. The residue thus obtained was treated with water and extracted with CH$_2$Cl$_2$ to afford Intermediate 231-III (468 mg) in a 70% yield, which was purified by column chromatography on silica gel using 21% NH$_3$ (aq) and MeOH as eluants.

A solution of 20% TFA/CH$_2$Cl$_2$ (5 mL) was added to a solution of Intermediate 231-III (468 mg) in CH$_2$Cl$_2$ (2 mL). The reaction mixture was stirred for 8 hours at room temperature and concentrated by removing the solvent. The resultant residue was purified by column chromatography on silica gel (21% NH$_3$ (aq)/MeOH=1/19) to afford Compound 231 (356 mg) in a 90% yield. Compound 231 was then treated with 1 M HCl (4 mL) in CH$_2$Cl$_2$ (2 mL) for 0.5 hour. After the solvents were removed, the residue was treated with ether and filtered to give hydrochloride salt of Compound 231.

CI-MS (M$^+$+1): 544.4.

EXAMPLE 232

Preparation of Compound 232

Compound 232 was prepared in a manner similar to that used to prepare compound 231.

CI-MS (M$^+$+1): 503.4.

EXAMPLE 233

Preparation of Compound 233

Compound 233 was prepared in a manner similar to that used to prepare compound 231.

CI-MS (M$^+$+1): 519.4.

EXAMPLE 234

Preparation of Compound 234

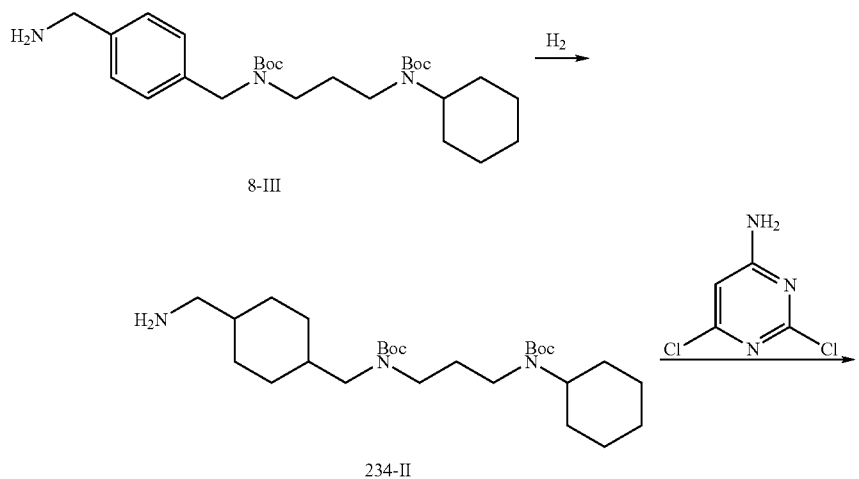

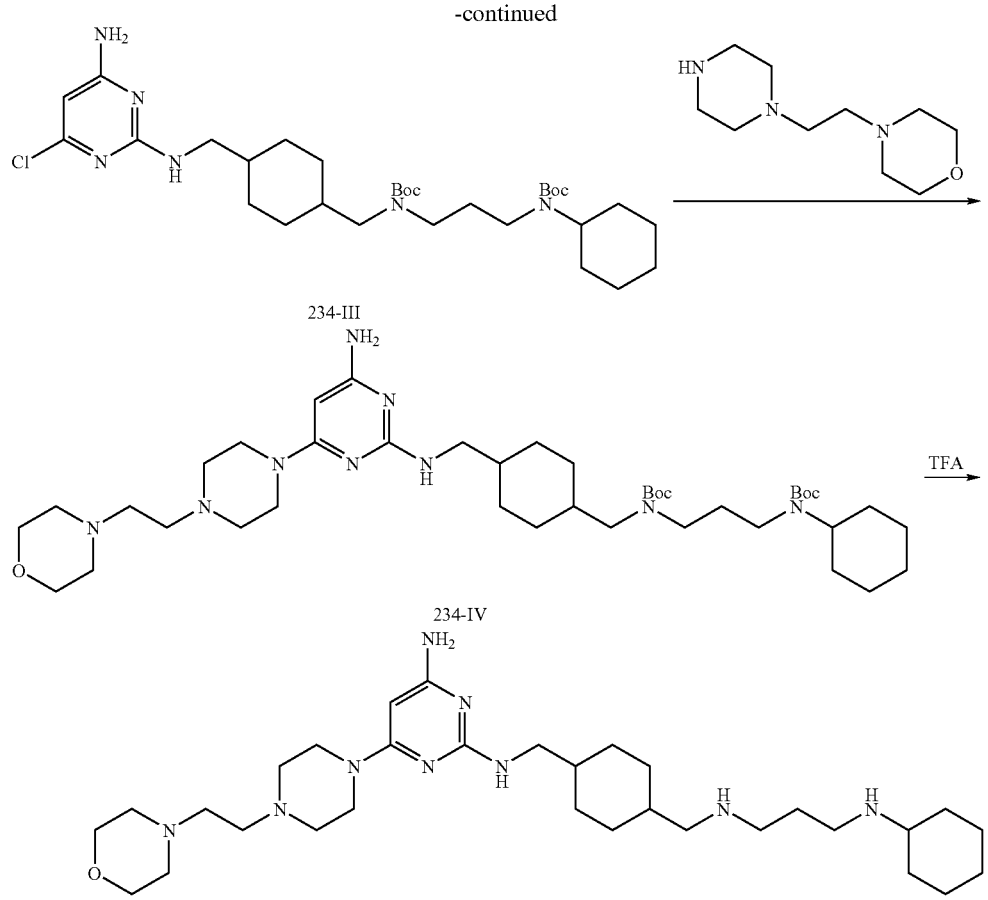

Compound 8-III (1.0 g) prepared in Example 8 in MeOH (20 mL) was hydrogenated in the presence of 10% Pd/C (200 mg) at 50 psi at room temperature for 18 hours. The mixture was then filtered and concentrated to afford Intermediate 234-II (500 mg) without further purification.

Crude Intermediate 234-II (0.5 g) in 1-pentanol (3 mL) was reacted with 2,4-dichloro-6-aminopyrimidine (0.2 g) at 120° C. for 15 hours. The solution was then concentrated and the resultant residue was purified by column chromatography on silica gel (EtOAc/Hexane=3/7) to give Intermediate 234-III (0.3 g) in a 65% yield.

$N^1$-Morpholine-$N^1$-piperazine ethane (0.3 g) was added to Intermediate 234-III (0.5 g) in 1-pentanol (1 mL). The mixture was stirred at 120° C. for 18 hours. The solution was concentrated to give the residue, which was then coated with $SiO_2$ and purified by column chromatography on silica gel (EtOAc/MeOH=7/3) to afford Intermediate 234-IV (0.23 g) in a 60% yield.

A solution of 20% $TFA/CH_2Cl_2$ (5 mL) was added to a solution of Intermediate 234-IV (230 mg) in $CH_2Cl_2$ (2 mL). The reaction mixture was stirred for 8 hours at room temperature and concentrated by removing the solvent. The resultant residue was purified by column chromatography on silica gel (21% $NH_3$ (aq)/MeOH=1/19) to afford Compound 234 (192 mg) in a 85% yield. Compound 234 was then treated with 1 M HCl (4 mL) in $CH_2Cl_2$ (2 mL) for 0.5 hour. After the solvents were removed, the residue was treated with ether and filtered to give hydrochloride salt of Compound 234.
CI-MS ($M^+$+1): 572.5.

EXAMPLE 235

Preparation of Compound 235

Compound 235 was prepared in a manner similar to that used to prepare compound 234.
CI-MS ($M^+$+1): 531.4.

EXAMPLE 236

Preparation of Compound 236

Compound 236 was prepared in a manner similar to that used to prepare compound 234.
CI-MS ($M^+$+1): 547.4.

EXAMPLE 237

Preparation of Compound 237

Compound 237 was prepared in a manner similar to that used to prepare compound 234.
CI-MS ($M^+$+1): 555.5.

EXAMPLE 238

Preparation of Compound 238

Compound 238 was prepared in a manner similar to that used to prepare compound 234.
CI-MS ($M^+$+1): 549.4.

EXAMPLE 239
Preparation of Compound 239
Compound 239 was prepared in a manner similar to that used to prepare compound 234.
CI-MS (M+1): 503.4.
EXAMPLE 240
Preparation of Compound 240
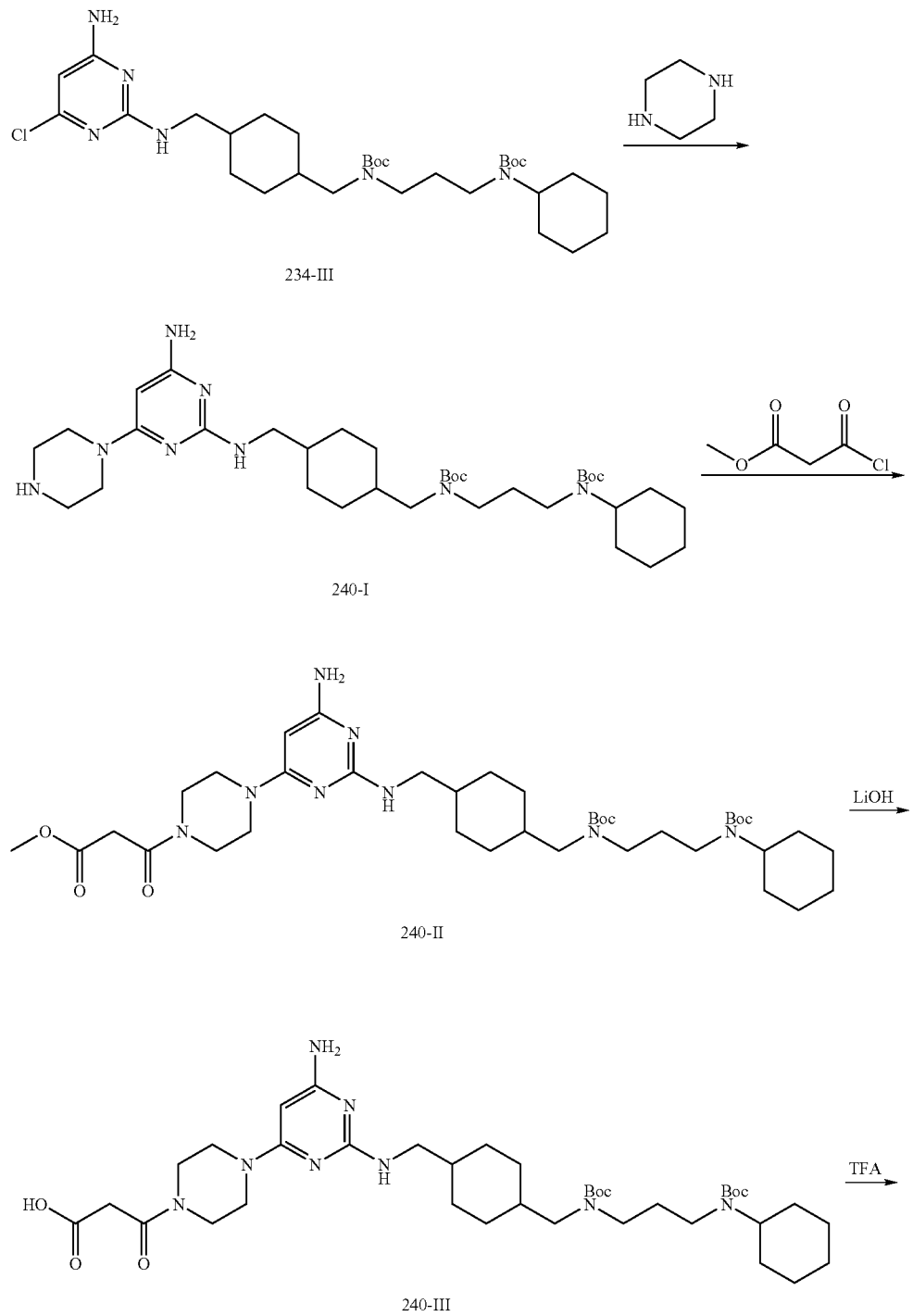

-continued

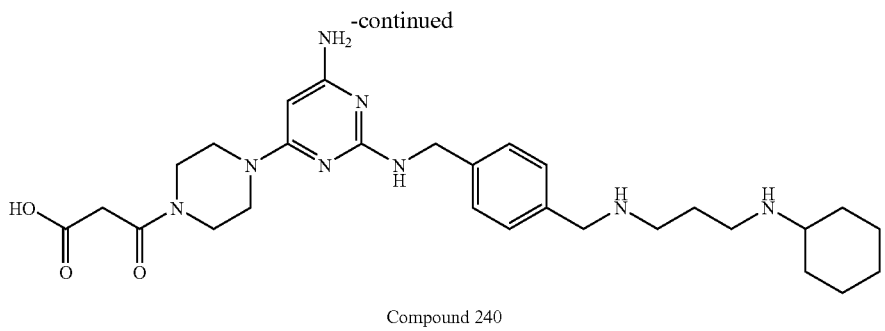

Compound 240

Intermediate 234-III (1.0 g) prepared from Example 3 was added to a stirred solution of piperazine (0.36 g) in 1-pentanol (1.0 mL). The solution was stirred at 120° C. for 18 hours. It was concentrated to give a residue, which was coated with $SiO_2$ and purified by column chromatography on silica gel (EtOAc/MeOH=9/1) to afford Intermediate 240-I (0.82 g) in a 75% yield.

Methoxycarbonylacetyl chloride (0.2 g) was added to a solution of Intermediate 240-I (0.82 g) in $CH_2Cl_2$ (50 mL) and $Et_3N$ (0.3 g) at 0° C. The mixture was stirred at 0° C. for 1 hour and then concentrated. The residue thus obtained was treated with water and extracted with $CH_2Cl_2$. The organic layer was separated and concentrated. The resultant residue was purified by column chromatography on silica gel (EtOAc/$Et_3N$=9/1) to give Intermediate 240-II (0.73 g) in a 80% yield.

Intermediate 240-II (0.5 g) dissolved in THF (10 mL) was added to 0.5 M of an LiOH aqueous solution (10 mL). The mixture was stirred at room temperature for 2 hours. It was then acidified with 2M HCl to obtain a crude product, which was purified by column chromatography on silica gel (EtOAc/MeOH=20/1) to afford Intermediate 240-III (170 mg) in a 35% yield.

Intermediate 240-III (170 mg) was treated with 20% TFA/$CH_2Cl_2$ (5 mL) at room temperature for 12 hours and then concentrated. The resultant residue was purified by column chromatography on silica gel (21% $NH_3$ (aq)/MeOH=1/19) to afford Compound 240 (100 mg) in a 85% yield. Compound 240 was then treated with 1 M HCl (3 mL) in $CH_2Cl_2$ (2 mL) for 0.5 hour. After the solvents were removed, the residue was treated with ether and filtered to give hydrochloride salt of Compound 240.

CI-MS ($M^+$+1): 545.4.

EXAMPLE 241

Preparation of Compound 241

Compound 241 was prepared in a manner similar to that used to prepare compound 240.
CI-MS ($M^+$+1): 558.5.

EXAMPLE 242

Preparation of Compound 242

Compound 242 was prepared in a manner similar to that used to prepare compound 240.
CI-MS ($M^+$+1): 560.4.

EXAMPLE 243

Preparation of Compound 243

Compound 243 was prepared in a manner similar to that used to prepare compound 240.
CI-MS ($M^+$+1): 576.4.

EXAMPLE 244

Preparation of Compound 244

Compound 244 was prepared in a manner similar to that used to prepare compound 240.
CI-MS ($M^+$+1): 559.4.

EXAMPLE 245

Preparation of Compound 245

Compound 245 was prepared in a manner similar to that used to prepare compound 240.
CI-MS ($M^+$+1): 531.4.

EXAMPLE 246

Preparation of Compound 246

Compound 246 was prepared in a manner similar to that used to prepare compound 240.
CI-MS ($M^+$+1): 517.4.

EXAMPLE 247

Preparation of Compound 247

Compound 247 was prepared in a manner similar to that used to prepare compound 240.
CI-MS ($M^+$+1): 515.4.

EXAMPLE 248

Preparation of Compound 248

Compound 248 was prepared in a manner similar to that used to prepare compound 240.
CI-MS ($M^+$+1): 531.4.

EXAMPLE 249
Preparation of Compound 249
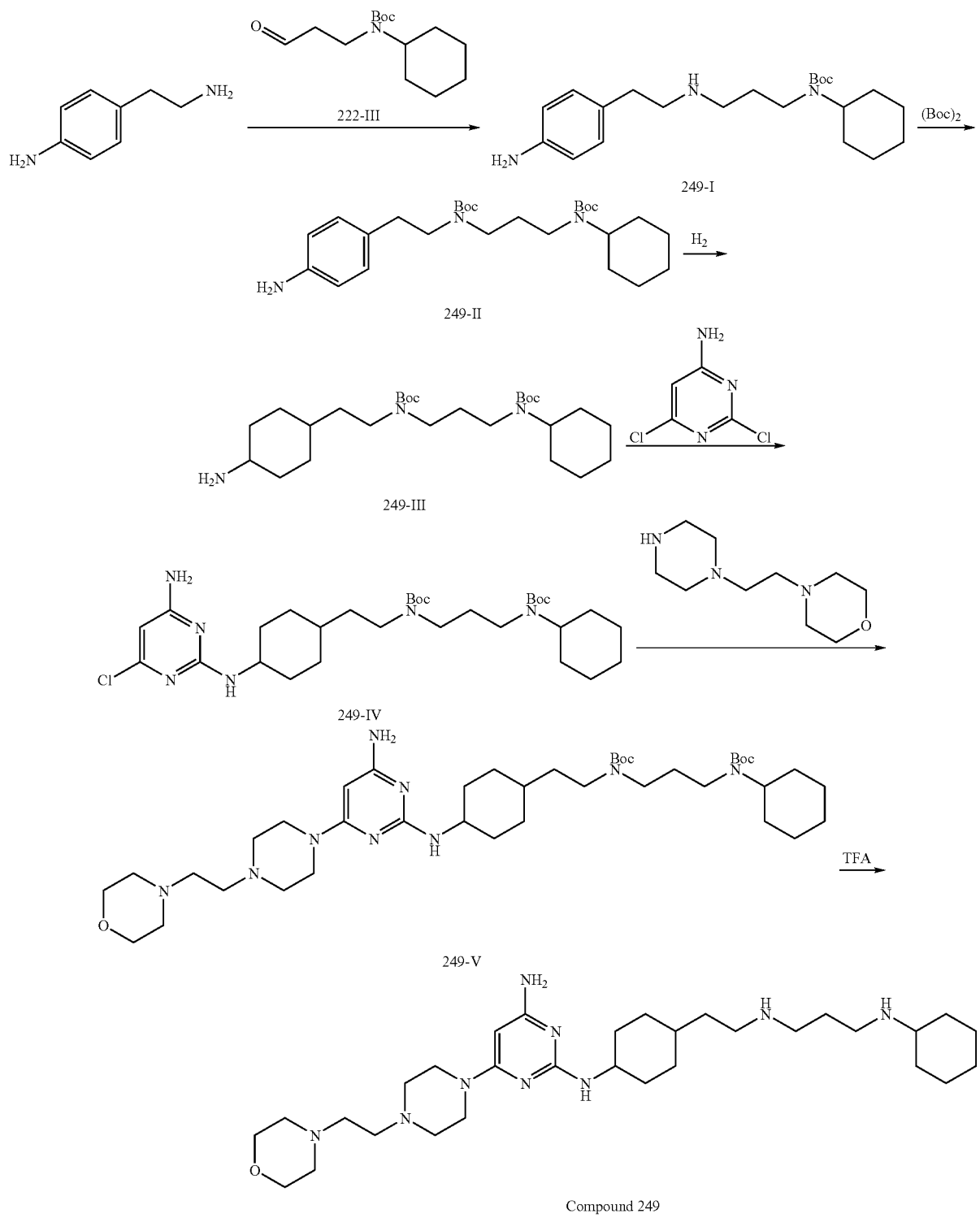
Intermediate 222-III (4.56 g) was added to a solution of 2-aminoethylaniline (2.92 g) in MeOH (300 mL). The mixture was stirred at 60° C. for 8 hours. NaBH$_4$ (0.68 g) was then added at 0° C. for 0.5 hour and the mixture was concentrated by removing the solvent. An aqueous solution of NH$_4$Cl (10%, 10 mL) was added to the resultant residue. The mixture was extracted with CH$_2$Cl$_2$, dried over anhydrous MgSO$_4$, filtered, and concentrated. The residue thus obtained was purified by column chromatography on silica gel (EtOAc/MeOH=1/1) to afford Intermediate 249-I (4.2 g) in a 63% yield.

A solution of Intermediate 249-I (4.2 g) and Boc$_2$O (2.8 g) in CH$_2$Cl$_2$ (250 mL) was added to Et$_3$N (1.4 mL) at 25° C. overnight. The solution was then concentrated and the resultant residue was purified by column chromatography on silica gel (EtOAc/Hexane=1/5) to give Intermediate 249-II (4 g) in a 75% yield.

Intermediate 249-II (4.0 g) in MeOH (20 mL) was hydrogenated in the presence of 10% Pd/C (800 mg) and 5% Rh/C (400 mg) at 50 psi at room temperature for 18 hours. The mixture was then filtered and concentrated. The residue was purified by column chromatography on silica gel (using EtOAc/MeOH as an eluant) to afford Intermediate 249-III (2.8 g) in a 69% yield.

Intermediate 249-III (900 mg) and Et$_3$N (0.4 mL) in 1-pentanol (5 mL) was reacted with 2,4-dichloro-6-aminopyrimidine (365 mg) at 120° C. for 24 hours. The solvent was then removed and the resultant residue was purified by column chromatography on silica gel (EtOAc/Hexane=1/1) to afford Intermediate 249-IV (842 mg) in a 74% yield.

N$^1$-Morpholine-N$^1$-piperazine ethane (300 mg) was added to Intermediate 249-IV (300 mg) in 1-pentanol (1 mL). The mixture was stirred at 120° C. for 18 hours. The solution was concentrated to give a residue, which was then coated with SiO$_2$ and purified by column chromatography on silica gel (EtOAc/MeOH=7/3) to afford Intermediate 249-V (243 mg) in a 64% yield.

A solution of 20% TFA/CH$_2$Cl$_2$ (5 mL) was added to a solution of Intermediate 249-V (243 mg) in CH$_2$Cl$_2$ (2 mL). The reaction mixture was stirred for 8 hours at room temperature and concentrated by removing the solvent. The resultant residue was purified by column chromatography on silica gel (21% NH$_3$ (aq)/MeOH=1/19) to afford Compound 249 (151 mg) in a 84% yield. Compound 249 was then treated with 1 M HCl (4 mL) in CH$_2$Cl$_2$ (2 mL) for 0.5 hour. After the solvents were removed, the residue was treated with either and filtered to give hydrochloride salt of Compound 249.

CI-MS (M$^+$+1): 572.5.

EXAMPLE 250

Preparation of Compound 250

Compound 250 was prepared in a manner similar to that used to prepare compound 249.

CI-MS (M$^+$+1): 531.4.

EXAMPLE 251

Preparation of Compound 251

Compound 251 was prepared in a manner similar to that used to prepare compound 249.

CI-MS (M$^+$+1): 547.4.

EXAMPLE 252

Preparation of Compound 252

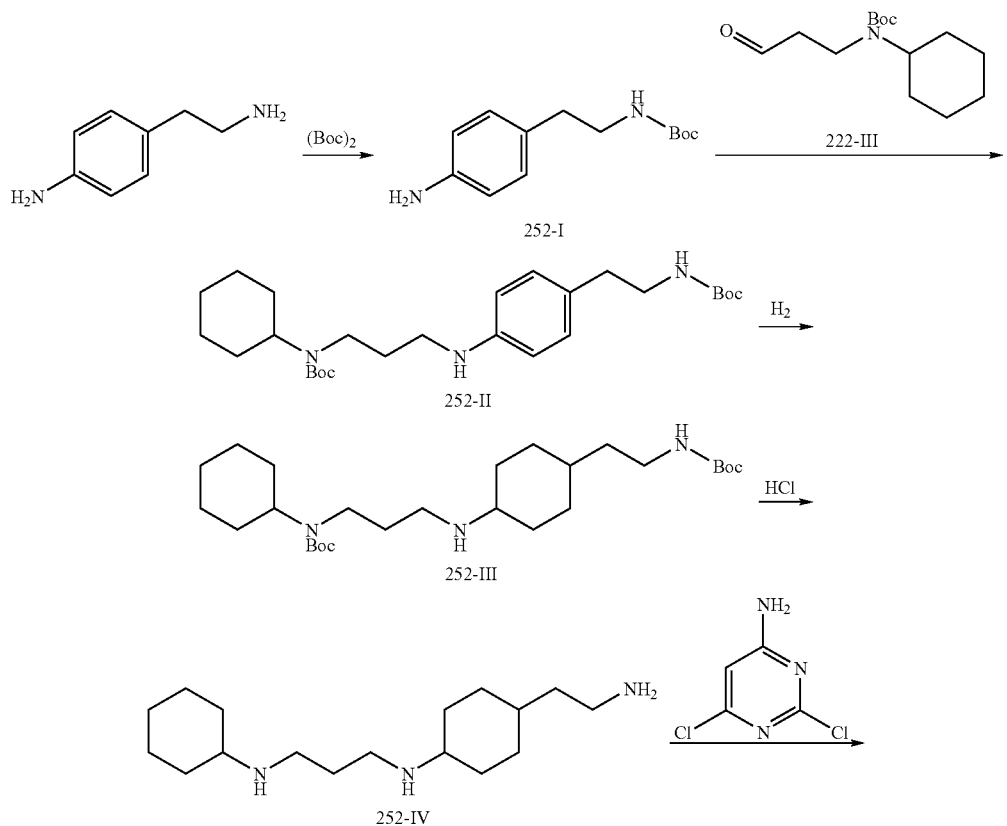

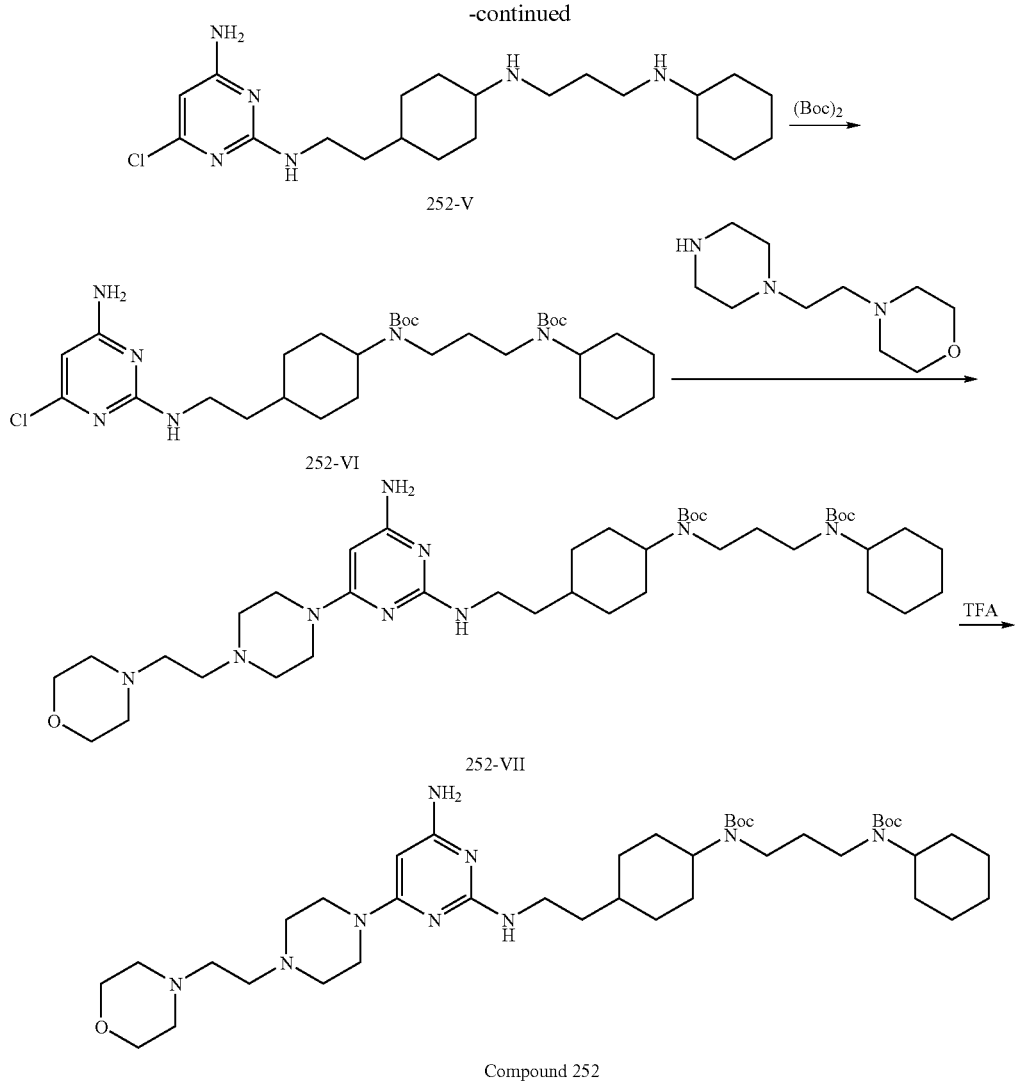

Compound 252

A solution of 2-aminoethylaniline (5.0 g) and Boc₂O (6.8 g) in CH₂Cl₂ (200 mL) was stirred at 25° C. overnight. The solution was then concentrated and the resultant residue was purified by column chromatography on silica gel (EtOAc/Hexane=1:1 as eluant) to give Intermediate 252-I (6.8 g) in a 83% yield.

222-III (7.3 g) prepared from Example 222 was added to a solution of Intermediate 252-I (6.8 g) in CH₂Cl₂ (250 mL). The mixture was stirred at 25° C. for 1.5 hour. NaBH(OAc)₃ (6.0 g) and a small amount of MeOH were added at 0° C. The mixture was stirred at room temperature overnight. After the solution was concentrated, a saturated solution of NaHCO₃ (250 mL) was added. The mixture was extracted with EtOAc, dried over anhydrous MgSO₄, filtered, and concentrated to afford crude Intermediate 252-II (6.0 g).

Crude Intermediate 252-II (3.0 g) in MeOH (15 mL) was hydrogenated in the presence of 5% Rh/C (300 mg) and 10% Pd/C (300 mg) at 50 psi at room temperature for 72 hours. The mixture was then filtered and concentrated. The resultant residue was purified by column chromatography on silica gel (EtOAc/MeOH=1:1) to afford Intermediate 252-III (2.6 g) in a 87% yield.

A solution of intermediate 252-III (1.5 g) treated with 1M HCl in ether (52 mL) and MeOH (10 mL) was stirred at room temperature for 8 hours. After additional ether was added, the solution was filtered. The solid thus obtained was dried under vacuum. K₂CO₃ was added to a suspension of the solid in CH₃CN at room temperature for 10 minutes. After water was added, the reaction mixture was stirred at room temperature for 2 hours, filtered, dried over anhydrous MgSO₄, and concentrated to afford crude Intermediate 252-IV (1.5 g).

Intermediate 252-IV (1.5 g) and Et₃N (0.5 mL) in 1-pentanol (14 mL) was allowed to react with 2,4-dichloro-6-aminopyrimidine (1.0 g) at 120° C. overnight. The solvent was then removed to afford crude Intermediate 252-V (2.0 g).

A solution of Intermediate 252-V (2.0 g) and Boc₂O (2.1 g) in CH₂Cl₂ (250 mL) was added to Et₃N (1.0 mL) at 25° C. overnight. The solution was then concentrated and the resultant residue was purified by column chromatography on silica gel (EtOAc/Hexane=1:1) to give Intermediate 252-VI (1.7 g) in a 56% yield.

N¹-Morpholine-N¹-piperazine ethane (300 mg) was added to Intermediate 252-VI (300 mg) in 1-pentanol (1 mL). The mixture was stirred at 120° C. overnight and then concentrated. The residue thus obtained was coated with SiO₂ and purified by column chromatography on silica gel (EtOAc/MeOH=1/1) to afford Intermediate 252-VII (260 mg) in a 70% yield.

A solution of 20% TFA/CH$_2$Cl$_2$ (5 mL) was added to a solution of Intermediate 252-VII (260 mg) in CH$_2$Cl$_2$ (2 mL). The reaction mixture was stirred for 8 hours at room temperature and concentrated by removing the solvent. The resultant residue was purified by column chromatography on silica gel (21% NH$_3$ (aq)/MeOH=1/19) to afford Compound 252 (175 mg) in a 91% yield. Compound 252 was then treated with 1 M HCl (4 mL) in CH$_2$Cl$_2$ (2 mL) for 0.5 hours. After the solvents were removed, the residue was treated with ether and filtered to give hydrochloride salt of Compound 252.
CI-MS (M$^+$+1): 572.5.

EXAMPLE 253

Preparation of Compound 253

Compound 253 was prepared in a manner similar to that used to prepare compound 252.
CI-MS (M$^+$+1): 531.4.

EXAMPLE 254

Preparation of Compound 254

Compound 254 was prepared in a manner similar to that used to prepare compound 252.
CI-MS (M$^+$+1): 547.4.

EXAMPLE 255

Preparation of Compound 255

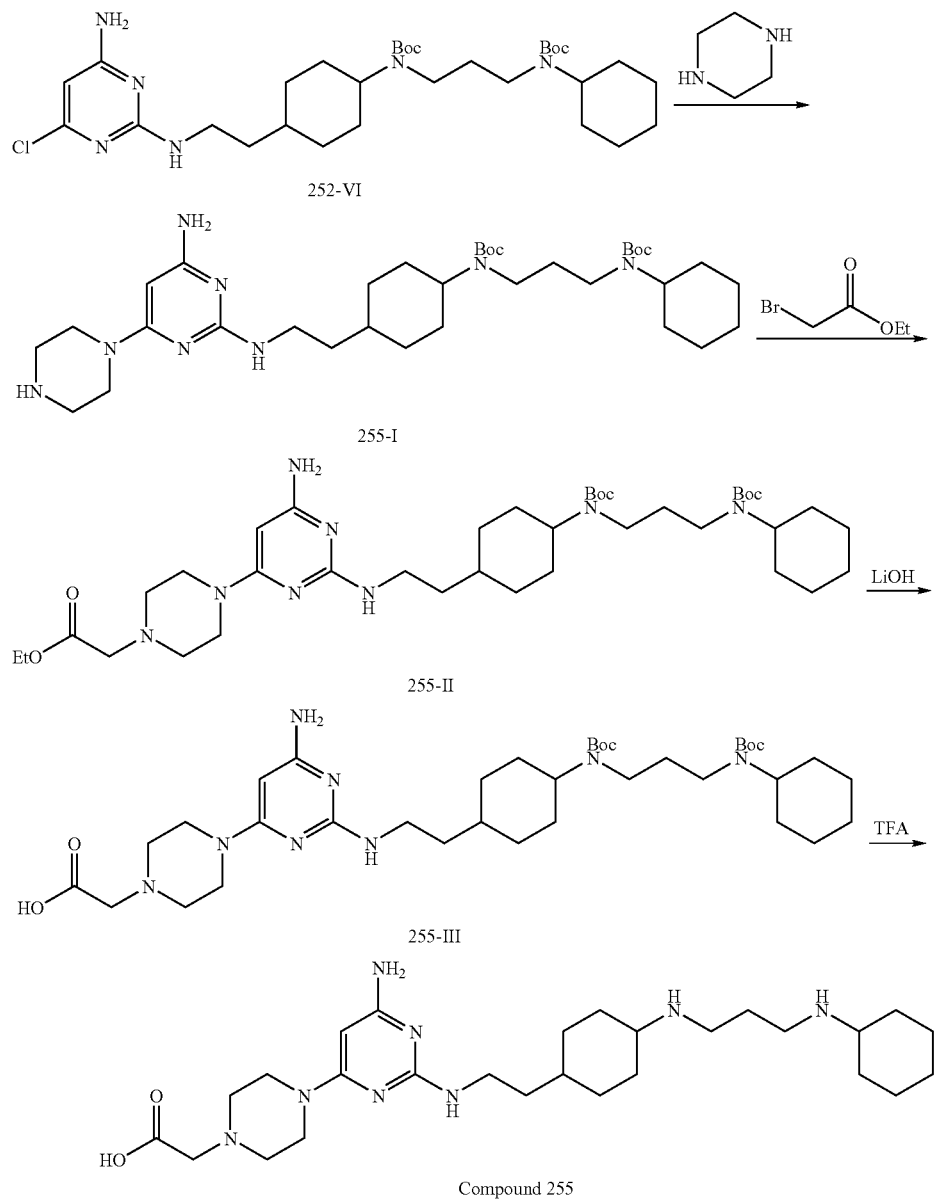

A solution of Intermediate 252-VI (1.0 g) and piperazine (0.42 g) in 1-pentanol (8 mL) was stirred at 120° C. overnight. After the solution was concentrated, the residue was treated with water and extracted with $CH_2Cl_2$. The organic layer was separated and concentrated. The residue thus obtained was purified by column chromatography on silica gel (EtOAc/MeOH=2/1) to afford Intermediate 255-I (0.9 g) in a 84% yield.

To a solution of Intermediate 255-I (0.4 g) in $CH_3CN$ (6 mL) were added ethyl bromoacetate (100 mg) and $K_2CO_3$ (400 mg). The mixture was stirred at 60° C. for 3 hours. After the solution was filtered and concentrated, the residue was purified by column chromatography on silica gel (EtOAc/MeOH=4/1) to afford Intermediate 255-I (0.17 g) in a 38% yield.

Intermediate 255-II (0.17 g) dissolved in THF (2 mL) was added to 0.5 M of an LiOH aqueous solution (2 mL). The mixture was stirred at room temperature for 15 hours. It was acidified with 2.5 M HCl (PH=9) and filtered to obtain yellow solid. The yellow solid was purified by column chromatography on silica gel (EtOAc/MeOH=1/5) to afford Intermediate 255-III (0.1 g) in a 61% yield.

20% $TFA/CH_2Cl_2$ (3 mL) was added to a solution of Intermediate 255-III (100 mg) in $CH_2Cl_2$ (2 mL). The solution was stirred at room temperature for 2 hours and then concentrated. The residue in acetone (3 mL) was added to HCl (4 M in dioxane, 1 mL) at room temperature and the mixture was stirred for 30 minutes. After the solvents were removed, the residue was treated with ether and filtered to give hydrochloride salt of Compound 255 (62 mg).

CI-MS ($M^+$+1): 517.4.

EXAMPLE 256

Preparation of Compound 256

Compound 256 was prepared in a manner similar to that used to prepare compound 255.

CI-MS ($M^+$+1): 531.7.

EXAMPLE 257

Preparation of Compound 257

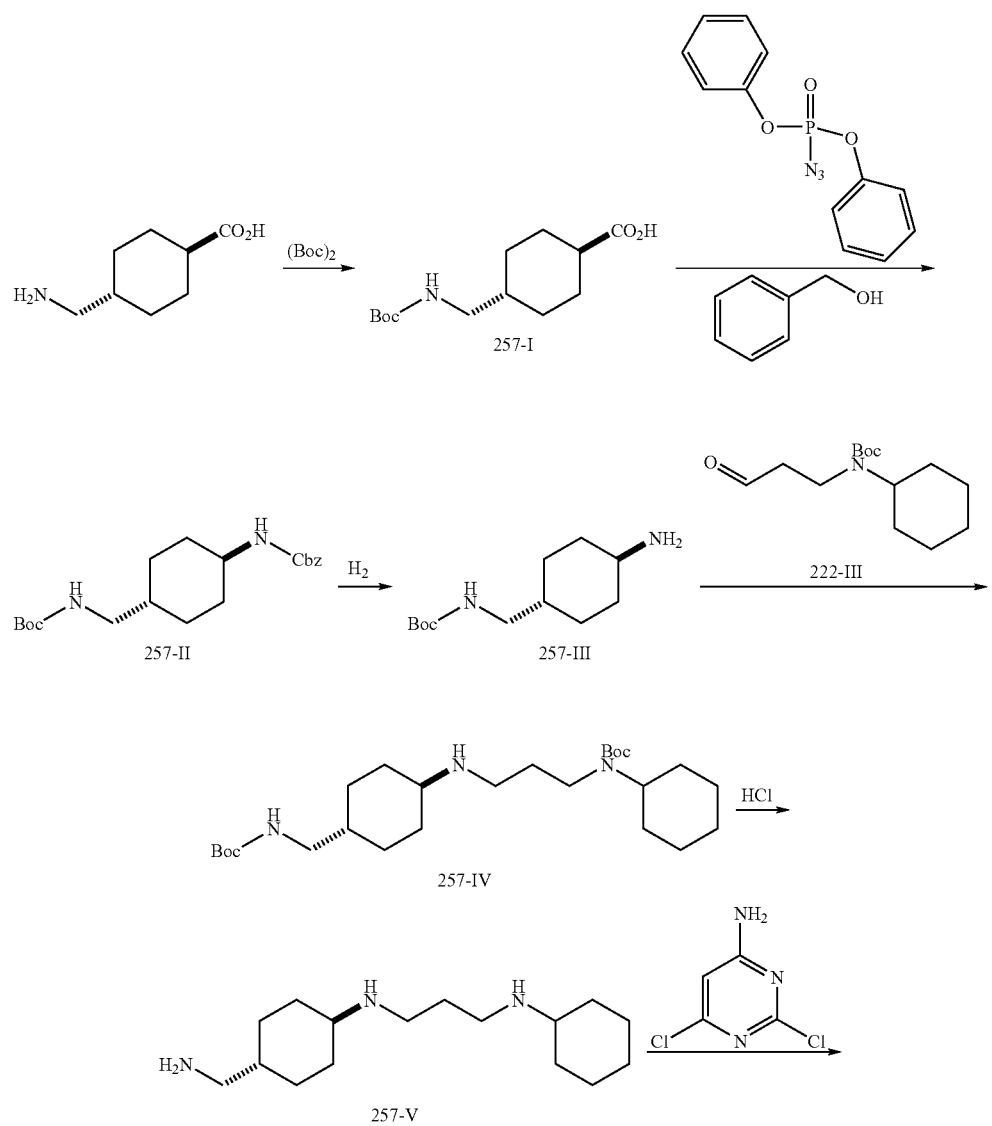

-continued
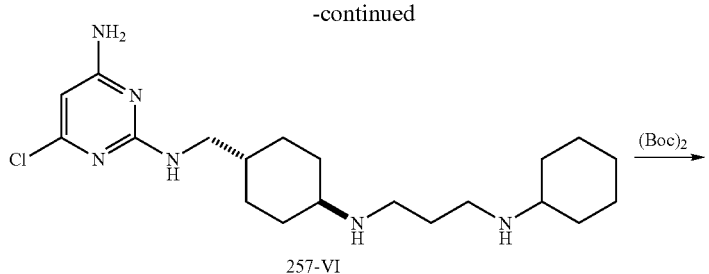
257-VI
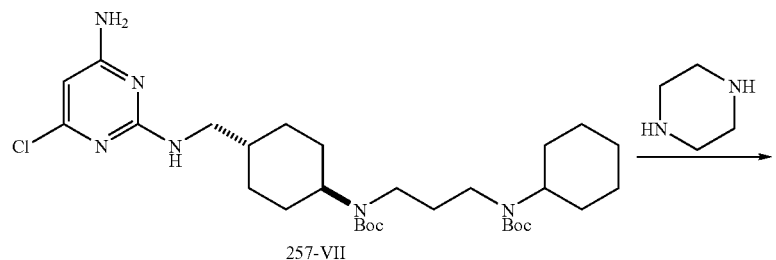
257-VII
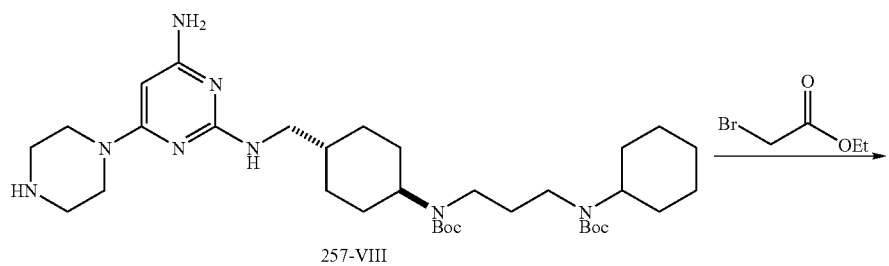
257-VIII
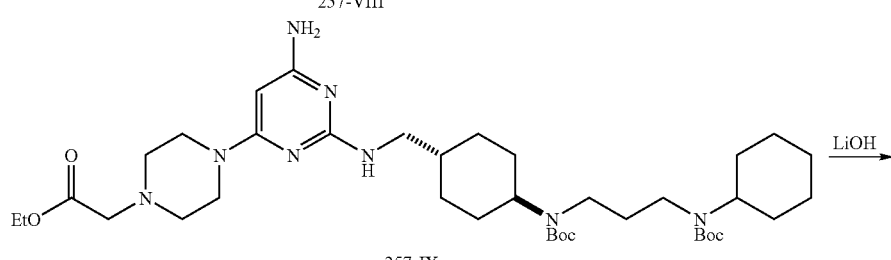
257-IX
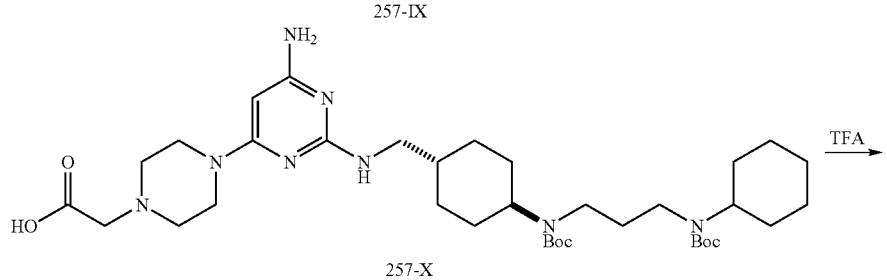
257-X
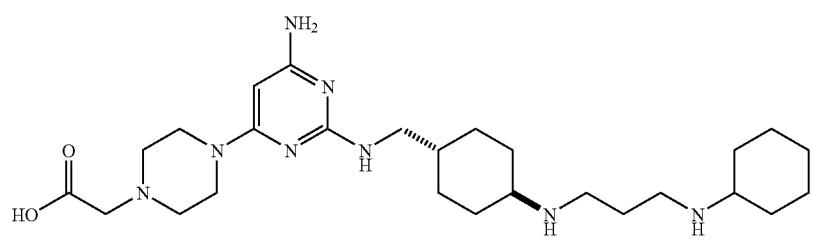
Compound 257

KOH (14 g) and Boc₂O (33.3 g) were added to a solution of trans-4-(Aminomethyl)cyclohexane-carboxylic acid (20 g) in dioxane (112 mL) at 0° C. The reaction was stirred at 25° C. overnight. The solution was concentrated to half of the original volume under vacuum, acidified with 2.5 N HCl (PH=3), and extracted with EtOAc. The combined organic layer was washed with brine, dried over anhydrous MgSO₄, filtered, and concentrated to give a white solid Intermediate 257-I (31.9 g).

To a suspension of the above solid in toluene (150 mL) were added phosphorazidic acid diphenyl ester (32.4 g) and Et₃N (11.9 g) at 25° C. for 1.0 hour. The reaction mixture was warmed to 80° C. for 3.0 hours and then cooled to 25° C. After benzyl alcohol (20 g) was added, the reaction mixture was stirred at 80° C. for another 3.0 hours and then warmed to 120° C. overnight. It was then concentrated and dissolved again in EtOAc and H₂O. The organic layer was then collected. The aqueous layer was extracted with EtOAc. The combined organic layer was washed with 2.5 N HCl, saturated aqueous NaHCO₃ and brine, dried over anhydrous MgSO₄, filtered, and concentrated. The residue thus obtained was purified by column chromatography on silica gel (EtOAc/Hexane=1/2) to give Intermediate 257-II (35 g) in a 79% yield.

To a suspension of Intermediate 257-II (1.9 g) in MeOH (10 mL) was added 10% Pd/C (190 mg). The mixture was stirred at ambient temperature under hydrogen atmosphere for 4.0 hours, filtered, and concentrated. The residue thus obtained was purified by column chromatography on silica gel (using EtOAc and MeOH as an eluant) to give Intermediate 257-III (750 mg) in a 60% yield.

222-III (1,198 mg) prepared from Example 222 was added to a solution of Intermediate 257-III (750 mg) in CH₂Cl₂ (30 mL). The mixture was stirred at 25° C. for 2 hours. NaBH(OAc)₃ (1,046 mg) was then added at 25° C. for 12 hours. After the solution was concentrated, a saturated aqueous NaHCO₃ solution was added to the resultant residue. The mixture was extracted with CH₂Cl₂. The organic layer was collected and concentrated. The residue thus obtained was purified by column chromatography on silica gel (using EtOAc and MeOH as an eluant) to afford Intermediate 257-IV (1,200 mg) in a 78% yield.

A solution of Intermediate 257-IV (5.2 g) treated with 4 N HCl/dioxane (39 mL) in MeOH (52 mL) was stirred at room temperature for 8 hours. After ether (104 mL) was added, the solution was filtered. The solid thus obtained was dried under vacuum. K₂CO₃ (21 g) was added to a suspension of this solid in CH₃CN (230 mL) at room temperature for 10 minutes. After water (9 mL) was added, the reaction mixture was stirred at room temperature for 2 hours. The mixture was then filtered, dried over anhydrous MgSO₄, and concentrated to afford crude Intermediate 257-V (2.8 g).

Crude Intermediate 257-V (2.8 g) and Et₃N (1.3 mL) in 1-pentanol (11.3 mL) was allowed to react with 2,4-dichloro-6-aminopyrimidine (1,633 mg) at 100° C. for 12 hours. The solvent was then removed and the residue was purified by column chromatography on silica gel (21% NH₃ (aq)/MeOH=1/19) to afford Intermediate 257-VI (3.3 g) in a 75% yield.

A solution of Intermediate 252-VI (3.3 g) and Boc₂O (4.189 g) in CH₂Cl₂ (60 mL) was added to Et₃N (1.0 mL) at 25° C. overnight. The solution was then concentrated and the resultant residue was purified by column chromatography on silica gel (using EtOAc and Hexane as an eluant) to give Intermediate 257-VII (3.2 g) in a 64% yield.

Intermediate 257-VII (2.6 g) and piperazine (1.127 g) in 1-pentanol (5.2 mL) was added to Et₃N (0.5 mL) at 120° C. for 18 hours. After the solution was concentrated, the residue was treated with water and extracted with CH₂Cl₂. The organic layer was collected and concentrated. The residue thus obtained was purified by column chromatography on silica gel (using EtOAc/MeOH to 21% NH₃ (aq)/MeOH as an eluant) to afford Intermediate 257-VIII (1.8 g) in a 64% yield.

To a solution of Intermediate 257-VIII (200 mg) in CH₃CN (20 mL) were added ethyl bromoacetate (52 mg) and K₂CO₃ (128 mg). The mixture was stirred at 60° C. for 2 hours. The solution was filtered and concentrated. The residue was purified by column chromatography on silica gel (using EtOAc and MeOH as an eluant) to afford Intermediate 257-IX (140 mg) in a 62% yield.

0.5 M of a LiOH aqueous solution (10 mL) was added to Intermediate 257-IX (500 mg) dissolved in THF (10 mL). The mixture was stirred at room temperature for 15 hours. It was then acidified with 2.5 M HCl (pH=9) and filtered to obtain a yellow solid. The yellow solid was purified by column chromatography on silica gel (using EtOAc/MeOH to 21% NH₃ (aq)/MeOH as an eluant) to afford Intermediate 257-X (337 mg) in a 70% yield.

20% TFA/CH₂Cl₂ (10 mL) was added to a solution of Intermediate 257-X (400 mg) in CH₂Cl₂ (8 mL). The solution was stirred at room temperature for 2 hours and then concentrated. To the residue in acetone (7 mL) was added HCl (4 M in dioxane, 1.3 mL) at room temperature for 30 minutes. After the solvents were removed, the residue was treated with ether and filtered to give hydrochloride salt of Compound 257 (257 mg).

CI-MS (M⁺+1): 503.4.

EXAMPLE 258

Preparation of Compound 258

Compound 258 was prepared in a manner similar to that used to prepare compound 257.

CI-MS (M⁺+1): 531.4.

EXAMPLE 259

Preparation of Compound 259

Compound 259 was prepared in a manner similar to that used to prepare compound 257.

CI-MS (M⁺+1): 517.4.

EXAMPLE 260
Preparation of Compound 260
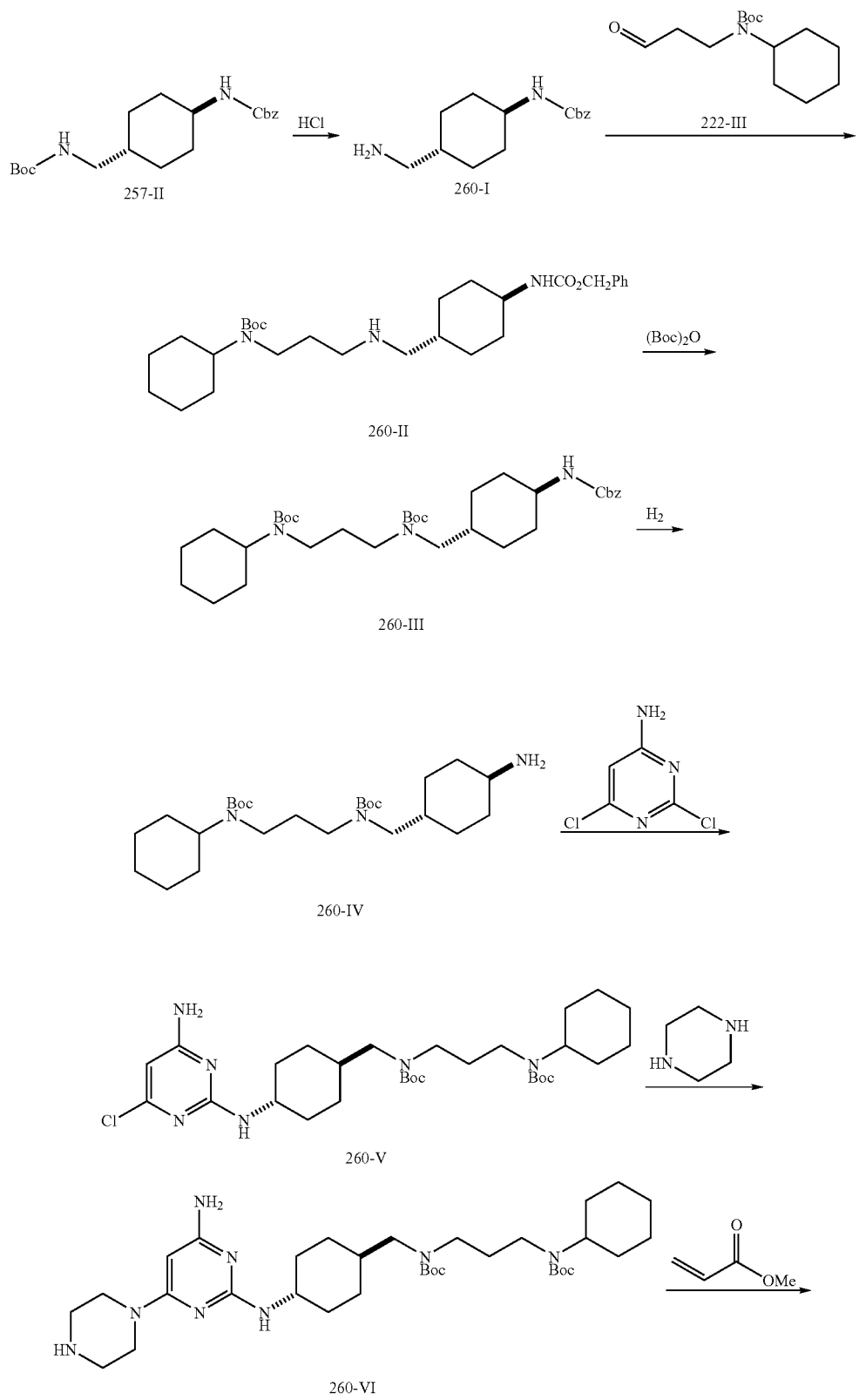

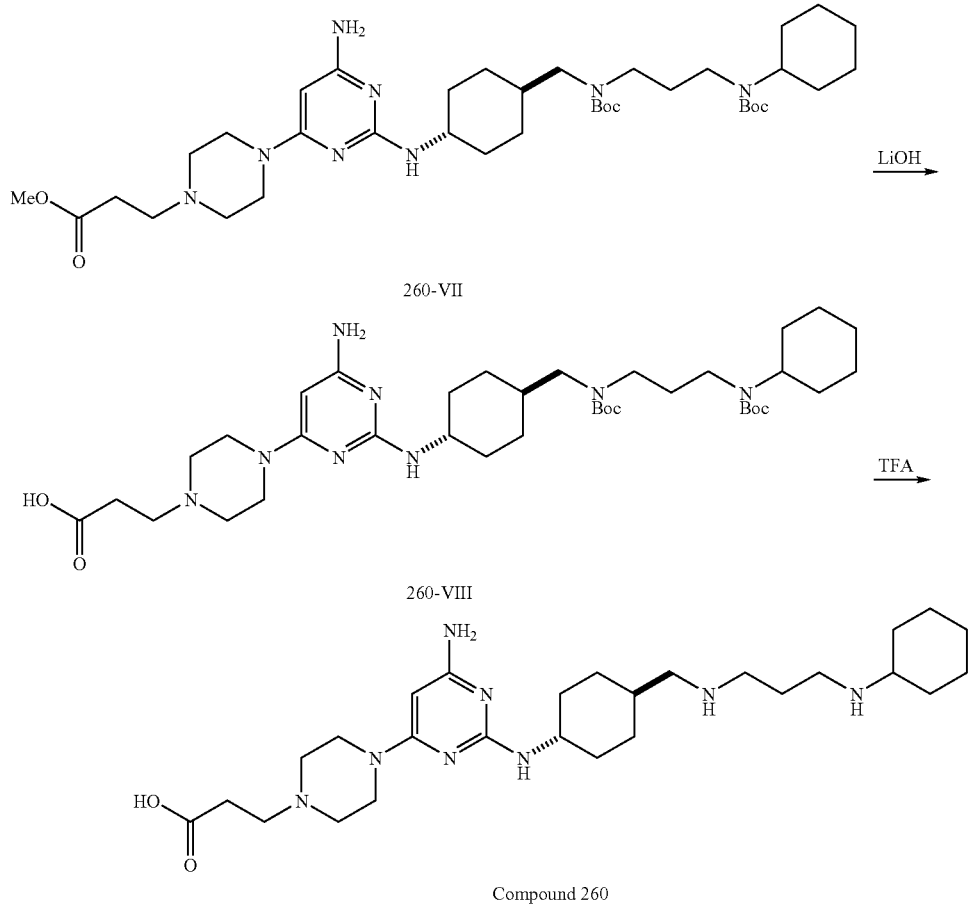

Compound 260

A solution of Intermediate 257-II (35 g) treated with 4 N HCl/dioxane (210 mL) in MeOH (350 mL) was stirred at room temperature overnight. After ether (700 mL) was added, the solution was filtered. The solid thus obtained was dried under vacuum. $K_2CO_3$ was added to a suspension of this solid in $CH_3CN$ and iso-propanol at room temperature for 10 minutes. After water was added, the reaction mixture was stirred at room temperature for 2 hours, filtered, dried over anhydrous $MgSO_4$, and concentrated. The resultant residue was purified by column chromatography on silica gel (using $CH_2Cl_2$ and MeOH as an eluant) to give Intermediate 260-I (19 g) in a 76% yield.

Intermediate 222-III (21 g) prepared from Example 222 was added to a solution of Intermediate 260-I (19 g) in $CH_2Cl_2$ (570 mL). The mixture was stirred at 25° C. for 2 hours. $NaBH(OAc)_3$ (23 g) was then added at 25° C. overnight. After the solution was concentrated, a saturated aqueous $NaHCO_3$ solution was added to the resultant residue. The mixture was then extracted with $CH_2Cl_2$. The solution was concentrated and the residue was purified by column chromatography on silica gel (using EtOAc and MeOH as an eluant) to afford Intermediate 260-II (23.9 g) in a 66% yield.

A solution of Intermediate 260-II (23.9 g) and $Boc_2O$ (11.4 g) in $CH_2Cl_2$ (200 mL) was added to $Et_3N$ (5.8 mL) at 25° C. for overnight. The solution was then concentrated and the resultant residue was purified by column chromatography on silica gel (using EtOAc and Hexane as an eluant) to give Intermediate 260-III (22 g) in a 77% yield.

10% Pd/C (2.2 g) was added to a suspension of Intermediate 260-III (22 g) in MeOH (44 mL). The mixture was stirred at ambient temperature under hydrogen atmosphere overnight, filtered, and concentrated. The residue thus obtained was purified by column chromatography on silica gel (using EtOAc and MeOH as an eluant) to afford Intermediate 260-IV (16.5 g) in a 97% yield.

Intermediate 260-IV (16.5 g) and $Et_3N$ (4.4 mL) in 1-pentanol (75 mL) was allowed to react with 2,4-dichloro-6-aminopyrimidine (21 g) at 120° C. overnight. The solvent was then removed and the residue was purified by column chromatography on silica gel (using EtOAc and hexane as an eluant) to afford Intermediate 260-V (16.2 g) in a 77% yield.

Intermediate 260-V (16.2 g) and piperazine (11.7 g) in 1-pentanol (32 mL) was added to $Et_3N$ (3.3 mL) at 120° C. overnight. After the solution was concentrated, the residue was treated with water and extracted with $CH_2Cl_2$. The organic layer was collected and concentrated. The residue thus obtained was purified by column chromatography on silica gel (using EtOAc/MeOH to 21% $NH_3$ (aq)/MeOH as an eluant) to afford Intermediate 260-VI (13.2 g) in a 75% yield.

Methylacrylate (532 mg) was added to a solution of Intermediate 260-VI (4 g) in MeOH (200 mL) at 25° C. for 5 hours. The solution was then concentrated and the resultant residue was purification by column chromatography on silica gel (using EtOAc and MeOH as an eluant) to afford Intermediate 260-VII (3 g) in a 66% yield.

Intermediate 260-VII (3 g) dissolved in THF (60 mL) was added 0.5 M of a LiOH aqueous solution (60 mL). The mixture was stirred at room temperature for 15 hours. It was then acidified with 2.5 M HCl (pH=8) and filtered to obtain a yellow solid. The yellow solid was purified by column chromatography on silica gel (using $CH_2Cl_2$ and MeOH as an eluant) to afford Intermediate 260-VIII (1.4 g) in a 48% yield 20% $TFA/CH_2Cl_2$ (34 mL) was added to a solution of Intermediate 260-VIII (1.4 g) in $CH_2Cl_2$ (17 mL). The solution was stirred at room temperature for 5 hours and then concentrated. To the residue in acetone (20 mL) was added HCl (4 M in dioxane, 4 mL) at room temperature for 30 minutes. After the solvents were removed, the residue was treated with ether and (20 mL) and filtered to give hydrochloride salt of Compound 260 (1.4 g).

CI-MS ($M^+$+1): 517.4.

EXAMPLE 261

Preparation of Compound 261

Compound 261 was prepared in a manner similar to that used to prepare compound 260.
CI-MS ($M^+$+1): 531.4.

EXAMPLE 262

Preparation of Compound 262

Compound 262 was prepared in a manner similar to that used to prepare compound 260.
CI-MS ($M^+$+1): 503.4.

EXAMPLE 263

Preparation of Compound 263

Compound 263 was prepared in a manner similar to that used to prepare compound 260.
CI-MS ($M^+$+1): 545.4.

EXAMPLE 264

Preparation of Compound 264

Compound 264 was prepared in a manner similar to that used to prepare compound 260.
CI-MS ($M^+$+1): 545.4.

EXAMPLE 265

Preparation of Compound 265

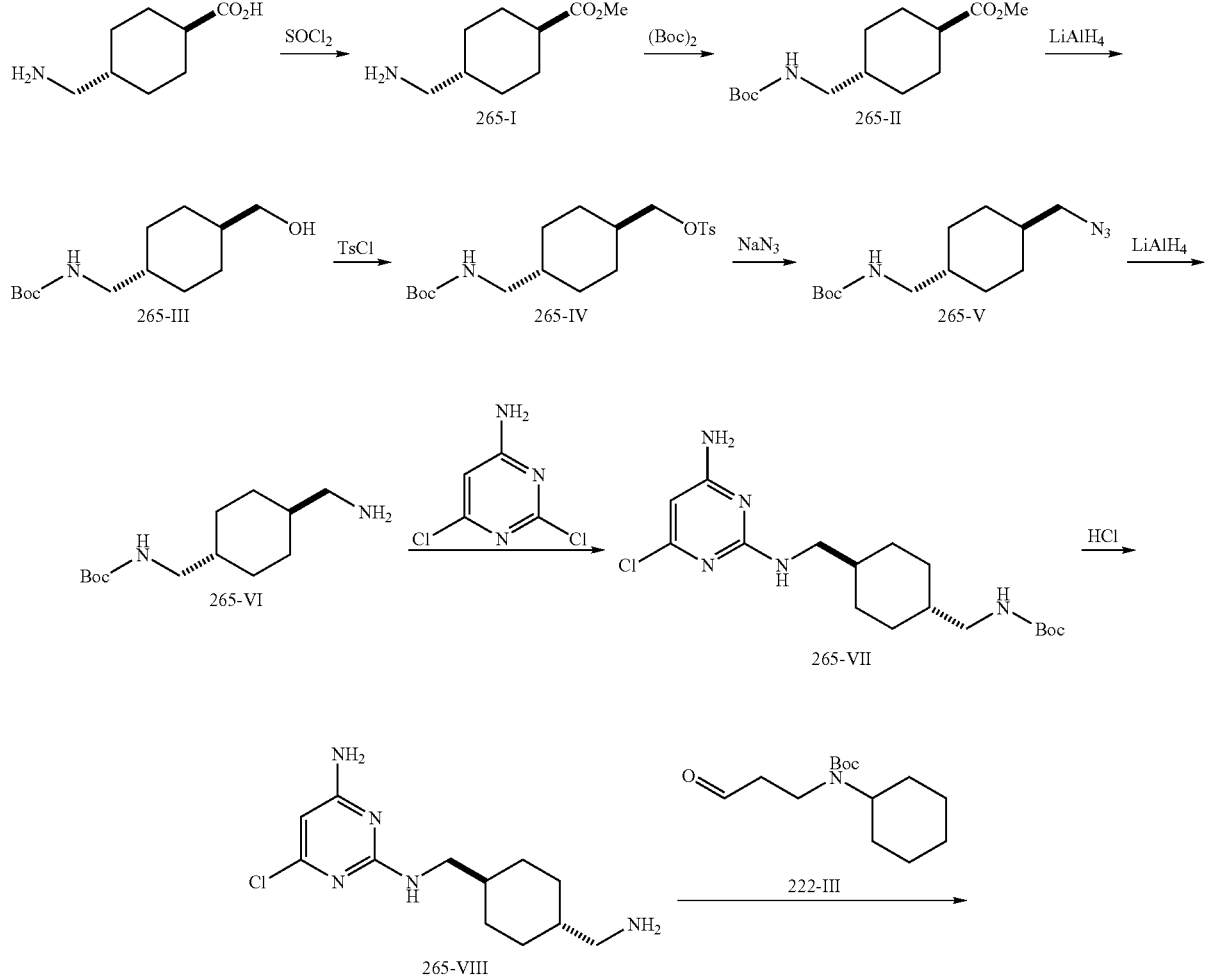

-continued
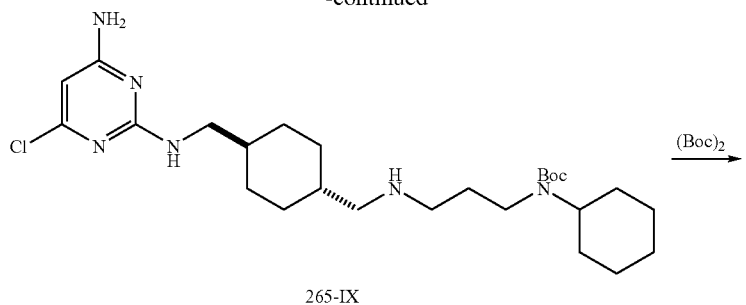
265-IX
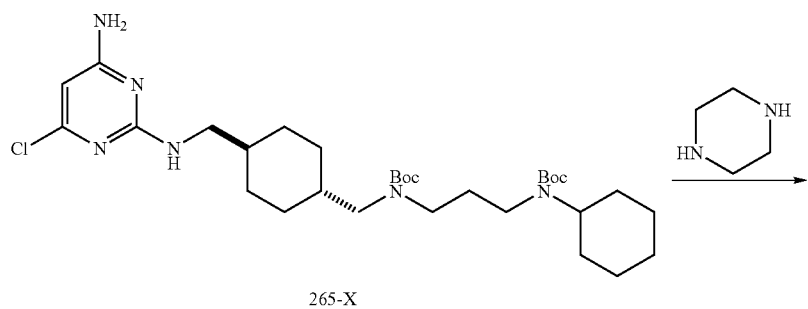
265-X
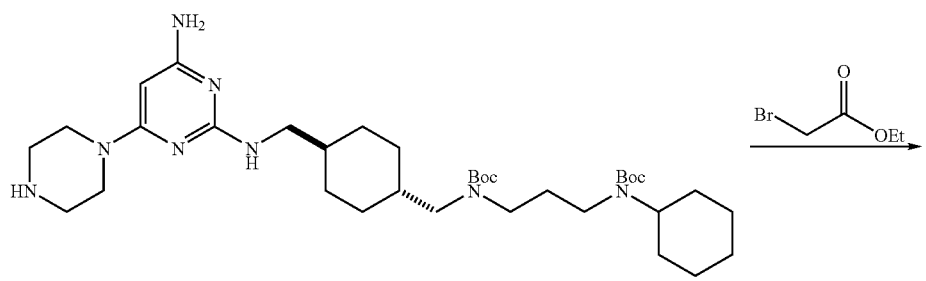
265-XI
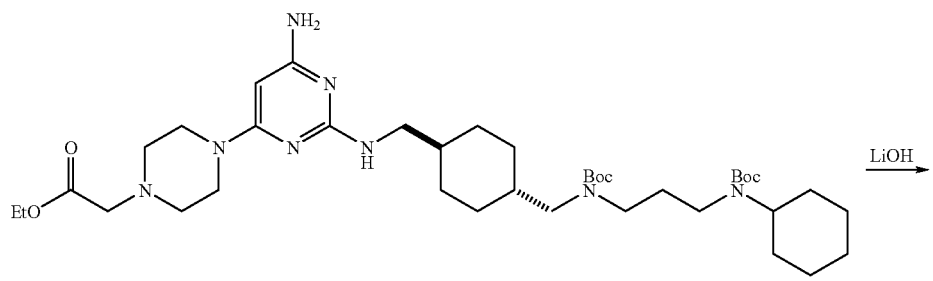
265-XII
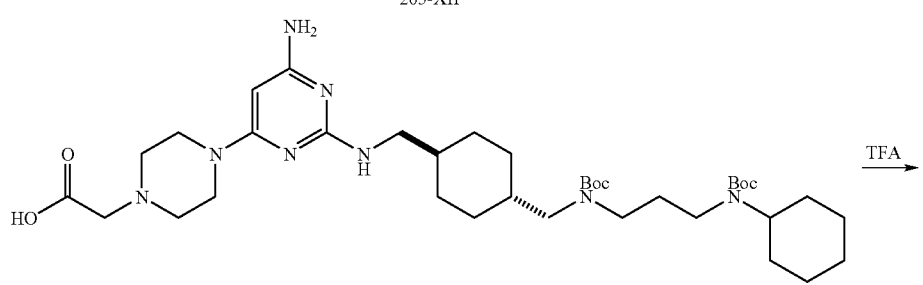
265-XIII

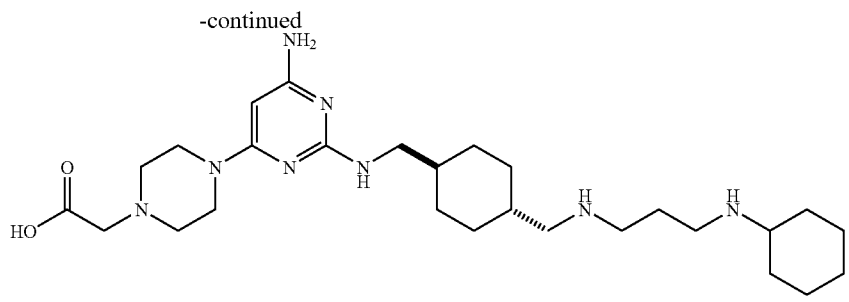

Compound 265

A suspension of cis-4-amino-cyclohexanecarboxylic acid (20 g) in MeOH (300 mL) was cooled to 0° C. Thionyl chloride (12.2 mL) was added dropwise to the suspension. The mixture was stirred at room temperature overnight and concentrated. To the he residue in $CH_3CN$ was added $K_2CO_3$ at room temperature for 10 minutes. After water was added, the mixture was stirred at room temperature for 2 hours, filtered, dried over anhydrous $MgSO_4$, concentrated to give a white solid Intermediate 265-I (25 g).

$Boc_2O$ (31.8 g) was added to a suspension of the crude Intermediate 265-I (25 g) in $CH_2Cl_2$ (300 mL) at 0° C. for 0.5 hour. The reaction mixture was stirred at 25° C. overnight and poured into water. The aqueous layer was extracted with $CH_2Cl_2$. The combined organic layer was collected, dried over anhydrous $MgSO_4$, filtered, and concentrated to give crude Intermediate 265-II (38 g).

A solution of crude Intermediate 265-II (38 g) in $Et_2O$ (100 mL) was added to a suspension of $LiAlH_4$ (6.7 g) in $Et_2O$ (400 mL) below 0° C. The reaction mixture was stirred at room temperature overnight. The mixture was quenched with $Na_2SO_4.10H_2O$, and filtered through a pad of celite. The filtrate was dried over anhydrous $MgSO_4$, filtered, dried under reduced pressure. The residue thus obtained was purified by column chromatography on silica gel (using $CH_2Cl_2$ and MeOH as an eluant) to afford Intermediate 265-III (28 g) in a 90% yield.

To a solution of Intermediate 265-III (28 g) in $CH_2Cl_2$ (300 mL) were added $Et_3N$ (30 mL), DMPA (0.7 g), and p-toluenesulfonyl chloride (25.8 g). The reaction mixture was stirred at 25° C. overnight. The resulting solution was concentrated and the residue was re-dissolved in EtOAc. The solution was then washed with water and extracted with EtOAc. The organic layer was collected, dried over anhydrous $MgSO_4$, concentrated to give Intermediate 265-IV (50 g).

$NaN_3$ (24 g) was added to a solution of Intermediate 265-IV (50 g) in DMF (300 mL). The resulting mixture was stirred at 60° C. overnight, filtered, and concentrated. The residue in $CH_2Cl_2$ was washed with a saturated aq. $NaHCO_3$ solution. The organic solution collected, dried, and concentrated to give a residue. The residue was purified by column chromatography on silica gel (using EtOAc as an eluant) to afford Intermediate 265-V (30 g) in a 97% yield.

To a suspension of $LiAlH_4$ (5.4 g) in $Et_2O$ (400 mL) was added a solution of crude Intermediate 265-V (30 g) in $Et_2O$ (100 mL) below 0° C. The reaction mixture was stirred at room temperature overnight. The reaction was quenched with $Na_2SO_4.10H_2O$, filtered through a pad of celite. The filtrate was dried over anhydrous $MgSO_4$, filtered, and dried under reduced pressure. The residue thus obtained was purified by column chromatography on silica gel (MeOH as an eluant) to afford Intermediate 265-VI (24.5 g) in a 90% yield.

A solution of Intermediate 265-VI (24.5 g) and $Et_3N$ (13 mL) in 1-pentanol (75 mL) was reacted with 2,4-dichloro-6-aminopyrimidine (19.6 g) at 120° C. overnight. The reaction mixture was stirred at 150° C. for 3 hours, filtered, and dried under reduced pressure. The residue thus obtained was purified by column chromatography on silica gel (EtOAc as an eluant) to afford Intermediate 265-VII (26.2 g) in a 68% yield.

A solution of Intermediate 265-VII (26.2 g) treated with 4 N HCl/dioxane (160 mL) in MeOH (200 mL) was stirred at room temperature overnight. After ether was added, the solution was filtered. The solid thus obtained was dried by vacuum. To a suspension of the above solid in $CH_3CN$ and iso-propanol was added $K_2CO_3$ at room temperature for 10 minutes. After water was added at room temperature for 2 hours, the reaction mixture was filtered, dried over anhydrous $MgSO_4$, filtered, and concentrated and to give Intermediate 265-VIII (15 g).

To a solution of Intermediate 265-VIII (15 g) in $CH_2Cl_2$ (500 mL) was added Intermediate 222-III (18.6 g). The mixture was stirred at 25° C. for 2 hours. $NaBH(OAc)_3$ (11.7 g) was then added at 25° C. and the mixture was stirred overnight. The solution was then concentrated and a saturated aqueous $NaHCO_3$ solution was added. The mixture was extracted with $CH_2Cl_2$. The organic layer was collected, dried over anhydrous $MgSO_4$, concentrated. The residue thus obtained was purified by column chromatography on silica gel (MeOH as an eluant) to afford Intermediate 265-IX (14.1 g) in a 39% yield.

$Et_3N$ (2.2 mL) was added to a solution of Intermediate 265-IX (14.1 g) and $Boc_2O$ (6.6 g) in $CH_2Cl_2$ (150 mL) at 25° C. The solution was stirred overnight and then concentrated. The resultant residue was purified by column chromatography on silica gel (EtOAc as an eluant) to give Intermediate 265-X (12 g) in a 71% yield.

$Et_3N$ (2.4 mL) was added to a mixture of Intermediate 265-X (12 g) and piperazine (5.1 g) in 1-pentanol (24 mL) 120° C. The solution was stirred overnight and then concentrated. The residue was treated with water and extracted with $CH_2Cl_2$. The organic layer was collected, dried over anhydrous $MgSO_4$. The residue thus obtained was purified by column chromatography on silica gel (MeOH as eluant) to afford Intermediate 265-XI (9.6 g) in a 74% yield.

To a solution of Intermediate 265-XI (500 mg) in $CH_3CN$ (50 mL) were added ethyl bromoacetate (127 mg) and $K_2CO_3$ (314 mg). The mixture was stirred at 60° C. for 2 hours. The solution was filtered and concentrated. The residue thus obtained was purified by column chromatography on silica gel (EtOAc as an eluant) to afford Intermediate 265-XII (230 mg) in a 41% yield.

0.5 M LiOH (5 mL) was added to a solution of Intermediate 265-XII (230 mg) in THF (10 mL). The mixture was stirred at room temperature for 15 hours. It was then acidified with 2.5

M HCl (pH=8) and filtered to obtain a yellow solid, which was purified by column chromatography on silica gel (MeOH as an eluant) to afford Intermediate 265-XIII (150 mg) in a 68% yield.

To a solution of Intermediate 265-XIII (150 mg) in $CH_2Cl_2$ (2 mL) was added 20% $TFA/CH_2Cl_2$ (3 mL). The solution was stirred at room temperature for 5 hours and then concentrated. HCl (4 M in dioxane, 2 mL) was added in the residue in acetone at room temperature for 30 minutes. After solvents were removed, the residue was treated with ether and filtered to give hydrochloride salt of compound 265 (94 mg).

CI-MS ($M^+$+1): 517.4.

Example 266

Preparation of Compound 266

Compound 266 was prepared in a manner similar to that used to prepare compound 265 (see example 264).

CI-MS ($M^+$+1): 531.4.

Example 267

Preparation of Compound 267

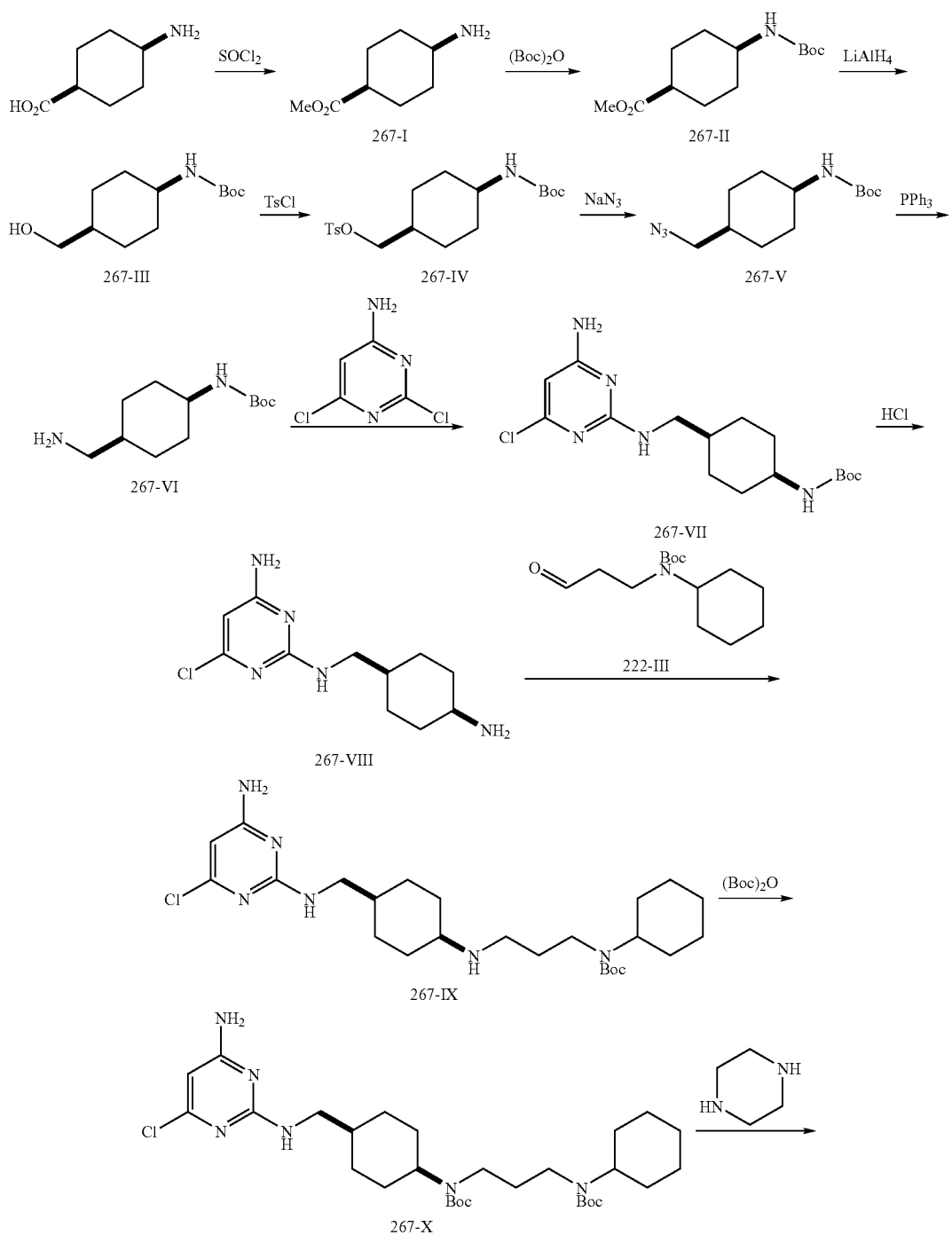

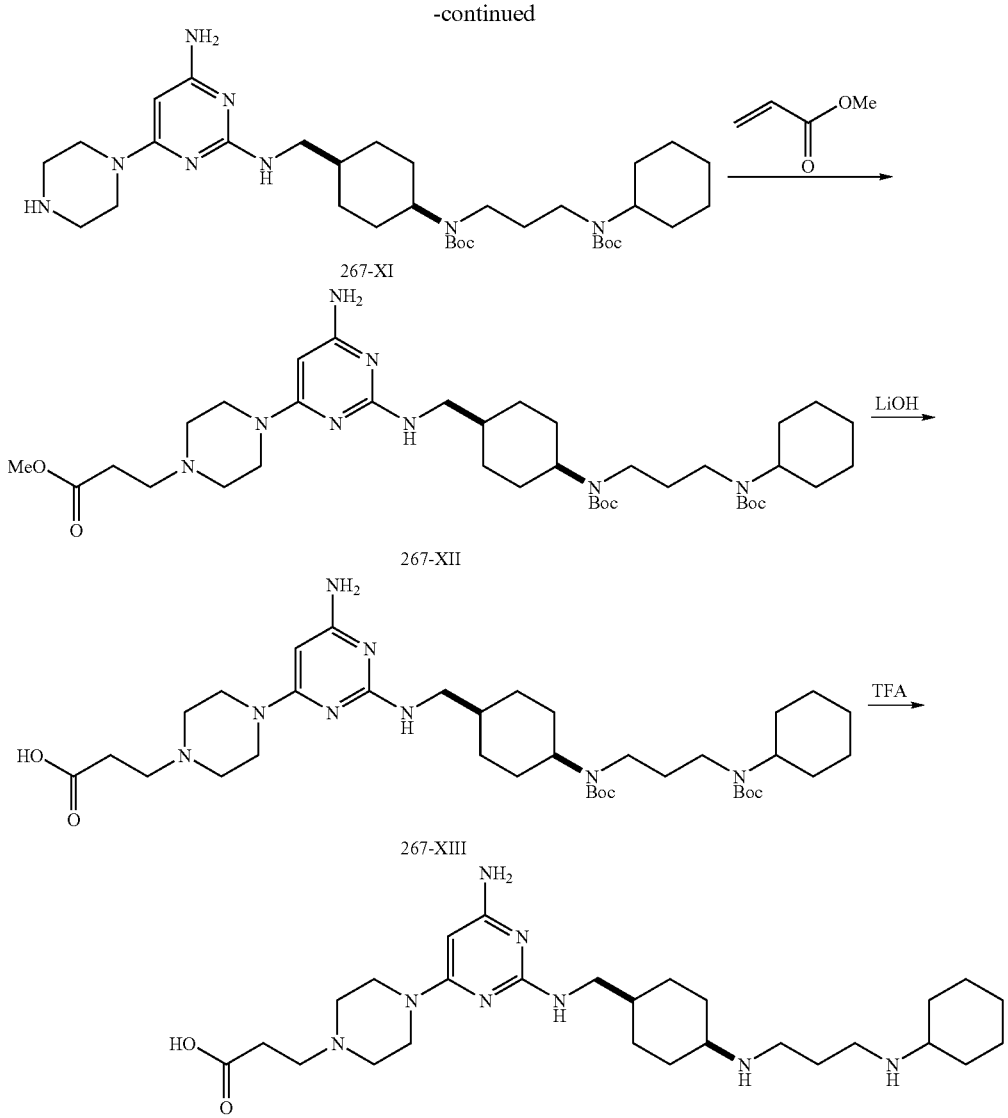

Compound 267

A suspension of cis-4-amino-cyclohexanecarboxylic acid (30 g) in MeOH (500 mL) was cooled to 0° C. Thionyl chloride (30.5 mL) was added dropwise. The mixture was stirred at room temperature overnight and concentrated to give a white solid Intermediate 267-I (32.6 g).

To a suspension of Intermediate 267-I (32.6 g) obtained above in $CH_2Cl_2$ (500 mL) were added $Et_3N$ (18 mL) and $Boc_2O$ (50 g) sequentially. The reaction mixture was stirred at 25° C. overnight and poured into water. The aqueous layer was extracted with $CH_2Cl_2$. The combined organic layer was dried over anhydrous $MgSO_4$, filtered, concentrated to give crude Intermediate 267-II (53.4 g).

A solution of crude Intermediate 267-II (53.4 g) in $Et_2O$ (100 mL) was added to a suspension cooled at 0° C. of $LiAlH_4$ (11 g) in $Et_2O$ (500 mL) below 0° C. The reaction mixture was stirred at room temperature overnight. The resulting solution was cooled in ice-bath, quenched with cold water, filtered through a pad of celite. The filtrate was dried over anhydrous $MgSO_4$, filtered, washed with hexane, and dried under reduced pressure to give crude Intermediate 267-III (43.21 g).

$Et_3N$ (32 mL), DMPA (4.6 g) and p-toluenesulfonyl chloride (40 g) were added to a solution of Intermediate 267-III (43.21 g) in $CH_2Cl_2$ (400 mL). The reaction mixture was stirred at 25° C. overnight. The resulting solution was concentrated and the residue was dissolved in EtOAc. The solution was washed with water and extracted with EtOAc. The organic layer was dried over anhydrous $MgSO_4$, and concentrated to give a residue. The residue was purified by column chromatography on silica gel (EtOAc/Hexane=1/4) to afford Intermediate 267-IV (57.34 g) in a 71% yield.

$NaN_3$ (29 g) was added to a solution of Intermediate 267-IV (57.34 g) in DMF (200 mL). The resulting mixture was stirred at 40° C. overnight, filtered, and concentrated. The residue was dissolved in $CH_2Cl_2$ and was washed with a saturated aqueous $NaHCO_3$ solution. The solution was concentrated to give a residue, which was purified by column chromatography on silica gel (EtOAc/Hexane=1/6) to afford Intermediate 267-V (30.48 g) in a 80% yield.

$PPh_3$ (12.9 g) and $H_2O$ (0.9 mL) were added to a solution of Intermediate 267-V (11.37 g) in THF (200 mL). After the solution was stirred at 25° C. overnight, the solution was concentrated to give a residue, which was purified by column chromatography on silica gel (EtOAc/MeOH=15/1) to afford Intermediate 267-VI (9.44 g) in a 93% yield.

A solution of Intermediate 267-VI (9.44 g) and Et$_3$N (4 mL) in 1-pentanol (40 mL) was reacted with 2,4-dichloro-6-aminopyrimidine (7.5 g). The solution was stirred at 120° C. overnight. The solvent was removed and the residue thus obtained was purified by column chromatography on silica gel (EtOAc/MeOH=1/2) to afford Intermediate 267-VII (10.5 g) in a 71% yield.

A solution of Intermediate 267-VII (2.0 g) treated with 4 N HCl/dioxane (10 mL) in MeOH (20 mL) was stirred at room temperature overnight. After ether was added, the solution was filtered. The solid was dried under vacuum. To a suspension of the above solid in CH$_3$CN and iso-propanol was added K$_2$CO$_3$ at room temperature and was stirred for 10 minutes. After water was added to the reaction mixture at room temperature, it was stirred for another 2 hours. The mixture was then filtered, dried over anhydrous MgSO$_4$, filtered, and concentrated. The resultant residue was purified by column chromatography on silica gel (CH$_2$Cl$_2$ and MeOH as eluant) to give Intermediate 267-VIII (1.1 g) in a 77% yield.

Intermediate 222-III (1.58 g) was added to a solution of Intermediate 267-VIII (1.10 g) in CH$_2$Cl$_2$ (40 mL). The mixture was stirred at 25° C. for 2 hours. NaBH(OAc)$_3$ (907 mg) was then added at 25° C. and the mixture was stirred overnight. The mixture was then concentrated and a saturated aqueous NaHCO$_3$ solution was added to the resultant residue. The mixture was extracted with CH$_2$Cl$_2$. The organic layer was collected and concentrated. The residue thus obtained was purified by column chromatography on silica gel (EtOAc and MeOH as eluant) to afford Intermediate 267-IX (1.30 g) in a 61% yield.

Et$_3$N (0.3 mL) was added to a solution of Intermediate 267-IX (1.30 g) and Boc$_2$O (0.63 g) in CH$_2$Cl$_2$ (150 mL) at 25° C. The solution was stirred overnight and then concentrated. The resultant residue was purified by column chromatography on silica gel (EtOAc/Hexane=1/1) to give Intermediate 267-X (1.30 g) in a 83% yield.

Et$_3$N (0.2 mL) was added to a solution of Intermediate 267-X (800 mg) and piperazine (347 mg) in 1-pentanol (2 mL) at 120° C. The solution was stirred overnight and then concentrated. The residue was treated with water and extracted with CH$_2$Cl$_2$. The organic layer was collected and concentrated. The residue thus obtained was purified by column chromatography on silica gel (EtOAc/MeOH=1/1) to afford Intermediate 267-XI (700 mg) in a 81% yield.

Methylacrylate (93 mg) was added to a solution of Intermediate 267-XI (700 mg) in MeOH (7 mL) at 30° C. The solution was stirred for 5 hours and then concentrated. The residue was purified by silica gel (EtOAc and MeOH as eluant) to afford Intermediate 267-XII (460 mg) in a 58% yield.

0.5 M LiOH (9.2 mL) was added to a solution of Intermediate 267-XII (460 mg) in THF (5 mL). The mixture was stirred at room temperature for 15 hours. It was then acidified with 2.5 M HCl (pH=8) and filtered to obtain a yellow solid. The solid was purified by column chromatography on silica gel (CH$_2$Cl$_2$ and MeOH as eluant) to afford Intermediate 267-XIII (266 mg) in a 59% yield 20% TFA/CH$_2$Cl$_2$ (5 mL) was added to a solution of Intermediate 267-XIII (266 mg) in CH$_2$Cl$_2$ (3 mL). The solution was stirred at room temperature for 5 hours. The solution was concentrated. HCl (4 M in dioxane, 3 mL) was added to the residue in acetone. The mixture was stirred at room temperature for 30 minutes. After solvents were removed, the residue was treated with ether and filtered to give the hydrochloride salt of Compound 267 (153 mg).

CI-MS (M$^+$+1): 517.4.

Example 268

Preparation of Compound 268

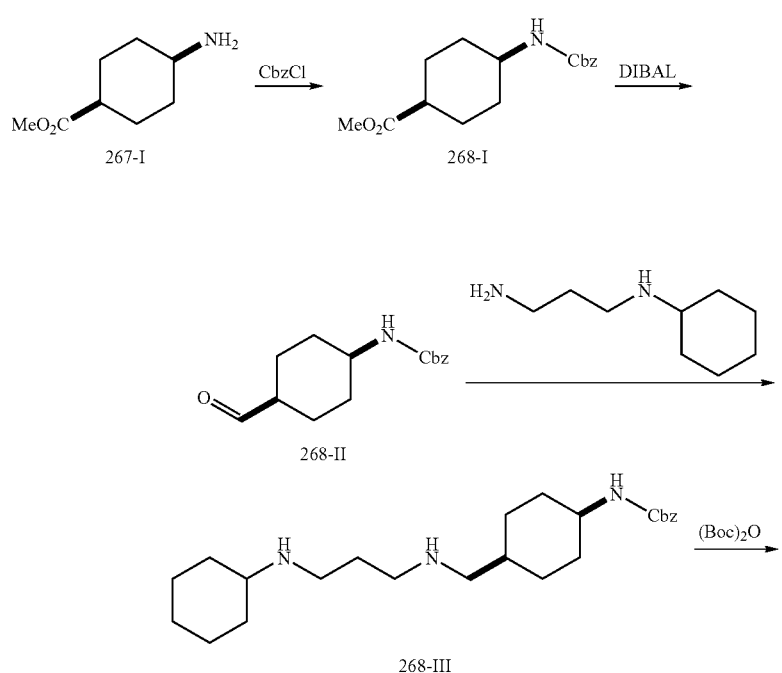

-continued
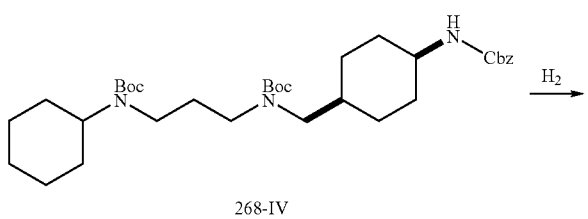
268-IV
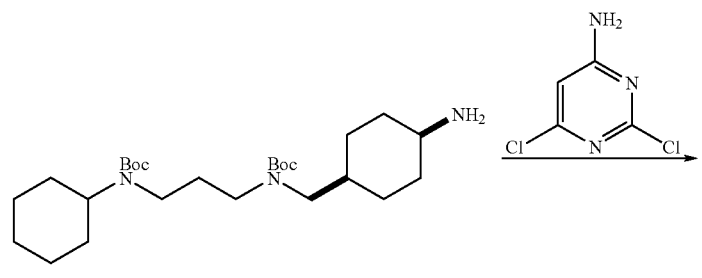
268-V
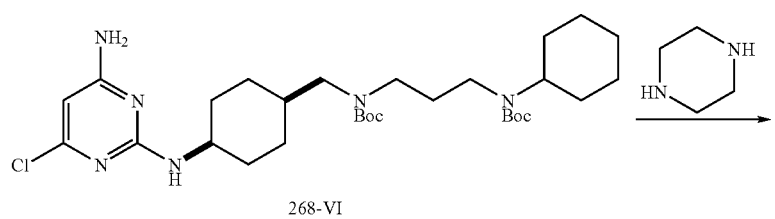
268-VI
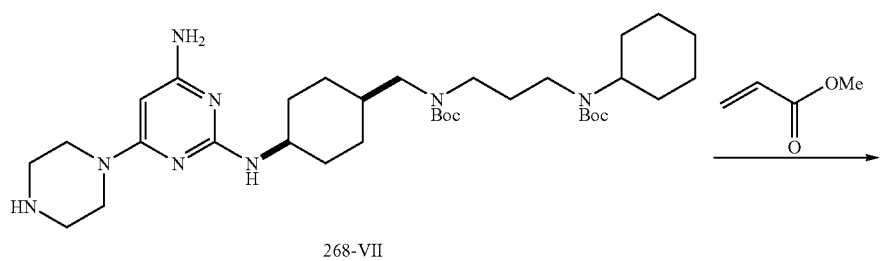
268-VII
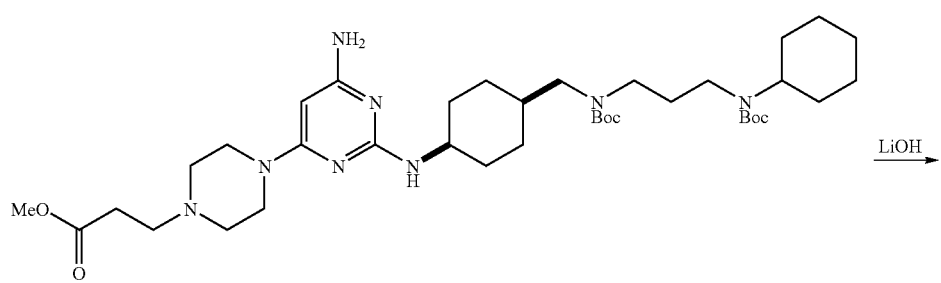
268-VIII
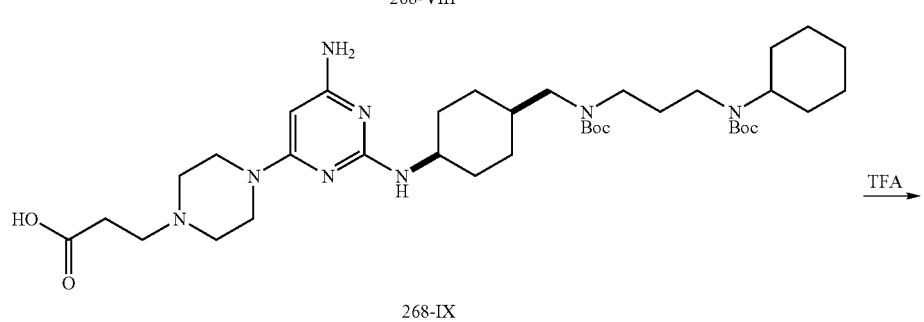
268-IX

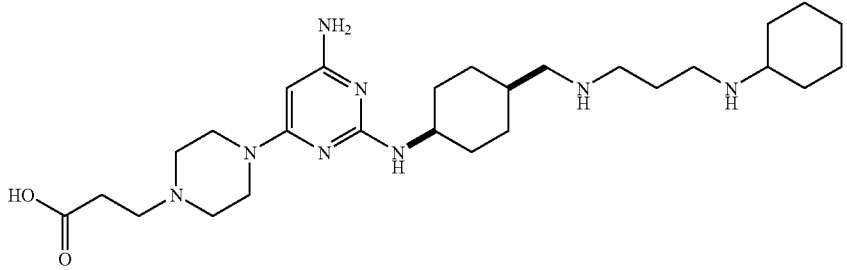

Compound 268

A solution of methyl cis-4-(amino)cyclohexylcarboxylate (267-I, 5.0 g) and PhCH$_2$OCOCl (6.5 g) in CH$_2$Cl$_2$ (64 mL) was stirred at 0° C. for 1 hour. The solution was allowed to warm-up to room temperature and stirred for another 12 hours. It was then concentrated and the residue was purified by column chromatography on silica gel (EtOAc/Hexane=1/4) to afford Intermediate 268-I (5.56 g) in a 60% yield.

DIBAL (1.0 M in Hexane, 34 mL) was added to a stirred solution of Intermediate 268-I (5.0 g) in dry toluene (170 mL) at −70~−78° C. under N$_2$ (g). The reaction mixture was stirred for 2 hours at this temperature. 5% HCl (aq) (34 mL) was then added to the solution at −60~−70° C. and the mixture was stirred for another 0.5 hour after the reaction temperature was increased to 25° C. The aqueous layer was extracted with CH$_2$Cl$_2$ twice. The organic layers were combined, dried with anhydrous MgSO$_4$, and concentrated by removing the solvent under vacuum to afford curd 268-II (3.14 g).

Intermediate 268-II (3.0 g) was then reacted at room temperature with cyclohexylaminopropylamine (1.8 g) in MeOH (30 mL). The mixture was stirred at 60° C. for 12 hours. NaBH$_4$ (0.43 g) was added at 0° C. After being stirred for 0.5 hour, an aqueous solution of NH$_4$Cl (10%, 20 mL) was added and the mixture was extracted with CH$_2$Cl$_2$. The organic layer was collected, dried over anhydrous MgSO$_4$, filtered, and concentrated to afford a residue. The residue was purified by column chromatography on silica gel (EtOAc/Hexane=4/1) to afford Intermediate 268-III (2.54 g) in a 55% yield.

A solution of Intermediate 268-III (2.5 g) and Boc$_2$O (3.0 g) in CH$_2$Cl$_2$ (130 mL) was stirred at 25° C. overnight. The solution was then concentrated and the resultant residue was purified by column chromatography on silica gel (EtOAc/Hexane=1/9) to give Intermediate 268-IV (3.2 g) in a 85% yield.

10% Pd/C (570 mg) was added to a suspension of Intermediate 268-IV (3.2 g) in EtOH (18 mL). The mixture was stirred at ambient temperature under hydrogen atmosphere for 2.0 hours, filtered, and concentrated to give crude Intermediate 268-V (2.4 g).

A solution of crude Intermediate 268-V (2.4 g) and Et$_3$N (0.85 mL) in 1-pentanol (17 mL) was reacted with 2,4-dichloro-6-aminopyrimidine (1.0 g) at 120° C. for 15 hours. The solvent was removed and the residue was purified by column chromatography on silica gel (EtOAc/Hexane=3/1) to afford Intermediate 268-VI (2.4 g) in a 80% yield.

Piperazine (1.0 g) was added to Intermediate 268-VI (2.4 g) in 1-pentanol (8 mL). The mixture was stirred at 120° C. for 15 hours. The solution was concentrated and the residue was treated with water and extracted with CH$_2$Cl$_2$. The organic layer was collected and concentrated to afford crude Intermediate 268-VII (2.2 g).

Methyl acrylate (0.1 mL) was added to a solution of crude Intermediate 268-VII (700 mg) in MeOH (10 mL). The mixture was stirred at 30° C. for 12 hours. After the mixture was concentrated, the residue was treated with water and extracted with CH$_2$Cl$_2$. The organic layer was collected and concentrated to give a residue, which was purified by column chromatography on silica gel (EtOAc/MeOH=4/1) to afford Intermediate 268-VIII (530 mg) in a 67% yield.

0.5 M LiOH (7.2 mL) was added to a solution of Intermediate 268-VIII (530 mg) in THF (7.2 mL). The mixture was stirred at room temperature for 2 hours. It was then acidified with 2M HCl (pH=8) and filtered to obtain a yellow solid, which was purified by column chromatography on silica gel (EtOAc/MeOH=1/9) to afford Intermediate 268-IX (470 mg) in a 90% yield.

Intermediate 268-IX (470 mg) was dissolved in CH$_2$Cl$_2$ (8 mL). TFA (2 mL) was added and the solution was stirred at room temperature overnight. The solution was then concentrated and HCl (4 M in dioxane, 1.3 mL) was added to the residue in acetone (7 mL) at room temperature for 30 minutes. After the solvents were removed, the residue was treated with ether and filtered to give a hydrochloride salt of compound 268 (390 mg).

CI-MS (M$^+$+1): 517.4.

Example 269

In Vitro Assay

The above-mentioned compounds were tested for their efficacy in binding to CXCR4 receptor using a DELFIA GTP-binding kit (Wallac Oy, Turku, Finland). The DELFIA GTP-binding assay is a time-resolved fluorometric assay based on GDP-GTP exchange on G-protein subunits followed by activation of a G protein-coupled receptor by its agonists. Eu-GTP, obtained from Wallac Oy, was used in this assay to allow monitoring of agonist-dependent activation of G-protein. Stimulation of CXCR4 receptor by SDF-1 leads to the replacement of GDP by GTP on the α-subunit of G-protein. This GTP-Gα complex represents the activated form of G-protein. Eu-GTP, a non-hydrolysable analog of GTP, can be used to quantify the amount of activated G-protein. (Peltonen et al., Eur. J. Pharmacol. (1998) 355:275.)

Plasma membrane of CXCR4-expressing HEK293 cells was suspended in an assay buffer (50 mM NaCl, 100 µg/mL saponin, 3 mM MgCl$_2$, 3 µM GDP, 5% BSA, 50 mM HEPES, pH 7.4). An aliquot (4 µg protein) was added to each well of an AcroPlate (Pall Life Sciences, Ann Arbor, Mich.). After the addition of the test compounds (10 µM in 0.1% DMSO) and stromal-derived factor-1 (4 nM in the assay buffer), the assay plate was incubated in the dark at room temperature with slow shaking for 10 minutes. Eu-GTP was added to each well and the plate was incubated again for 60 minutes. The assay was terminated by washing the plate twice with a wash solution provided in the assay kit. Binding of Eu-GTP was determined based on the fluorescence signal from a Victor 2 multi-label reader.

Unexpectedly, 196 of the tested compounds showed $IC_{50}$ values between 0.003 µM and 0.1 µM; 56 of the tested compounds showed $IC_{50}$ values between 0.1 µM and 1 µM, and 16 of the test compounds showed $IC_{50}$ values between 1 µM and 5 µM.

Example 270

Radioligand Binding Assay

Competition binding assays between test compounds and human stromal-derived factor-1 were carried out using glass fiber filter plates (Millipore, Billerica, Mass.). The glass fiber filter plates were pre-coated with 90 µl of 0.2% polyethyleneimine for 30 minutes and rinsed with 100 µl of distilled water for four times to reduce non-specific binding. Membranes of human CXCR4-transfected HEK293 cells (5-10 µg protein/well) in a 70 µl assay buffer (50 mM HEPES, pH 7.4, 0.5% bovine serum albumin, 90 mM NaCl, 5 mM $MgCl_2$, 1 mM $CaCl_2$) were incubated with 20 µl of a test compound solution and 10 µl of a [$^{125}$I]-SDF-1 solution (each having a final concentration 150 pM) in U-bottom assay plates (Corning, Corning, N.Y.). After the membranes were incubated at room temperature for 120 minutes, the incubation was terminated by transferring 80 µl of each reaction mixture to each glass fiber plate well and filtered by vacuum filtration (MultiScreen Vacuum Maniford, Millipore). Each plate was washed 4 times with 80 µl/well of a wash buffer (20 mM HEPES, pH 7.4 and 90 mM NaCl) and then air dried overnight. After 35 µl/well of a Supermix cocktail to each plate, the radioactivity retained on the plate was counted with Trilux MicroBeta (PerkinElmer, Boston, Mass.).

The 196 compounds with $IC_{50}$ values between 0.003 µM and 0.1 µM in GTP-binding assay were further screened in radioligand binding assay. The results show that they exhibited inhibitory activities in the range of 10-1200 nM.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for enhancing migration of bone marrow-derived cells to blood, comprising administering to a subject in need thereof an effective amount of a compound of formula (I):

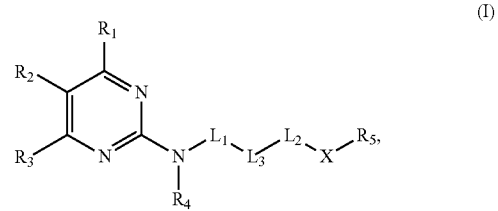

wherein
X is —NH—;
each of $L_1$ and $L_2$, independently, is $C_1$-$C_{10}$ alkylene, —C(O)—, or deleted;
$L_3$ is —N($R_b$)—, —O—, aryl, heteroaryl, or $C_3$-$C_{20}$ cycloalkyl;
$R_1$ is H, $C_1$-$C_{10}$ alkyl, $C_3$-$C_{20}$ cycloalkyl, $C_3$-$C_{20}$ heterocycloalkyl, or $NR_cR_d$;
$R_2$ is H, $C_1$-$C_{10}$ alkyl, $C_3$-$C_{20}$ heterocycloalkyl, halo, or CN;
$R_3$ is H, $C_3$-$C_{20}$ heterocycloalkyl, halo, or $NR_cR_d$;
$R_4$ is H; and
$R_5$ is

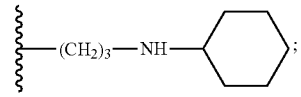

in which each of $R_b$, $R_c$, and $R_d$, independently, is H, $C_1$-$C_{10}$ alkyl, $C_3$-$C_{20}$ cycloalkyl, $C_3$-$C_{20}$ heterocycloalkyl, aryl, or heteroaryl.

2. The method of claim 1, wherein $L_3$ is —N($R_b$)—.
3. The method of claim 2, wherein $R_1$ is $C_3$-$C_{20}$ heterocycloalkyl.
4. The method of claim 3, wherein $R_1$ is

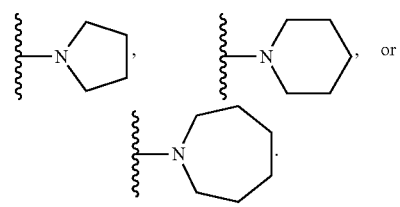

5. The method of claim 1, wherein $L_3$ is aryl.
6. The method of claim 5, wherein $L_3$ is phenylene.
7. The method of claim 1, wherein $L_3$ is $C_3$-$C_{20}$ cycloalkyl.
8. The method of claim 7, wherein $L_3$ is cyclohexylene.
9. The method of claim 7, wherein $R_3$ is $C_3$-$C_{20}$ heterocycloalkyl substituted with $C_1$-$C_{10}$ alkyl, $C_3$-$C_{20}$ cycloalkyl, $C_3$-$C_{20}$ heterocycloalkyl, aryl, OR', C(O)R', COOR', C(O)N(R'R''), $SO_2$R', or C(S)N(R'R''), in which each of R' and R'', independently, is H, $C_1$-$C_{10}$ alkyl, $C_3$-$C_{20}$ cycloalkyl, $C_3$-$C_{20}$ heterocycloalkyl, aryl, or heteroaryl.
10. The method of claim 1, wherein the bone marrow-derived cells are CD34+ cells or CD133+ cells.
11. The method of claim 1, wherein the bone marrow-derived cells are stem cells or endothelial progenitor cells.
12. The method of claim 1, further comprising concurrently administering to the subject an effective amount of a granulocyte-colony stimulating factor.

13. The method of claim 1, further comprising administering to the subject an effective amount of a very later antigen-4 inhibitor.
14. The method of claim 1, wherein $R_3$ is
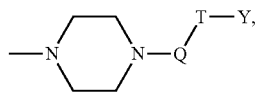
wherein Q is C(O) or a bond, T is alkylene, and Y is OH or COOH.
15. The method of claim 1, wherein the compound is one of the following compounds:
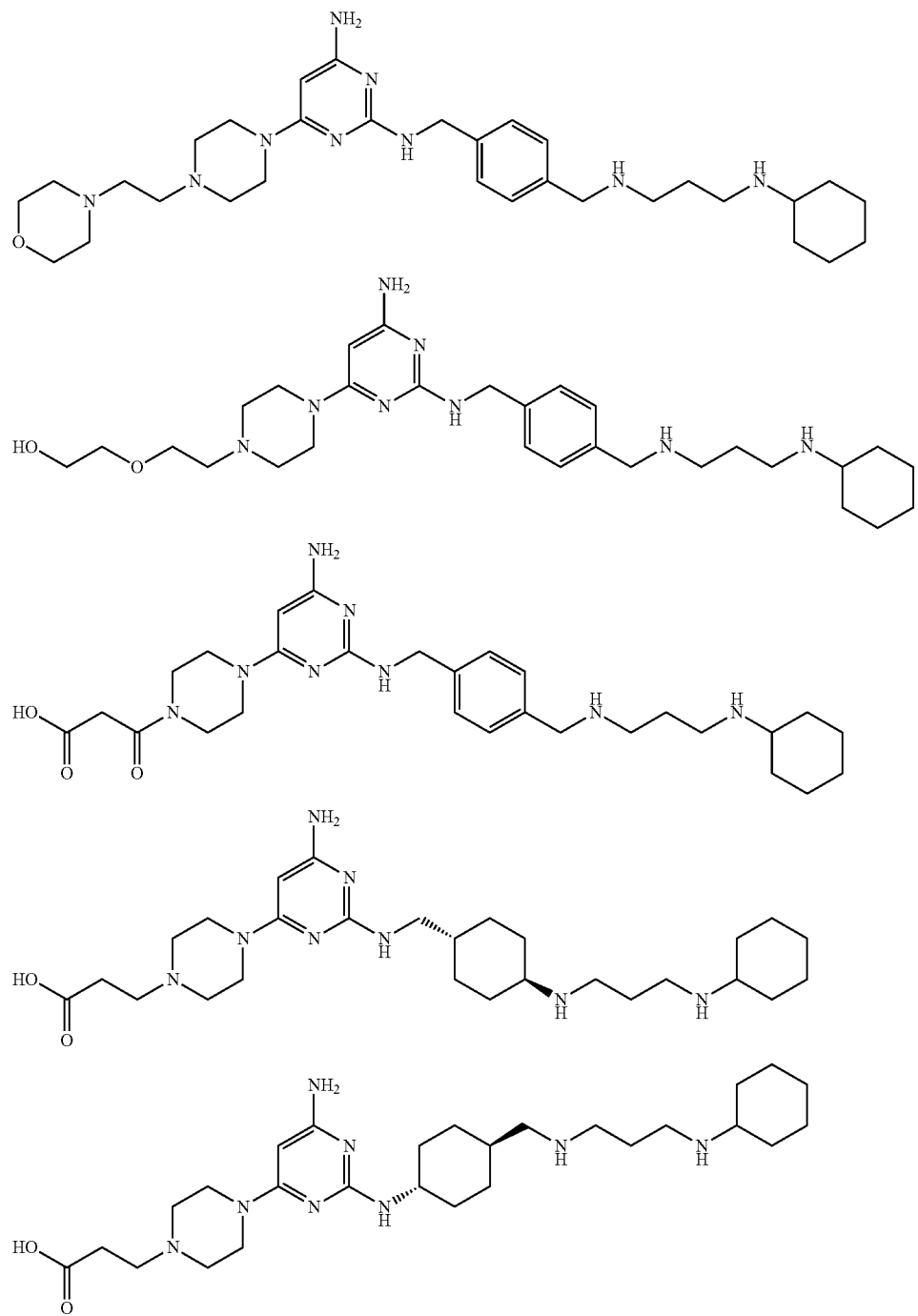

-continued
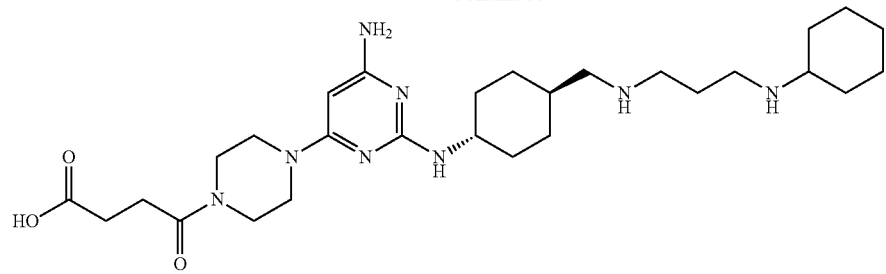
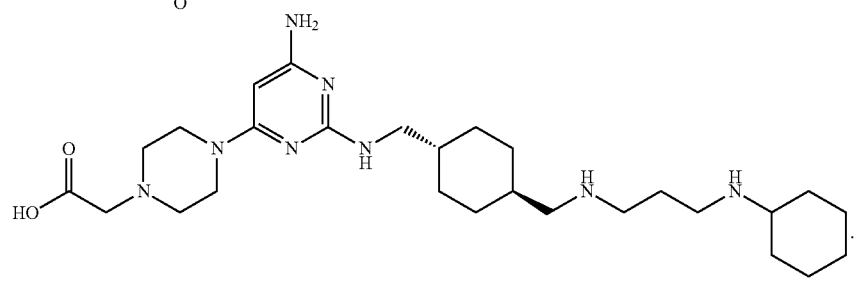
* * * * *